US011787781B2

(12) United States Patent
Drummond et al.

(10) Patent No.: US 11,787,781 B2
(45) Date of Patent: *Oct. 17, 2023

(54) INHIBITING ATAXIA TELANGIECTASIA AND RAD3-RELATED PROTEIN (ATR)

(71) Applicant: Celator Pharmaceuticals, Inc., Palo Alto, CA (US)

(72) Inventors: Daryl C. Drummond, Lincoln, MA (US); Bolin Geng, Andover, MA (US); Dmitri B. Kirpotin, Revere, MA (US); Suresh K. Tipparaju, Arlington, MA (US); Alexander Koshkaryev, Newton, MA (US); Ozan Alkan, Cambridge, MA (US)

(73) Assignee: CELATOR PHARMACEUTICALS, INC., Palo Alto, CA (US)

( * ) Notice: Subject to any disclaimer, the term of this patent is extended or adjusted under 35 U.S.C. 154(b) by 218 days.

This patent is subject to a terminal disclaimer.

(21) Appl. No.: 17/314,753

(22) Filed: May 7, 2021

(65) Prior Publication Data

US 2021/0300905 A1 Sep. 30, 2021

Related U.S. Application Data

(63) Continuation of application No. 16/745,709, filed on Jan. 17, 2020, now Pat. No. 11,028,076, which is a continuation of application No. 16/069,092, filed as application No. PCT/US2017/012939 on Jan. 11, 2017, now Pat. No. 10,570,119.

(60) Provisional application No. 62/444,172, filed on Jan. 9, 2017, provisional application No. 62/420,258, filed on Nov. 10, 2016, provisional application No. 62/277,262, filed on Jan. 11, 2016.

(51) Int. Cl.
| | |
|---|---|
| *C07D 403/12* | (2006.01) |
| *A61K 9/127* | (2006.01) |
| *A61K 31/496* | (2006.01) |
| *A61K 31/555* | (2006.01) |
| *A61K 31/4745* | (2006.01) |
| *A61K 31/7068* | (2006.01) |
| *A61K 31/497* | (2006.01) |
| *A61K 31/4965* | (2006.01) |
| *A61P 35/00* | (2006.01) |
| *A61K 47/14* | (2017.01) |

(52) U.S. Cl.
CPC .......... *C07D 403/12* (2013.01); *A61K 9/1271* (2013.01); *A61K 31/4745* (2013.01); *A61K 31/496* (2013.01); *A61K 31/497* (2013.01); *A61K 31/4965* (2013.01); *A61K 31/555* (2013.01); *A61K 31/7068* (2013.01); *A61K 47/14* (2013.01); *A61P 35/00* (2018.01)

(58) Field of Classification Search
None
See application file for complete search history.

(56) References Cited

U.S. PATENT DOCUMENTS

| | | |
|---|---|---|
| 4,990,610 A | 2/1991 | Lazaridis et al. |
| 5,043,164 A | 8/1991 | Huang et al. |
| 7,199,123 B2 | 4/2007 | Munchhof |
| 7,595,319 B2 | 9/2009 | Berg et al. |
| 8,147,867 B2 | 4/2012 | Hong et al. |
| 8,410,112 B2 | 4/2013 | Charrier et al. |
| 8,623,869 B2 | 1/2014 | Charrier et al. |
| 8,703,181 B2 | 4/2014 | Hong et al. |
| 8,765,751 B2 | 7/2014 | Charrier et al. |
| 8,822,469 B2 | 9/2014 | MacCormick et al. |
| 8,841,308 B2 | 9/2014 | Charrier et al. |
| 8,841,337 B2 | 9/2014 | Charrier et al. |
| 8,841,449 B2 | 9/2014 | Charrier et al. |
| 8,841,450 B2 | 9/2014 | Charrier et al. |
| 8,846,686 B2 | 9/2014 | Charrier et al. |
| 8,846,917 B2 | 9/2014 | Charrier et al. |
| 8,846,918 B2 | 9/2014 | Charrier et al. |
| 8,853,217 B2 | 10/2014 | Charrier et al. |
| 8,877,759 B2 | 11/2014 | Charrier et al. |
| 8,912,198 B2 | 12/2014 | Charrier et al. |
| 8,999,632 B2 | 4/2015 | Falcon et al. |
| 9,701,674 B2 | 7/2017 | Charrier et al. |
| 10,570,119 B2 | 2/2020 | Drummond et al. |
| 11,028,076 B2 | 6/2021 | Drummond et al. |
| 2006/0052396 A1 | 3/2006 | Berg et al. |
| 2007/0027135 A1 | 2/2007 | Bruncko et al. |
| 2008/0076779 A1 | 3/2008 | Elmore et al. |
| 2008/0318974 A1 | 12/2008 | Gaudino et al. |
| 2010/0215582 A1 | 8/2010 | Isoda |
| 2011/0053923 A1 | 3/2011 | Foote et al. |
| 2012/0165298 A1 | 6/2012 | Miller-Moslin et al. |
| 2013/0089626 A1 | 4/2013 | Pollard et al. |
| 2013/0115310 A1 | 5/2013 | Charrier et al. |

(Continued)

FOREIGN PATENT DOCUMENTS

| | | |
|---|---|---|
| CN | 101115727 A | 1/2008 |
| CN | 102325764 A | 1/2012 |

(Continued)

OTHER PUBLICATIONS

Zheng, L., Biochemistry, 2015, p. 33 (with English translation, 4 pages).

(Continued)

*Primary Examiner* — Brian J Davis

(74) *Attorney, Agent, or Firm* — COOLEY LLP

(57) ABSTRACT

Novel compounds inhibiting ATR protein kinase include compounds of formula (I) disclosed herein, as well as liposome formulations comprising ATR protein kinase inhibitor compounds. The compositions are useful for the treatment of cancer.

20 Claims, 86 Drawing Sheets

(56) References Cited

U.S. PATENT DOCUMENTS

| | | | |
|---|---|---|---|
| 2013/0115311 A1 | 5/2013 | Charrier et al. |
| 2013/0115312 A1 | 5/2013 | Charrier et al. |
| 2013/0115313 A1 | 5/2013 | Charrier et al. |
| 2013/0115314 A1 | 5/2013 | Charrier et al. |
| 2013/0184292 A1 | 7/2013 | Charrier et al. |
| 2014/0044802 A1 | 2/2014 | Pollard et al. |
| 2014/0107093 A1 | 4/2014 | Charrier et al. |
| 2015/0182460 A1 | 7/2015 | Hong et al. |
| 2015/0359797 A1 | 12/2015 | Helleday et al. |
| 2018/0303829 A1 | 10/2018 | Pollard et al. |
| 2020/0399247 A1 | 12/2020 | Drummond et al. |

FOREIGN PATENT DOCUMENTS

| | | | |
|---|---|---|---|
| CN | 102485212 A | 6/2012 |
| CN | 102485213 A | 6/2012 |
| HK | 1162482 | 2/2018 |
| JP | 2007528863 A | 10/2007 |
| JP | 2007538247 A | 12/2007 |
| JP | 2014528419 A | 10/2014 |
| JP | 2015502925 A | 1/2015 |
| WO | WO 2003/004472 A1 | 1/2003 |
| WO | WO-2005007196 A2 | 1/2005 |
| WO | WO-2005112752 A1 | 12/2005 |
| WO | WO 2006/120573 A2 | 11/2006 |
| WO | WO 2007/015632 A1 | 2/2007 |
| WO | WO-2008140081 A1 | 11/2008 |
| WO | WO 2010/054398 A1 | 5/2010 |
| WO | WO 2010/071837 A1 | 6/2010 |
| WO | WO-2010073034 A1 | 7/2010 |
| WO | WO 2011/143399 A1 | 11/2011 |
| WO | WO 2011/143419 A1 | 11/2011 |
| WO | WO 2011/143422 A1 | 11/2011 |
| WO | WO 2011/143423 A2 | 11/2011 |
| WO | WO 2011/143425 A2 | 11/2011 |
| WO | WO 2011/143426 A1 | 11/2011 |
| WO | WO 2011/163527 A1 | 12/2011 |
| WO | WO 2012/138938 A1 | 10/2012 |
| WO | WO 2012/178123 A1 | 12/2012 |
| WO | WO 2012/178124 A1 | 12/2012 |
| WO | WO 2012/178125 A1 | 12/2012 |
| WO | WO 2013/049719 A1 | 4/2013 |
| WO | WO 2013/049722 A1 | 4/2013 |
| WO | WO 2013/049726 A2 | 4/2013 |
| WO | WO 2013/049859 A1 | 4/2013 |
| WO | WO-2013071085 A1 | 5/2013 |
| WO | WO 2013/152298 A1 | 10/2013 |
| WO | WO 2014/055756 A1 | 4/2014 |
| WO | WO 2014/089379 A1 | 6/2014 |
| WO | WO 2014/143240 A1 | 9/2014 |
| WO | WO 2014/143241 A1 | 9/2014 |
| WO | WO 2014/143242 A1 | 9/2014 |
| WO | WO 2016/004043 A1 | 1/2016 |

OTHER PUBLICATIONS

Bao et al., "ATR/ATM-mediated phosphorylation of human Rad17 is required for genotoxic stress responses," Nature. (2001) 411:969-974.
Barsanti et al., "Structure-Based Drug Design of Novel Potent and Selective Tetrahydropyrazolo[1,5-a] pyrazines as ATR Inhibitors," ACS Med. Chem. Lett. (Nov. 20, 2014) 6(1):37-41.
Barsanti et al., "Structure-Based Drug Design of Novel, Potent, and Selective Azabenzimidazoles (ABI) as ATR Inhibitors," ACS Med. Chem. Lett. (Oct. 30, 2014) 6(1):42-46.
Boucher et al., "Abstract LB-299: Comprehensive preclinical evaluation of VE-822, the first ATR-targeted drug candidate: a novel approach to transforming the efficacy of DNA damaging agents," Cancer Res. (Apr. 15, 2013) 73: LB-299, 5 pages.
Boucher et al., "Potent Radiation Enhancement With VX-984, a Selective DNA-PKcs Inhibitor for the Treatment of NSCLC" Presentation Abstract In; AACR Annual Meeting, 2016. (Apr. 16-20, 2016) Abstract No. 3716, 1 page.
Boucher et al., "Potent Radiation Enhancement With VX-984, a Selective DNA-PKcs Inhibitor for the Treatment of NSCLC" Poster Presented In; AACR Annual Meeting, 2016. (Apr. 16-20, 2016) Poster 3716, 1 page.
Casper et al., "Chromosomal instability at common fragile sites in Seckel syndrome," Am. J. Hum. Genet. (2004) 75:654-660.
Cattrell et al., "Discovery of VX-984: Mitigation of aldehyde oxidase metabolism through the use of targeted deuteration," Presentation Abstract In; 251st American Chemical Society National Meeting & Exposition, Mar. 13-17, 2016. San Diego, California. Abstract No. MEDI 283, 1 page.
Chan et al., "Protein microarrays for multiplex analysis of signal transduction pathways," Nat. Med. (2004) 10 (12):1390-1396.
Charrier et al., "Discovery of Potent and Selective Inhibitors of Ataxia Telangiectasia Mutated and Rad3 Related (ATR) Protein Kinase as Potential Anticancer Agents," Journal of Medicinal Chemistry, (2011) vol. 54, pp. 2320-2330.
Chen et al. (Oct. 9, 2014) "Development of pharmacodynamic biomarkers for ATR inhibitors," Molecular Oncology. 9 (2):463-472.
Cimprich et al., "ATR: an essential regulator of genome integrity," Nat. Rev. Mol. Cell. Biol. (2008) 9:616-627.
ClinicalTrials.gov "An Open-Label, First-in-Human Study of the Safety, Tolerability, and Pharmacokinetics of VX-970 in Combination With Cytotoxic Chemotherapy," Accessible on the Internet at URL: https://clinicaltrials.gov/ct2/show/NCT02157792. [Last Accessed Oct. 10, 2016], 5 pages.
Cortez et al., "ATR and ATRIP: partners in checkpoint signaling," Science. (2001) 294:1713-1716.
Davidson et al., "Small Molecules, Inhibitors of DNA-PK, Targeting DNA Repair, and Beyond," Front. Pharmacol. (Jan. 2013) 4:5, 7 pages.
Dobbs et al., "A structural model for regulation of NHEJ by DNA-PKcs autophosphorylation," DNA Repair. (2010) 9:1307-1314.
Einhorn, "Curing metastatic testicular cancer," Proc. Natl. Acad. Sci. USA. (2002) 99:4592-4595.
Extended European Search Report for European Application No. 17738831.1 dated Aug. 12, 2019, 8 pages.
Finlay and Griffin, "Modulation of DNA repair by pharmacological inhibitors of the PIKK protein kinase family," Bioorganic & Medicinal Chemistry Letters, 2012, vol. 22, pp. 5352-5359.
Fokas et al., "Targeting ATR in vivo using the novel inhibitor VE-822 results in selective sensitization of pancreatic tumors to radiation," Cell Death Dis. (Dec. 6, 2012) 3:e441, 10 pages.
Foote et al., "Discovery of 4-{4-[(3R)-3-Methylmorpholin-4-yl]-6-[1-(methylsulfonyl)cyclopropyl] pyrimidin-2-yl}-1H-indole (AZ20): a potent and selective inhibitor of ATR protein kinase with monotherapy in vivo antitumor activity," J. Med. Chem. (2013) 56, 2125-2138.
Geran et al., "Protocols for screening chemical agents and natural products against animal tumors and natural other biological systems," Cancer Chemother. Rep. (1972) Part 3. 3:1-88.
Hall et al., "Potentiation of tumor responses to DNA damaging therapy by the selective ATR inhibitor VX-970," Oncotarget. (Jul. 3, 2014) 5(14):5674-5685—with supplementary information, 19 pages.
Hall-Jackson et al., "ATR is a caffeine-sensitive, DNA-activated protein kinase with a substrate specificity distinct from DNA-PK," Oncogene. (1999) 18:6707-6713.
Hammel et al. "Ku and DNA-dependent Protein Kinase Dynamic Conformations and Assembly Regulate DNA Binding and the Initial Non-homologous End Joining Complex," J. Biol. Chem. (2010) 285:1414-1423.
Helleday et al., "DNA repair pathways as targets for cancer therapy," Nat. Rev. Cancer. (2008) 8:193-204.
Helleday, "The underlying mechanism for the PARP and BRCA synthetic lethality: clearing up the misunderstandings," Mol. Oncol. (2011) 5:387-393.
Hill "The DNA-dependent protein kinase (DNA-PK): More than just a case of making ends meet?" Cell Cycle. (2010) 9:3460-3469.
International Search Report and Written Opinion of PCT/US2017/012939 dated Apr. 6, 2017, 9 pages.

(56) References Cited

OTHER PUBLICATIONS

International Search Report and Written Opinion of PCT/US2017/012992 dated Apr. 3, 2017, 9 pages.
Jackson et al., "The DNA-damage response in human biology and disease," Nature. (2009) 461:1071-1078.
Jossé et al., "ATR inhibitors VE-821 and VX-970 sensitize cancer cells to topoisomerase I inhibitors by disabling DNA replication initiation and fork elongation responses," Cancer Res. (2014) 74:6968-6979.
Koshkaryev et al., "Development of Liposomal ATR Inhibitor" Poster Presentation. Merrimack Pharmaceuticals Inc. (Feb. 29, 2016) 11 pages.
Kumagai et al., "TopBP1 activates the ATR-ATRIP complex," Cell. (2006) 124:943-955.
Li et al., "3D-QSAR Analysis on ATR Protein Kinase Inhibitors Using CoMFA and CoMSIA," Curr. Comput. Aided Drug Des. (2014), 10(4), 327-334.
Lu et al., "Rationally Designed PI3Kα Mutants to Mimic ATR and Their Use to Understand Binding Specificity of ATR Inhibitors," J. Mol. Biol. (2017), 429(11): 1684-1704.
Luo et al., "Molecular dynamics-based self-organizing molecular field analysis on 3-amino-6-arylpyrazines as the ataxia telangiectasia mutated and Rad3 related (ATR) protein kinase inhibitors," Medicinal Chemistry Research, (2014) vol. 23, pp. 747-758.
Maxwell et al., "Discovery of VX-984: A novel, selective DNA-PK inhibitor for the treatment of cancer," Presentation Abstract In; 251st American Chemical Society National Meeting & Exposition, Mar. 13-17, 2016. San Diego, California.
Mohni et al., "A Synthetic Lethal Screen Identifies DNA Repair Pathways that Sensitize Cancer Cells to Combined ATR Inhibition and Cisplatin Treatments," PLoS One. (May 12, 2015) 10:e0125482. pp. 1-22.
Murai et al., "Stereospecific PARP trapping by BMN 673 and comparison with olaparib and rucaparib," Mol. Cancer Ther. (2013) 13:433-443.
Murai et al., "Rationale for poly(ADP-ribose) polymerase (PARP) inhibitors in combination therapy with camptothecins or temozolomide based on PARP trapping versus catalytic inhibition," J. Pharmacol. Exp. Ther., (Jun. 2014) 349:408-416.
Murai et al., "Trapping of PARP1 and PARP2 by Clinical PARP Inhibitors," Cancer Res. (Nov. 1, 2012) 72:5588-5599.
Claussen et al., "DNA repair by ERCC1 in non-small-cell lung cancer and cisplatin-based adjuvant chemotherapy," New Eng. J. Med. (2006) 355:983-991.
Peasland et al., "Identification and evaluation of a potent novel ATR inhibitor, NU6027, in breast and ovarian cancer cell lines," Br. J. Cancer. (Jul. 5, 2011) 105(3):372-381.
Pires et al., "Targeting radiation-resistant hypoxic tumour cells through ATR inhibition," Br. J. Cancer. (Jun. 19, 2012) 10:291-299.
Pollard et al., "Defining Optimal Dose Schedules for ATR Inhibitors in Combination With DNA-Damaging Drugs: Informing Clinical Studies of VX-970, the First-in-Class ATR Inhibitor" Presentation Abstract In; The AACR Annual Meeting, Apr. 16-20, 2016, 1 page.
Pollard et al. "Defining Optimal Dose Schedules for ATR Inhibitors in Combination With DNA-Damaging Drugs: Informing Clinical Studies of VX-970, the First-in-Class ATR Inhibitor" Poster Presented In; The AACR Annual Meeting, Apr. 16-20, 2016, 1 page.
Pollard "The Science of Possibility," Vertex Pharmaceuticals Incorporated. (Sep. 2013) Document No. VXR-EU-ONC-00003, pp. 1-47.
Prevo et al., "The novel ATR inhibitor VE-821 increases sensitivity of pancreatic cancer cells to radiation and chemotherapy," Cancer Biol. Ther. (Sep. 2012) 13(11):1072-1081.
Radhakrishnan et al., "Non-homologous end joining: emerging themes and unanswered questions," DNA Repair. (May 2014) 17:2-8.
Reaper et al., "Selective killing of ATM- or p53-deficient cancer cells through inhibition of ATR," Nat. Chem. Biol. (Apr. 13, 2011) 7:428-430.
Reaper et al., "Preclinical Combinations of ATR and PARP Inhibitors: Defining Target Patient Populations and Dose Schedule" Poster Presented In; AACR Annual Meeting, Apr. 16-20, 2016. Poster 3711, 1 page.
Schoppy et al., "Oncogenic stress sensitizes murine cancers to hypomorphic suppression of ATR," J. Clin. Inves. (Jan. 2012) 122:241-252.
Sibanda et al., "Crystal Structure of DNA-PKcs Reveals a Large Open-Ring Cradle Comprised of HEAT Repeats" Nature. (2010) 463:118-121.
Toledo et al., "Targeting ATR and Chk1 kinases for cancer treatment: a new model for new (and old) drugs," Molecular Oncology. (Jul. 2011) 5:368-373.
Toledo et al., "A cell-based screen identifies ATR inhibitors with synthetic lethal properties for cancer- associated mutations," Nat. Struct. Mol. Biol. (May 8, 2011) 18(6):721-727.
Turner et al. "A synthetic lethal siRNA screen identifying genes mediating sensitivity to a PARP inhibitor," EMBO J. (2008) 27:1368-1377.
Ünsal-Kaçmaz et al., "Preferential binding of ATR protein to UV-damaged DNA," Proc. Natl. Acad. Sci. USA. (2002) 99(10):6673-6678.
Ünsal-Kaçmaz et al., "Quaternary structure of ATR and effects of ATRIP and replication protein A on its DNA binding and kinase activities," Molecular and Cellular Biology. (2004) 24(3):1292-1300.
Wagner et al., "Prospects for the Use of ATR Inhibitors to Treat Cancer," Pharmaceuticals. (2010) 3:1311-1334.
Weber et al., "ATM and ATR as therapeutic targets in cancer," Pharmacology and Therapeutics. (2015) 149:124-138.
Yap et al. "Phase I trial of first-in-class ataxia telangiectasia-mutated and Rad3-related (ATR) inhibitor VX-970 as monotherapy (mono) or in combination with carboplatin (CP) in advanced cancer patients (pts) with preliminary evidence of target modulation and antitumor activity" Presentation Abstract In; AACR-NCI-EORTC, Nov. 6, 2015, 1 page.
Zenke et al., "M3814, a novel investigational DNA-PK inhibitor: enhancing the effect of fractionated radiotherapy leading to complete regression of tumors in mice" Abstract Presented In; AACR Annual Meeting, Apr. 16-20, 2016. Abstract No. 1658, 1 page.
Zou et al. "Sensing DNA damage through ATRIP recognition of RPA-ssDNA complexes," Science. (2003) 300:1542-1548.

Scheme 2

A549

| Gemcitabine | Compound A | Compound 5 |
|---|---|---|
| responder | A549, HCC827, H2170, H358, H460 | A549, HCC827, H2170, H358, H460 |
| non-responder | H2170, H358, H596 | H2170, H358, H596 |

| SN38 | Compound A | Compound 5 |
|---|---|---|
| responder | A549, DMS-114, H1299, H23, H460, Calu-6 | A549, DMS-114, H1299, H23, H460, Calu-6 |
| non-responder | Calu-6, H1993, H23, H596 | Calu-6, H1993, H23, H596 |

*Fig. 24*

| Kinase | ATR IC$_{50}$ (nM) | ATM IC$_{50}$ (nM) |
|---|---|---|
| Compound 6 | 470.8 | > 10,000 |
| Compound 2 | 139.8 | 4817 |
| Compound 5 | 233.9 | > 10,000 |
| Compound 4 | 353.4 | 6869 |
| Compound 3 | 196.1 | > 10,000 |
| Compound A | < 1 * | 42 |
| Compound 1 *** | 49.6 ** | 3864 |

Lit. ref.  EuroFin, UK, cell freesystem
* KI < 0.2nM
** KI = 6 nM
   IC50 = 120nM
*** discontinued

*Fig. 25A*

| Kinase | Compound 5 IC$_{50}$ (nM) | Compound A IC$_{50}$ (nM) |
|---|---|---|
| GSK3α | 206 | 126 |
| GSK3β | 876 | 210 |
| MLK1 | 74 | 59 |
| MLK2 | 91 | 76 |

EuroFin, UK, cell freesystem

*Fig. 25B*

INHIBITING ATAXIA TELANGIECTASIA AND RAD3-RELATED PROTEIN (ATR)

RELATED APPLICATIONS

This application is a continuation of U.S. patent application Ser. No. 16/745,709, filed on Jan. 17, 2020, now U.S. Pat. No. 11,028,076, which is a continuation of U.S. patent application Ser. No. 16/069,092, filed on Jul. 10, 2018, now U.S. Pat. No. 10,570,119, which is a 35 U.S.C. § 371 filing of International Application No. PCT/US2017/012939, filed Jan. 11, 2017, which claims priority to U.S. Provisional Patent Application No. 62/277,262, filed Jan. 11, 2016, U.S. Provisional Patent Application No. 62/420,258, filed Nov. 10, 2016, and U.S. Provisional Patent Application No. 62/444,172, filed Jan. 9, 2017, each of which are incorporated by reference into the present application in their entirety and for all purposes.

FIELD

This disclosure relates to compounds and related methods of inhibiting ataxia telangiectasia and Rad3-related protein (ATR), including methods and compounds useful for the treatment of cancer.

BACKGROUND

The ataxia-telangiectasia and Rad3-related (ATR) kinase is a serine/threonine protein kinase believed to be involved in the cellular DNA damage repair processes and cell cycle signaling. ATR kinase acts with ATM ("ataxia telangiectasia mutated") kinase and other proteins to regulate a cell's response to DNA damage, commonly referred to as the DNA Damage Response ("DDR"). The DDR is believed to stimulate DNA repair, promote survival and stalls cell cycle progression by activating cell cycle checkpoints, which provide time for repair. Without the DDR, cells are much more sensitive to DNA damage and readily die from DNA lesions induced by endogenous cellular processes such as DNA replication or exogenous DNA damaging agents commonly used in cancer therapy.

The disruption of ATR function (e.g. by gene deletion) has been shown to promote cancer cell death both in the absence and presence of DNA damaging agents. Mutations of ATR have been linked to cancers of the stomach and endometrium, and lead to increased sensitivity to ionizing radiation and abolished cell cycle checkpoints. ATR is essential for the viability of somatic cells, and deletion of ATR has been shown to result in loss of damage checkpoint responses and cell death. See Cortez et al., Science 294: 1713-1716 (2001). ATR is also essential for the stability of fragile sites, and low ATR expression in Seckel syndrome patients results in increased chromosomal breakage following replication stress. See Casper et al., Am. J. Hum. Genet 75: 654-660 (2004). The replication protein A (RPA) complex recruits ATR, and its interacting protein ATRIP, to sites of DNA damage, and ATR itself mediates the activation of the CHK1 signaling cascade. See Zou et al., Science 300:1542-1548 (2003). ATR, like its related checkpoint kinase ATM, phosphorylates RAD17 early in a cascade that is critical to for checkpoint signaling in DNA-damaged cells. See Bao et al., Nature 411: 969-974 (2001). It is believed that ATR is particularly essential in the early mammalian embryo, to sense incomplete DNA replication and prevent mitotic catastrophe.

However, while DNA-damaging chemotherapy agents and ionizing radiation (IR) therapy have provided initial therapeutic benefits to cancer patients, existing therapies have lost clinical efficacy (e.g., due to tumor cell DNA repair responses). In vivo effects of an ATR inhibitor and a DNA damaging agent have shown some promise in the selective treatment of cancer compared to normal cells, particularly in treating tumor cells deficient in the G1 check point control (which may depend more on the ATR for survival).

There remains a need for the development of potent and selective therapies to deliver ATR inhibitors for the treatment of cancer, either as single agents or as part of combination therapies (e.g., in combination with chemotherapy and/or radiation therapy).

SUMMARY

Applicants have discovered novel chemical compounds useful for inhibiting ataxia-telangiectasia and Rad3-related (ATR) kinase and the treatment of cancer, and liposome formulations of certain inhibitors of ATR protein kinase having desirable properties (e.g., extended half-life in blood circulation and efficacy in treating tumors). The inventions are based in part on the discovery of certain novel compounds for inhibiting ATR protein kinase, as well as extended plasma half-lives and enhanced antitumor efficacy of certain liposomal formulations of ATR protein kinase inhibitor compounds.

In a first embodiment, novel compounds of formula (I) are useful for inhibiting ataxia-telangiectasia and Rad3-related (ATR) kinase and the treatment of cancer:

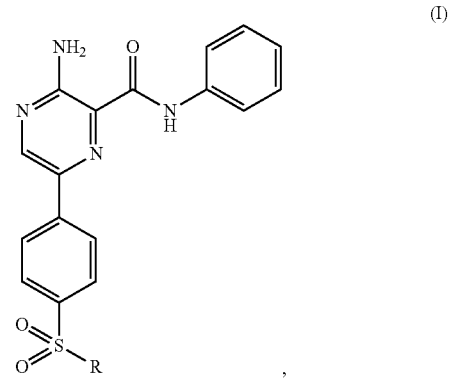

or a pharmaceutically acceptable salt thereof, wherein R is a moiety comprising an amine with a $pK_a$ of greater than 7.0 (preferably greater than 8.0, and most preferably at least about 9.5). The compounds of formula (I) preferably include one or more tertiary amine moieties at R selected to provide desired inhibition of ATR and/or liposome formation and stability characteristics. In some examples, R is a heterocyclic moiety comprising a first tertiary substituted nitrogen, preferably substituted with an alklyamino moiety comprising a second tertiary substituted nitrogen. In particular, compounds of formula (I) include those where R can be a moiety of the formula:

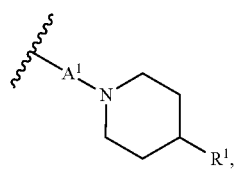

wherein $A^1$ is either absent or is an alkyl (e.g., $C_1$-$C_4$ alkyl (preferably —$(CH_2)_2$—), and $R^1$ is lower (e.g., $C_1$-$C_4$) alkylamino. In one embodiment, $R^1$ is ($C_1$-$C_4$ alkyl)-$NR^aR^b$, wherein $R^a$ and $R^b$ are each independently $C_1$-$C_4$ alkyl, e.g., $R^1$ is —$(CH_2)_2$—$N(CH_3)(CH_3)$. In another embodiment, $R^1$ is $NR^aR^b$, wherein $R^a$ and $R^b$ are each independently $C_1$-$C_4$ alkyl, e.g., $R^1$ is —$N(CH_2CH_3)(CH_2CH_3)$.

In another embodiment of formula (I), R is —$N(H)(C_1$-$C_4$ alkyl)-$NR^aR^b$, wherein $R^a$ and $R^b$ are each independently $C_1$-$C_4$ alkyl, or R is -(G)-$NR^aR^b$, wherein $R^a$ and $R^b$ are each independently $C_1$-$C_4$ alkyl, wherein G is $C_1$-$C_4$ alkyl, and wherein G can be further substituted with $C_1$-$C_4$ alkyl.

In another embodiment of formula (I), R can be a moiety of the formula:

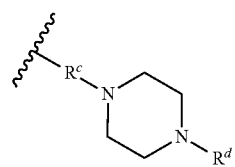

wherein $R^c$ and $R^d$ are each independently $C_1$-$C_4$ alkyl.

Preferred examples include liposomes comprising compounds selected from the group consisting of compounds 1, 2, 3, 4, 5, or 6:

Compound 1

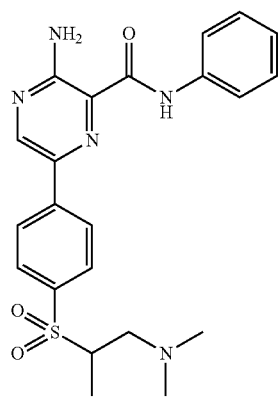

MW: 439.53

Compound 2

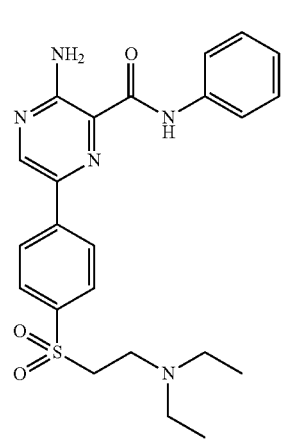

MW: 453.56

Compound 3

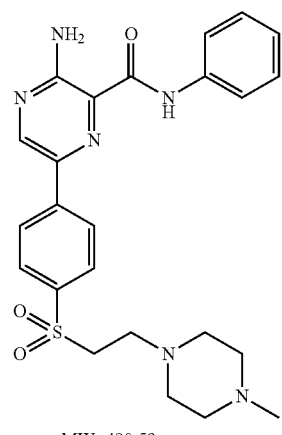

MW: 480.59

Compound 4

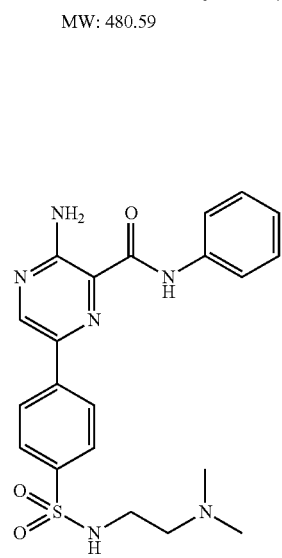

MW: 440.52

Compound 5

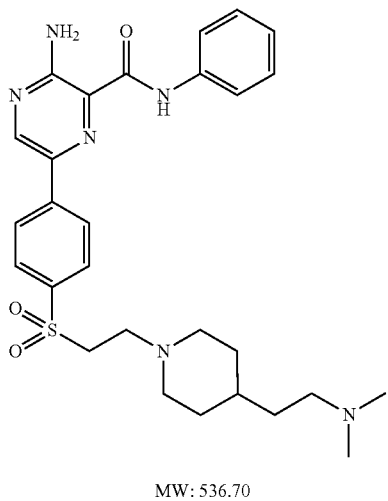

MW: 536.70

Compound 6

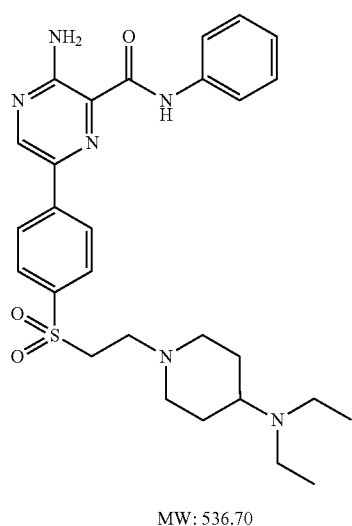

MW: 536.70 sulfate. In some examples, the liposome encapsulates the compound of formula (I) and sucrose octasulfate in a ratio at or near the stoichiometric ratio of the compound of formula (I) and the sucrose octasulfate.

One specific example provides a liposome having a vesicle formed from HSPC, cholesterol and PEG2000-DSG in a 3:2:0.15 molar ratio, encapsulating sucrose octasulfate and Compound 5. Another example provides a liposome having a vesicle formed from HSPC, cholesterol and PEG2000-DSG in a 3:2:0.15 molar ratio, encapsulating sucrose octasulfate and Compound 5.

Another specific example provides a liposome having a vesicle formed from HSPC, cholesterol and PEG2000-DSG in a 3:2:0.15 molar ratio, encapsulating sucrose octasulfate and Compound 6.

Another specific example provides a liposome having a vesicle formed from HSPC, cholesterol and PEG2000-DSG in a 3:2:0.15 molar ratio, encapsulating sucrose octasulfate and Compound A.

The ATR inhibitor compounds and/or liposome formulations thereof disclosed herein can be used in therapy and methods of treatment. In some embodiments, the therapy is treatment of cancer. When used as a therapy, the liposome composition may be used in a treatment regimen with one or more other compounds or compositions (e.g., in combination with an irinotecan

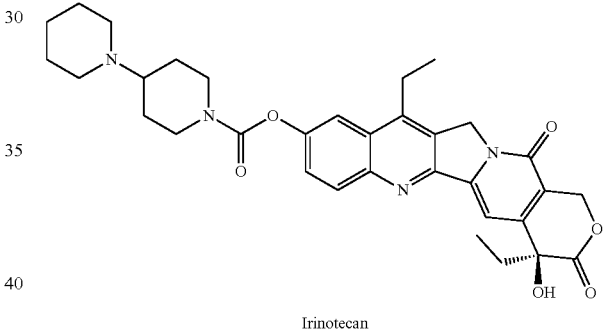

Irinotecan liposome formulation such as MM-398). The administration of the liposome composition with one or more other compounds or compositions may be simultaneous, separate or sequential. The one or more other compounds or compositions may be further therapeutics, e.g. further anticancer agents, or may be compounds which are designed to ameliorate the negative side effects of the therapeutic agents.

In a second embodiment, liposome formulations of ATR inhibitor compounds can include a compound of formula (I) or other ATR inhibitor compound(s) (e.g., comparative Compound A) encapsulated with a polyanion (e.g., a polyanionized sugar such as sucrose octasulfate, or a suitable polyanionized polyol) in a unilamellar vesicle formed from one or more liposome-forming lipids (e.g., hydrogenated soy phosphatidylcholine (HSPC)), cholesterol and a polymer-conjugated lipid (e.g., methoxy-poly(ethylene glycol)-1,2-distearoyl-sn-glyceryl (PEG2000-DSG). The liposome-forming lipid preferably comprises one or more phospholipids, with the ratio of the phospholipid(s) and the cholesterol selected to provide a desired amount of liposome membrane rigidity while maintaining a sufficiently reduced amount of leakage of the compound of formula (I) from the liposome. The type and amount of polymer-conjugated lipid can be selected to provide desirable levels of protein binding, liposome stability and circulation time in the blood stream. In some examples, the liposome vesicle comprises HSPC and cholesterol in a 3:2 molar ratio. In particular, the liposome can comprise a vesicle consisting of HSPC, cholesterol and PEG2000-DSG in a 3:2:0.15 molar ratio. The compound of formula (I) can be entrapped within the liposome with a suitable polyanion, such as sucrose octa-

DESCRIPTION OF THE DRAWINGS

FIG. 21A is a heat map illustrating the effect of combining Compound A or Compound 5 with Gemcitabine at various concentrations in U2OS, H358, and A549 cell lines. Microscopy images of cells treated with set concentrations of Compound 5 and Gemcitabine or Compound A and Gemcitabine in cells are shown (FIG. 21B). Proliferation assays of USO2 and H358 cells with set concentrations are shown as well (FIG. 21C).

FIG. 24 shows a summary of the lung cancer cell lines that are responsive to Compound A or Compound 5 in combination with Gemcitabine or SN38.

FIG. 25A-B show various ATR inhibitors tested for their ability to inhibit ATR (on-target) and ATM (off-target). Inhibition is reported as IC50 in nM (FIG. 25A). Additional "off-target" kinases are tested with Compound A or Compound 5 as well (FIG. 25B).

DETAILED DESCRIPTION

Figure 1:
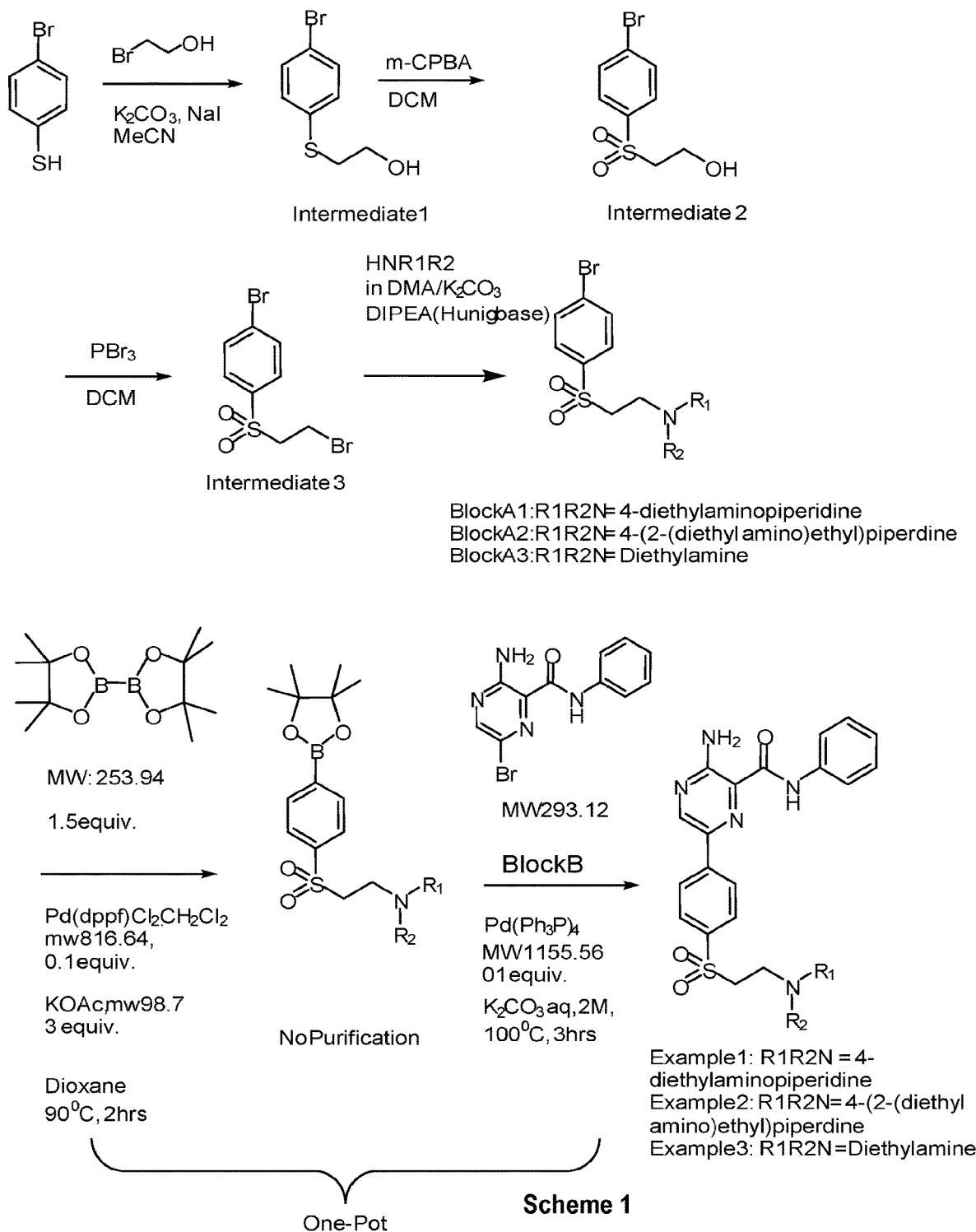
FIG. 1 is a first chemical reaction scheme useful in manufacturing certain compounds disclosed herein.

Novel compounds for inhibiting ATR protein kinase are described by formula (I):

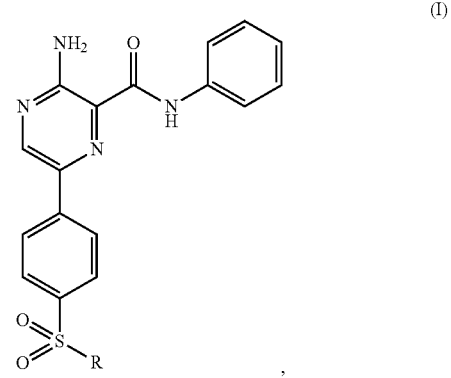

(I)

or a pharmaceutically acceptable salt thereof, wherein R is a moiety comprising an amine with a $pK_a$ of greater than 7.0 (preferably greater than 8.0, and most preferably at least about 9.5), selected to provide a plasma half-life of at least about 5 hours in mice (obtained according to Example 7). Preferably, R includes an amine-substituted alkyl moiety with 4-12 carbons. R can be selected to include only a combination of tertiary-substituted amine and hydrogenated alkyl groups. R preferably further includes a tertiary-alkyl substituted amine having a $pK_a$ of at least 7, but most preferably at least about 9.5 (e.g., a $pK_a$ of about 9.5-10.5). Examples of compounds of formula (I), or pharmaceutically acceptable salts thereof, include Compounds 1-6 (see Examples 1-6):

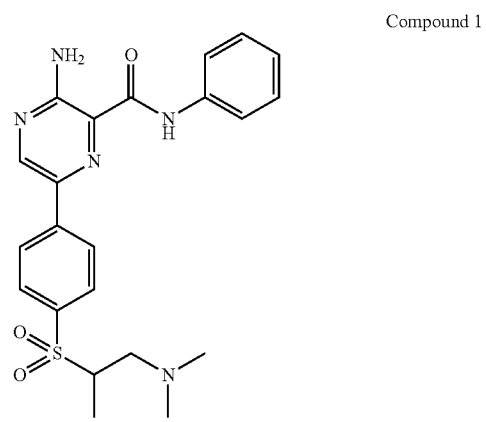

Compound 1

MW: 439.53

Compound 2

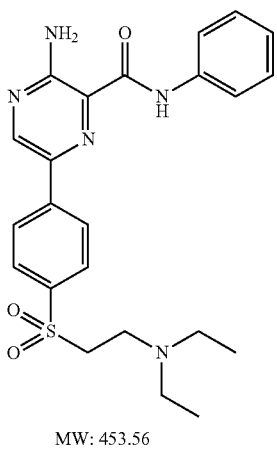

MW: 453.56

Compound 3

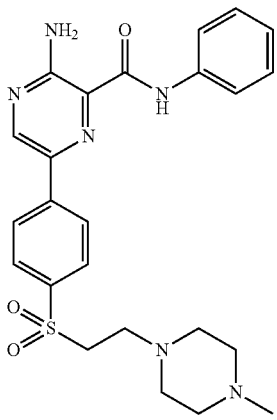

MW: 480.59

Compound 4

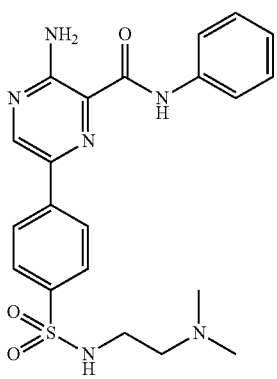

MW: 440.52

Compound 5

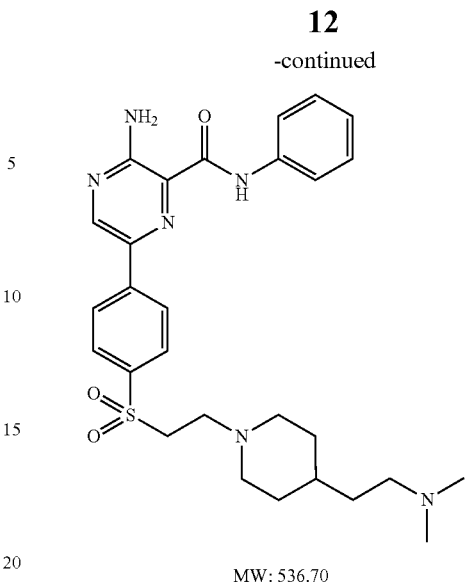

MW: 536.70

Compound 6

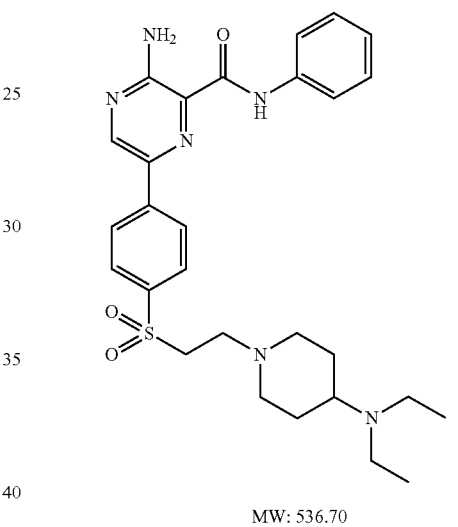

MW: 536.70

The compounds of formula (I) preferably include one or more tertiary amine moieties at R selected to provide desired inhibition of ATR and/or liposome formation and stability characteristics. In some examples, R is a heterocyclic moiety comprising a first tertiary substituted nitrogen, preferably substituted with an alklyamino moiety comprising a second tertiary substituted nitrogen. In particular, compounds of formula (I) include those where R can be a moiety of the formula:

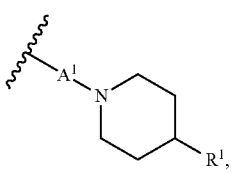

wherein $A^1$ is either absent or is an alkyl (e.g., $C_1$-$C_4$ alkyl (preferably —$(CH_2)_2$—), and $R^1$ is lower (e.g., $C_1$-$C_4$) alkylamino. In one embodiment, $R^1$ is ($C_1$-$C_4$ alkyl)-$NR^aR^b$, wherein $R^a$ and $R^b$ are each independently $C_1$-$C_4$ alkyl, e.g., $R^1$ is —$(CH_2)_2$—$N(CH_3)(CH_3)$. In another embodiment, $R^1$ is $NR^aR^b$, wherein $R^a$ and $R^b$ are each independently $C_1$-$C_4$ alkyl, e.g., $R^1$ is —N(CH$_2$CH$_3$)(CH$_2$CH$_3$).

In another embodiment of formula (I), R is —N(H)(C$_1$-C$_4$ alkyl)-$NR^aR^b$, wherein $R^a$ and $R^b$ are each independently $C_1$-$C_4$ alkyl, or R is -(G)-$NR^aR^b$, wherein $R^a$ and $R^b$ are each independently $C_1$-$C_4$ alkyl, wherein G is $C_1$-$C_4$ alkyl, and wherein G can be further substituted with $C_1$-$C_4$ alkyl.

In another embodiment of formula (I), R can be a moiety of the formula:

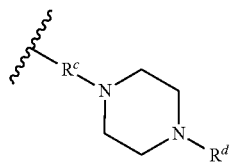

wherein $R^c$ and $R^d$ are each independently $C_1$-$C_4$ alkyl.

Preferred examples include liposomes comprising compounds selected from the group consisting of compounds 1, 2, 3, 4, 5, or 6 above. In some examples, the compound is compound 5 or compound 6.

The compound of formula (I) can have the chemical structure of formula (Ia), or a pharmaceutically acceptable salt thereof, wherein R' is a tertiary alkyl substituted amine having a $pK_a$ of about 9.5 or greater:

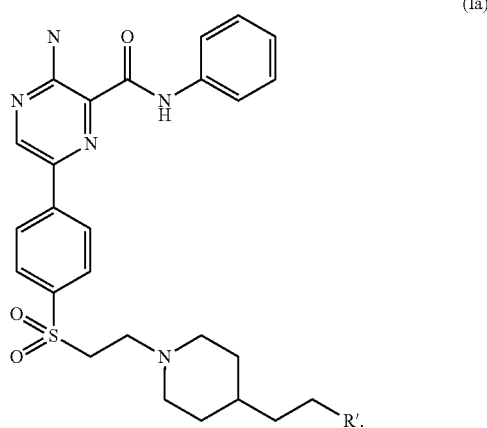

Examples of compounds of formula (Ia) include compound 5 disclosed herein (e.g., Examples 1). In one embodiment of formula (Ia), R' is $NR^aR^b$, wherein $R^a$ and $R^b$ are each independently $C_1$-$C_4$ alkyl.

Liposome formulations of ATR protein kinase inhibitor compounds (e.g., as described in Example 7) can provide desirable pharmacokinetic properties such as enhanced plasma half-life of 5 hours or more in the mouse model described in Example 8. The liposomes typically comprise vesicles containing one or more lipid bilayers enclosing an aqueous interior. Liposome compositions usually include liposomes in a medium, such as an aqueous fluid exterior to the liposome. Liposome lipids can include amphiphilic lipid components that, upon contact with aqueous medium, spontaneously form bilayer membranes, such as phospholipids, for example, phosphatidylcholines. Liposomes also can include membrane-rigidifying components, such as sterols, for example, cholesterol. In some cases, liposomes also include lipids conjugated to hydrophilic polymers, such as, polyethyleneglycol (PEG) lipid derivatives that may reduce the tendency of liposomes to aggregate and also have other beneficial effects.

The liposome formulation can include a compound of formula (I) encapsulated with a polyanion (e.g., a polyanionized sugar such as sucrose octasulfate, or a suitable polyanionized polyol) in a unilamellar vesicle formed from one or more liposome-forming lipids (e.g., hydrogenated soy phosphatidylcholine (HSPC)), cholesterol and a polymer-conjugated lipid (e.g., methoxy-poly(ethylene glycol)-1,2-distearoyl-sn-glyceryl (PEG2000-DSG). The liposome-forming lipid preferably comprises one or more phospholipids, with the ratio of the phospholipid(s) and the cholesterol selected to provide a desired amount of liposome membrane rigidity while maintaining a sufficiently reduced amount of leakage of the compound of formula (I) from the liposome.

Liposomes typically have the size in a micron or submicron range and are well recognized for their capacity to carry pharmaceutical substances, including anticancer drugs, such as irinotecan, and to change their pharmaceutical properties in various beneficial ways. Methods of preparing and characterizing pharmaceutical liposome compositions are known in the field (see, e.g., Lasic D. Liposomes: From physics to applications, Elsevier, Amsterdam 1993; G. Greroriadis (ed.), Liposome Technology, 3$^{rd}$ edition, vol. 1-3, CRC Press, Boca Raton, 2006; Hong et al., U.S. Pat. No. 8,147, 867, incorporated by reference herein in their entirety for all purposes).

In some examples (e.g., Example 7), ATR protein kinase inhibitor compositions can include a liposome comprising a ATR protein kinase inhibitor compound encapsulated in a liposome with polyanion such as a polysulfated sugar (e.g., sucrose octasulfate). Sucrosofate, a fully substituted sulfate ester of sucrose having, in its fully protonated form, the following structure:

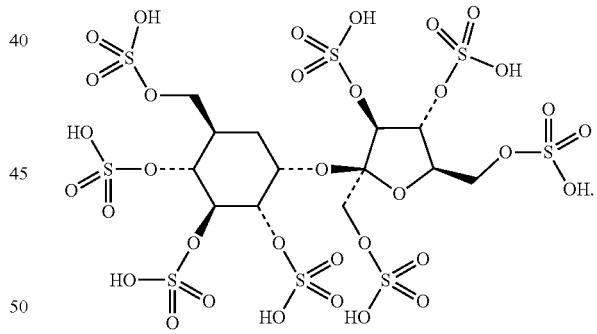

Sucrosofate is also referred to as sucrose octasulfate or sucrooctasulfate (SOS). Methods of preparing sucrosofate in the form of various salts, e.g., ammonium, sodium, or potassium salts, are well known in the field (e.g., U.S. Pat. No. 4,990,610, incorporated by reference herein in its entirety).

The ATR protein kinase inhibitor liposomes can be prepared in multiple steps comprising the formation of a TEA containing liposome, followed by loading of an ATR protein kinase inhibitor compound (e.g., Compound A or a compound of formula (I)) into the liposome as the TEA leaves the liposome. For example, the ATR protein kinase inhibitor liposomes can be prepared by a process that includes the steps of (a) preparing a liposome containing triethylamine (TEA) as a triethylammonium salt of sucrosofate (TEA- SOS), and (b) subsequently contacting the TEA-SOS liposome with irinotecan under conditions effective for the irinotecan to enter the liposome and to permit a corresponding amount of TEA to leave the liposome (thereby exhausting or reducing the concentration gradient of TEA across the resulting liposome).

The first step can include forming the TEA-sucrosofate containing liposome by hydrating and dispersing the liposome lipids in the solution of TEA sucrosofate. This can be performed, for example, by dissolving the lipids, including HSPC and cholesterol, in heated ethanol, and dispersing the dissolved and heated lipid solution in the TEA-sucrosofate aqueous solution at the temperature above the transition temperature ($T_m$) of the liposome lipid, e.g., 60° C. or greater. The lipid dispersion can be formed into liposomes having the average size of 75-125 nm (such as 80-120 nm, or in some embodiments, 90-115 nm), by extrusion through track-etched polycarbonate membranes with the defined pore size, e.g., 100 nm. The TEA-sucrosofate can include at least 8 molar equivalents of TEA to each molar equivalent of sucrosofate to obtain a solution that can have a concentration of about 0.40-0.50 N, and a pH (e.g., about 6.5) that is selected to prevent unacceptable degradation of the liposome phospholipid during the dispersion and extrusion steps (e.g., a pH selected to minimize the degradation of the liposome phospholipid during these steps). Then, the non-entrapped TEA-SOS can be removed from the liposome dispersion, e.g., by dialysis, gel chromatography, ion exchange or ultrafiltration prior to the drug encapsulation. The resulting liposomes can contain ATR protein kinase inhibitor sucrosofate. These ATR inhibitor liposomes can be stabilized by loading enough drug into the liposomes to reduce the amount of TEA in the resulting liposome composition to a level that results in less than a given maximum level of lyso-PC formation after 180 days at 4° C., or less than a given maximum level of lyso-PC accumulation rate in the liposome composition during storage in a refrigerator at about 4° C., or, more commonly, at 5±3° C., measured, e.g., in mg/mL/month, or % PC conversion into a lyso-PC over a unit time, such as, mol % lyso-PC/month. Next, the TEA exchanged from the liposomes into the external medium during the loading process, along with any unentrapped ATR inhibitor, is typically removed from the liposomes by any suitable known process(es) (e.g., by gel chromatography, dialysis, diafiltration, ion exchange or ultrafiltration). The liposome external medium can be exchanged for an injectable isotonic fluid (e.g. isotonic solution of sodium chloride), buffered at a desired pH.

The antitumor efficacy of various liposome formulations comprising liposome encapsulated ATR protein kinase inhibitor compounds was tested in human cervical cancer cell lines (e.g., MS751, C33A and SiHa cell lines, as shown in Example 9), and various lung cancer cell lines including lung squamous cell carcinoma cell line (e.g., NCI-H2170 cell line in Example 10), small cell lung carcinoma cell line (e.g., DMS-114 cell line in Example 10), and human Calu-6 and COLO-699 cell lines (Example 11).

Referring to FIGS. 6-9 and Example 9, a liposome formulation of the ATR inhibitor Compound A (Example 7) was tested against three human cervical cancer cell lines in mouse xenograph model (Example 9A), alone and in combination with the irinotecan liposome formulation MM398 (Example 9B). Greater tumor volume was observed over time for the liposomal Compound A formulation of Example 7 compared to the control experiment for 2 of the 3 cervical cancer cell lines (MS571 and C33A). However, administering the irinotecan liposome MM398 (Example 9B) in combination with the Compound A liposome formulation (Example 7) resulted in greater suppression of tumor volume in all three cervical cancer cell lines than either administration of MM398 alone or liposomal Compound A alone.

Figure 10A:
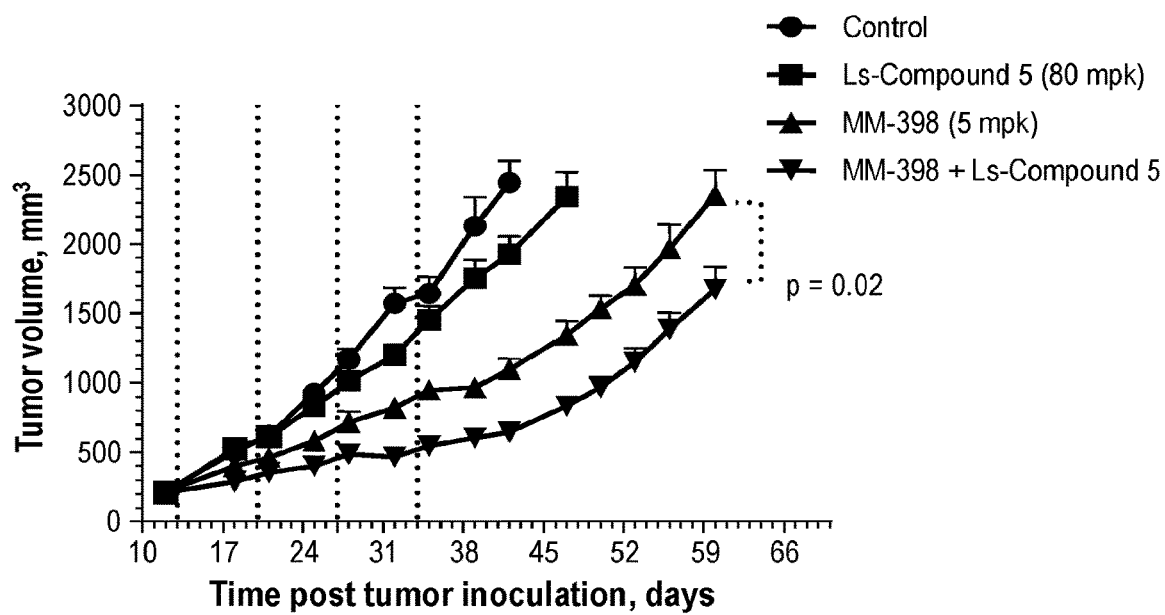
FIG. 10A and FIG. 10B are each a graph, showing the efficacy of liposomal Compound 5 in combination with MM-398 in NCI-H2170 (FIG. 10A) or DMS-114 (FIG. 10B) mice xenograft models, as discussed in Example 10.
Figure 10B:
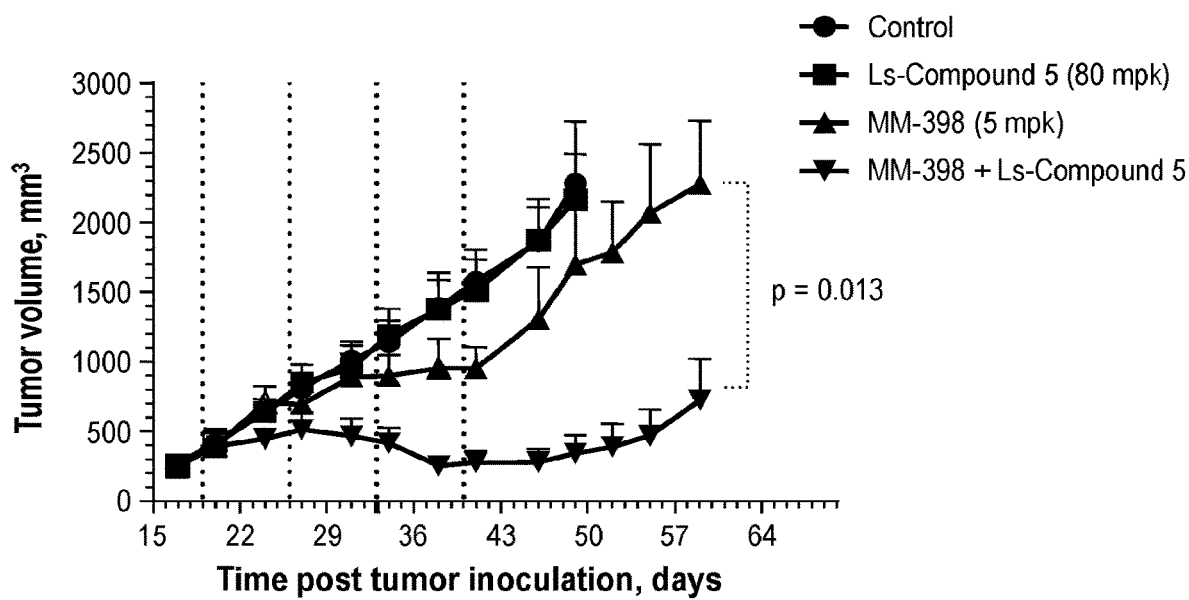

Referring to FIGS. 10A-10B and FIGS. 11A-11B, a liposome formulation of the ATR inhibitor Compound 5 of formula (I) and formula (Ia) (the compound of Example 1 formulated as a liposome as described in Example 7) was tested against two lung cancer cell lines in a mouse xenograph model (Example 10), alone and in combination with the irinotecan liposome formulation MM398 (Example 9B). Referring to FIG. 10A and FIG. 10B, the administration of the liposome formulation of Compound 5 reduced tumor volume in each cell line tested compared to the control experiment in Example 10, the combination of MM398 and the Compound 5 liposome composition of Example 7 reduced the tumor volume in the mouse model to a greater degree than either compound administered independently of the other. Similarly, the Kaplan-Meyer survival curves presented in Example 10 (FIG. 11A and FIG. 11B) demonstrate increased survival in mouse lung cancer xenograph testing when a combination of both the irinotecan liposome MM398 of Example 9B was administered in combination with the Compound 5 liposome formulation of Example 7 using two different cell lines.

Figure 12A:
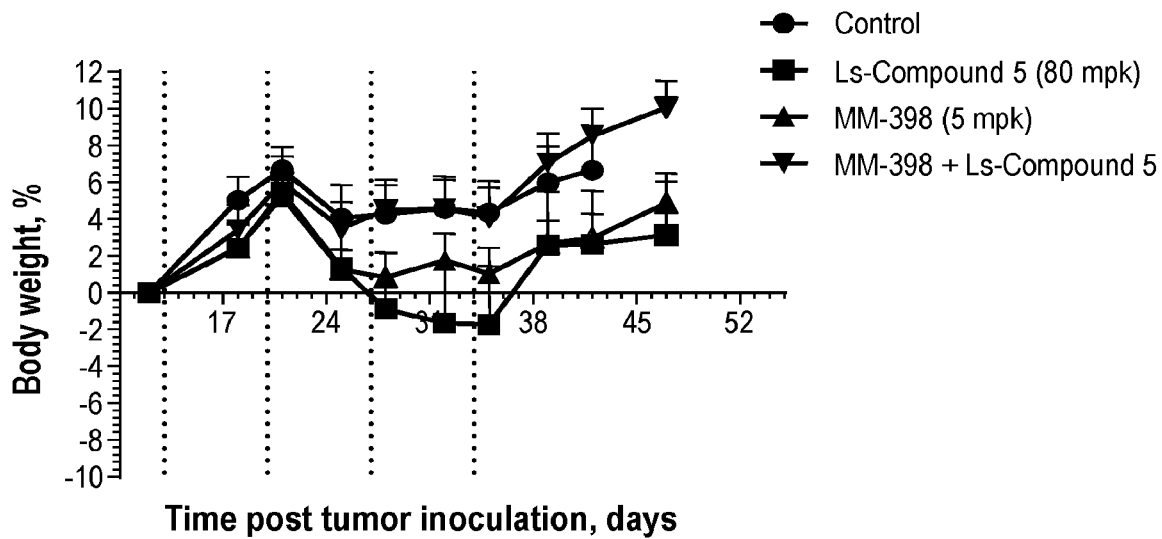
FIG. 12A and FIG. 12B are each a graph showing Tolerability of liposomal Compound 5 in combination with MM-398 in NCI-H2170 (FIG. 12A) or DMS-114 (FIG. 12B) in a mouse xenograft model.
Figure 12B:
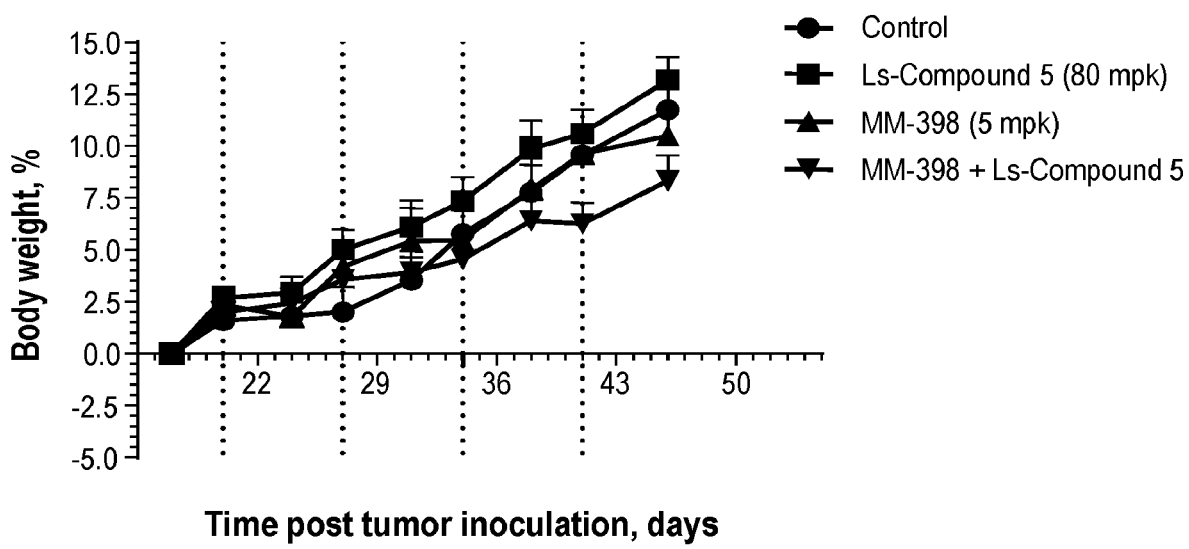

Referring to FIG. 12A and FIG. 12B, the tolerability of various liposome formulations of ATR protein kinase inhibitor compounds was assessed in Example 10. Referring to FIG. 12A, the decline in mouse bodyweight tested in the NCI-H2170 mouse xenograph model was lowest over time for the liposome formulation of Compound 5 (Example 7), compared to the irinotecan liposome MM398 (Example 9B), the control or the combination of the liposome formulation of Compound 5 in combination with MM398. Referring to FIG. 12B, the decline in mouse bodyweight tested in the DMS-114 mouse xenograph model was lowest over time for the combination of the liposome formulation of Compound 5 in combination with MM398, compared to the liposome formulation of Compound 5 (Example 7), or the irinotecan liposome MM398 (Example 9B) administered independently.

Figure 13A:
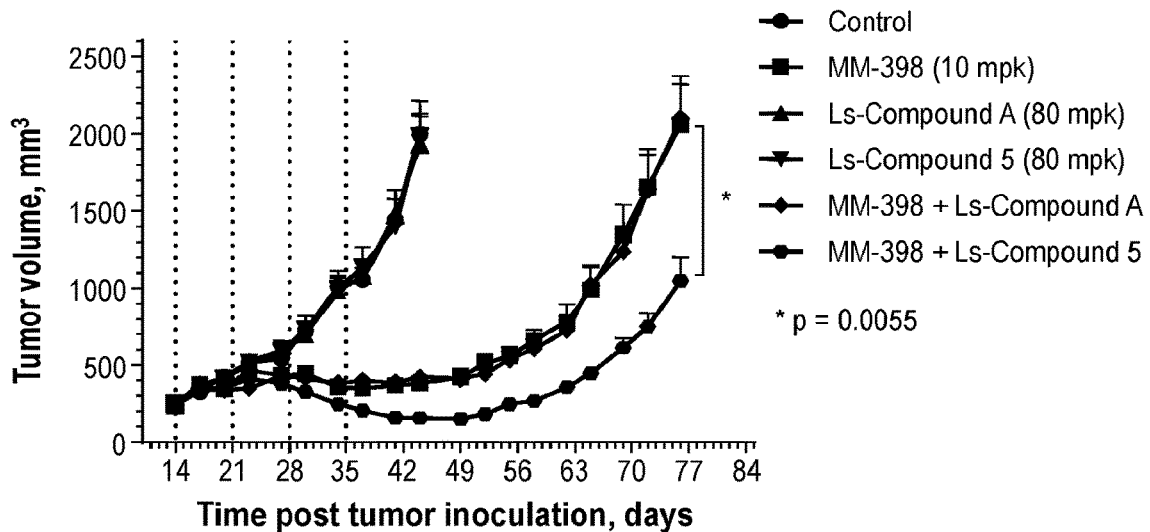
FIG. 13A and FIG. 13B are graphs showing the efficacy of liposomal Compound 5 in combination with MM-398 in Calu-6 (FIG. 13A) or COLO-699 (FIG. 13B) mice xenograft models, as described in Example 11.
Figure 13B:
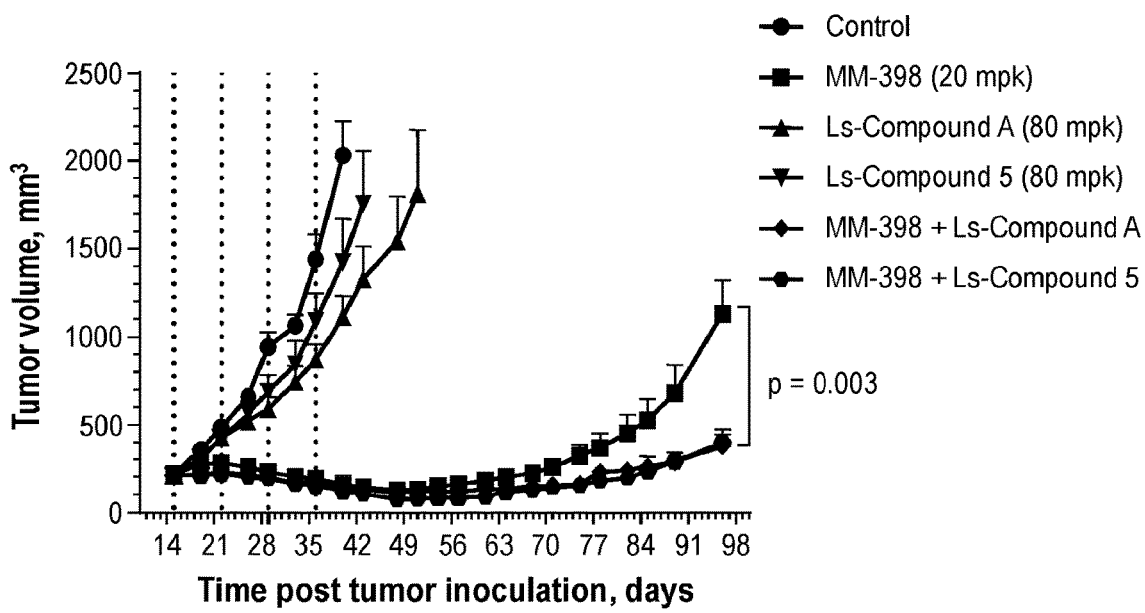

Referring to FIG. 13A and FIG. 13B, administering a combination of the irinotecan liposome MM398 (Example 9B) with the liposome formulation of ATR protein kinase inhibitor Compound 5 resulted in the greatest reduction in tumor volume in both the Calu-6 and COLO699 cell lines in mice xenograft models, compared to the control, the administration of MM398 irinotecan liposome alone, administration of the Compound A liposome formulation (Example 7) or the combination of the MM398 irinotecan liposome (Example 9B) with the Compound A liposome formulation (Example 7).

EXAMPLES

The following examples illustrate some embodiments of the invention. The examples and preparations which follow are provided to enable those skilled in the art to more clearly understand and to practice these and other embodiments present invention. They should not be considered as limiting the scope of the invention, but merely as being illustrative and representative thereof.

ATR peptide can be expressed and isolated using a variety of methods known in the literature (see e.g., Unsal-Kagmaz et al, PNAS 99: 10, pp 6673-6678, May 14, 2002; see also Kumagai et al. Cell 124, pp 943-955, Mar. 10, 2006;

Unsal-Kacmaz et al. Molecular and Cellular Biology, February 2004, p 1292-1300; and Hall-Jackson et al. Oncogene 1999, 18, 6707-6713).

Compound A can be obtained by methods disclosed (for example) in publication WO2010/071827A1 (published Jun. 24, 2010), portions of which relating to the synthesis and use of compound II-A-7 are incorporated herein by reference. The structure of Compound A is as follows:

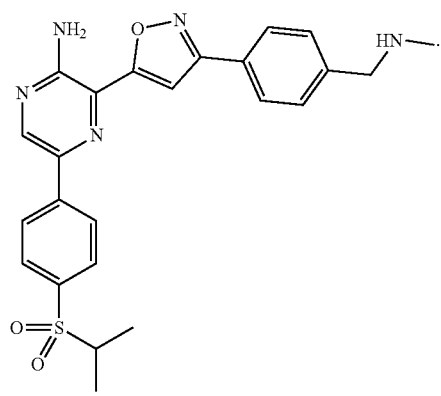

Compound A

Various compounds of formula (I) can be prepared as described herein, and summarized in the table below.

TABLE 1

Selected Compounds of Formula (I)

| Compound | R | Example |
|---|---|---|
| Compound 5 | ⸺N(piperidine-CH₂CH₂N(CH₃)₂) | 1 |
| Compound 6 | ⸺N(piperidine-N(Et)₂) | 2 |
| Compound 2 | ⸺CH₂CH₂CH₂N(Et)₂ | 3 |
| Compound 4 | ⸺NHCH₂CH₂N(CH₃)₂ | 4 |
| Compound 3 | ⸺CH₂CH₂-(4-methylpiperazine) | 5 |
| Compound 1 | ⸺CH₂CH(CH₃)N(CH₃)₂ | 6 |

The examples 1, 2, 3 and 6 were prepared in a one-pot Suzuki cross-coupling using boronic ester generated in-situ shown in Scheme 1 in FIG. 1. Referring to FIG. 1, the synthesis of Intermediate 3: 1-bromo-4-(2-bromoethylsulfonyl)benzene can be obtained as described below.

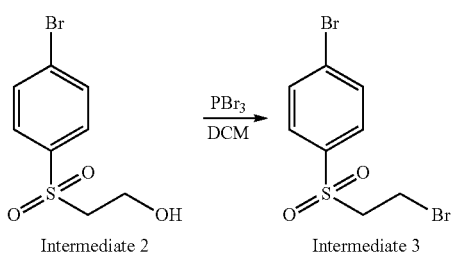 [SMILES: O=S(=O)(CCO)c1ccc(Br)cc1 ; "PBr3" ; O=S(=O)(CCBr)c1ccc(Br)cc1]

Intermediate 2          Intermediate 3

To a solution of Intermediate 2 (35 g, 133 mmol) in DCM (400 mL) was added PBr₃ (40 g, 146 mmol) at 0° C. dropwise. Then the mixture was stirred at rt overnight. Water (15 mL) was added to quench the reaction. Then the resultant was washed with water (120 mL) and brine (120 mL). The organic phase was concentrated to afford 20 g of crude 3 as yellow oil, which was used in the next step without further purification.

Referring to FIG. 1, the synthesis of intermediate 2 can be performed as described below:

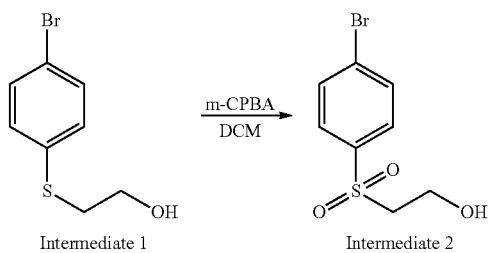 [SMILES: OCCSc1ccc(Br)cc1 ; "m-CPBA" ; O=S(=O)(CCO)c1ccc(Br)cc1]

To a solution of Intermediate 1 (45 g, 194 mmol) in DCM (500 ml) was added m-CPBA (134 g, 776 mmol) at rt in several batches. Then the mixture was stirred at rt overnight. The reaction mixture was filtered and DCM (500 ml) was added to wash the solid. The filtrate was washed with NaOH (1M, 300 mL×3) and brine (300 mL). The organic layer was concentrated to dryness to afford 36 g of 2 (70%) as white solid.

Referring to FIG. 1, the synthesis of intermediate 1 can be performed as described below.

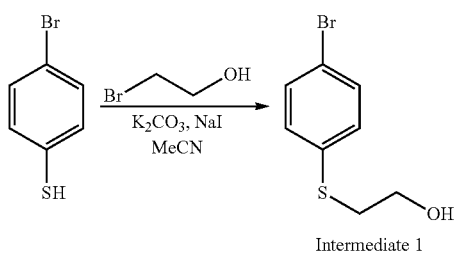

To a solution of 4-bromobenzenethiol (45 g, 238 mmol) in MeCN (600 ml) was added K$_2$CO$_3$ (60 g, 476 mmol) and NaI (36 g, 238 mmol). The mixture was stirred at rt for 10 minutes. Then 2-bromoethanol was added dropwise. After addition, the mixture was stirred at rt overnight. The reaction mixture was filtered and the filtrate was concentrated to dryness. The residue was purified by silica-gel column to afford 45 g of 1 (81%) as light yellow oil.

Figure 2:
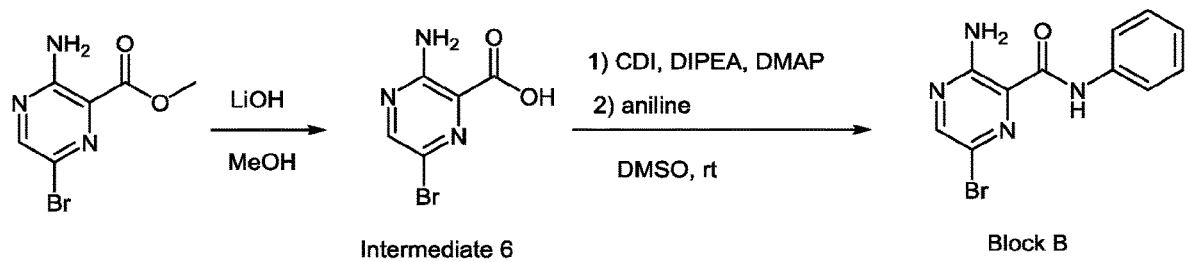
FIG. 2 is a second chemical reaction scheme useful in manufacturing certain compounds disclosed herein.

Block B can be prepared according to scheme 2 in FIG. 2. Referring to FIG. 2, the synthesis of Block B can be performed as described below.

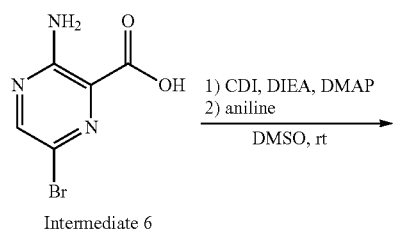

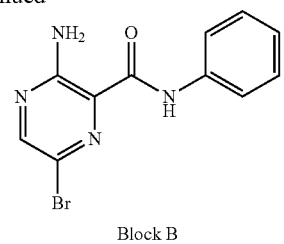

Block B

To a solution of Intermediate 6 (6.0 g, 27.4 mmol) in DMSO (30 mL) was added CDI (8.9 g, 54.8 mmol), DIPEA (3.8 g, 30.1 mmol) and DMAP (0.17 g, 1.37 mmol). The solution was stirred at rt for 4 hours. Aniline (2.5 g, 27.4 mmol) was added and the mixture was stirred at rt overnight. Water was added and the formed solid was collected by filtration. The crude product was purified by silica-gel column to afford 2.5 g of Block B (31%) as yellow solid.

LC-MS (M+1): 293.2; $^1$H NMR (400 MHz, DMSO-d$_6$) δ10.28 (s, 1H), 8.42 (s, 1H), 7.78 (d, J=8.0 Hz, 2H), 7.74 (s, 2H), 7.36 (t, J=8.0 Hz, 2H), 7.13 (t, J=7.6 Hz, 1H).

Referring again to FIG. 2, the synthesis of Intermediate 6 can be performed as described below.

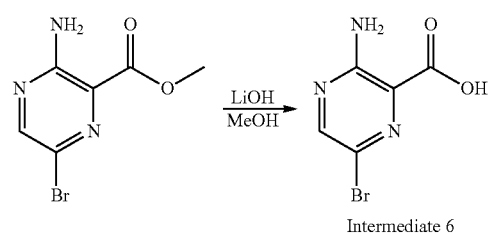

To the solution of methyl 3-amino-6-bromopyrazine-2-carboxylate (10.0 g 43.1 mmol) in MeOH (70 mL) was added a solution of LiOH (9.0 g, 215 mmol) in water (70 mL). The mixture was stirred at 90° C. for 3 hours. The reaction mixture was cooled to rt and acidified to PH=4-5 with HCl (2 M). The mixture was filtered to afford 7.4 g of 6 (79%) as yellow solid.

LC-MS (M+1): 218.0; 1H NMR (400 MHz, DMSO-d6) δ 8.39 (s, 1H), 7.59 (br, 2H).

Example 1: Synthesis of Compound 5 (3-amino-6-(4-((2-(4-(2-(dimethylamino)ethyl)piperidin-1-yl)ethyl)sulfonyl)phenyl)-N-phenylpyrazine-2-carboxamide)

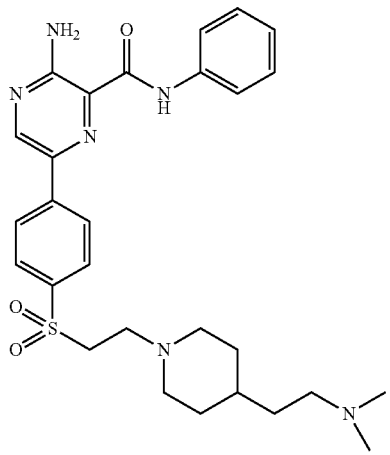 [SMILES: CN(C)CCC1CCN(CCS(=O)(=O)c2ccc(-c3cnc(N)c(C(=O)Nc4ccccc4)n3)cc2)CC1]

Exact Mass: 536.26; Molecular Weight: 536.70; Compound 5; More basic; 143 mg; Yield 8.2%; pK$_a$ 10.00.

To a solution of 2-(1-(2-((4-bromophenyl)sulfonyl)ethyl)piperidin-4-yl)-N,N-dimethylethan-1-amine (Block A1) (261 mg, 0.648 mmol) in anhydrous dioxane (3 ml) was added potassium acetate (191 mg, 1.944 mmol) and Bis(pinacolato) diborane (246 mg, 0.971 mmol), the reaction vessel was degassed by repeating vacuum/nitrogen cycle and then was added Pd(dppf)$_2$Cl$_2$·CH$_2$Cl$_2$ (53 mg, 0.0648 mmol), again was degassed and the reaction was heated at 90° C. for 2 hours under nitrogen. The reaction was then cooled down to room temperature and was added 3-amino-6-bromo-N-phenylpyrazine-2-carboxamide (Block B), 2M K$_2$CO$_3$ (1 ml) and degassed and purged with nitrogen. The Pd(PPh$_3$)$_4$ (75 mg, 0.0648 mmol) was added. The reaction was heated at 100° C. for 4 hrs. The reaction was cooled to room temperature and diluted with ethyl acetate and washed with brine three times and organic layer was dried over Na$_2$SO$_4$. Upon removal of solvent on the rotovap, a dark oil residual crude product was obtained and it was purified on silica-gel column chromatography (Reveleris Flash Chromatography System) using 0-15% methanol in dichloromethane as an eluent. Desired product was obtained as a yellow solid (149 mg, yield 43%). MS (M+H)+537; $^1$H NMR (400 MHz, DMSO-d$_6$): δ 10.45 (s, 1H), 9.03 (s, 1H), 8.49 (d, 2H, 6.8 Hz), 7.95 (d, 2H, 6.8 Hz), 7.88 (s, br, 2H), 7.81 (d, 2H, 8.8 Hz), 7.40 (t, 2H, 7.2 Hz), 7.18 (t, 1H, 7.2 Hz), 3.53 (t, 2H, 7.2 Hz), 2.64 (d, 2H, 11.6 Hz), 2.55 (t, 2H, 7.2 Hz), 2.05 (m, 2H), 1.98 (s, 6H), 1.17 (m, 2H), 1.42 (d, 2H, 12.0 Hz), 1.18 (m, 3H), 0.78 (m, 2H).

High resolution mass (Thermo Scientific™ Q Exactive™ hybrid quadrupole-Orbitrap mass spectrometer): Calculated for C$_{28}$H$_{36}$N$_6$O$_3$S+Proton (1.00728)=537.2642; theoretical m/z of single charged ion: 537.2642; Found: 537.2636.

Example 2: Synthesis of Compound 6 (3-amino-6-(4-((2-(4-(diethylamino)piperidin-1 yl)ethyl)sulfonyl)phenyl)-N-phenylpyrazine-2-carboxamide)

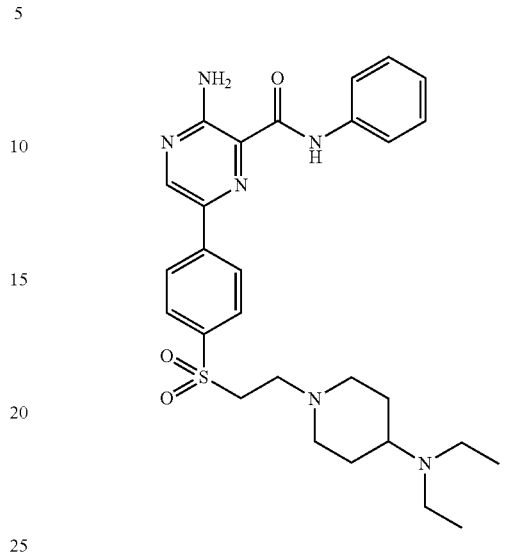

Exact Mass: 536.26; Molecular Weight: 536.70; Compound 6; More basic; 53 mg; Yield 11.10%; pK$_a$ 9.81.

The example 2 was prepared in a similar fashion using Block A2 (1-(2-((4-bromophenyl)sulfonyl)ethyl)-N,N-diethylpiperidin-4-amine), a yellow solid was obtained (52 mg, yield 24%). MS (M+H)+537; $^1$H NMR (400 MHz, DMSO-d$_6$): δ 10.45 (s, 1H), 9.05 (s, 1H), 8.51 (d, 2H, 8.4 Hz), 7.94 (d, 2H, 8.8 Hz), 7.87 (s, br, 2H), 7.79 (d, 2H, 8.8 Hz), 7.42 (t, 2H, 8.4 Hz), 7.18 (t, 1H, 7.2 Hz), 3.54 (t, 2H, 6.4 Hz), 2.65 (d, 2H, 11.2 Hz), 2.56 (t, 2H, 6.4 Hz), 2.20 (q, 4H, 6.8 Hz), 1.71 (t, 2, 10.4 Hz), 1.33 (d, 2H, 12.4 Hz), 0.85 (qd, 2H, 12.4 Hz), 0.74 (t, 6H, 7.2 Hz).

1-(2-((4-bromophenyl)sulfonyl)ethyl)-N,N-diethylpiperidin-4-amine (Block A2) was prepared in a similar fashion using corresponding 4-diethylaminopiperidine. A colorless oil was obtained (661 mg, 47% yield), MS (M+H)+ 403, 405.

Example 3: Synthesis of Compound 2 (3-amino-6-(4-((2-(diethylamino)ethyl)sulfonyl)phenyl)-N phenylpyrazine-2-carboxamide)

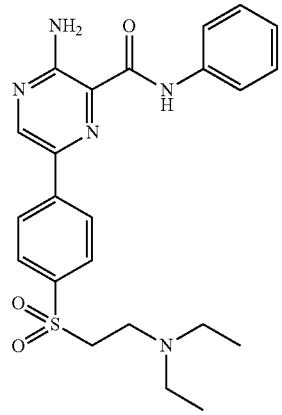 [SMILES: CCN(CC)CCS(=O)(=O)c1ccc(-c2cnc(N)c(C(=O)Nc3ccccc3)n2)cc1]

Exact Mass: 453.18; Molecular Weight: 453.56; Compound 2; Less basic; 98 mg; Yield 7.7%; $pK_a$ 7.46.

The compound of example 3 was prepared in a similar fashion using intermediate Block A3, 2-((4-bromophenyl)sulfonyl)-N,N-diethylethan-1-amine, a yellow solid was obtained (98 mg, yield 11%). MS (M+H)+454; $^1$H NMR (400 MHz, DMSO-$d_6$): δ 10.46 (s, 1H), 9.05 (s, 1H), 8.51 (d, 2H, 6.8 Hz), 7.98 (d, 2H, 6.8 Hz), 7.88 (s, br, 2H), 7.81 (d, 2H, 8.8 Hz), 7.41 (t, 2H, 7.2 Hz), 7.17 (t, 1H, 7.2 Hz), 3.48 (dd, 2H, 6.8 Hz), 2.73 (m, 2H), 2.33 (q, 4H, 6.8 Hz), 0.81 (t, 6H, 6.8 Hz).

Block A3 (2-((4-bromophenyl)sulfonyl)-N,N-diethylethan-1-amine) was prepared in a similar fashion using corresponding 4-diethylamine. A colorless oil was obtained (1.42 g, 73% yield), MS (M+H)+320, 322

Example 4: Synthesis of Compound 4 (3-amino-6-(4-(((2-(dimethylamino)ethyl)-λ$^2$-azanyl)sulfonyl)phenyl)-N-phenylpyrazine-2-carboxamide)

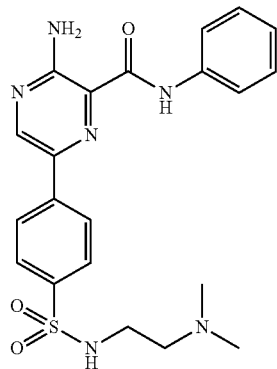 [SMILES: CN(C)CCNS(=O)(=O)c1ccc(-c2cnc(N)c(C(=O)Nc3ccccc3)n2)cc1]

Exact Mass: 439.16; Molecular Weight: 439.51; Compound 4; $pK_a$ 8.36.

Figure 3:
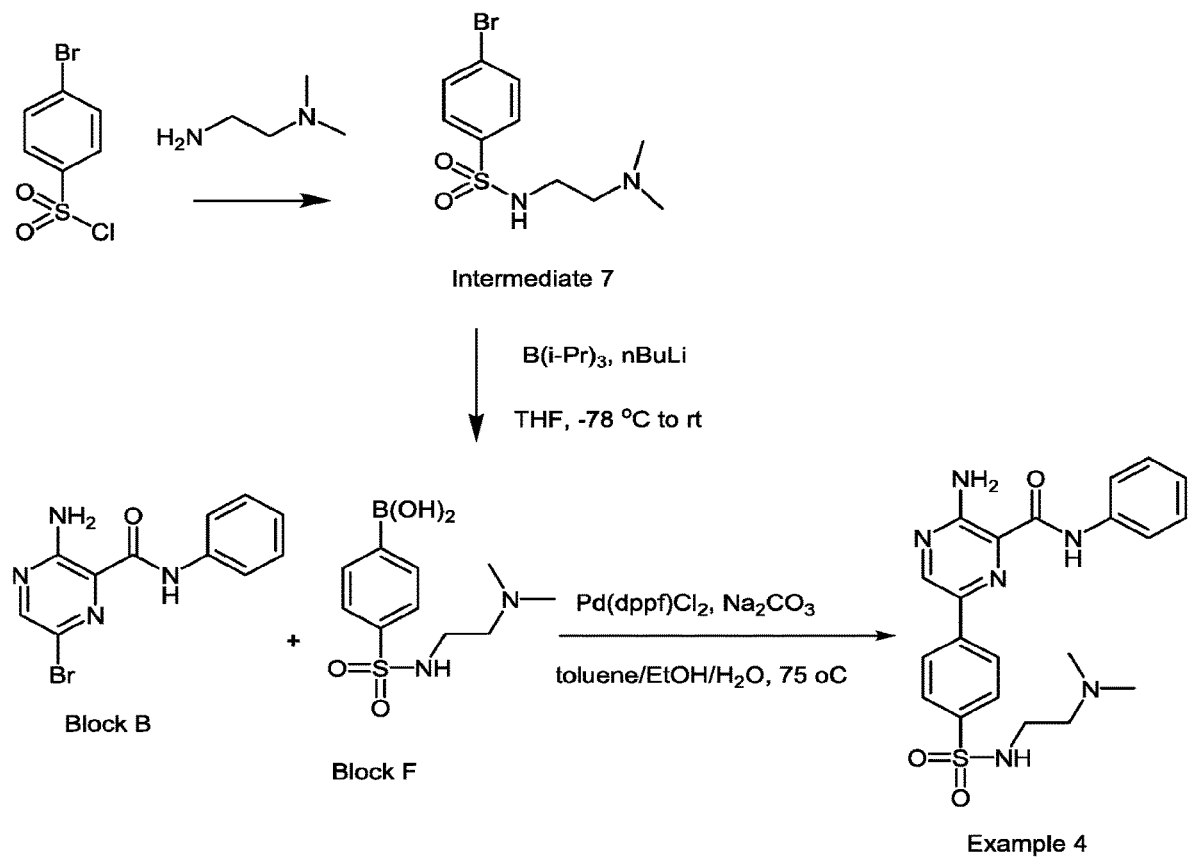
FIG. 3 is a third chemical reaction scheme useful in manufacturing certain compounds disclosed herein.

Compound 4 can be prepared as shown in scheme 3 in FIG. 3. To a mixture of Block B (150 mg, 0.51 mmol), Block F (153 mg, 0.56 mmol) and Na$_2$CO$_3$ (216 mg, 2.0 mmol) in toluene/ethanol/water (2 mL/2 mL/2 mL) was added Pd(dppf)Cl$_2$ (30 mg). The mixture was stirred at 75° C. under argon atmosphere for 4 hours. The reaction mixture was concentrated to dryness. The residue was purified by prep-HPLC to afford 100 mg of TM4 (45%) as white solid.

LC-MS (M+1): 441.4; $^1$H NMR (400 MHz, CD$_3$OD) δ 8.88 (s, 1H), 8.33 (dd, J=6.8 Hz, 1.6 Hz, 2H), 8.00 (dd, J=6.8 Hz, 1.6 Hz, 2H), 7.80 (dd, J=8.4 Hz, 1.2 Hz, 2H), 7.41 (t, J=7.6 Hz, 2H), 7.19 (t, J=7.6 Hz, 1H), 3.10 (t, J=6.4 Hz, 2H), 2.73 (t, J=6.4 Hz, 2H), 2.46 (s, 6H).

Referring again to Scheme 3 in FIG. 3, the synthesis of Block F can be performed as described below.

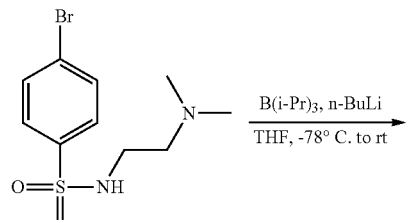

Intermediate 7

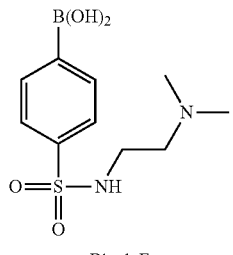

Block F

To a solution of Intermediate 7 (10.0 g, 32.6 mmol) in THF (200 mL) at −78° C. under argon atmosphere was added B(i-Pr)$_3$ (30.6 g, 163 mmol). Then n-BuLi (2.5 M, 65 mL) was added dropwise. The mixture was stirred at −78° C. for 2 hours and at then rt for another 16 hours. Water was added to quench the reaction. The mixture was concentrated to dryness. The residue was purified by prep-HPLC to afford 5.2 g of Block F (59%) as white solid.

LC-MS (M+1): 273.4; $^1$H NMR (400 MHz, DMSO-$d_6$) δ 7.90-7.45 (m, 4H), 2.91 (s, 2H), 2.69 (t, J=6.4 Hz, 2H), 2.18 (t, J=6.8 Hz, 2H), 2.03 (s, 6H).

Referring again to Scheme 3 in FIG. 3, the synthesis of Intermediate 7 can be performed as described below.

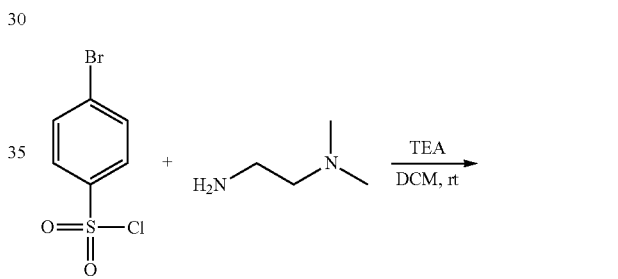

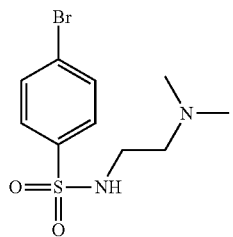

Intermediate 7

To a solution of 4-bromobenzene-1-sulfonyl chloride (20 g, 78.3 mmol) in DCM (300 mL) at 0° C. was added TEA (22 mL, 158 mmol), followed by N,N'-dimethylethane-1,2-diamine (8.3 g, 94.0 mmol). The resulting solution was stirred at rt for 1 hour and then diluted with DCM (300 mL). The solution was washed with water (200 mL) and brine (200 mL). The organic layer was concentrated to dryness. The residue was purified by silica-gel column to afford 17.0 g of 7 (71%) as off-white solid.

Example 5: Synthesis of Compound 3 (3-amino-6-(4-((2-(4-methylpiperazin-1-yl)ethyl)sulfonyl)phenyl)-N-phenylpyrazine-2-carboxamide)

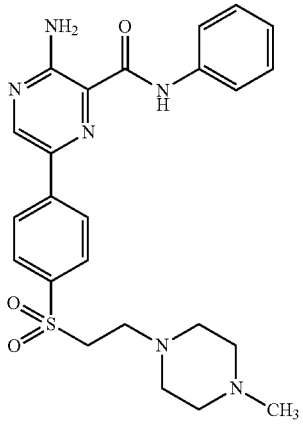 [SMILES: CN1CCN(CCS(=O)(=O)c2ccc(-c3cnc(N)c(C(=O)Nc4ccccc4)n3)cc2)CC1]

Exact Mass: 480.19; Molecular Weight: 480.59; Compound 3; pK$_a$ 7.73.

Figure 4:
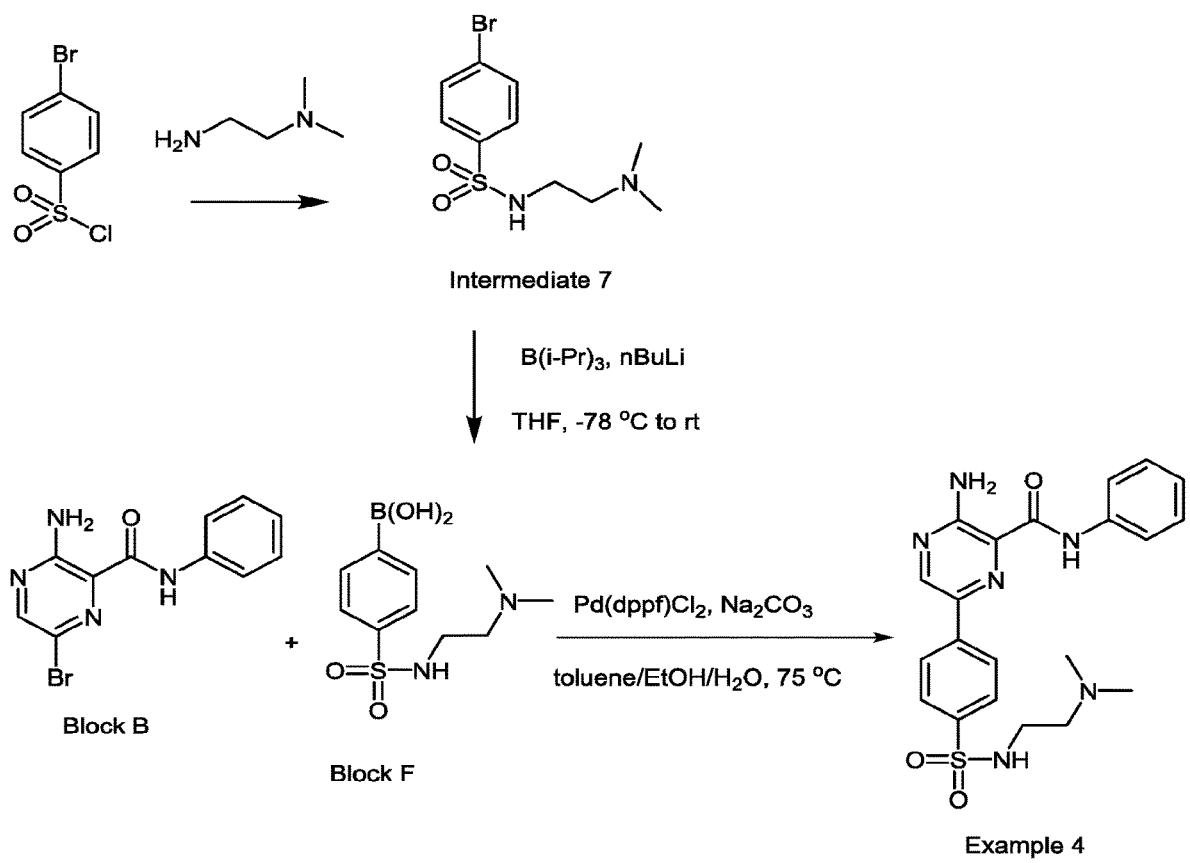
FIG. 4 is a fourth chemical reaction scheme useful in manufacturing certain compounds disclosed herein.

The compound of Example 5 can be obtained by Scheme 4 shown in FIG. 4. Intermediate 5 in Scheme 4 can be obtained as described below.

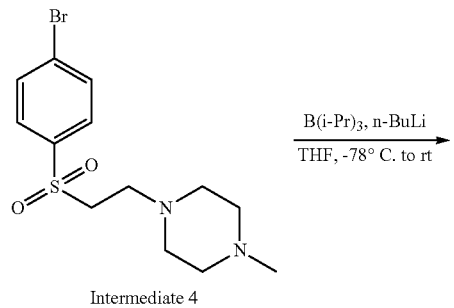

Referring again to FIG. 4, Intermediate 4 in Scheme 4 can be obtained as described below.

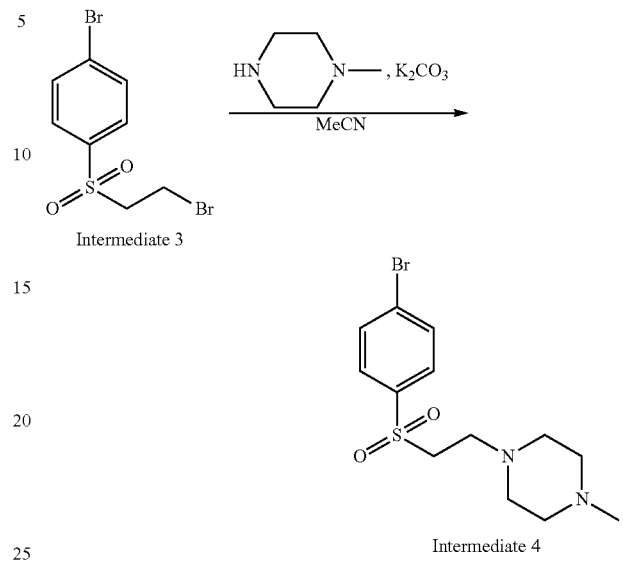

To a solution of Intermediate 3 (20 g, 60 mmol) in MeCN (300 mL) was added 1-methylpiperazine (9.0 g, 90 mmol) and K$_2$CO$_3$ (16.6 g, 120 mmol). The mixture was stirred at rt overnight. The reaction mixture was filtered and the filtrate was concentrated to dryness. The residue was purified by silica-gel column to afford 15 g of 4 (71%) as pale solid.

Example 6: Synthesis of Compound 1 (3-amino-6-(4-((1-(dimethylamino)propan-2-yl)sulfonyl)phenyl)-N-phenylpyrazine-2-carboxamide)

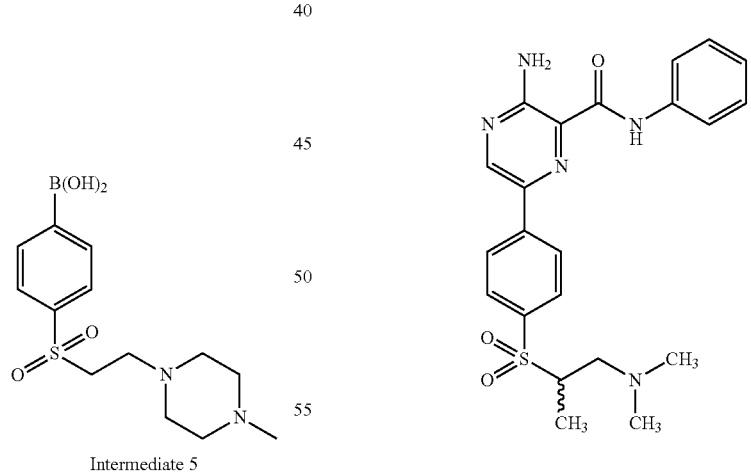

Exact Mass: 439.17; Molecular Weight: 439.53; Compound 1; Less basic; 427 mg; Yield 12.9%; pK$_a$ 7.04.

The compound of Example 6 was prepared according to the procedure for preparing Compound 1 given in J. Med. Chem. 2011, 54, 2320 (supplementary materials) except using 1-bromo-4-(2-bromoethylsulfonyl)benzene. A yellow solid was obtained (427 mg, yield 11%). MS (M+H)+440; $^1$H NMR (400 MHz, DMSO-d$_6$): δ 10.46 (s, 1H), 9.05 (s, 1H), 8.52 (d, 2H, 6.8 Hz), 7.93 (d, 2H, 6.8 Hz), 7.89 (s, br, 2H), 7.82 (d, 2H, 8.0 Hz), 7.40 (t, 2H, 7.2 Hz), 7.18 (t, 1H, To a solution of Intermediate 4 (1.7 g, 5.0 mmol) in THF (30 mL) at −78° C. under argon atmosphere was added B(i-Pr)$_3$ (4.7 g, 25 mmol). Then n-BuLi (2.5 M, 10 mL) was added dropwise. The mixture was stirred at −78° C. for 2 hours and at then rt for another 16 hours. Water was added to quench the reaction. The mixture was concentrated to dryness. The residue was purified by prep-HPLC to afford 300 mg of 5 (19%) as white solid.

7.2 Hz), 3.53 (t, 2H, 7.2 Hz), 2.64 (d, 2H, 11.6 Hz), 2.55 (t, 2H, 7.2 Hz), 2.05 (m, 2H), 1.98 (s, 6H), 1.17 (m, 2H), 1.42 (d, 2H, 12.0 Hz), 1.18 (m, 3H), 0.78 (m, 2H).

Example 7: Preparation of Liposomes with Entrapped Triethylammonium SOS Salts and Loading of ATRi into the Liposome Sodium sucrose octasulfate (equivalent weight 144.8) is a sodium salt of sucrose derivate in which all hydroxyl groups have formed sulfuric acid esters. Sixty gram of sucrose octasulfate (SOS) sodium salt were dissolved in in 150 ml of di water, heated with shaking (swirling) of a 50° C. water bath. The solution was passed through a column packed with sulfonated polystyrene divinylbenzene copolymer cation exchange resin beads (Dowex 50Wx8-100-200 mesh, Dow Chemical Co.). The column was pre-equilibrated with aqueous 3-3.6 M HCl to bring the resin in the hydrogen form and washed with deionized water until the outflow shows conductivity of <1 µS/cm. The eluent was monitored using a conductivity detector. The SOS fraction was collected corresponding to conductivity peak and immediately titrated with neat triethylamine (TEA) solution to pH 6-6.5. The solution was analyzed for residual sodium by potentiometry using a sodium-sensitive electrode and for SOS concentration using a refractometer. The solution having residual sodium less than 0.25% was diluted with di water to final SOS concentration 1.1 M and then sterile-filtered using Millipore 0.22 µm Steri-Top filter.

Cholesterol (Chol) was purchased from Avanti Polar Lipids, Alabaster, Ala., USA, hydrogenated soy phosphocholine (HSPC) and methoxy-poly(ethylene glycol)-1,2-distearoyl-sn-glyceryl (PEG2000-DSG) were obtained from Lipoid GmbH, Ludwigshafen, Germany.

Chol, HSPC and PEG2000-DSG were co-dissolved in 100% ethanol (200-proof, Sigma cat #: 459828) at a molar ratio of 3:2:0.15 at 65° C. The solution of TEA-SOS (10 times the volume of added ethanol) was mixed with the lipid solution at 60-65° C. and stirred at this temperature until a homogeneous milky suspension of multilamellar vesicles was formed. This suspension was extruded 3 times through 5 stacked polycarbonate track-etched filters (Corning Nuclepore) with the pore size of 100 nm using argon pressure extruder (Lipex Biomembranes) at 60-65° C., and resulting unilamellar liposomes were quickly chilled in ice and then stored at 4-6° C. before use. Concentration of phospholipids was measured by phosphate assay and particle diameter was recorded on a Malvern Nanosizer.

Prior to drug loading, the TEA-SOS gradient was created by removing excess of un-trapped TEA-SOS using gel-chromatography (Sepharose CL-4B, Pharmacia). Osmolarity of liposomes was balanced using 50% dextrose solution. Final dextrose concentration was 15%.

ATR inhibitors were dissolved in 15% dextrose solutions in di water by titration with 1 M HCl and heating at 45° C. and then filtered with 0.2 micron NALGENE 13 mm Syringe Filters. Drug concentration in the solution was detected by HPLC. A stock solution of ATR inhibitors containing 9-10 mg/mL of drugs was added to the liposomes at a drug/lipid ratio of 800 mg/mmol phospholipids and pH was adjusted to pH 6.5 with 1M Hepes buffer and 0.1 N NaOH.

The liposome-drug mixture was incubated with occasional agitation for 30 minutes at 65° C. The incubation mixture was quickly cooled down and incubated for 10 minutes at 0° C., then allowed to attain ambient temperature. Un-encapsulated drug was removed by gel chromatography on Sephadex G-25 (Amersham Pharmacia) eluted with HBS-6.5 buffer (5 mM 2-(4-(2-hydroxyethyl)-piperazino)-ethylsulfonic acid (HEPES), 144 mM NaCl, pH 6.5). Liposome fractions eluted in the void volume were combined, sterilized by 0.2 micron filtration, and stored at 4-6° C. before use. The liposomes were characterized by lipid concentration, drug concentration, and particle size (Table 2). All ATR inhibitors showed good loading efficacy except Compound 1, which at drug to lipid ration higher than 400 g/mol formed aggregates and participated.

TABLE 2

Characterization of Liposome loaded with ATR inhibitors.
Example 8: General description of PK study of liposomal ATRi

| ATR inhibitor | Drug/lipid ratio before loading | Drug/lipid ratio after loading | Loading efficiency (%) | Liposome size, (mean ± SD) nm |
|---|---|---|---|---|
| Compound 6 | 743 ± 89 | 550 ± 64 | 74 ± 0.3 | 119 ± 28 |
| Compound 2 | 642 ± 10 | 639 ± 22 | 100 ± 5 | 130 ± 34 |
| Compound 5 | 732 ± 58 | 619 ± 110 | 84 ± 8 | 120 ± 29 |
| Compound 3 | 646 ± 28 | 628 ± 6 | 97 ± 5 | 120 ± 27 |
| Compound A | 736 ± 57 | 716 ± 41 | 97 ± 2 | 121 ± 26 |
| Compound 1 | 600-800 | Not loadable. Formed aggregates and precipitated | | |
| | 379 | 369 | 98 | 122 ± 24 |

Figure 5:
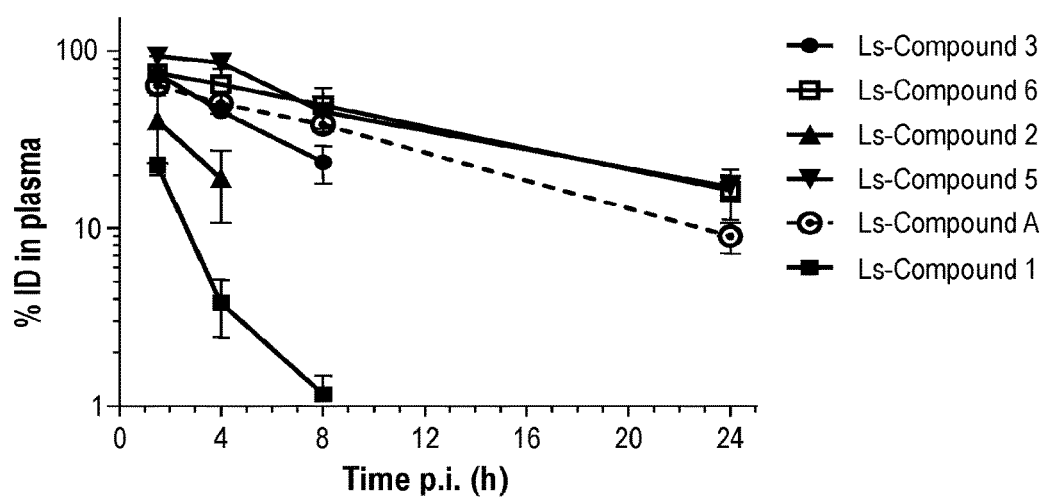
FIG. 5 is a graph showing the blood pharmacokinetics of liposomal ATR inhibitors, as discussed in Example 8.

FIG. 5 is a graph showing the blood pharmacokinetics of liposomal ATR inhibitors. Liposomal formulations of ATR inhibitors were prepared as described in Example 7. The liposomes were administered intravenously at a dose of 20 mg drug/kg to three 7-9-week-old female CD-1 mice (Charles River) (body weight about 25 g). Blood samples were collected into lithium heparin tubes by bleeding from saphenous vein at 0.08, 1.5, 4, 8 and 24 h time points. Plasma was separated from the cell fraction by centrifugation at 10000 rpm for 5 min. Drugs were extracted by incubation of plasma samples with 200 µl of 1% acidic acid in methanol (10% Ac/MeOH) to at least 2 hours at −80° C. Plasma proteins were spun down by centrifugation at 15000 rpm for 20 min. Then 75 µl of supernatant was transferred to HPLC vials (Thermo Scientific, Cat #C4011-LV1) and additional 75 µl of 1% Ac/MeOH were added. Drug content was analyzed by HPLC with each sample measured in duplicate. The data were expressed as the % injected dose plotted against post injection time. As shown in FIG. 5, liposomal formulation of Compound 1, Compound 3 and Compound 2 were unstable in the circulation with liposomal Compound 1 and Compound 3 un-detectable by HPLC analysis at 24 hour time point and liposomal Compound 2 un-detectable already at 8 h time point. Two liposomal formulations Compound 6 and Compound 5 have good circulation longevity with above 16% of the initial injected doze after 24 hours. Table 2 below summarizes the blood PK curves. Liposomal Compound 6 and Compound 5 show the highest plasma half-lives compare to other liposomal examples.

TABLE 3

Pharmacokinetics parameters of liposomal ATR inhibitors

| Drug | $C_{max}$ (mg/ml) | AUC (mg/ml*h) | Vd (ml) | Cl (ml/h) | $T_{1/2}$ (h) | % of ID after 24 h |
|---|---|---|---|---|---|---|
| Ls-Compound 3 | 0.271 | 1.659 | 2.020 | 0.330 | 4.24 | 0.0 |
| Ls-Compound 6 | 0.303 | 3.021 | 1.655 | 0.166 | 6.91 | 16.4 |
| Ls-Compound 2 | 0.080 | 0.160 | 5.806 | 2.890 | 1.39 | 0.0 |

TABLE 3-continued

Pharmacokinetics parameters of liposomal ATR inhibitors

| Drug | $C_{max}$ (mg/ml) | AUC (mg/ml*h) | Vd (ml) | Cl (ml/h) | $T_{1/2}$ (h) | % of ID after 24 h |
|---|---|---|---|---|---|---|
| Ls-Compound 5 | 0.227 | 2.504 | 2.012 | 0.182 | 7.65 | 17.2 |
| Ls-Compound A | 0.237 | 1.902 | 0.712 | 0.089 | 5.56 | 9.0 |
| Ls-Compound 1 | 0.053 | 0.043 | 6.358 | 7.841 | 0.56 | 0.0 |

Figure 6:
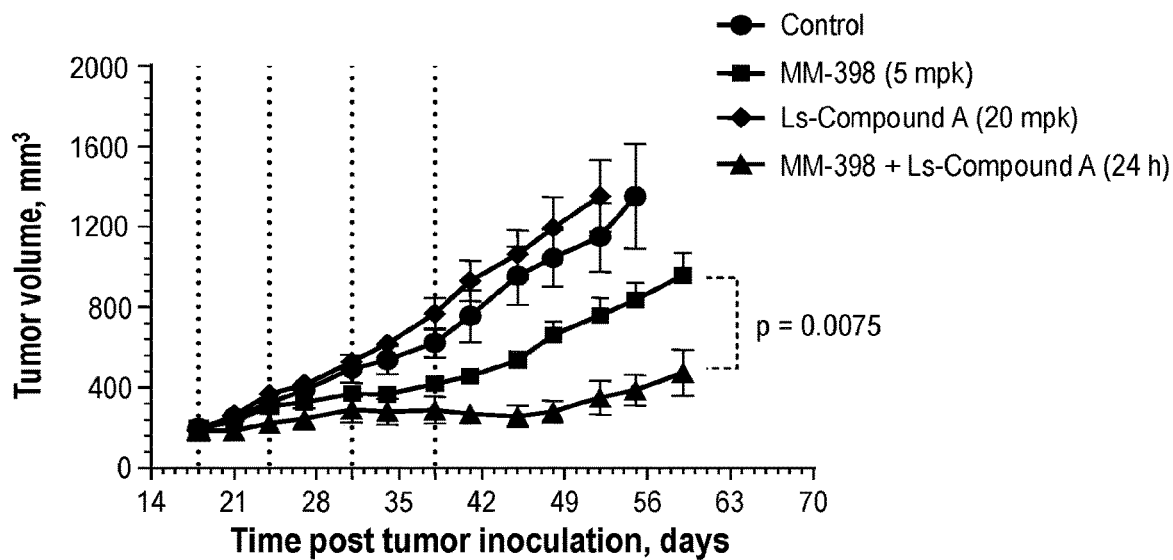
FIG. 6 is a graph showing the antitumor efficacy of liposomal Compound A in combinations with MM-398 in cervical MS751 xenograft model, as described in Example 9A.

Example 9A: In Vivo Antitumor Efficacy and Tolerability of LS-Compound a Prepared Using TEA.SOS Against Cervical Cancer Xenografts in Mice FIG. 6 is a graph showing the antitumor efficacy of liposomal Compound A in combinations with MM-398 in cervical MS571 xenograft model, as described in Example 9A.

Figure 7:
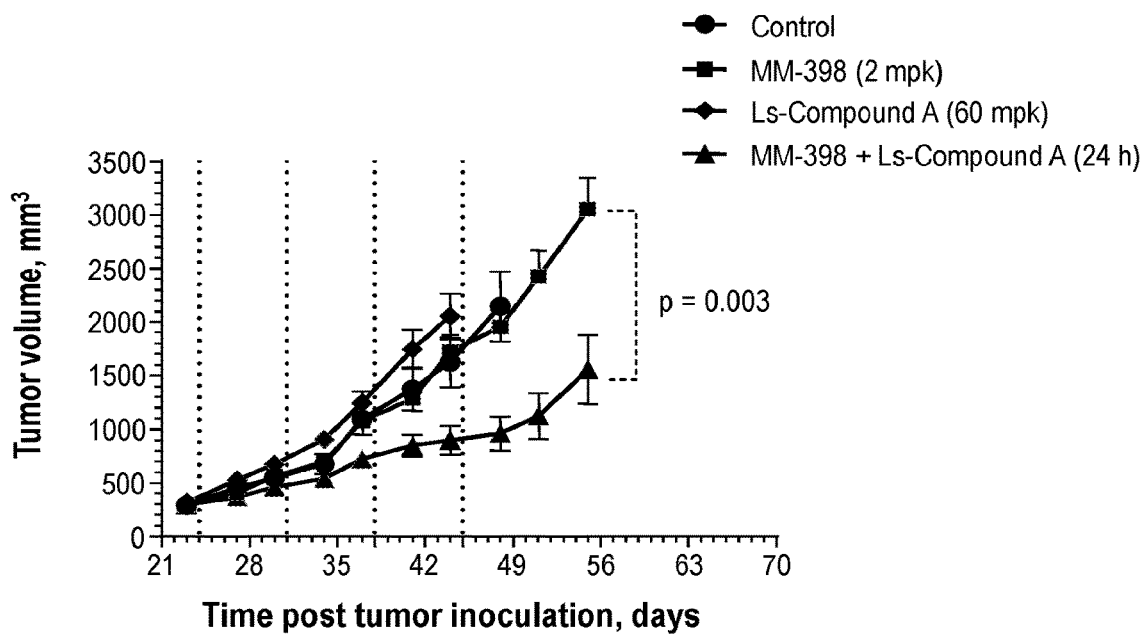
FIG. 7 is a graph showing the antitumor efficacy of liposomal Compound A in combinations with MM-398 in cervical C33A xenograft model, as described in Example 9A.

FIG. 7 is a graph showing the antitumor efficacy of liposomal Compound A in combinations with MM-398 in cervical C33A xenograft model, as described in Example 9A.

Figure 8:
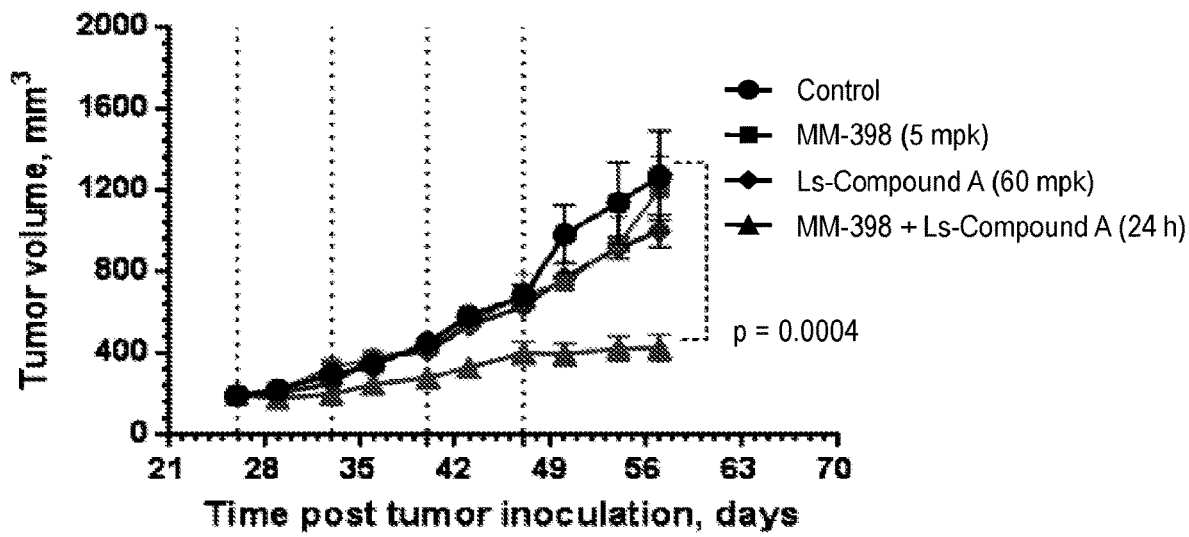
FIG. 8 is a graph showing the antitumor efficacy of liposomal Compound A in combinations with MM-398 in cervical C33A xenograft model, according to Example 9A.

FIG. 8 is a graph showing the antitumor efficacy of liposomal Compound A in combinations with MM-398 in cervical C33A xenograft model, according to Example 9A.

Figure 9:
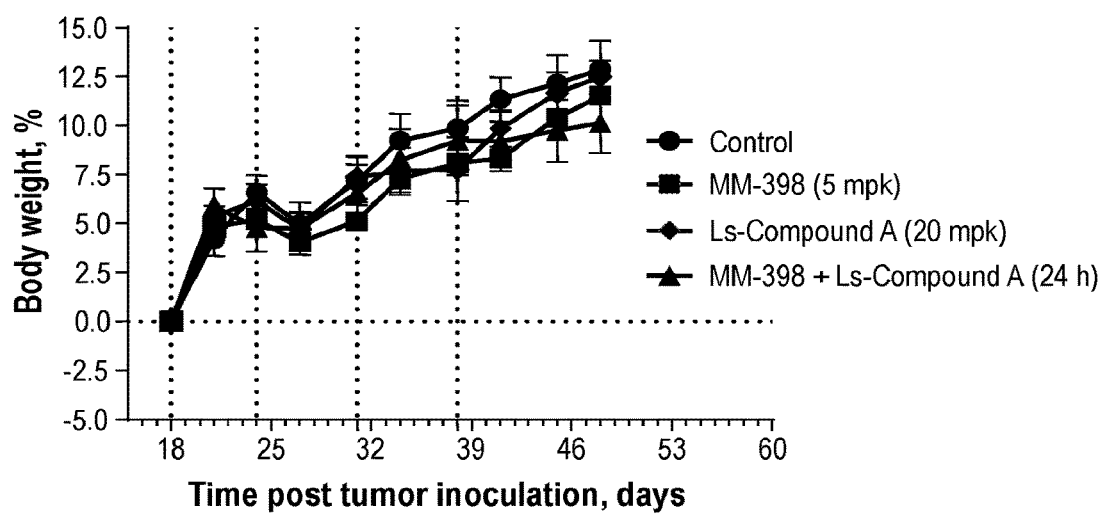
FIG. 9 is a graph showing the tolerability of liposomal Compound A in combination with MM-398 in cervical MS751, according to Example 9A.

FIG. 9 is a graph showing the tolerability of liposomal Compound A in combination with MM-398 in cervical MS751, according to Example 9A.

Antitumor efficacy of liposomes loaded with an ATR inhibitor Compound A (Ls-Compound A) in combinations with MM-398 (liposomal Irinotecan) was studied in the model of human cervical MS751, C33A and SiHa cell line. The cells were obtained from American Type Culture Collection (Rockville, Md.) and propagated in RPMI medium supplemented with 10% fetal calf serum, 50 U/mL penicillin G, and 50 pg/mL of streptomycin sulfate at 37° C., 5% $CO_2$ as recommended by the supplier. NCR nu/nu homozygous athymic male nude mice (4-5 week old, weight at least 16 g) were obtained from Charles River. The mice were inoculated subcutaneously in the right flank with 0.1 mL of the suspension containing 5×106 cells suspended in PBS supplemented with 30% Matrigel. When tumors achieved the size between 150 $mm^3$ and 350 $mm^3$ the animals were assigned to the treatment groups according to the following method. The animals were ranked according to the tumor size, and divided into 6 categories of decreasing tumor size. Four treatment groups of 10 animals/group were formed by randomly selecting one animal from each size category, so that in each treatment group all tumor sizes were equally represented.

The animals received four tail vein injections, at the intervals of 7 days, of the following preparations: 1) Control (HEPES-buffered saline pH 6.5); 2) MM-398 at dose 2 or 5 mg/kg per injection; 3) Liposomal Compound A at 20 or 60 mg/kg per injection; 4) MM-398 followed by injections of liposomal Compound A with a 24 h interval. Liposomes for injections were prepared as described in Example 7. The animal weight and tumor size were monitored twice weekly. The tumor progression was monitored by palpation and caliper measurements of the tumors along the largest (length) and smallest (width) axis twice a week. The tumor sizes were determined twice weekly from the caliper measurements using the formula (Geran, R. I., et al., 1972 Cancer Chemother. Rep. 3:1-88):

Tumor volume=[(length)×(width)$^2$]/2

To assess treatment-related toxicity, the animals were also weighted twice weekly. The animals were observed for 60 days following tumor inoculation. When the tumors in the group reached 10% of the mouse body weight, the animals in the group were euthanized. Average tumor volumes across the groups were plotted together and compared over time. As shown in FIGS. 6, 7, and 8, combination of liposomal ATR inhibitor Compound A with MM-398 has a significantly stronger antitumor effect compare to MM-398 and liposomal Compound A alone in all three xenograft models. The treatment related toxicity was assessed by the dynamics of animals' body weight (FIG. 9). Neither group revealed any significant toxicity. The weight of the animals in all treated groups was comparable to the control group and was consistently increasing. Thus, the liposome formulation of ATR inhibitor Compound A showed increased antitumor activity in the studied tumor models without an appreciable increase in toxicity.

Example 9B: MM-398 Irinotecan Liposome Manufacturing

The MM398 used in Example 9A and elsewhere herein is an irinotecan liposome that can be prepared in a multi-step process. First, lipids are dissolved in heated ethanol. The lipids can include DSPC, cholesterol and MPEG-2000-DSPE combined in a 3:2:0.015 molar ratio. Preferably, the liposomes can encapsulate irinotecan sucrose octasulfate (SOS) encapsulated in a vesicle consisting of DSPC, cholesterol and MPEG-2000-DSPE combined in a 3:2:0.015 molar ratio. The resulting ethanol-lipid solution is dispersed in an aqueous medium containing substituted amine and polyanion under conditions effective to form a properly sized (e.g. 80-120 nm) essentially unilamellar liposome containing the substituted amine (in the ammonium form) and polyanion encapsulated within a vesicle formed from the dissolved lipids. The dispersing can be performed, e.g., by mixing the ethanolic lipid solution with the aqueous solution containing a substituted amine and polyanion at the temperature above the lipid transition temperature, e.g., 60-70° C., and extruding the resulting hydrated lipid suspension (multilamellar liposomes) under pressure through one or more track-etched, e.g. polycarbonate, membrane filters with defined pore size, e.g. 50 nm, 80 nm, 100 nm, or 200 nm. The substituted amine can be triethylamine (TEA) and the polyanion can be sucrose octasulfate (SOS) combined in a stoichiometric ratio (e.g., $TEA_8SOS$) at a concentration of about 0.4-0.5N. All or substantially all non-entrapped TEA or SOS is then removed (e.g., by gel-filtration, dialysis or ultrafiltration) prior to contacting the liposome with irinotecan under conditions effective to allow the irinotecan to enter the liposome in exchange with TEA leaving the liposome. The conditions can include one or more conditions selected from the group consisting of: addition of the osmotic agent (e.g., 5% dextrose) to the liposome external medium to balance the osmolality of the entrapped TEA-SOS solution and/or prevent osmotic rupture of the liposomes during the loading, adjustment and/or selection of the pH (e.g, to 6.5) to reduce the drug and/or lipid degradation during the loading step, and increase of the temperature above the transition temperature of the liposome lipids (e.g., to 60-70° C.) to accelerate the transmembrane exchange of TEA and irinotecan. The loading of irinotecan by exchange with TEA across the liposome preferably continues until all or substantially all of the TEA is removed from the liposome, thereby exhausting its concentration gradient across the liposome. Preferably, the irinotecan liposome loading process continues until the gram-equivalent ratio of irinotecan to sucrooctasulfate is at least 0.9, at least 0.95, 0.98, 0.99 or 1.0 (or ranges from about 0.9-1.0, 0.95-1.0, 0.98-1.0 or 0.99-1.0). Preferably, the irinotecan liposome loading process continues until the TEA is at least 90%, at least 95%, at least 98%, at least 99% or more of the TEA is removed from the liposome interior. The irinotecan can form irinotecan sucrosofate within the liposome, such as irinotecan and sucrose octasulfate in a molar ratio of about 8:1. Next, any remaining extra-liposomal irinotecan and TEA is removed to obtain the irinotecan liposome using, e.g., gel (size exclusion) chromatography, dialysis, ion exchange, or ultrafiltration methods. The liposome external medium is replaced with injectable, pharmacologically acceptable fluid, e.g., buffered isotonic saline. Finally, the liposome composition is sterilized, e.g., by 0.2-micron filtration, dispensed into dose vials, labeled and stored, e.g., upon refrigeration at 2-8° C., until use. The liposome external medium can be replaced with pharmacologically acceptable fluid at the same time as the remaining extra-liposomal irinotecan and TEA is removed. The extra-liposomal pH of the composition can be adjusted or otherwise selected to provide a desired storage stability property (e.g., to reduce formation of the lyso-PC within the liposome during storage at 4° C. over 180 days), for example by preparing the composition at a pH of about 6.5-8.0, or any suitable pH value there between (including, e.g., 7.0-8.0, and 7.25).

DSPC, cholesterol (Chol), and PEG-DSPE were weighed out in amounts that corresponded to a 3:2:0.015 molar ratio, respectively (e.g., 1264 mg/412.5 mg/22.44 mg). The lipids were dissolved in chloroform/methanol (4/1 v/v), mixed thoroughly, and divided into 4 aliquots (A-D). Each sample was evaporated to dryness using a rotary evaporator at 60° C. Residual chloroform was removed from the lipids by placing under vacuum (180 µtorr) at room temperature for 12 h. The dried lipids were dissolved in ethanol at 60° C., and pre-warmed $TEA_8SOS$ of appropriate concentration was added so that the final alcohol content was 10% (v/v). The lipid concentration was 75 mM. The lipid dispersion was extruded at about 65° C. through 2 stacked 0.1 µm polycarbonate membranes (Nucleopore) 10 times using Lipex thermobarrel extruder (Northern Lipids, Canada), to produce liposomes with a typical average diameter of 95-115 nm (determined by quasielastic light scattering). The pH of the extruded liposomes was adjusted with 1 N NaOH to pH 6.5 as necessary. The liposomes were purified by a combination of ion-exchange chromatography and size-exclusion chromatography. First, DOWEX IRA 910 resin was treated with 1 N NaOH, followed by 3 washes with deionized water and then followed by 3 washes of 3 N HCl, and then multiple washes with water. The liposomes were passed through the prepared resin, and the conductivity of the eluted fractions was measured by using a flow-cell conductivity meter (Pharmacia, Upsalla, Sweden). The fractions were deemed acceptable for further purification if the conductivity was less than 15 µS/cm. The liposome eluate was then applied to a Sephadex G-75 (Pharmacia) column equilibrated with deionized water, and the collected liposome fraction was measured for conductivity (typically less than 1 µS/cm). Cross-membrane isotonicity was achieved by addition of 40% dextrose solution to a final concentration of 5% (w/w) and the buffer (Hepes) added from a stock solution (0.5 M, pH 6.5) to a final concentration of 10 mM.

A stock solution of irinotecan was prepared by dissolving irinotecan-HCl trihydrate powder in deionized water to 15 mg/mL of anhydrous irinotecan-HCl, taking into account water content and levels of impurities obtained from the certificate of analysis of each batch. Drug loading was initiated by adding irinotecan at 500 g/mol liposome phospholipid and heating to 60±0.1° C. for 30 min in a hot water bath. The solutions were rapidly cooled upon removal from the water bath by immersing in ice cold water. Extraliposomal drug was removed by size exclusion chromatography, using Sephadex G75 columns equilibrated and eluted with Hepes buffered saline (10 mM Hepes, 145 mM NaCl, pH 6.5). The samples were analyzed for irinotecan by HPLC and phosphate by the method of Bartlett (see Phosphate Determination).

One preferred example of a storage stable irinotecan liposome described herein is the product that will be marketed as ONIVYDE (irinotecan liposome injection). ONIVYDE is a topoisomerase inhibitor, formulated with irinotecan hydrochloride trihydrate into a liposomal dispersion, for intravenous use. ONIVYDE indicated for the treatment of metastatic adenocarcinoma of the pancreas after disease progression following gemcitabine-based therapy.

ONIVYDE is a storage stabilized liposome having a pH of about 7.25. The ONIVYDE product contains irinotecan sucrosofate encapsulated in a liposome, obtained from an irinotecan hydrochloride trihydrate starting material. The chemical name of irinotecan is (S)-4,11-diethyl-3,4,12,14-tetrahydro-4-hydroxy-3,14-dioxolH-pyrano[3',4':6,7]-indolizino[1,2-b]quinolin-9-yl-[1,4'bipiperidine]-1'-carboxylate. The dosage of ONIVYDE can be calculated based on the equivalent amount of irinotecan trihydrate hydrochloride starting material used to prepare the irinotecan liposomes, or based on the amount of irinotecan in the liposome. There are about 866 mg of irinotecan per gram of irinotecan trihydrate hydrochloride. For example, an ONIVYDE dose of 80 mg based on the amount of irinotecan hydrochloride trihydrate starting material actually contains about 0.866×(80 mg) of irinotecan in the final product (i.e., a dose of 80 mg/m² of ONIVYDE based on the weight of irinotecan hydrochloride starting material is equivalent to about 70 mg/m² of irinotecan in the final product). ONIVYDE is a sterile, white to slightly yellow opaque isotonic liposomal dispersion. Each 10 mL single-dose vial contains 43 mg irinotecan free base at a concentration of 4.3 mg/mL. The liposome is a unilamellar lipid bilayer vesicle, approximately 110 nm in diameter, which encapsulates an aqueous space containing irinotecan in a gelated or precipitated state as the sucrose octasulfate salt. The vesicle is composed of 1,2-distearoyl-sn-glycero-3-phosphocholine (DSPC) 6.81 mg/mL, cholesterol 2.22 mg/mL, and methoxy-terminated polyethylene glycol (MW 2000)-distearoylphosphatidyl ethanolamine (MPEG-2000-DSPE) 0.12 mg/mL. Each mL also contains 2-[4-(2-hydroxyethyl) piperazin-1-yl]ethanesulfonic acid (HEPES) as a buffer 4.05 mg/mL and sodium chloride as an isotonicity reagent 8.42 mg/mL. Each vial of ONIVYDE contains 43 mg/10 mL irinotecan free base as a white to slightly yellow, opaque, liposomal dispersion in a single-dose vial.

In one example of the invention, an ONIVYDE unit dosage form is a pharmaceutical composition comprising an amount of irinotecan encapsulated in a liposome that provides a total amount of about 70 mg/m² of irinotecan, providing an amount of irinotecan equivalent to 80 mg/m² irinotecan hydrochloride trihydrate, and less than about 20% lyso-PC. The unit dosage form can be an intravenous formulation having a total volume of about 500 mL. ONIVYDE is prepared for administering by diluting the isotonic liposomal dispersion from the vial as follows: withdraw the calculated volume of ONIVYDE from the vial.

ONIVYDE is diluted in 500 mL 5% Dextrose Injection, USP or 0.9% Sodium Chloride Injection, USP and mix diluted solution by gentle inversion; protect diluted solution from light and administer diluted solution within 4 hours of preparation when stored at room temperature or within 24 hours of preparation when stored under refrigerated conditions [2° C. to 8° C. (36° F. to 46° F.)].

ONIVYDE (irinotecan liposome injection) is indicated, in combination with 5-fluorouracil and leucovorin, for the treatment of patients with metastatic adenocarcinoma of the pancreas that has progressed following gemcitabine-based therapy. Administer ONIVYDE prior to leucovorin and fluorouracil. The recommended dose of ONIVYDE is 70 mg/m2 irinotecan administered by intravenous infusion over 90 minutes every 2 weeks. The recommended starting dose of ONIVYDE in patients known to be homozygous for the UGT1A1*28 allele is 50 mg/m$^2$ irinotecan administered by intravenous infusion over 90 minutes. The dose of ONIVYDE can be increased to 70 mg/m$^2$ as tolerated in subsequent cycles. There is no recommended dose of ONIVYDE for patients with serum bilirubin above the upper limit of normal. ONIVYDE is infused as a diluted solution intravenously over 90 minutes.

Suitable treatment regimens include ONIVYDE 70 mg/m$^2$ with (l+d racemic form) leucovorin 400 mg/m$^2$ (or 200 mg/m$^2$ of the active l form of leucovorin) and fluorouracil 2,400 mg/m$^2$ over 46 hours every 2 weeks (ONIVYDE/5-FU/LV; n=117), ONIVYDE 100 mg/m$^2$ every 3 weeks (n=147), or leucovorin 200 mg/m$^2$ and fluorouracil 2000 mg/m$^2$ over 24 hours weekly for 4 weeks followed by 2 week rest (5-FU/LV; n=134).

Example 10: In Vivo Antitumor Efficacy and Tolerability of Ls-Compound 5 Prepared Using TEA.SOS Against Lung Cancer Xenografts in Mice FIG. 10A and FIG. 10B are each a graph, showing the efficacy of liposomal Compound 5 in combination with MM-398 in NCI-H2170 (FIG. 10A) or DMS-114 (FIG. 10B) mice xenograft models, as discussed in Example 10.

Figure 11A:
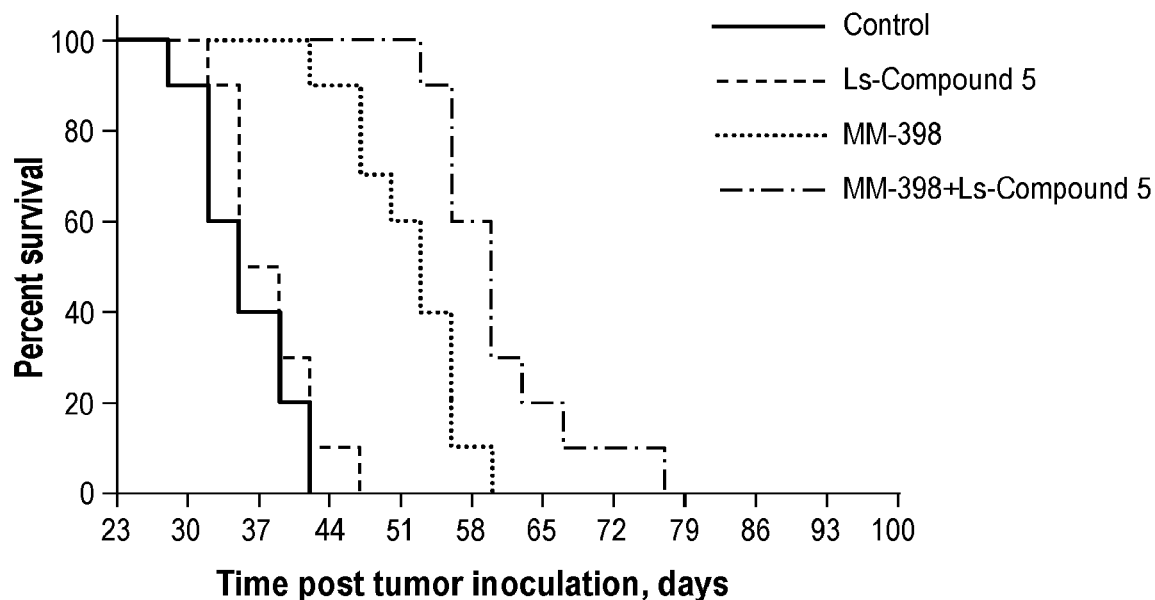
FIG. 11A and FIG. 11B are each a graph showing the Kaplan-Meyer survival curves representing efficacy of liposomal Compound 5 in combination with MM-398 in NCI-H2170 (FIG. 11A) and DMS-114 (FIG. 11B) a mouse xenograft model, as discussed in Example 10.
Figure 11B:
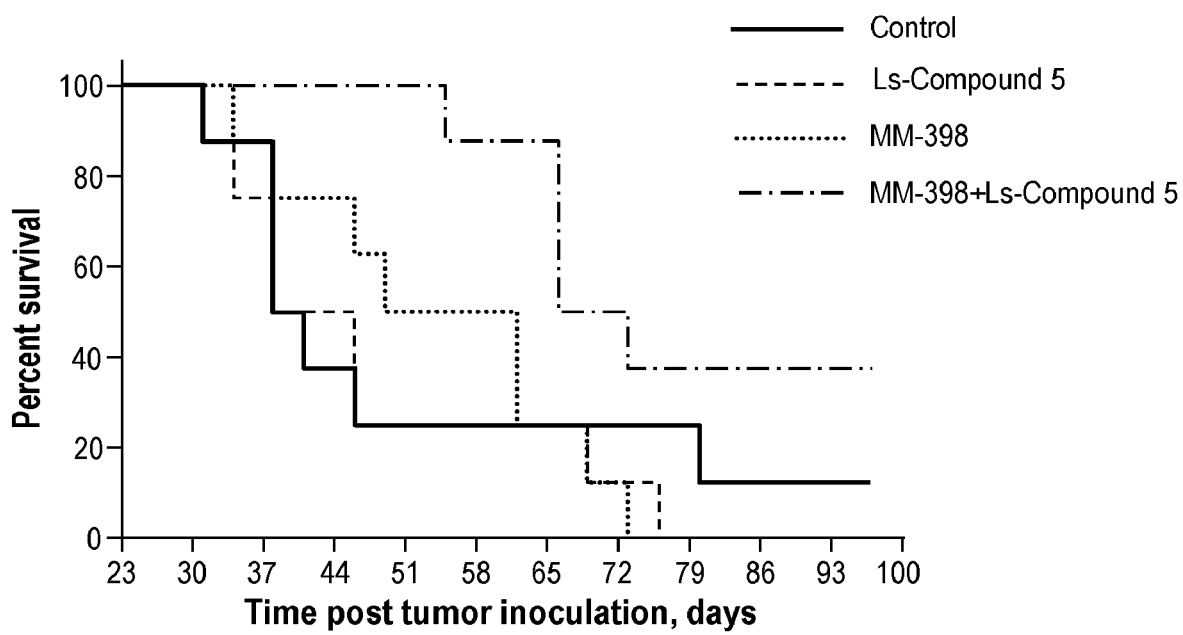

FIG. 11A and FIG. 11B are each a graph showing the Kaplan-Meyer survival curves representing efficacy of liposomal Compound 5 in combination with MM-398 in NCI-H2170 (FIG. 11A) and DMS-114 (FIG. 11B) a mouse xenograft model, as discussed in Example 10.

FIG. 12A and FIG. 12B are each a graph showing Tolerability of liposomal Compound 5 in combination with MM-398 in NCI-H2170 (FIG. 12A) or DMS-114 (FIG. 12B) in a mouse xenograft model.

Antitumor efficacy of liposomes loaded with an ATR inhibitor Compound 5 in combinations with MM-398 (liposomal Irinotecan) and was studied in the model of human NCI-H2170 (lung squamous cell carcinoma) and DMS-114 (small cells lung carcinoma) lung cell lines.

The cells were obtained from American Type Culture Collection (Rockville, Md.) and propagated in RPMI medium supplemented with 10% fetal calf serum, 50 U/mL penicillin G, and 50 pg/mL of streptomycin sulfate at 37° C., 5% $CO_2$ as recommended by the supplier. NCR nu/nu homozygous athymic male nude mice (4-5 week old, weight at least 16 g) were obtained from Charles River. The mice were inoculated subcutaneously in the right flank with 0.1 mL of the suspension containing 5×10$^6$ cells suspended in PBS supplemented with 30% Matrigel. When tumors achieved the size between 150 mm$^3$ and 350 mm$^3$ the animals were assigned to the treatment groups according to the following method. The animals were ranked according to the tumor size, and divided into 6 categories of decreasing tumor size. Four treatment groups of 10 animals/group were formed by randomly selecting one animal from each size category, so that in each treatment group all tumor sizes were equally represented. The animals received four tail vein injections, at the intervals of 7 days, of the following preparations: 1) Control (HEPES-buffered saline pH 6.5); 2) MM-398 at dose 5 mg/kg per injection; 3) Liposomal Compound 5 at 80 mg/kg per injection; 4) MM-398 followed by injections of liposomal Compound 5 with a 24 h interval. Liposomes for injections were prepared as described in Example 7. MM-398 is described in Example 9B.

The animal weight and tumor size were monitored twice weekly. The tumor progression was monitored by palpation and caliper measurements of the tumors along the largest (length) and smallest (width) axis twice a week. The tumor sizes were determined twice weekly from the caliper measurements using the formula:

Tumor volume=[(length)×(width)$^2$]/2

To assess treatment-related toxicity, the animals were also weighted twice weekly. When the tumors in the group reached 10% of the mouse body weight, the animals in the group were euthanized. Average tumor volumes across the groups were plotted together and compared over time.

As demonstrated in FIGS. 10A and 10B and FIGS. 11A and 11B, liposomal ATR inhibitor Compound 5 significantly improved antitumor efficacy of MM-398 in both lung xenograft models. The combinational treatment of liposomal ATR inhibitor and MM-398 did not affect the animals' body weight (FIGS. 12A and 12B).

Example 11: Comparison of In Vivo Antitumor Efficacy of Liposomal Inhibitors Ls-Compound 5 and LS-Compound a in Combination with MM-398 Against Lung Cancer Xenografts in Mice FIGS. 13A and 13B are graphs showing the efficacy of liposomal Compound 5 in combination with MM-398 in Calu-6 (FIG. 13A) or COLO-699 (FIG. 13B) mice xenograft models. For example, the data in FIGS. 13A and 13B show that while liposomal ATR inhibitor Compound 5 significantly improved the antitumor efficacy of MM-398 in both models, Compound A formulated in liposomes was active only in COLO-699 xenograft model.

Antitumor efficacy of liposomes loaded with an ATR inhibitor Compound 5 in combinations with MM-398 (liposomal Irinotecan) was compared with liposomal formulation of Compound A in the xenograft model of human Calu-6 and COLO-699 lung cell lines.

The cells were obtained from American Type Culture Collection (Rockville, Md.) and propagated in RPMI medium supplemented with 10% fetal calf serum, 50 U/mL penicillin G, and 50 pg/mL of streptomycin sulfate at 37° C., 5% $CO_2$ as recommended by the supplier. NCR nu/nu homozygous athymic male nude mice (4-5 week old, weight at least 16 g) were obtained from Charles River. The mice were inoculated subcutaneously in the right flank with 0.1 mL of the suspension containing 5×106 cells suspended in PBS supplemented with 30% Matrigel. When tumors achieved the size between 150 mm$^3$ and 350 mm$^3$ the animals were assigned to the treatment groups according to the following method. The animals were ranked according to the tumor size, and divided into 6 categories of decreasing tumor size. Four treatment groups of 10 animals/group were formed by randomly selecting one animal from each size category, so that in each treatment group all tumor sizes were equally represented. The animals received four tail vein injections, at the intervals of 7 days, of the following preparations: 1) Control (HEPES-buffered saline pH 6.5); 2) MM-398 at dose 10 or 20 mg/kg per injection; 3) Liposomal Compound 5 at 80 mg/kg per injection; 4) Liposomal Compound A at 80 mg/kg per injection; 5) MM-398 followed by injections of liposomal Compound 5 with a 24 h interval. 6) MM-398 followed by injections of liposomal Compound A with a 24 h interval. Liposomes for injections were prepared as described in Example 7.

The animal weight and tumor size were monitored twice weekly. The tumor progression was monitored by palpation and caliper measurements of the tumors along the largest (length) and smallest (width) axis twice a week. The tumor sizes were determined twice weekly from the caliper measurements using the formula:

Tumor volume=[(length)×(width)$^2$]/2

To assess treatment-related toxicity, the animals were also weighted twice weekly. When the tumors in the group reached 10% of the mouse body weight, the animals in the group were euthanized. Average tumor volumes across the groups were plotted together and compared over time.

Example 12: Free Drug Combination Screening Study

Figure 14A:
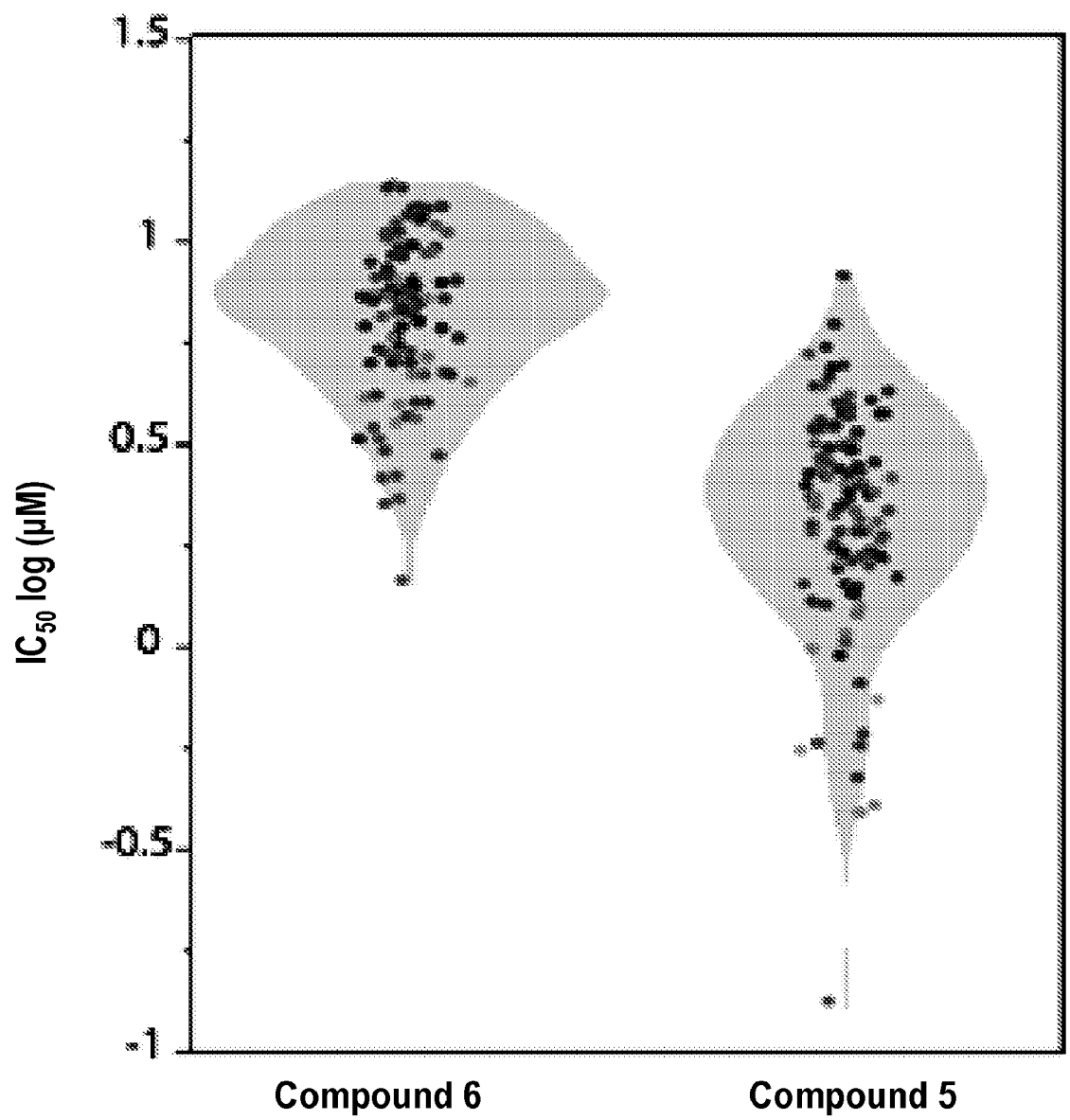
FIG. 14A is a graph illustrating the in vitro monotherapy cell kill of Compound 6 and Compound 5 in a panel of lung cancer cell lines.
Figure 14B:
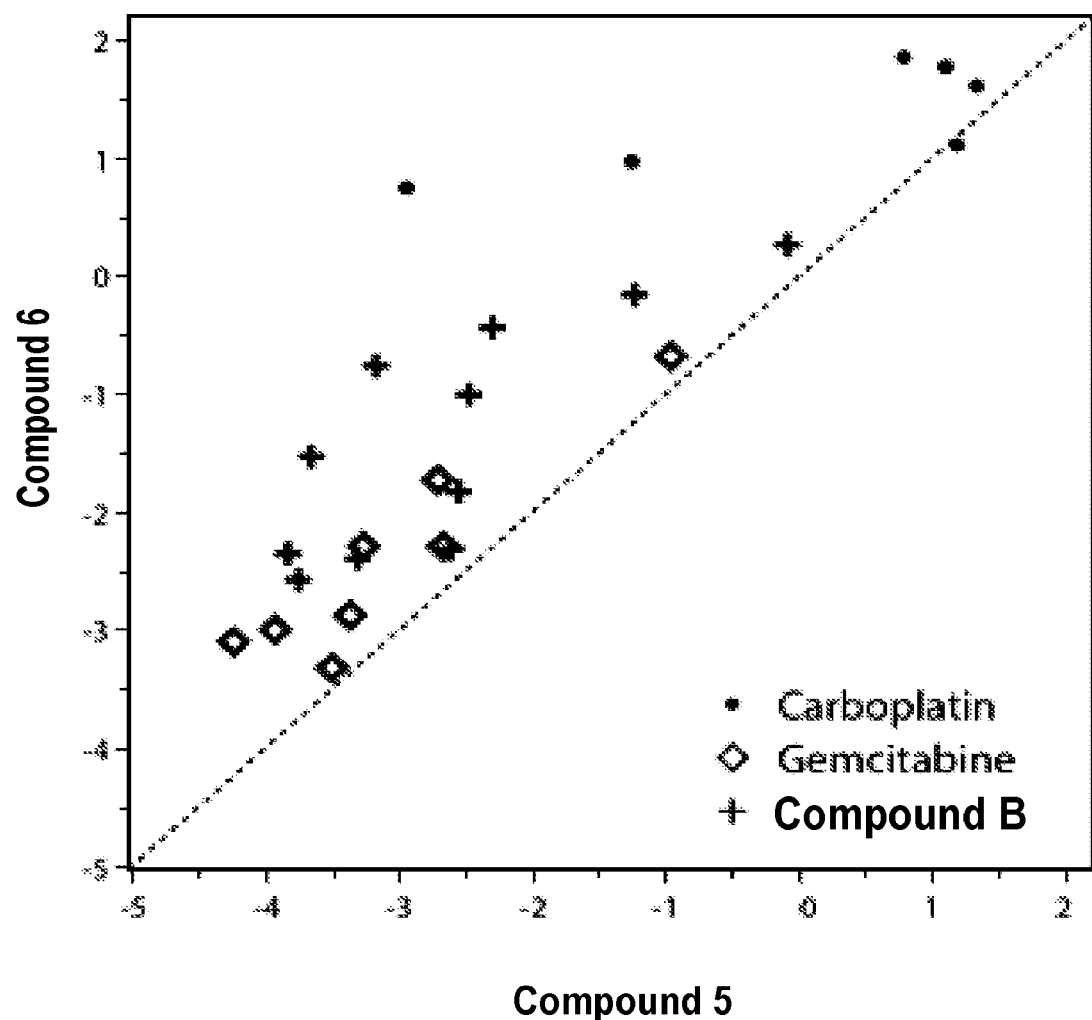
FIG. 14B is a graph illustrating the effect of Compound 5 and Compound 6 in combination with three chemotherapeutic agents (Carboplatin, Gemcitabine, Compound B).

FIG. 14A. is a graph showing the in vitro monotherapy cell kill of Compound 6 and Compound 5 in a panel of lung cancer cell lines. Compound 5 is more efficacious with IC$_{50}$ ~3 (=100.5) folds lower than Compound 6. FIG. 14B is a graph showing the effect of Compound 5 vs. Compound 6 in combination with three chemotherapeutic agents (Carboplatin, Gemcitabine, Compound B). The figure compares the IC$_{50}$ in log (pM) of the combination of the chemotherapeutic agents with 1 μg/ml of Compound 6 or Compound 5. The addition of Compound 5 to the chemotherapeutic agents was more potent (lower IC$_{50}$) than Compound 6 in all tested cytotoxic agents and in all cell lines except one.

Figure 15:
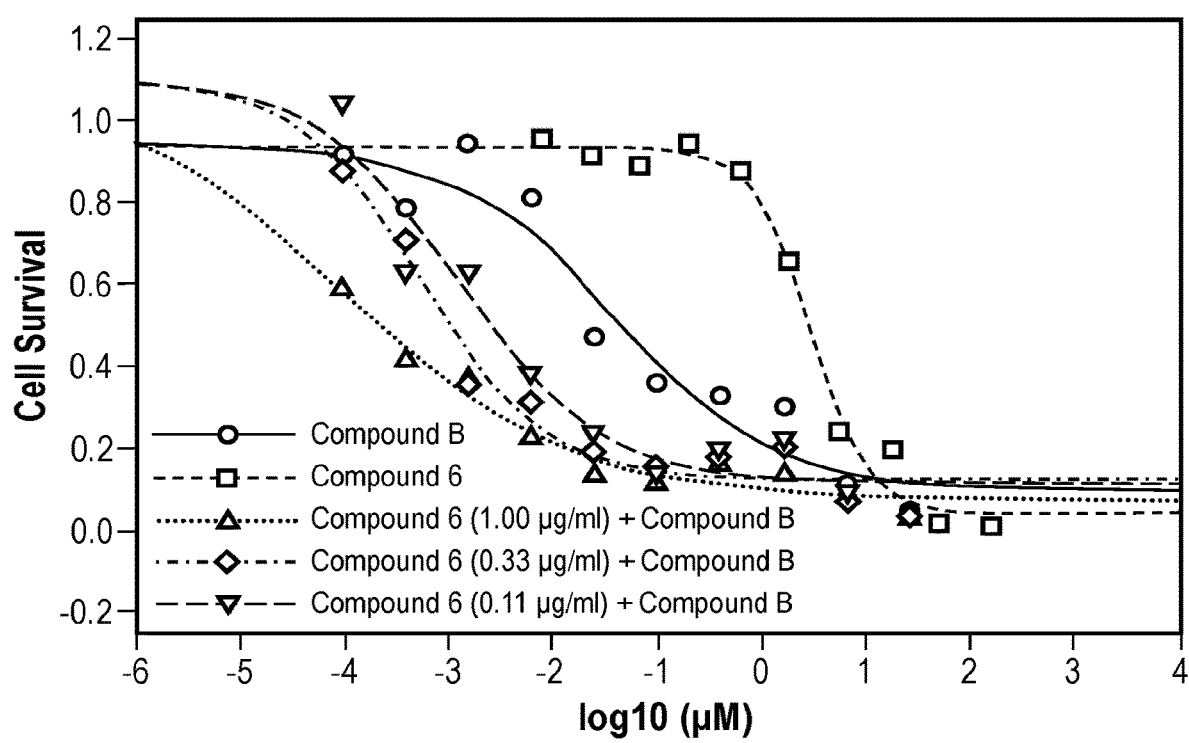
FIG. 15 is a graph showing the $IC_{50}$ shift values measured in Sum190PT cell line (Triple Negative Breast Cancer, TNBC) for the ATR protein kinase inhibitor Compound 6 of Example 2, with and without various concentrations of Compound B.

FIG. 15 is a graph showing the combination (Example 2+Compound B) IC$_{50}$ shift in Sum190PT cell line (TNBC).

Figure 16A:
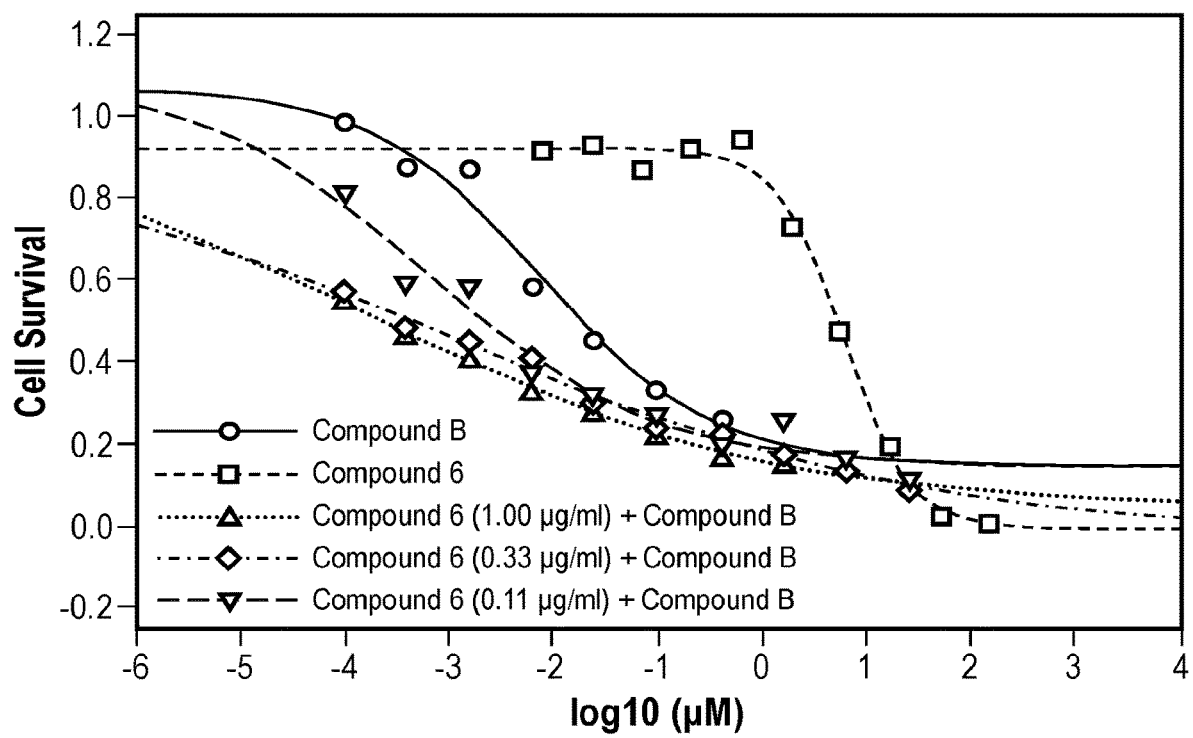
FIG. 16A is a graph showing the $IC_{50}$ shift values of a combination of ATR protein kinase inhibitor Compound 6 of Example 2, measured in MDA-MB-453 TNBC cancer cell line.
Figure 16B:
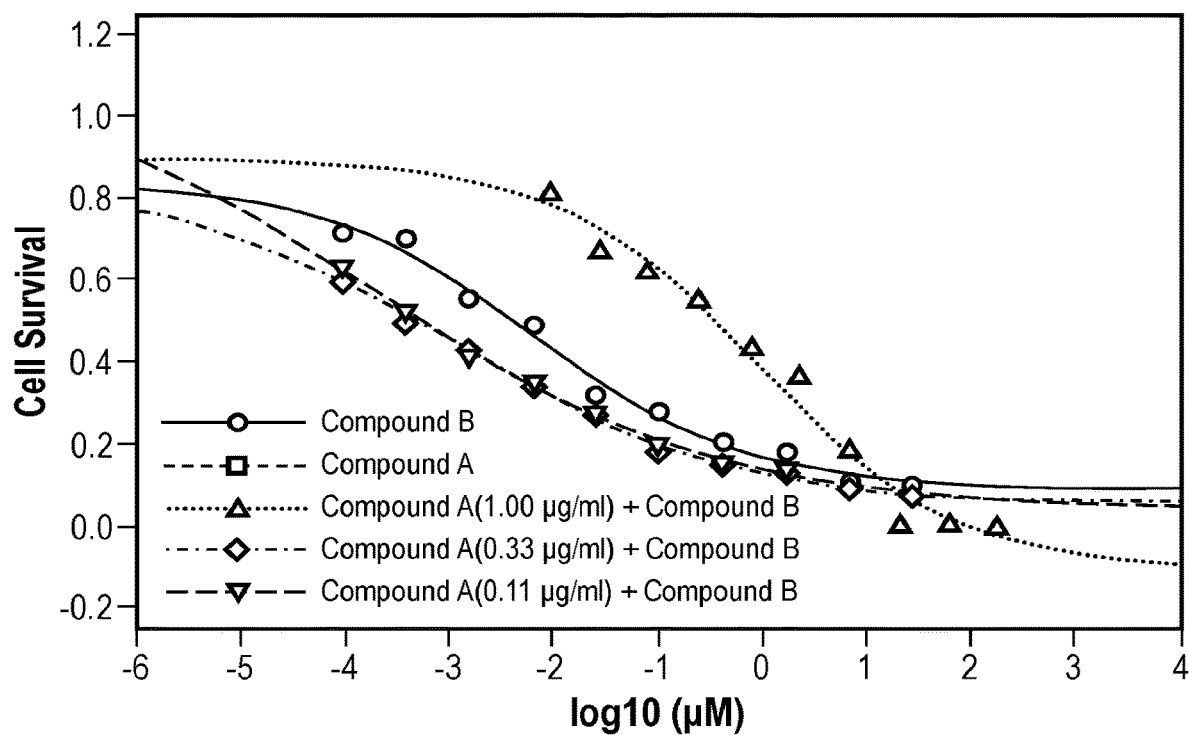
FIG. 16B is a graph showing the $IC_{50}$ shift values of a combination of ATR protein kinase inhibitor Compound A, measured in MDA-MB-453 TNBC cancer cell line.

FIG. 16A and FIG. 16B are graphs showing a comparison of IC50 shifts of the compound of Example 2 with Compound B vs combination of Compound A with Compound B in MDA-MB-453 cell line (TNBC).

Culture/Treatment Condition

In vitro efficacy study was done using CELLTITER-GLO Luminescent Cell Viability Assay (Promega) with Corning Cat #3707 384 well White Clear bottom plates. Cells were plated (1000 cells/well) in 384 well format and allowed to incubate at 37° C. for 24 hours. Monotherapy drugs were added at the 24 hr time point and then allowed to incubate at 37° C. for 24 hours. At the 48 hr time point the drugs in media were removed, washed with PBS, and fresh media was added. Cells were then allowed to incubate at 37° C. for 72 hours. For combination studies, cells were exposed to Carboplatin or Compound B or Gemcitabine for 24 hours, then the chemotherapeutic agent was removed and cells were exposed to the secondary compound (ATR inhibitor) for 24 hours. Cells were cultured in fresh media for an additional 48 hours.

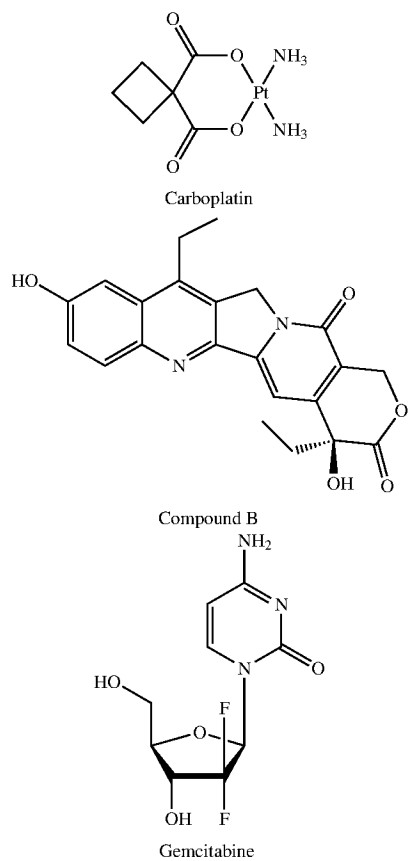

Carboplatin

Compound B

Gemcitabine

At the 120 hr time point media was removed and CELLTITER-GLO (CTG) reagent was added (1:1 ratio with PBS). Plates were read using a luminometer (Envision Multilabel reader).

Data Analysis:

Data was analyzed using an in-house algorithm developed using Matlab (Mathworks, Natick Mass.). In summary, average CTG mean luminescent values were computed for 4 replicate wells. Outlier detection was performed by computing the coefficient of variation (CV>20%) and outliers were removed from the average. CTG values were normalized based on a control non-treated well. Drug concentration in microMolar (pM) was log transformed prior to fitting to a 4 parameter logistic curve.

$$y = b + \frac{(a - b)}{(1 + 10^{(IC50-C)*slope})}$$

Where C: concentration of drug, y: normalized CTG value, a: top asymptote (represents maximum cell kill), b: bottom asymptote (constrained 0.8-1.2), IC50, slope: logistic curve slope.

Data quality control was performed to ensure that the concentration range is optimal according to these rules: (1) if the lowest concentration kills more than 70% of the cells the concentration range is deemed too potent (2) if the highest concentration kills less than 30% of the cells, the concentration range is deemed low or the cell line is too resistant. Additionally, goodness of the fit was evaluated using $R^2$ and $R^2<0.9$ is flagged as a bad fit.

Statistical analysis was performed using JMP (SAS Institute Inc., NC) and p<0.05 was considered significant.

Example 13: ATR Activity Determination

An $EC_{50}$ determination was conducted for the supplied set of compounds against the kinase ATR/ATRIP(h), using a linear enzyme concentration in the Eurofins ATR/ATRIP HTRF assay using GST tagged full length p53 as the substrate.

The activity of ATR/ATRIP(h) at an ATP concentration within 15 µM of the Km was determined at 9 concentrations of compound with semi-log dilutions from 10 µM. ATR/ATRIP phosphorylation of p53 on Ser15 was measured via formation of an energy transfer complex consisting of a Europium-labelled anti-phospho Ser15 p53 antibody and an anti-GST-d2 antibody. All data points were performed in duplicate with DMSO controls and EDTA blanks.

ATR/ATRIP(h) was pre-diluted in 25 mM HEPES pH 8.0, 0.01% Brij-35, 1% Glycerol, 5 mM DTT, 1 mg/mL BSA and assayed in 25 mM HEPES pH 8.0, 0.01% Brij-35, 1% Glycerol, 10 mM $MnCl_2$ using 30 nM GST, cMyc p53-(hu, FL) as the substrate. The reaction was initiated with the addition of ATP to a final concentration of 10 µM.

The individual replicates were expressed in terms of the % of the DMSO positive control activity. The mean activity (% control) of each inhibitor concentration was plotted against the inhibitor concentration, and $EC_{50}$ values were determined using GRAPHPAD PRISM.

The data expressed as % control activity were plotted against inhibitor concentration, and fitted to a four parameter logistic using GRAPHPAD PRISM. Graphs for each compound are shown alongside the data in the accompanying Excel report. A summary of the compound potencies is shown below.

TABLE 4

| Compound ID | Kinase | ATP µM | $EC_{50}$* nM | Top | Bottom | Hill | $r^2$ |
|---|---|---|---|---|---|---|---|
| Compound 6 | ATR ATRIP(h) | 10 | 470.8 | 101 | −2 | −0.768 | 0.998 |
| Compound 2 | ATR ATRIP(h) | 10 | 139.8 | 94 | 1 | −0.911 | 0.998 |
| Compound 5 | ATR ATRIP(h) | 10 | 233.9 | 95 | 1 | −0.819 | 0.996 |
| Compound 1 | ATR ATRIP(h) | 10 | 49.6 | 95 | −1 | −0.772 | 0.994 |
| Compound 4 | ATR ATRIP(h) | 10 | 353.4 | 97 | 1 | −0.860 | 0.997 |
| Compound 3 | ATR ATRIP(h) | 10 | 196.1 | 98 | −3 | −0.776 | 0.999 |
| Compound A | ATR ATRIP(h) | 10 | <1 | ND | ND | ND | ND |

Example 14: ATM Activity Determination

Estimated $IC_{50}$ values are as follows (obtained using STANDARD KINASEPROFILER):

TABLE 5

| Compound | Kinase | $IC_{50}$ (nM) |
|---|---|---|
| Compound 6 | ATM(h) | >10,000 |
| Compound 2 | ATM(h) | 4817 |
| Compound 5 | ATM(h) | >10,000 |
| Compound 1 | ATM(h) | 3864 |
| Compound 4 | ATM(h) | 6869 |
| Compound 3 | ATM(h) | >10,000 |
| Compound A | ATM(h) | 42 |

Example 15: Detecting Total and Phospho-ATR with Western Blot Analysis

Figure 17:
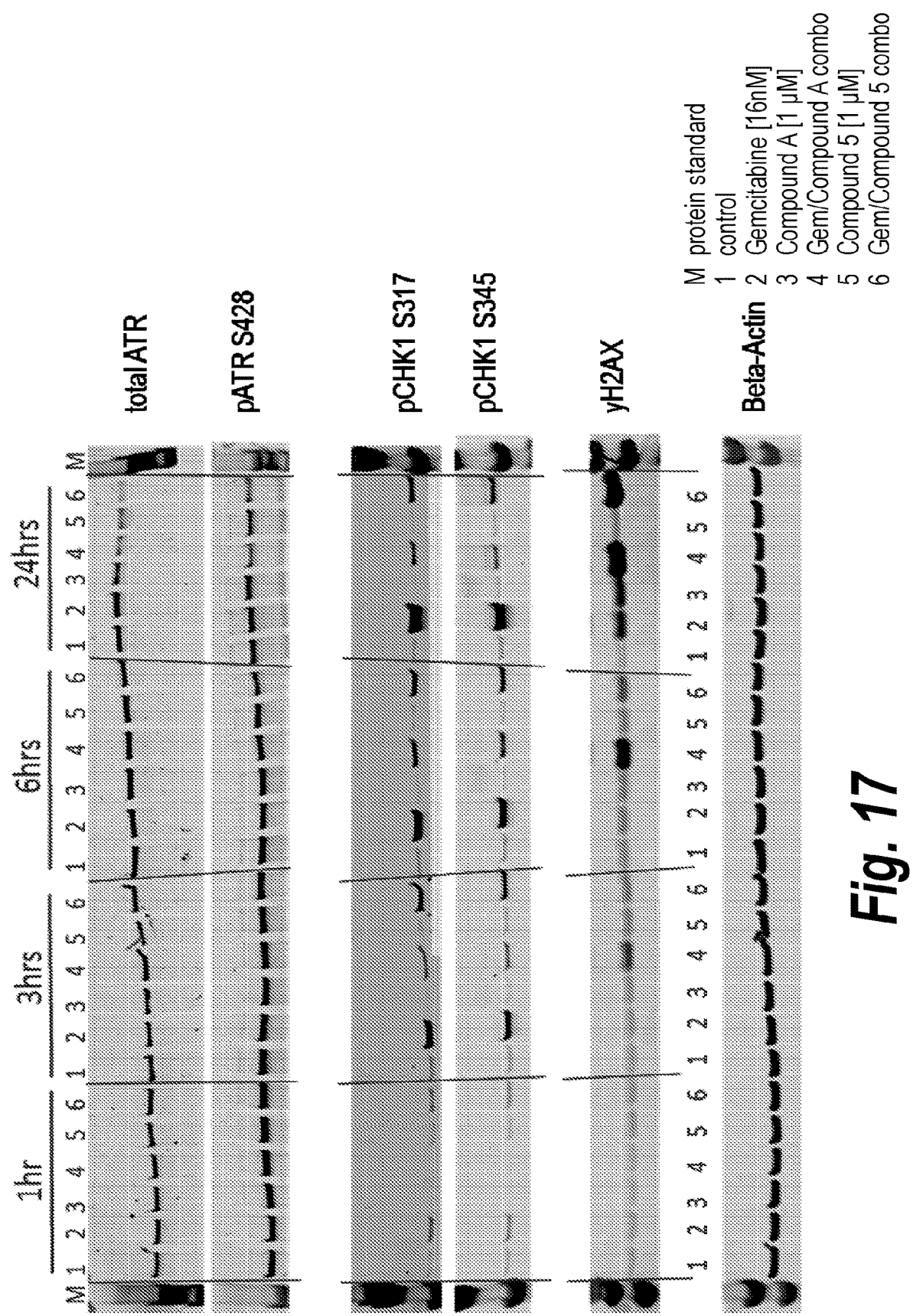
FIG. 17 is a western blot analysis of obtained from lung cancer cells DMS-114 exposed either to Gemcitabine [16 nM] or ATR inhibitor (Compound A or Compound 5 [1 uM]) alone or in combination in-vitro.

Referring to FIG. 17: Lung cancer cells DMS-114 were exposed either to Gemcitabine [16 nM] or ATR inhibitor (Compound A or Compound 5 [1 µM]) alone or in combination in vitro. Whole cell protein lysates were generated after 1, 3, 6 and 24 hours using a 2% SDS containing cell lysis buffer and stored at −80° C. until all samples were collected and run together at the same time for the WesternBlot analysis. The following proteins and phosphoproteins of interest were detected by antibodies purchased from Cell Signaling Technology (see methods and materials part below): total and phospho-ATR (S428), phospho-CHK1 (S317 and S345), γH2AX, beta-actin.

Results in FIG. 17: Total and phospho-ATR signal is strongly reduced over time with the addition of either of the two ATR inhibitors (Compound A and Compound 5) and not in control or Gemcitabine alone treatment (compare e.g. lane 1, 2 with 3, 4 or 5, 6 at 24 hrs). In response to Gemcitabine, the phospho-CHK1 (S317 and S345) signaling is significantly increased over the period of 24 hrs. The addition of any of the used ATR inhibitors (Compound A or Compound 5) abrogates the phosphorylation signal of CHK1. The reduction of the ATR protein and downstream CHK1 signaling by both inhibitors confirms the specific on-target effects of both molecules. More importantly, our hypothesis is that the loss of the cell cycle check-point, driven by the CHK1 phosphorylation signaling that supposed to lead to cell cycle arrest and repair of DNA damage, induces cell death by accumulation of DNA damage. The increased γH2AX signal can be seen as a surrogate for the measurement of increased toxicity and accumulation of DNA damage.

Cell Culture

U20S and all other cells were grown in (RPMI) supplemented with 10% fetal bovine serum (FBS) and antibiotics. Imaging and time-lapse compatible NucLight red cell lines were generated as recommend by Essen Bioscience Inc. using lentiviral particles, infection and puromycin selection protocols.

Antibodies and Western-Blots

All target and phospho-specific antibodies were purchased from Cell Signaling and/or Epitomics and were used at 1:1000 dilutions. A list of all antibodies is available in Table 6. Standard antibody based Western blot and immunohistochemistry protocols were used. Briefly, 2% SDS based cell lysis buffer was used to collect whole cell lysate for Western Blotting. Secondary antibodies and staining protocols were purchased and followed regarding LiCor Biosciences and/or BD Bioscience.

TABLE 6

| Target | Company | Catalog # |
|---|---|---|
| ATR | Cell Signaling Technology | 2790 |
| ATR phospho (S428) | Cell Signaling Technology | 2853 |
| CHK1 phospho (S317) | Cell Signaling Technology | 12302 |
| CHK1 phospho (S345) | Cell Signaling Technology | 2348 |
| H2AX phospho (S139) | Cell Signaling Technology | 9718 |
| beta-actin | Cell Signaling Technology | 4970 |

Whole Cell Lysis Protocol

Cells were grown and treated in a 6 cm dish scale. To harvest cells, medium was removed and quickly replaced by ice cold PBS. PBS was then replaced with 250 μL of 2% SDS lysis buffer. After five minutes of incubation, the lysed cells were scraped off and loaded onto a cell lysate homogenizer microcentrifuge spin-column (QIAshredder, Qiagen, Cat.-Nr. 79656). The filtrate was then loaded onto a 0.2 μm centrifugal filter column (Nanosep MF 0.2_m, Pall, Cat.-Nr. ODM02C34). The lysates were then stored at −80° C.

2% SDS containing lysis buffer (Table 7) was modified according to Steven et al., "Protein microarrays for multiplex analysis of signal transduction pathways," Nat Med 10, no. 12 (December 2004): 1390-1396.

TABLE 7

| Titrated pH = 6.8 | Final Conc. |
|---|---|
| Trizma-Base | 50 mM |
| SDS | 2% |
| Glycerol | 5% |
| EDTA | 5 mM |
| NaF | 1 mM |

Example 16: Broad Kinase Panel Screening (359)

Major hits out of 359 were: ALK, ARK, c-MER, CLK1, DYRK, GSK3a, GSK3b, FLT2, FLT3, MLK1, SIK2, TNIK, and YSK4.

TABLE 8

| Kinase: | Compound 5 (M) | Log IC$_{50}$ | Kinase: | nM |
|---|---|---|---|---|
| ALK1/ACVRL1 | 3.57E−08 | −7.45 | ALK1/ACVRL1 | 35.7 |
| ALK2/ACVR1 | 1.66E−08 | −7.78 | ALK2/ACVR1 | 16.6 |
| ARK5/NUAK1 | 1.68E−08 | −7.78 | ARK5/NUAK1 | 16.8 |
| CLK1 | 1.34E−07 | −6.87 | CLK1 | 134 |
| CLK4 | 8.86E−08 | −7.05 | CLK4 | 88.6 |
| DDR1 | 1.91E−07 | −6.72 | DDR1 | 191 |
| DYRK2 | 7.18E−08 | −7.14 | DYRK2 | 71.8 |
| FLT4/VEGFR3 | 6.34E−08 | −7.20 | FLT4A/VEGFR3 | 63.4 |
| GSK3a | 5.73E−09 | −8.24 | GSK3a | 5.73 |
| GSK3b | 6.30E−08 | −7.20 | GSK3b | 63 |
| MLK1/MAP3K9 | 1.13E−08 | −7.95 | MLK1/MAP3K9 | 11.3 |
| MLK2/MAP3K10 | 9.58E−09 | −8.02 | MLK2/MAP3K10 | 9.58 |
| MLK3/MAP3K11 | 5.90E−09 | −8.23 | MLK3/MAP3K11 | 5.9 |
| PIM1 | 7.26E−08 | −7.14 | PIM1 | 72.6 |
| PKCmu/PRKD1 | 1.34E−07 | −6.87 | PKCmu/PRKD1 | 134 |
| PKD2/PRKD2 | 1.57E−07 | −6.80 | PKD2/PRKD2 | 157 |
| RET | 7.74E−08 | −7.11 | RET | 77.4 |

TABLE 8-continued

| Kinase: | Compound 5 (M) | Log IC$_{50}$ | Kinase: | nM |
|---|---|---|---|---|
| SIK2 | 1.49E−07 | −6.83 | SIK2 | 149 |
| TNIK | 1.10E−07 | −6.96 | TNIK | 110 |
| YSK4/MAP3K19 | 2.92E−08 | −7.53 | YSK4/MAP3K19 | 29.2 |

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features set forth herein.

Example 17: Data Using Compound a as a Comparator

Figure 18A:
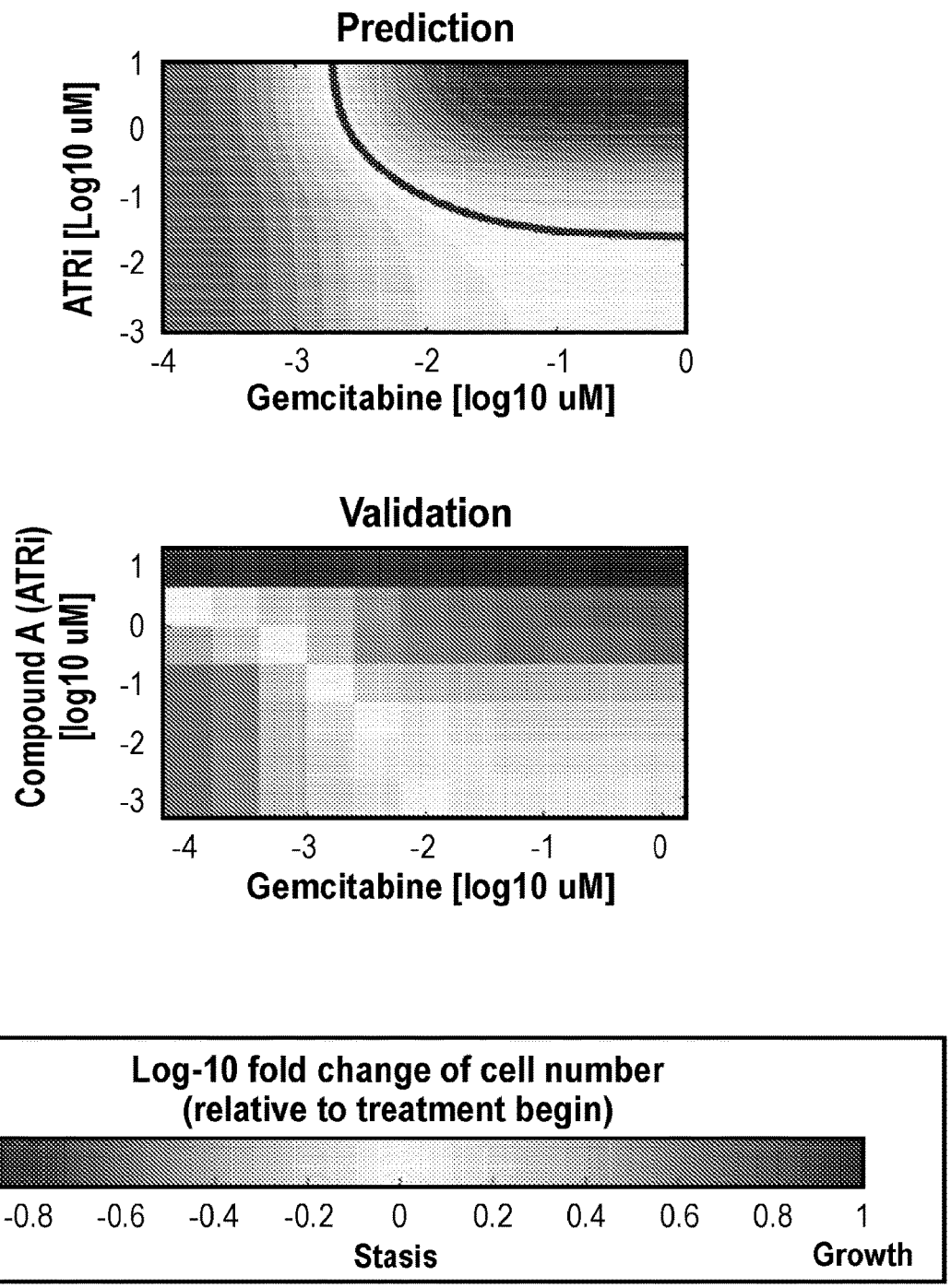
FIG. 18A-B is cell death and growth assay performed combining Compound A and Gemcitabine at various concentrations in U2OS cells. The results are compared back to a prediction of cell growth and death with the combination of the two compounds (FIG. 18A). The number of living and apoptotic cells is also determined at set concentrations of Compound A (1 µM) and Gemcitabine (0.04 µM) in USO2 cells (FIG. 18B).
Figure 18B:
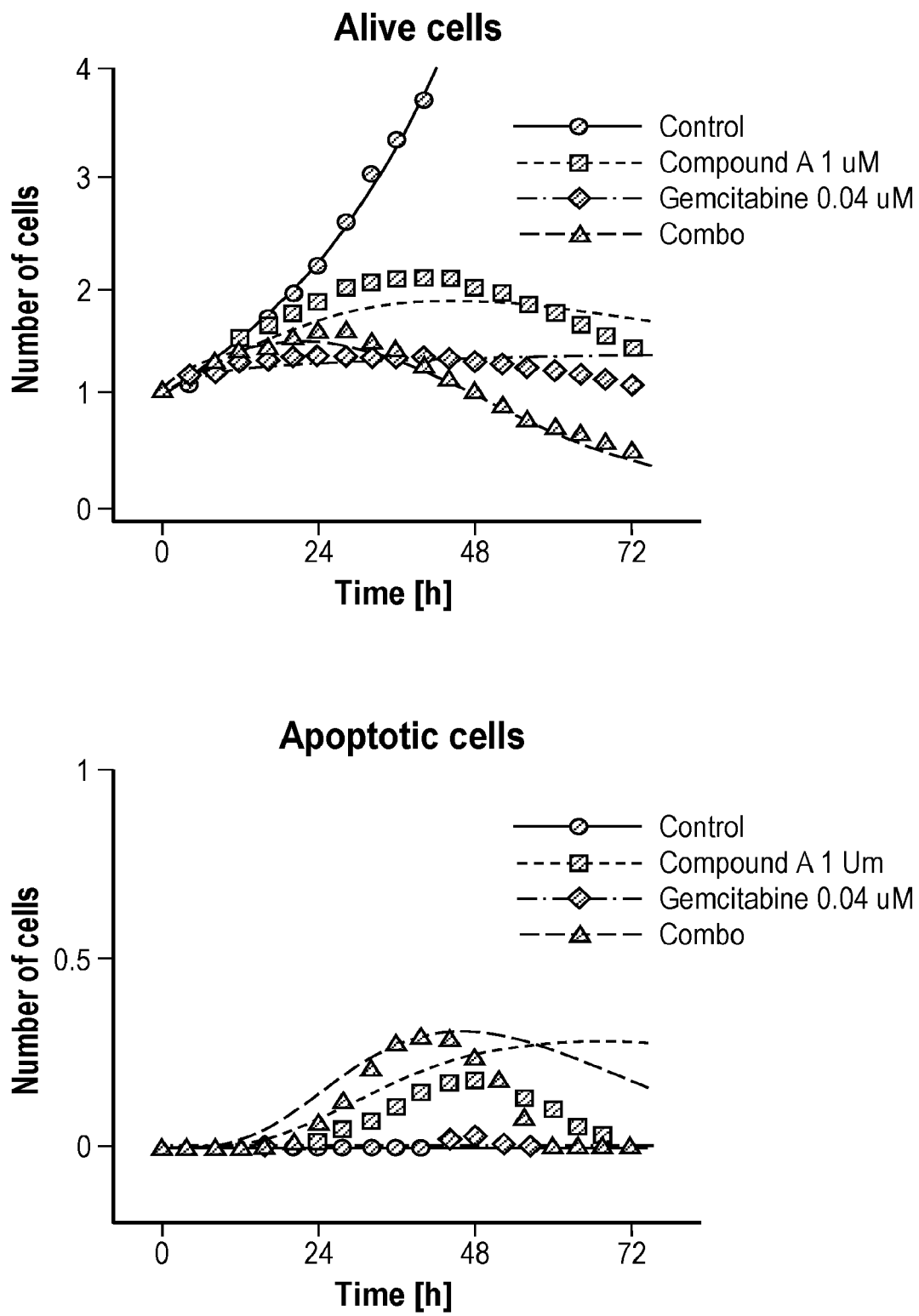

A cell death and growth assay was performed combining Compound A and Gemcitabine at various concentrations in U20S cells. The results were compared back to a prediction of cell growth and death with the combination of the two compounds (FIG. 18A). The number of living and apoptotic cells were also determined at set concentrations of Compound A (1 μM) and Gemcitabine (0.04 μM) in USO2 cells (FIG. 18B). The results show that the combination of Compound A and Gemcitabine are better at promoting cell death than either compound alone.

Figure 19:
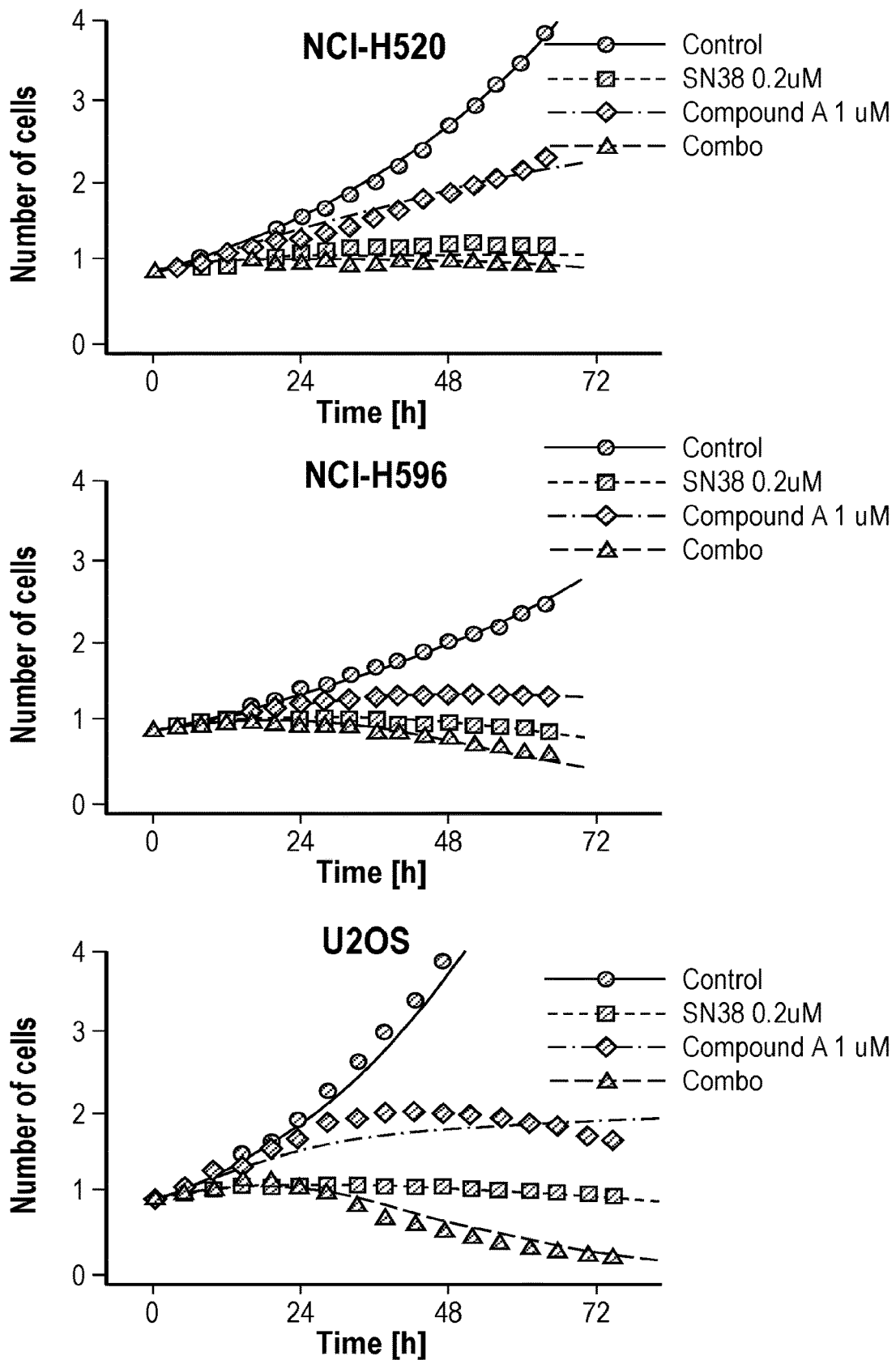
FIG. 19 shows Compound A being tested alone and in combination with SN38 at set concentrations (1 µM and 0.2 µM, respectively) in several lung cancer cell lines (NCI-H520 and NCI-H596) and U2OS cells, with the number of cells monitored over time.

Compound A was also tested alone and in combination with SN38 at set concentrations (1 μM and 0.2 μM, respectively) in several lung cancer cell lines (NCI-H520 and NCI-H596) and U2OS cells, with the number of cells monitored over time. The results indicate that the combination is more effective at maintaining or reducing cell numbers over time than either Compound A or SN38 in isolation (FIG. 19).

Figure 20:
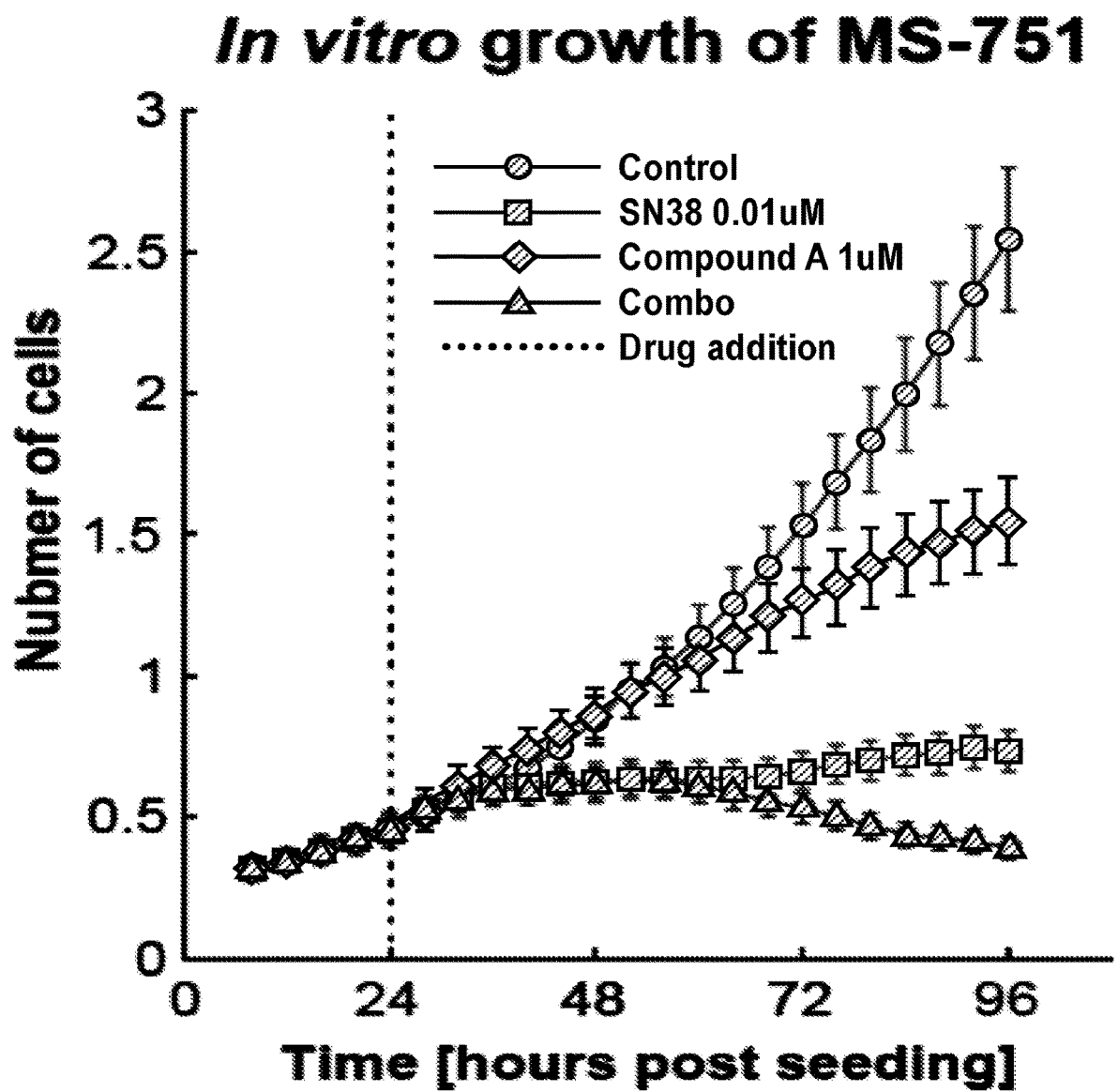
FIG. 20 is a graph illustrating the effect of Compound A and SN38 in combination and alone in the cervical cancer cell line MS751.

In vitro growth assays were also performed with Compound A and SN38 in combination and alone in the cervical cancer cell line MS-751. The in vitro assay shows a reduction in cell number over time with the combination as compared to either compound alone (FIG. 20).

Example 18: Comparison of Compound A and Compound 5 in Combination with Gemcitabine or SN38

Figure 21A:
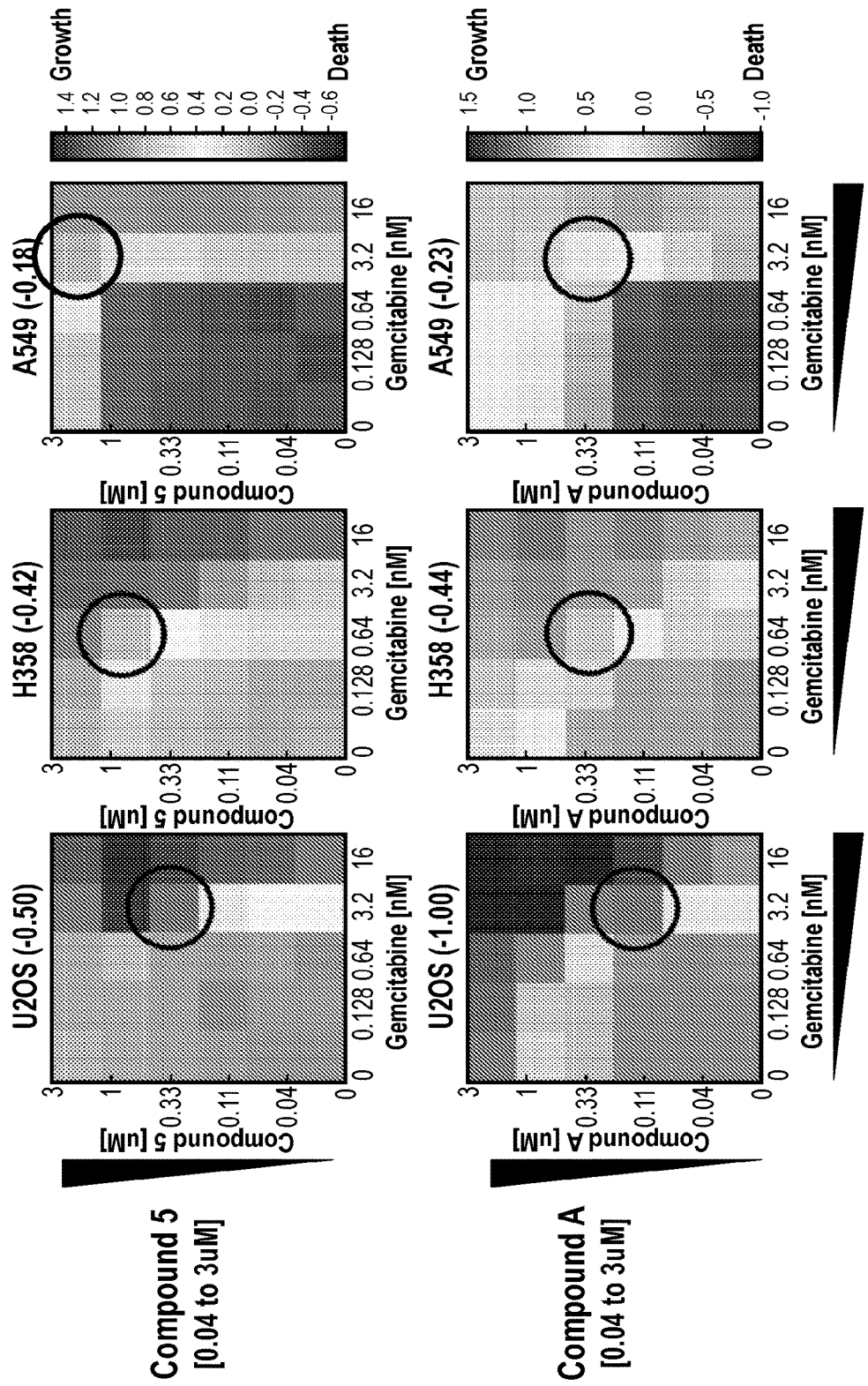
FIG. 21A-C demonstrates the effects of combining Compound A or Compound 5 with Gemcitabine.
Figure 21B:
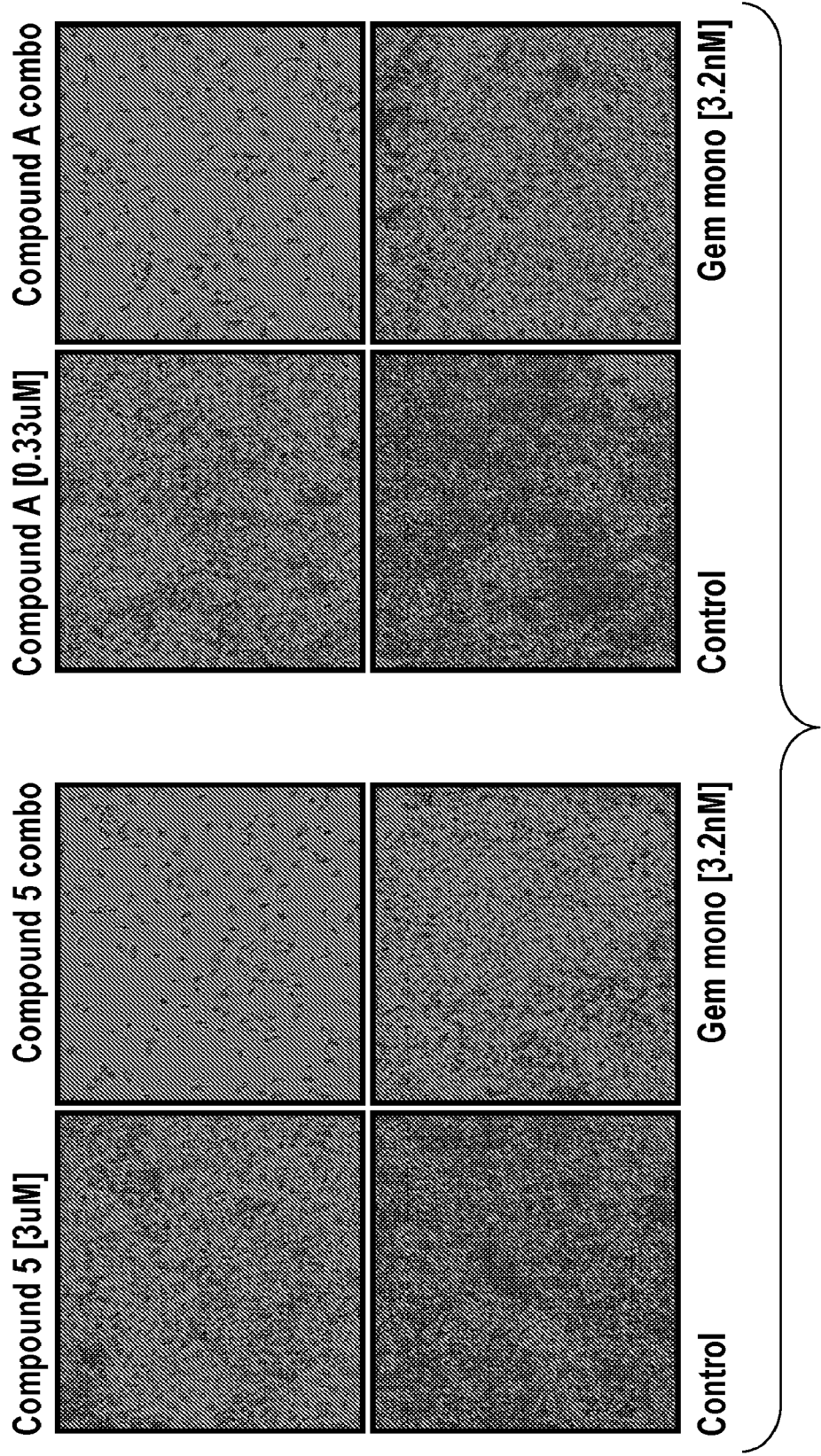
Figure 21C:
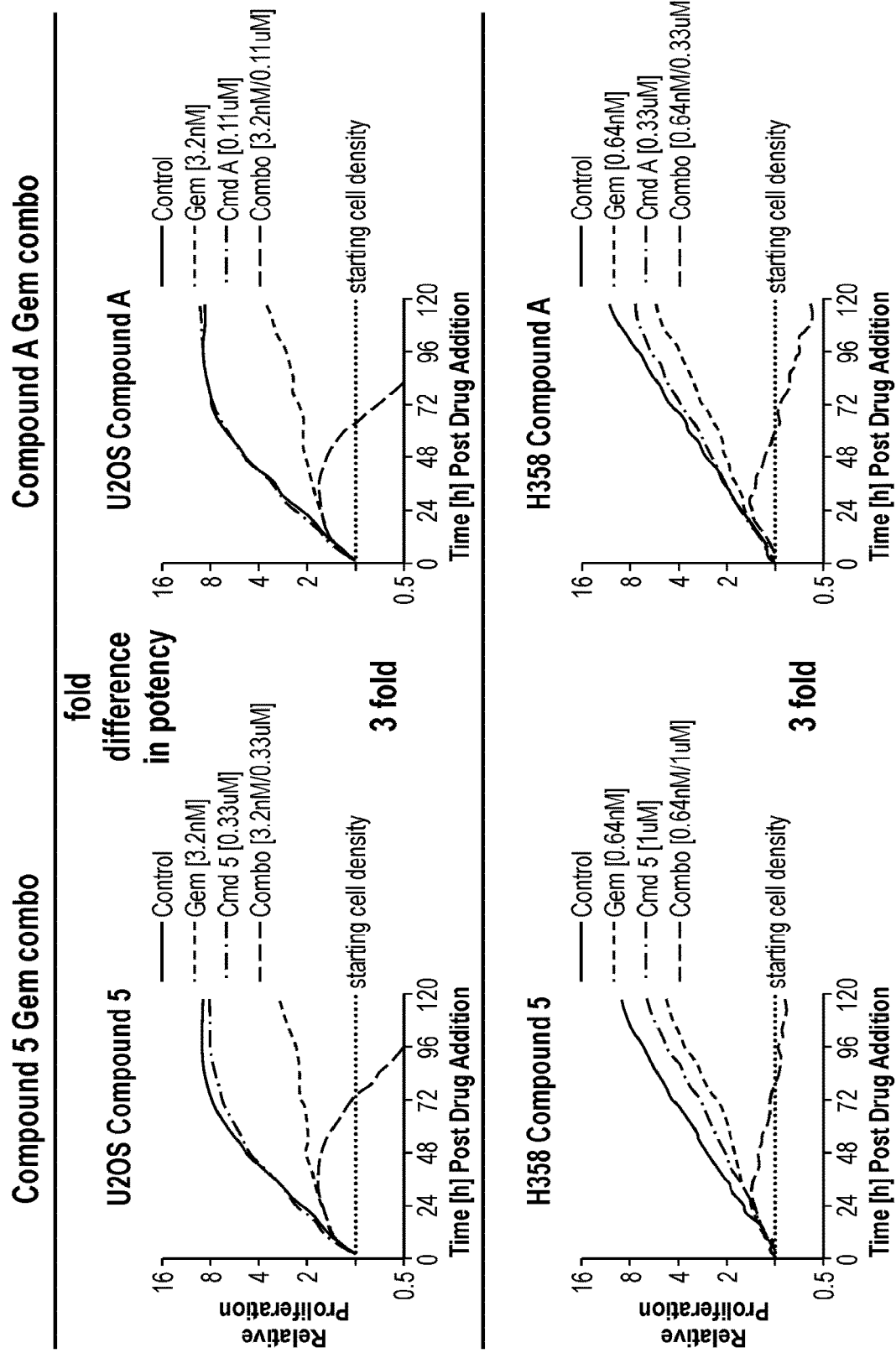

In vitro cell death and growth assays were performed combining Compound A or Compound 5 with Gemcitabine at various concentrations in U2OS, H358, and A549 cell lines. The results indicate the concentrations of each compound and Gemcitabine that are required to trigger cell death (FIG. 21A). Set concentrations of Compound 5 and Gemcitabine or Compound A and Gemcitabine were tested in USO2 and H358 cells as well. In all cases, relative cell proliferation is reduced with the combinations compared to the drugs alone (FIG. 21B-C).

Figure 22A:
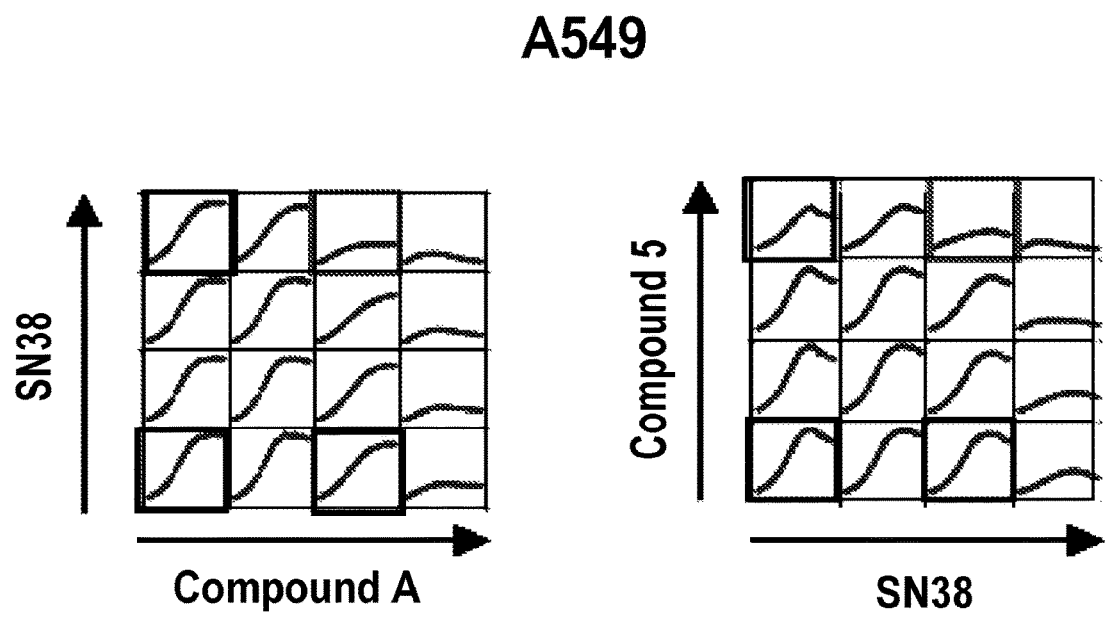
FIG. 22A-B illustrate growth curves of A549 cells with Compound A or Compound 5 in combination with SN38 (FIG. 22A) or alone (FIG. 22B).
Figure 22B:
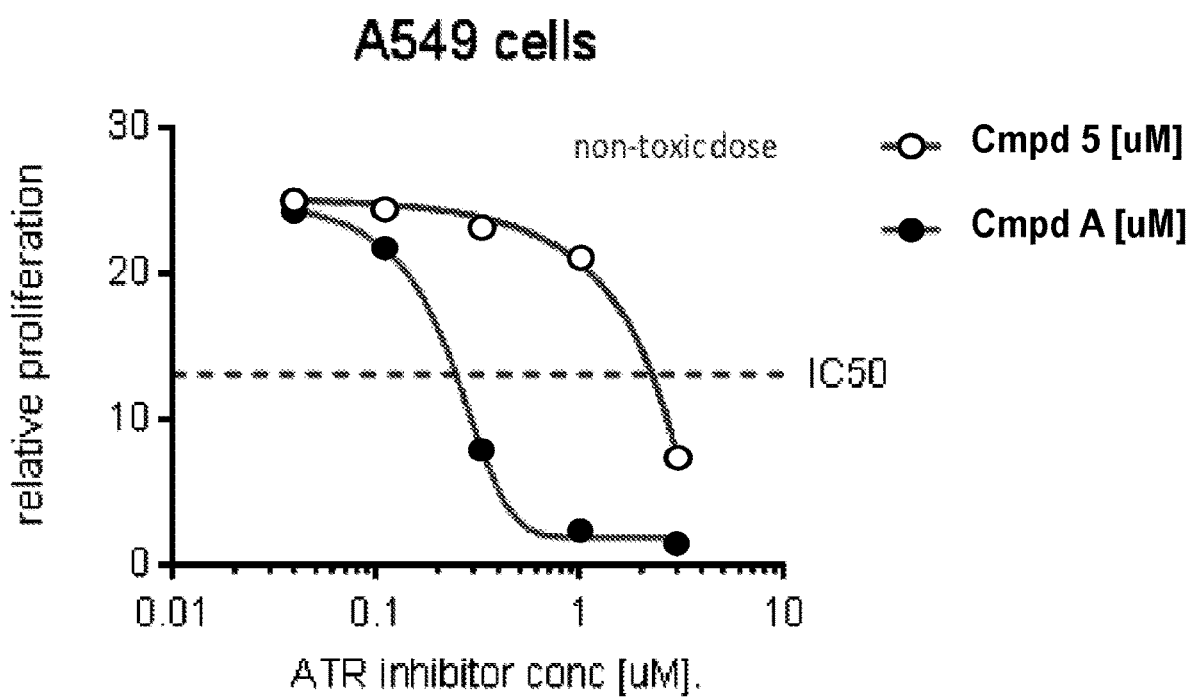

Compound A or Compound 5 was used in combination with SN38 in A549 cells. Cell growth was measured over time and at a range of concentrations. The growth curve at the optimal Compound/SN38 concentration is highlighted (FIG. 22A). Relative proliferation of A549 cells was measured with either Compound A or Compound 5 alone at a range of concentrations (FIG. 22B).

Figure 23:
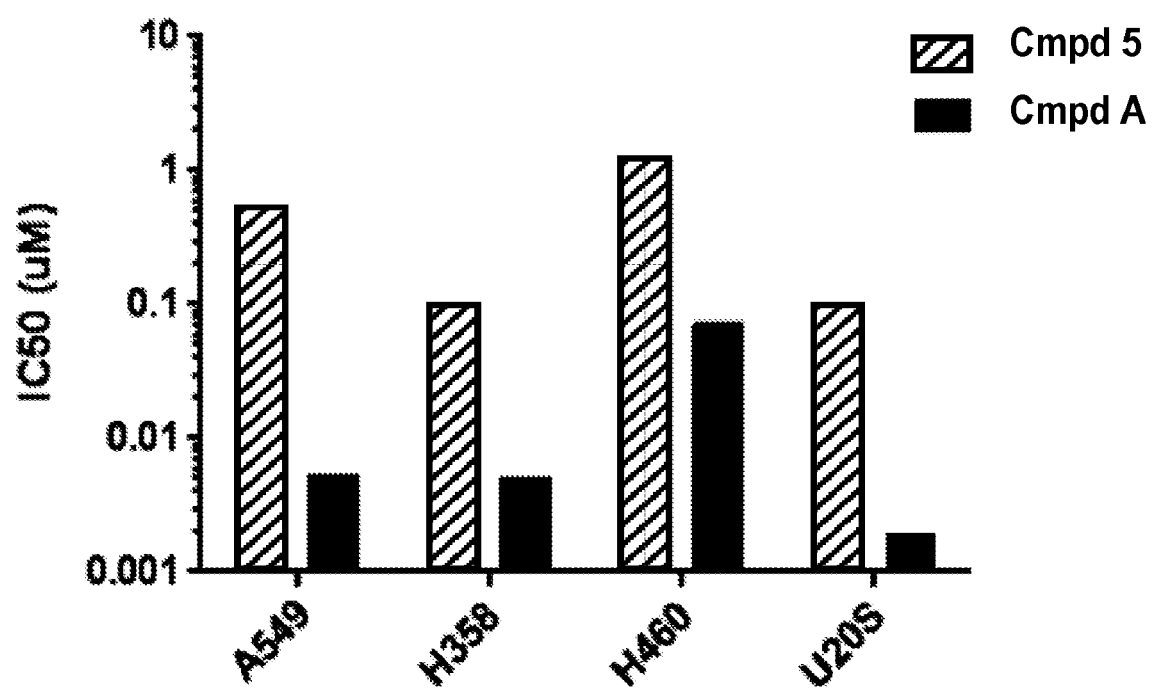
FIG. 23 shows IC50 values (pM) in several cell lines using a set concentration of Gemcitabine with varying concentrations of Compound A or Compound 5.

The IC50 values were determined in several cell lines using a set concentration of Gemcitabine with varying concentrations of Compound A or Compound 5 (FIG. 23).

A summary of the lung cancer cell lines that are responsive to Compound A or Compound 5 in combination with Gemcitabine or SN38 is provide in FIG. 24.

Example 19: On-Target and Off-Target Comparisons of Compound a and Compound 5

Various ATR inhibitors were tested for their ability to inhibit ATR (on-target) and ATM (off-target). Inhibition is reported as IC50 in nM (FIG. 25A). Additional "off-target" kinases were tested with Compound A or Compound 5 as well (FIG. 25B).

Figure 26A:
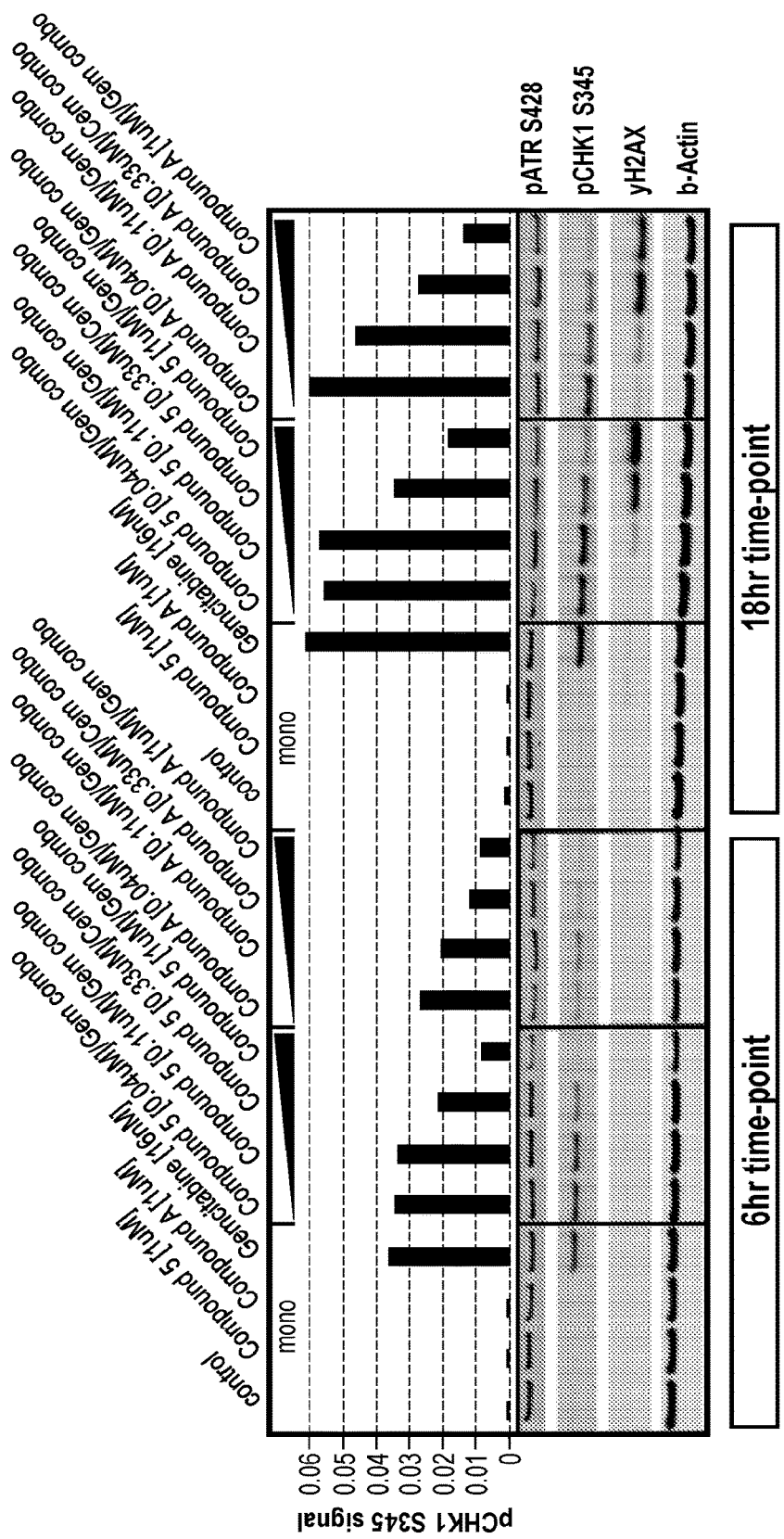
FIG. 26A-F shows on-target results with Compound A or Compound 5 in A549 lung cancer cells (FIG. 26A-B), H23 lung cancer cells (FIG. 26C-D), and DMS-114 cells (FIG. 26E-F). CHK1 S345 phosphorylation, a readout of ATR inhibition, is measured by western blot. Each compound is used with a fixed concentration of Gemcitabine as well.
Figure 26B:
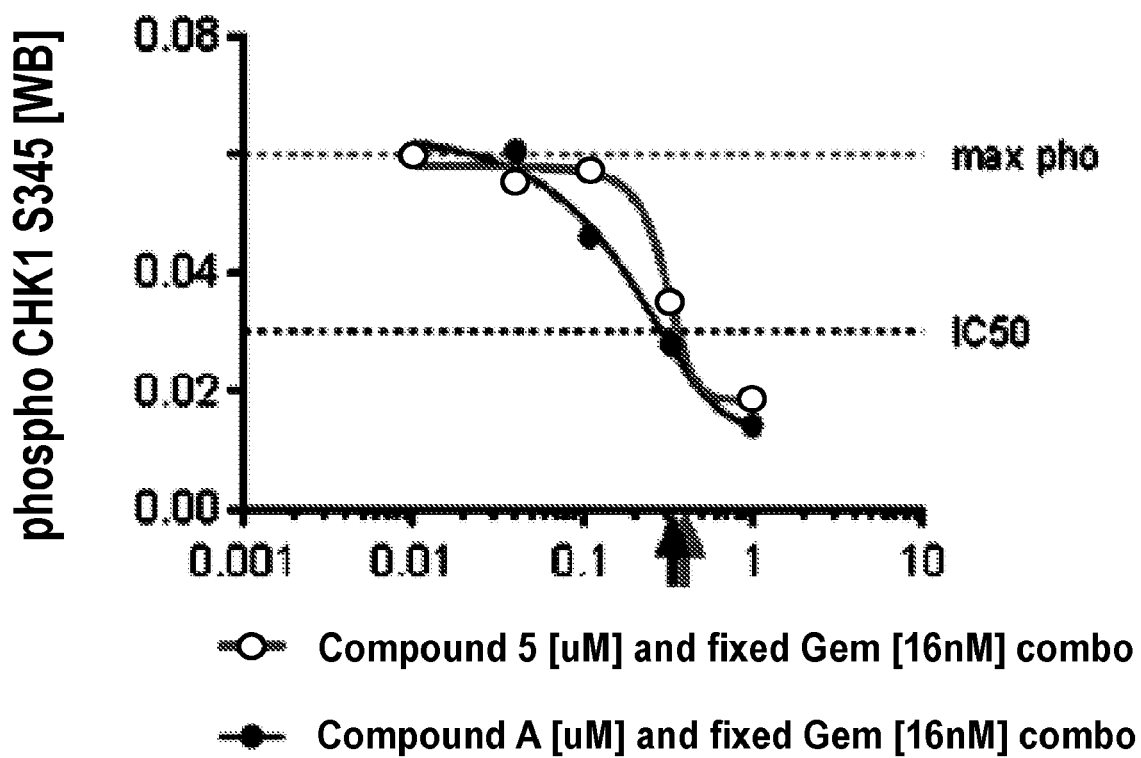
Figure 26C:
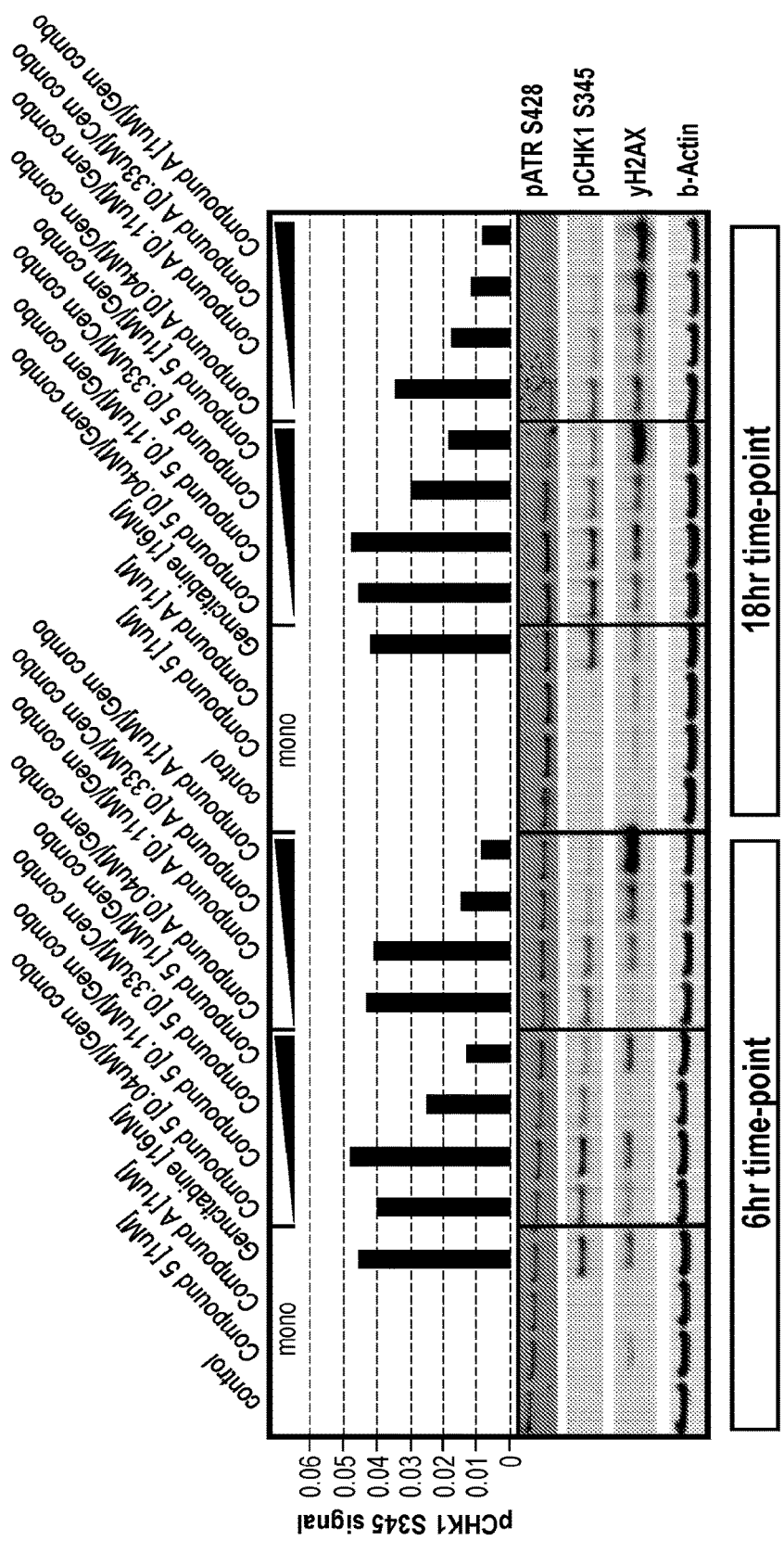
Figure 26D:
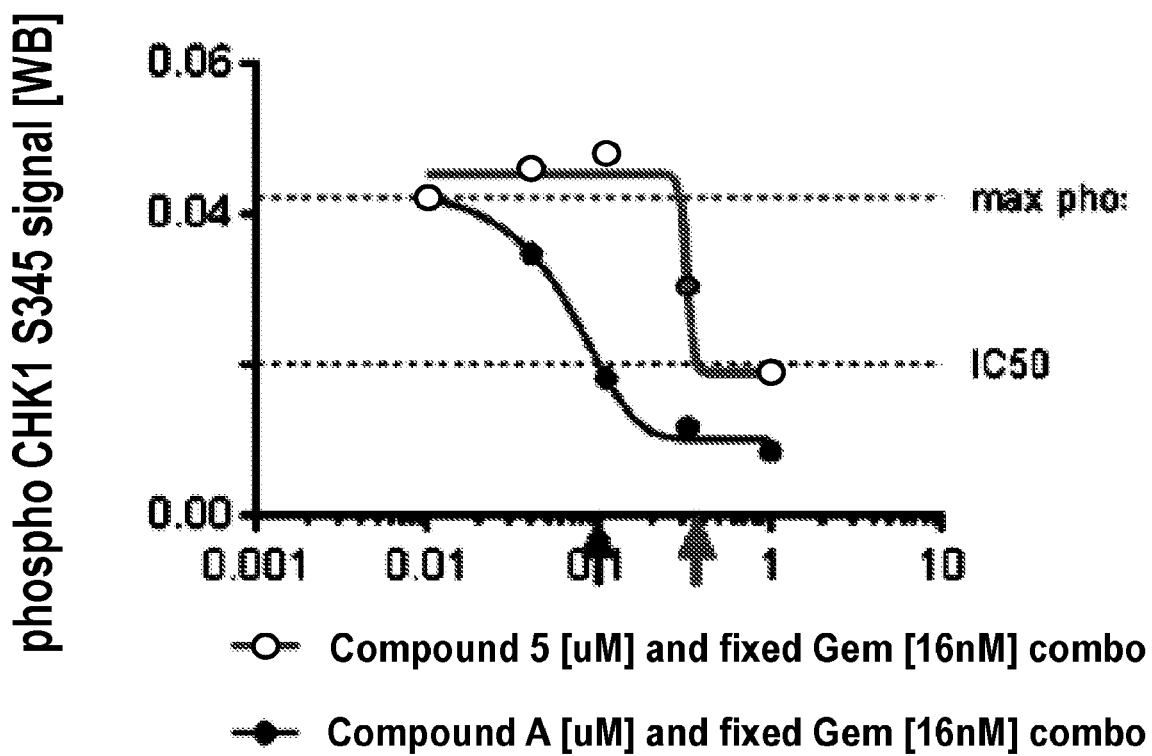
Figure 26E:
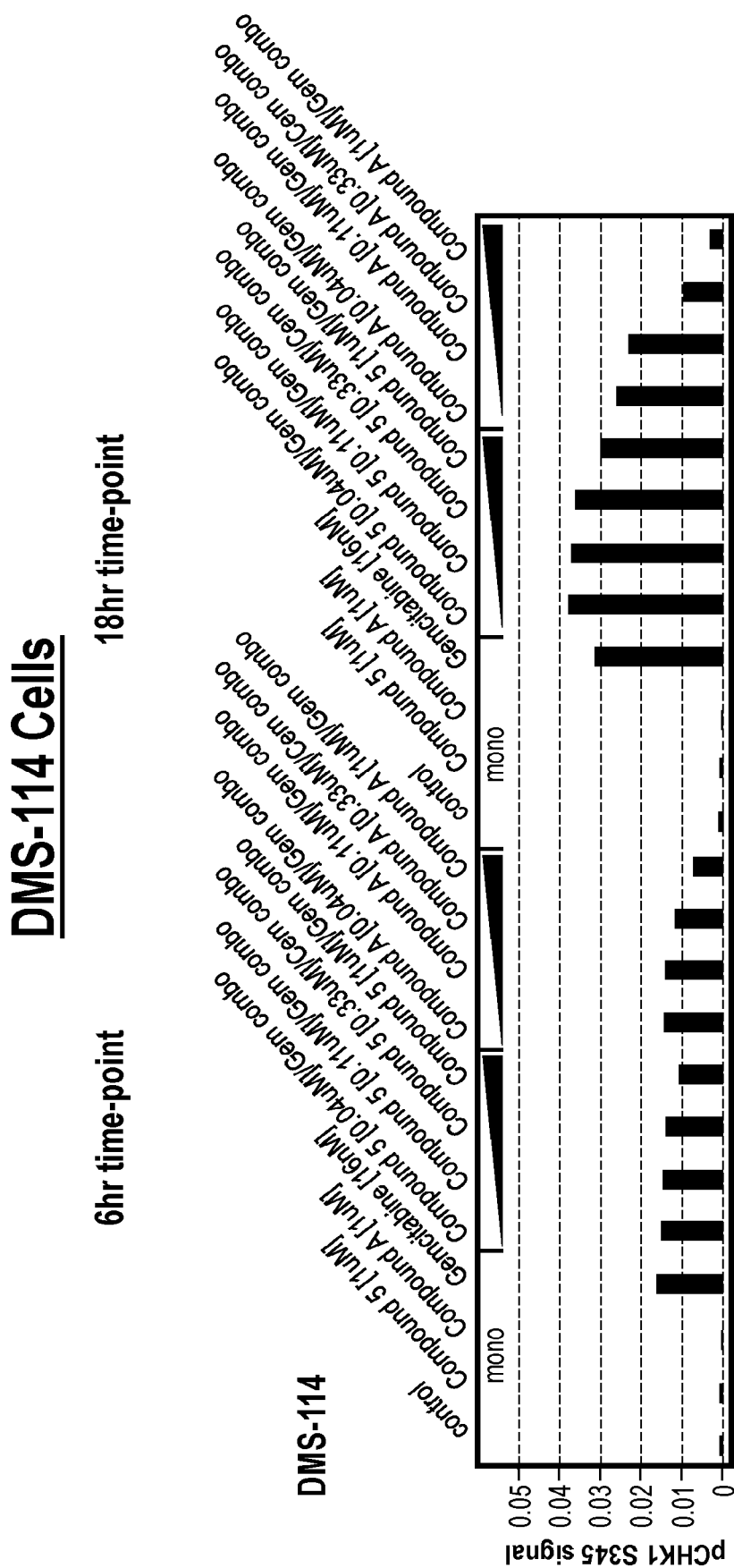
Figure 26F:
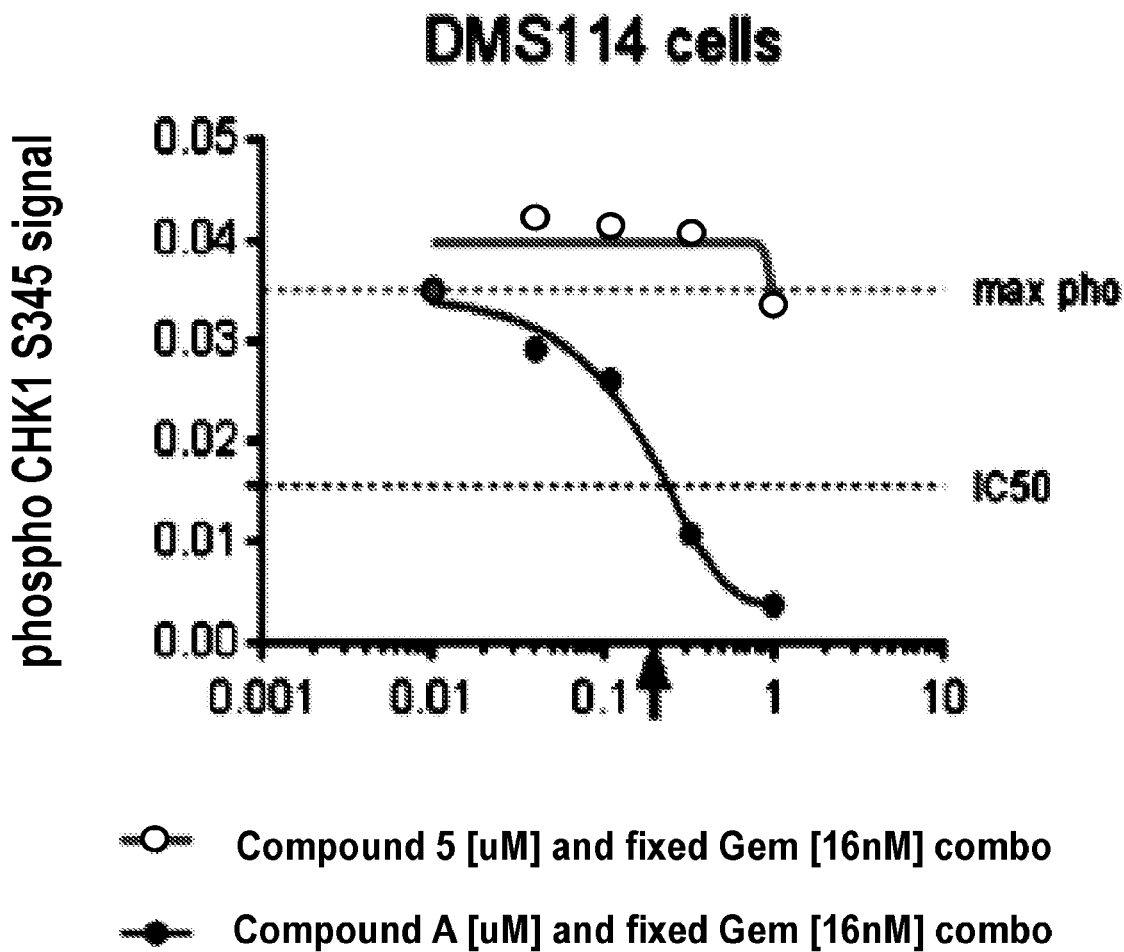

On-target testing was performed with Compound A or Compound 5 in A549 lung cancer cells (FIG. 26A-B), H23 lung cancer cells (FIG. 26C-D), and DMS-114 cells (FIG. 26E-F). CHK1 S345 phosphorylation, a readout of ATR inhibition, was measured by western blot. Each compound was used with a fixed concentration of Gemcitabine as well.

Figure 27A:
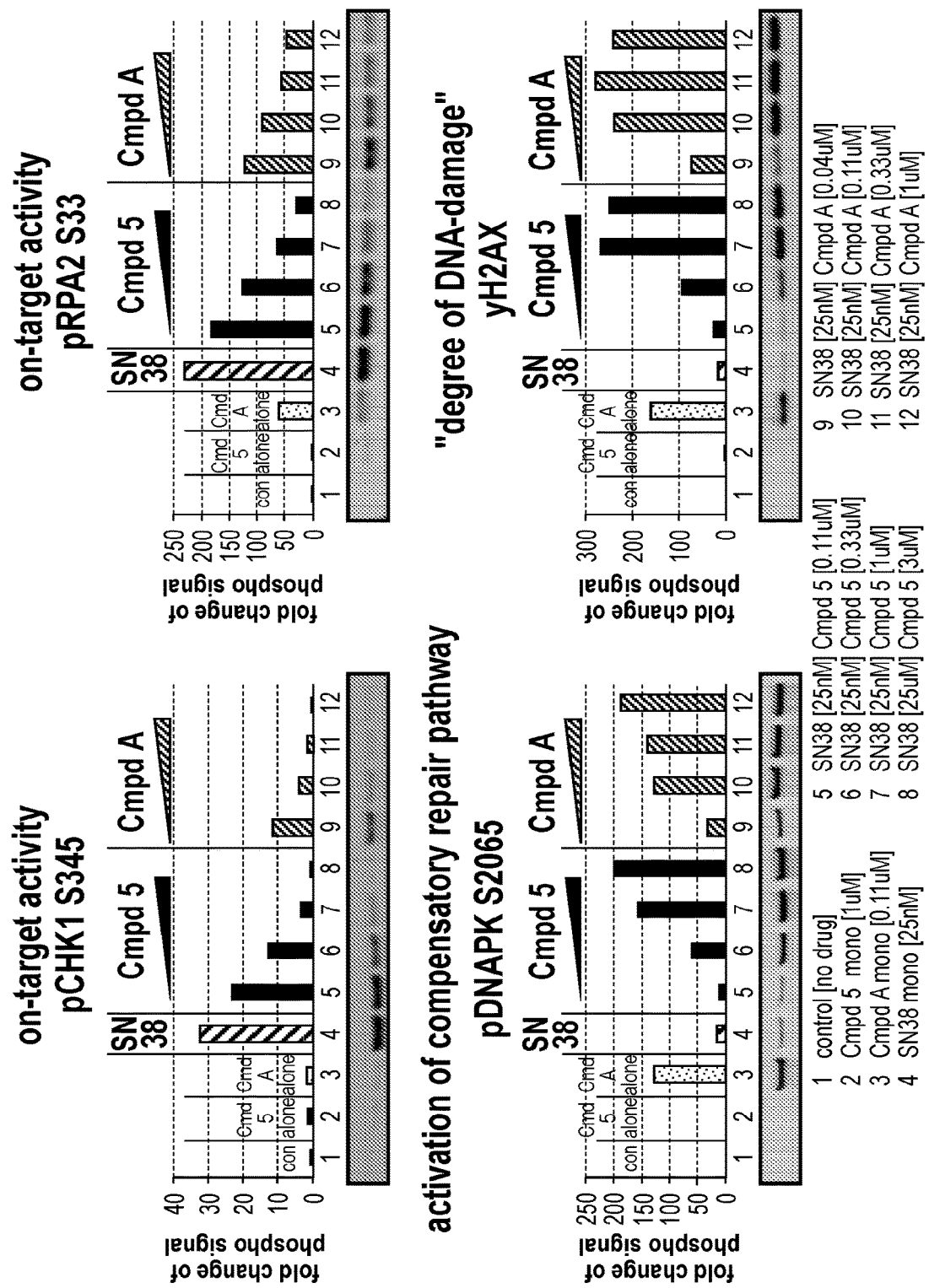
FIG. 27A-B shows further on-target analysis on the HCC-70 TNBC, MDA-MB-468 TNBC, and DMS-114 cell lines. A set concentration of SN38 is used with a range of Compound A or Compound 5 concentrations. Various on-target activity parameters are tested and measured by western blot (FIG. 27A-B)
Figure 27B:
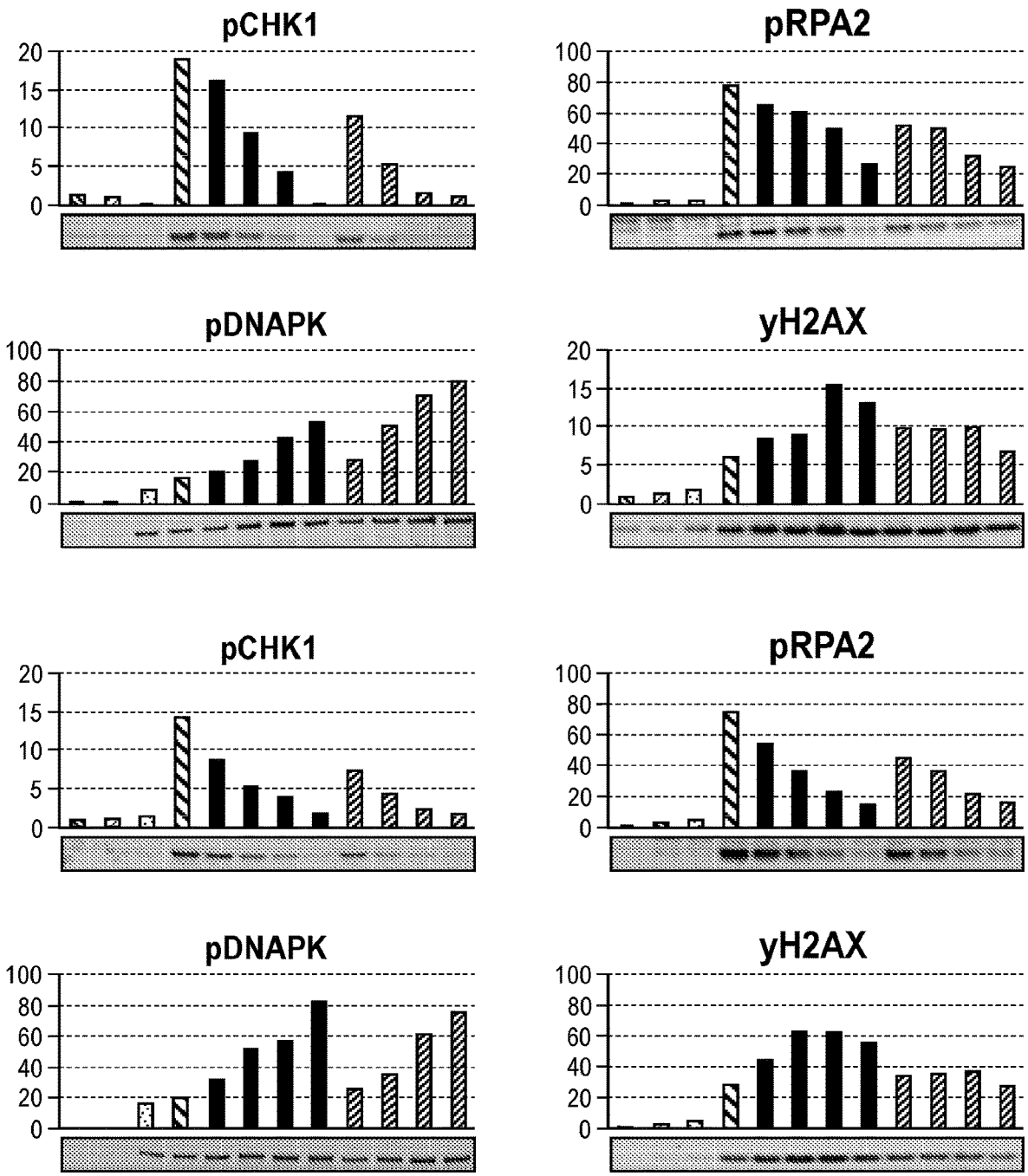

Further on-target studies were performed on the HCC-70 TNBC, MDA-MB-468 TNBC, and DMS-114 cell line. A set concentration of SN38 was used with a range of Compound A or Compound 5 concentrations. Various on-target activity parameters were tested and measured by western blot (FIG. 27A-B)

Figure 28:
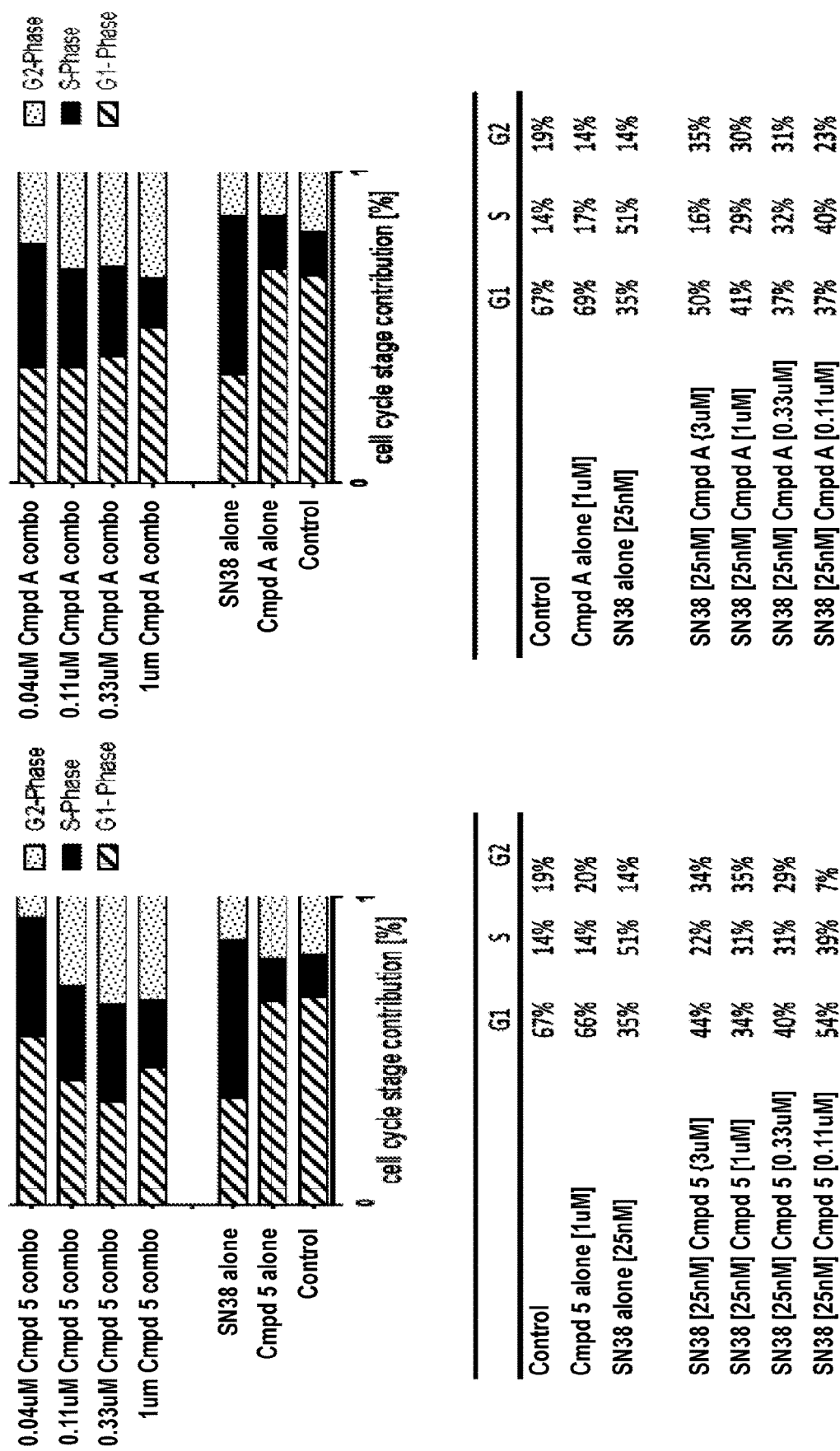
FIG. 28 shows cell cycle stage profiles of SUM149 cells 24 hours after addition of SN38 and Compound A or Compound 5.

Cell cycle stage profiles of SUM149 cells were determined 24 hours after addition of SN38 and Compound A or Compound 5 (FIG. 28). A larger percentage of cells are arrested in G2 phase when receiving the combination of drugs as compared to controls.

Example 20: Comparison of Liposomal Formulations of Compound a and Compound 5 Combined with MM398

Figure 29:
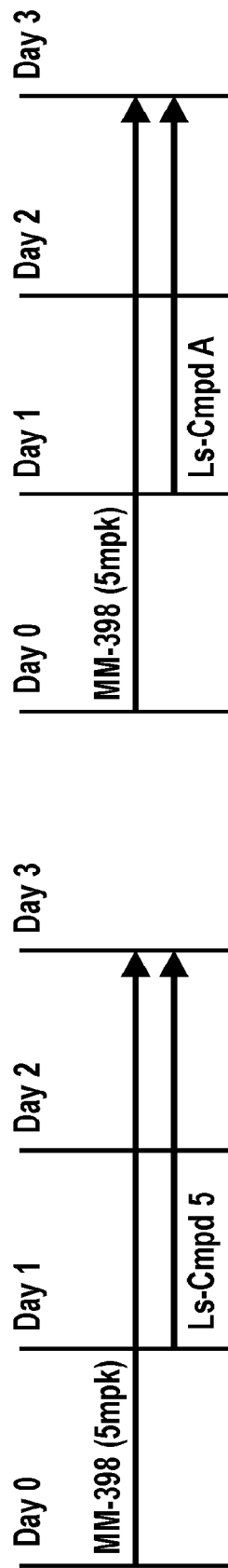
FIG. 29 shows DMS-114 lung xenograft models used to measure the effects of Ls-Compound A or Ls-Compound 5 in combination with MM398. A set dosage of MM398 is used (5 mpk) with two different dosages of Compound A or Compound 5 (20 mpk or 80 mpk). The effects of treatment are assayed by measuring the levels of CHK1 S345 phosphorylation.
Figure 29:
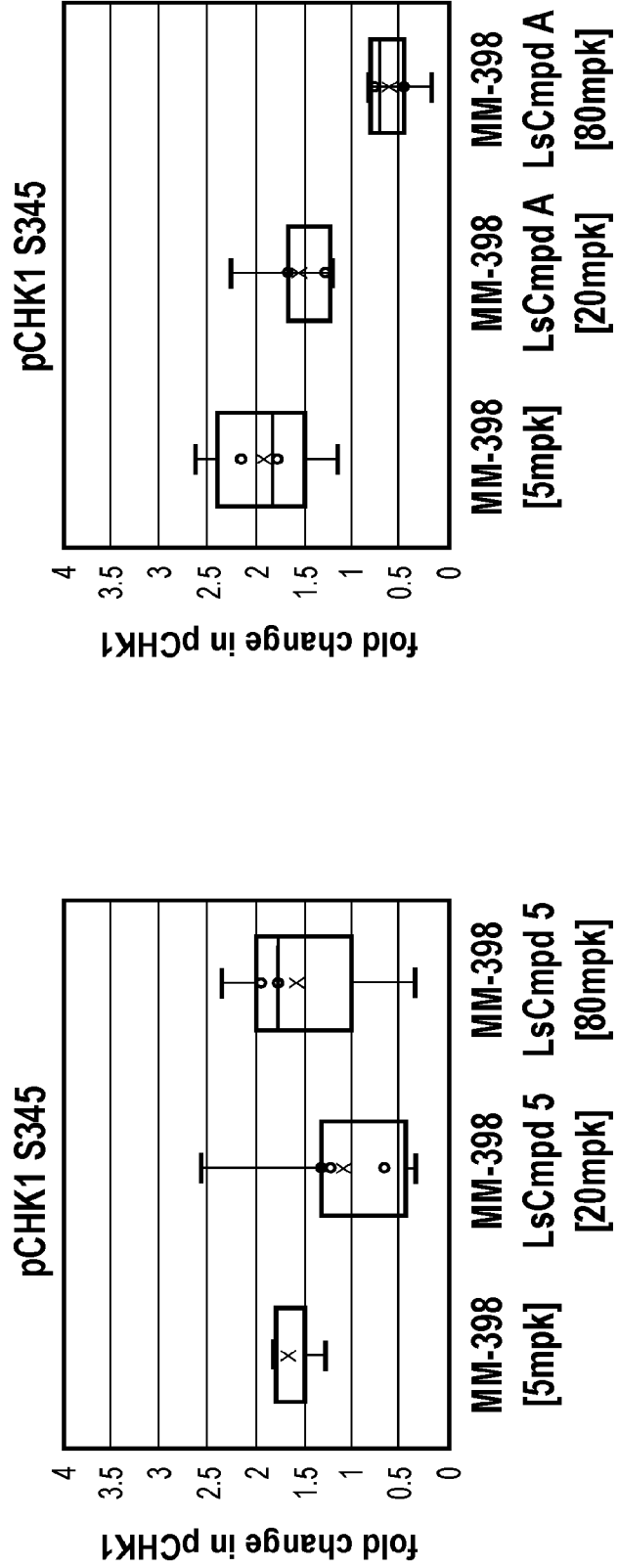

DMS-114 lung xenograft models were used to measure the effects of Ls-Compound A or Ls-Compound 5 in combination with MM398. A set dosage of MM398 was used (5 mpk) with two different dosages of Compound A or Compound 5 (20 mpk or 80 mpk). The effects of treatment were assayed by measuring the levels of CHK1 S345 phosphorylation (FIG. 29).

Figure 30A:
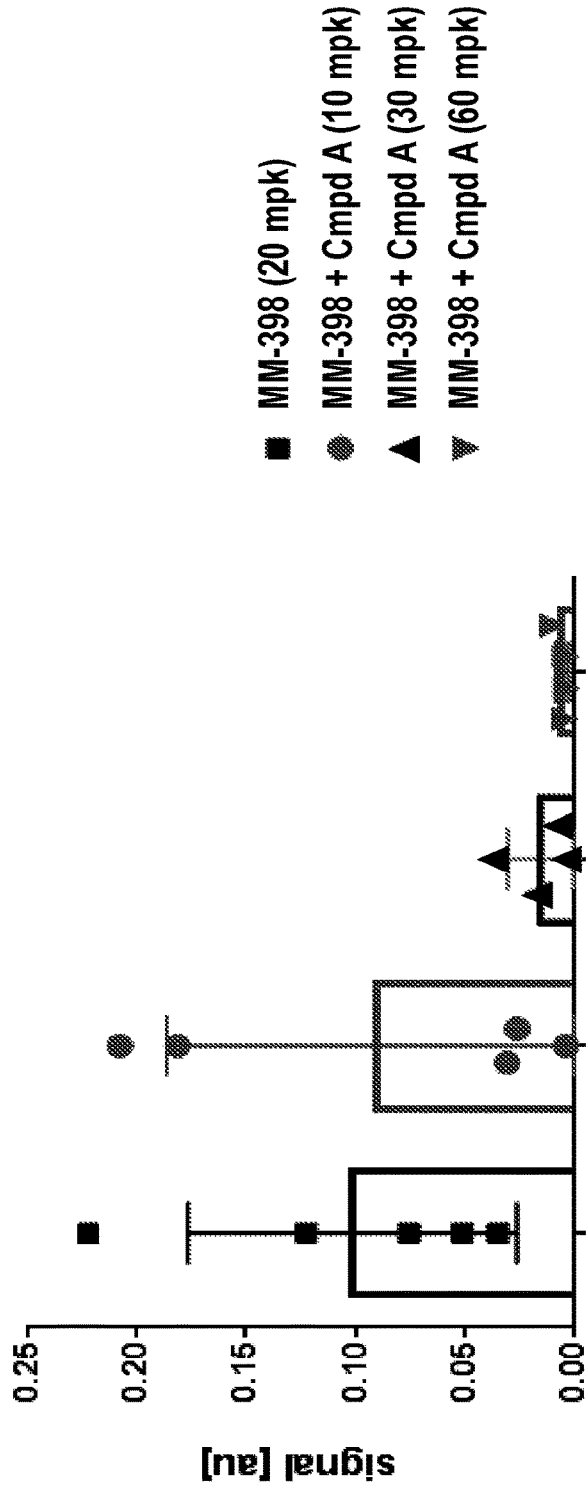
FIG. 30A-C illustrates the effects of Ls-Compound A with MM398 in the SUM-149 cell line. The effects of the treatment are assayed by measuring phosphorylated levels of RPA2 (FIG. 30A), DNAPK, CHK1, and γH2AX (FIG. 30B). Ls-Compound 5 is also tested without the combination of MM398 (FIG. 30C).
Figure 30A:
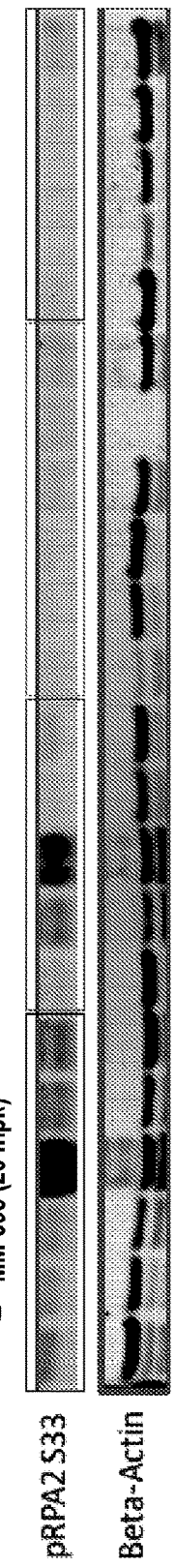
Figure 30B:
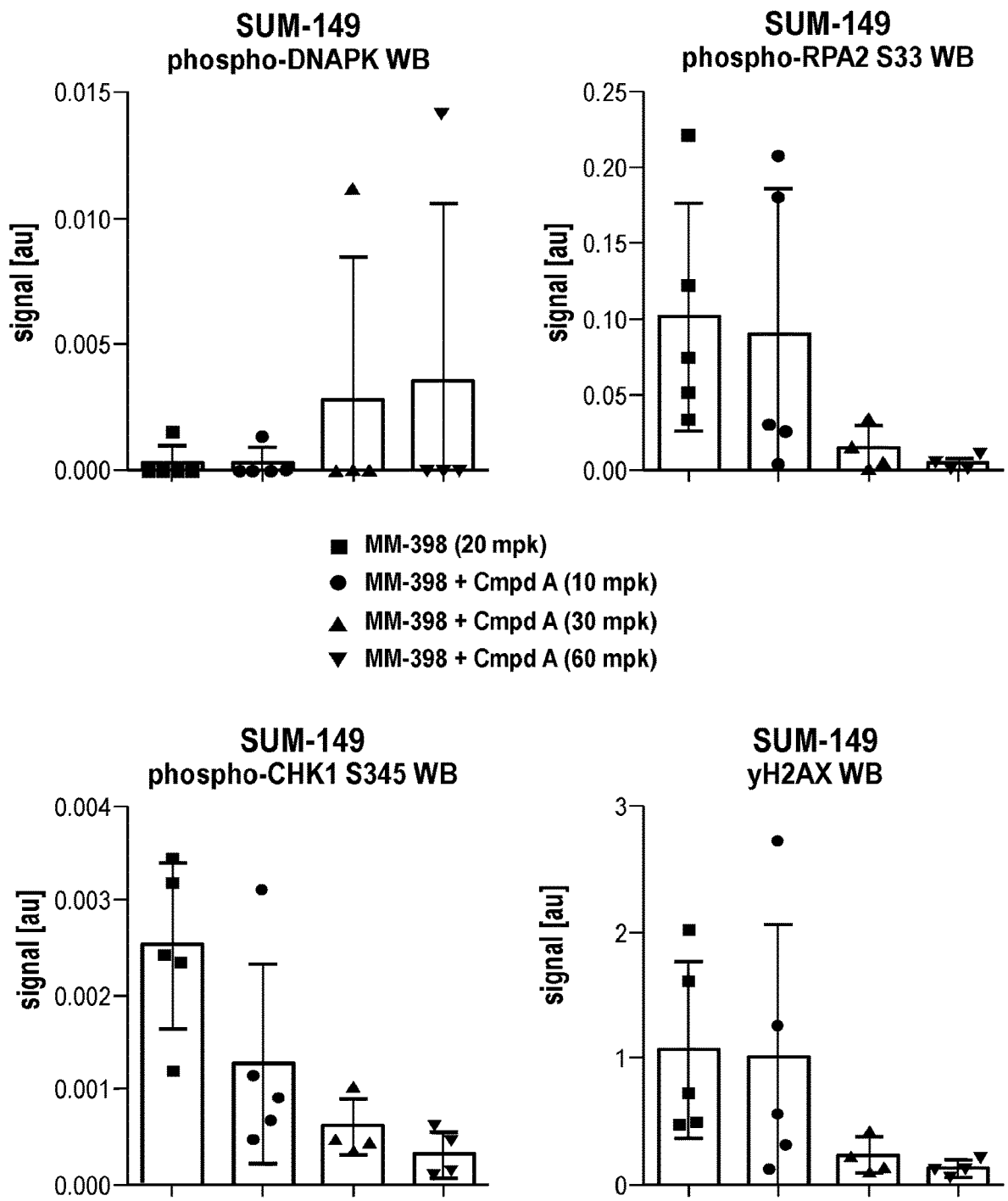
Figure 30C:
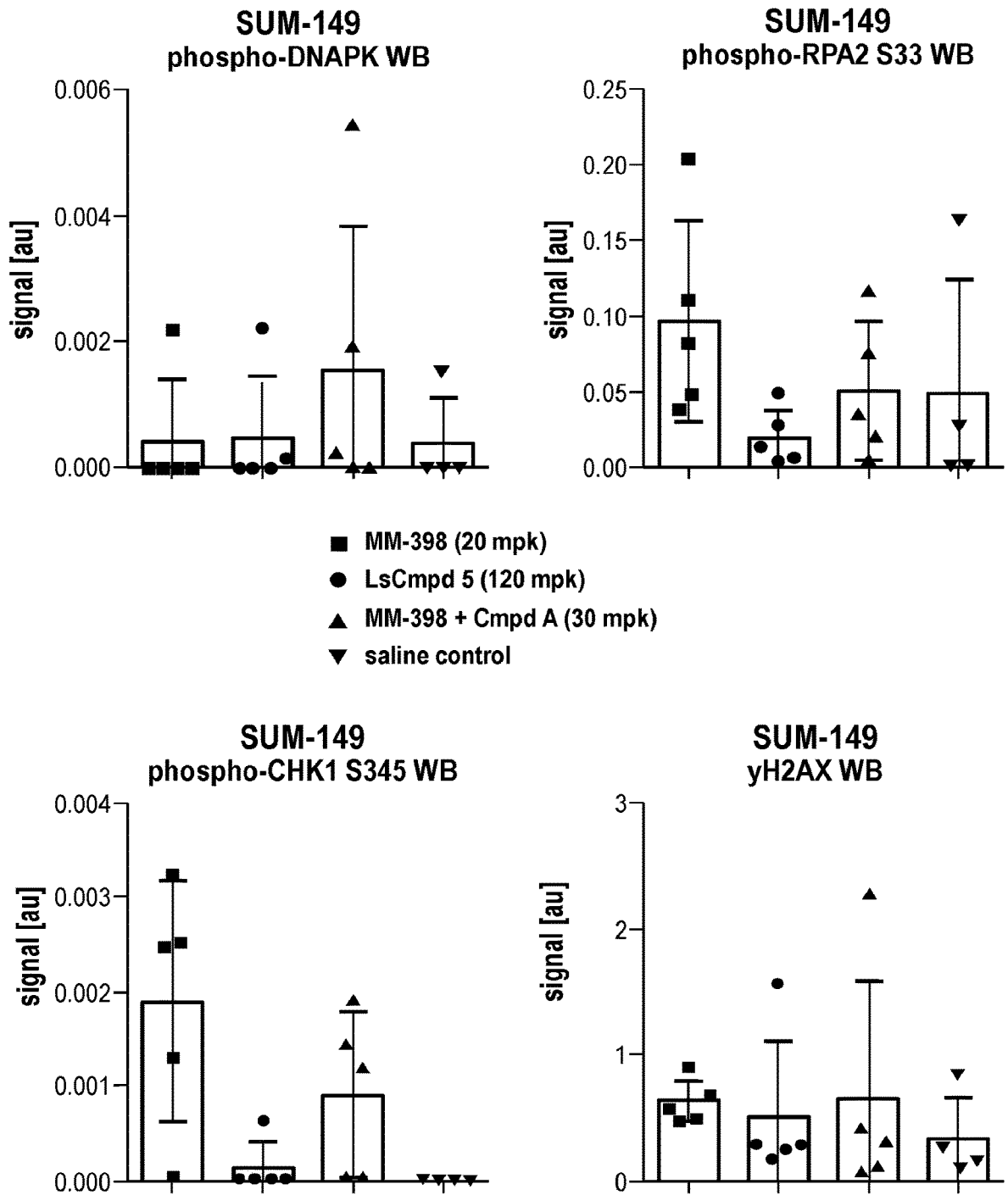

The effects of the Ls-Compound A with MM398 was also tested in the SUM-149 cell line. The effects of the treatment were assayed by measuring phosphorylated levels of RPA2, DNAPK, CHK1, and γH2AX. Ls-Compound 5 was also tested without the combination of MM398 (FIG. 30A-C).

Example 21: In Vivo Antitumor Efficacy and Tolerability of Ls-Compound 5 Prepared Using TEA.SOS Against Triple Negative Breast Cancer Xenografts in Mice Antitumor efficacy of liposomes loaded with an ATR inhibitor Compound 5 in combinations with MM-398 (liposomal Irinotecan) and was studied in the model of human SUM-149 (triple negative breast cancer) cell line.

The cells were obtained from American Type Culture Collection (Rockville, Md.) and propagated in RPMI medium supplemented with 10% fetal calf serum, 50 U/ml penicillin G, and 50 μg/mL of streptomycin sulfate at 37° C., 5% $CO_2$ as recommended by the supplier. NCR nu/nu homozygous athymic male nude mice (4-5 week old, weight at least 16 g) were obtained from Charles River. The mice were inoculated subcutaneously in the right flank with 0.1 mL of the suspension containing 107 cells suspended in PBS supplemented with 30% Matrigel. When tumors achieved the size between 150 mm3 and 350 mm3 the animals were assigned to the treatment groups according to the following method. The animals were ranked according to the tumor size, and divided into 6 categories of decreasing tumor size. Four treatment groups of 10 animals/group were formed by randomly selecting one animal from each size category, so that in each treatment group all tumor sizes were equally represented. The animals received five tail vein injections, at the intervals of 7 days, of the following preparations: 1) Control (HEPES-buffered saline pH 6.5); 2) MM-398 at dose 5 mg/kg per injection; 3) Liposomal Compound 5 at 80 mg/kg per injection; 4) MM-398 followed by injections of liposomal Compound 5 with a 24 h interval; 5)) MM-398 followed by injections of free un-capsulated ATR inhibitor Compound A. Liposomes for injections were prepared as described in Example 10.

The animal weight and tumor size were monitored twice weekly. The tumor progression was monitored by palpation and caliper measurements of the tumors along the largest (length) and smallest (width) axis twice a week. The tumor sizes were determined twice weekly from the caliper measurements using the formula:

$$\text{Tumor volume} = [(\text{length}) \times (\text{width})^2]/2$$

To assess treatment-related toxicity, the animals were also weighted twice weekly. When the tumors in the group reached 10% of the mouse body weight, the animals in the group were euthanized. Average tumor volumes across the groups were plotted together and compared over time.

Figure 31:
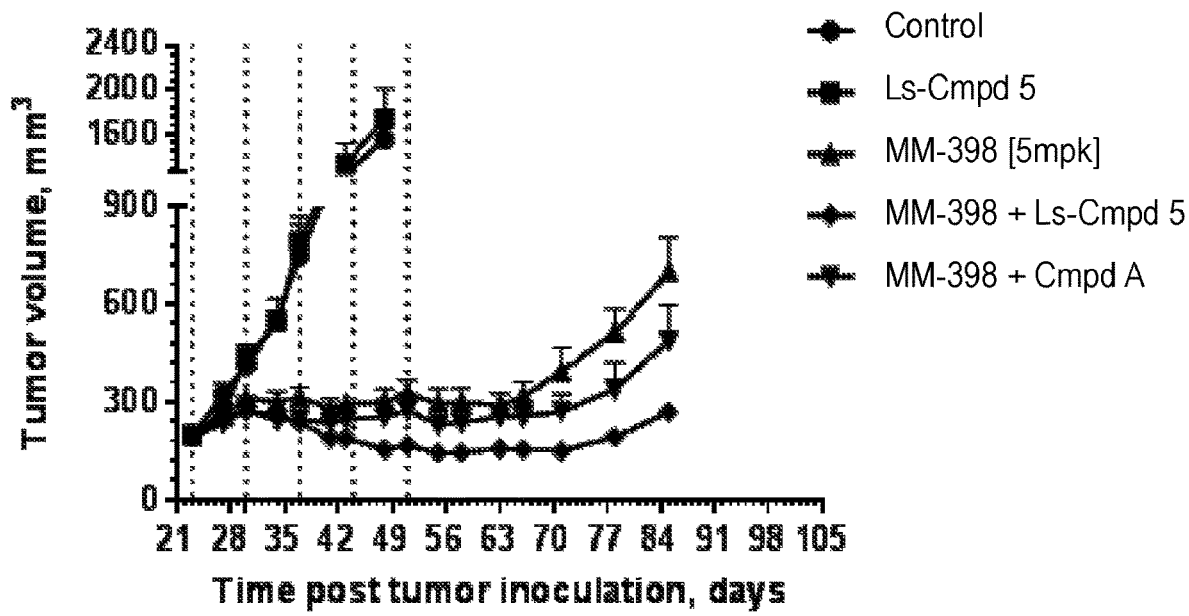
FIG. 31 is a graph showing the efficacy of liposomal Compound 5 in combination with MM-398 in SUM-149 mice xenograft model.
Figure 32:
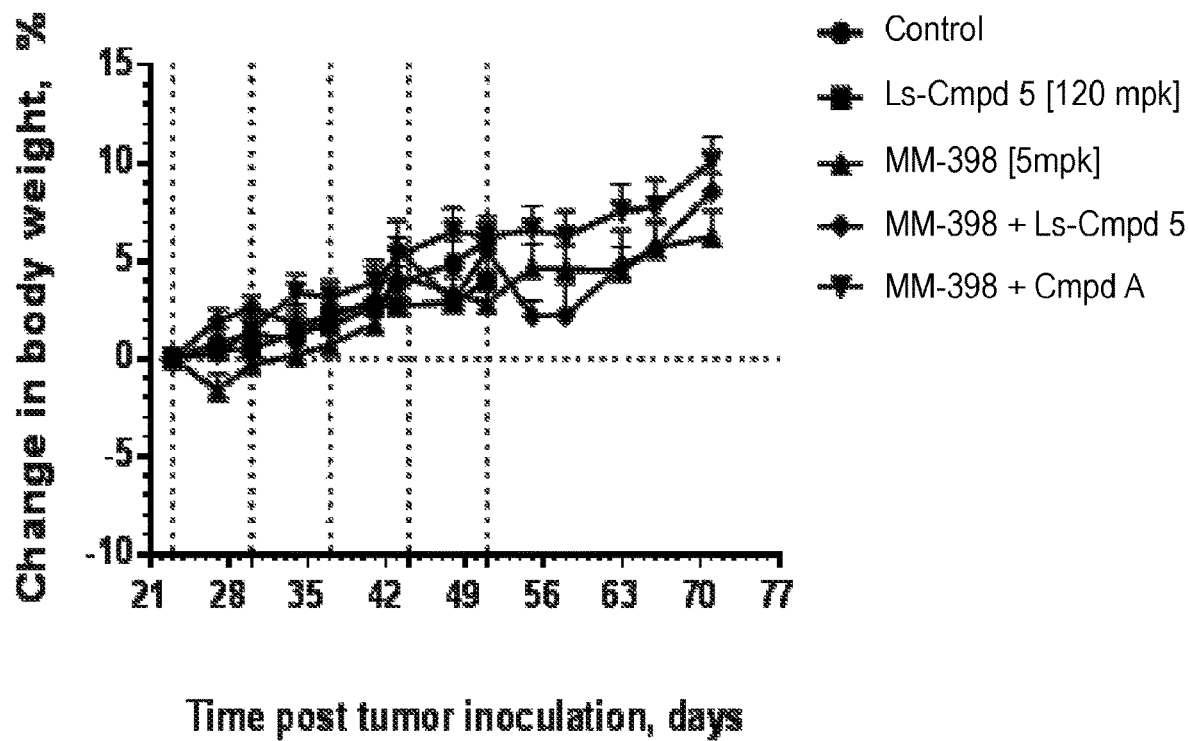
FIG. 32 is a graph showing the tolerability of liposomal Compound 5 in combination with MM-398 in SUM-149 mice xenograft models FIG. 33 Basal levels of various PD markers associated with the DNA damage response pathway, quantified by Western blot over a panel of cell lines.

As demonstrated in FIG. 31, liposomal ATR inhibitor Compound 5 significantly improved antitumor efficacy of MM-398 in the xenograft model. The combinational treatment of liposomal ATR inhibitor and MM-398 did not affect the animals' body weight (FIG. 32).

Example 22: Cell Line Profiling and Comparison with Incucyte Data

Figure 33:
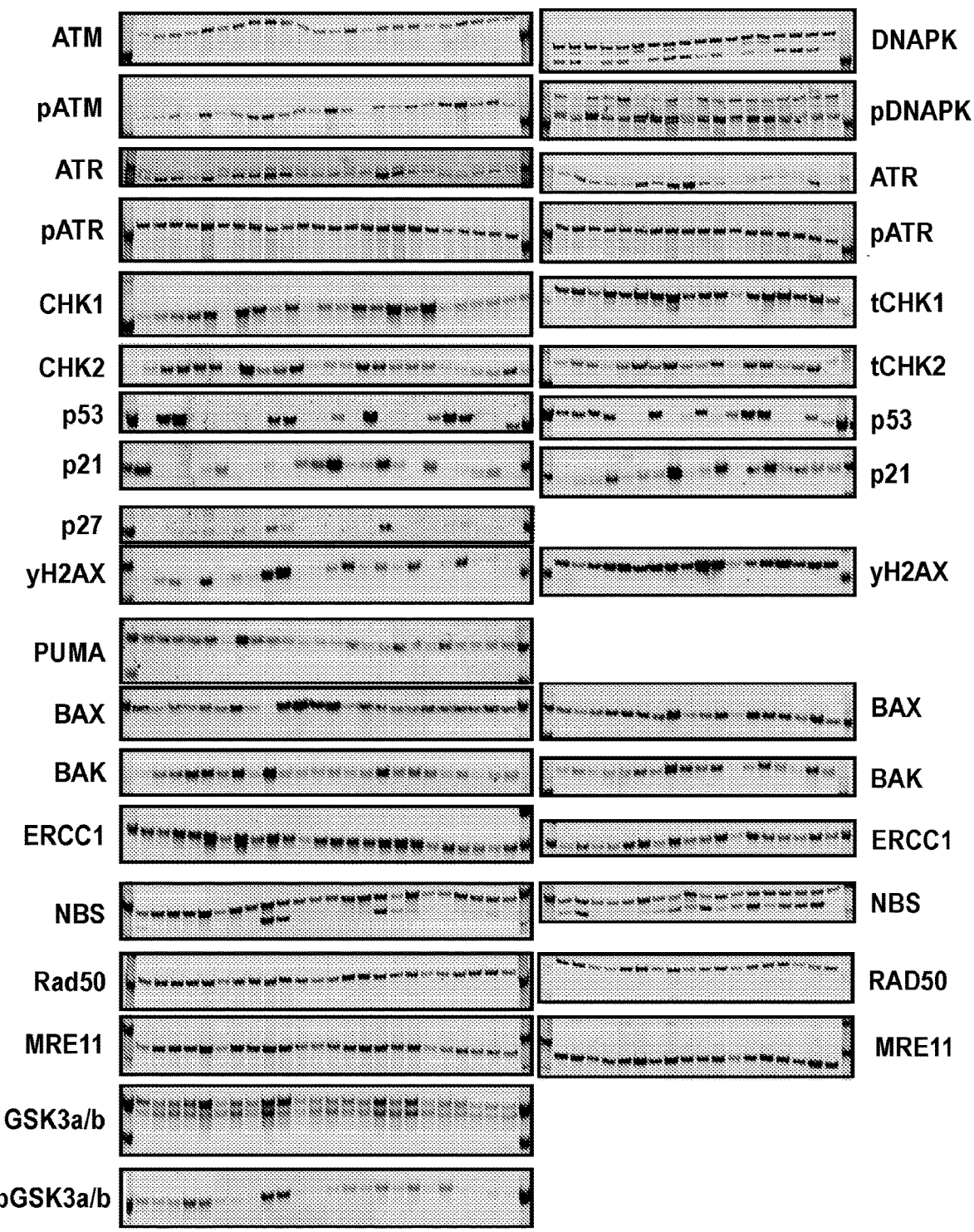
Figure 34:
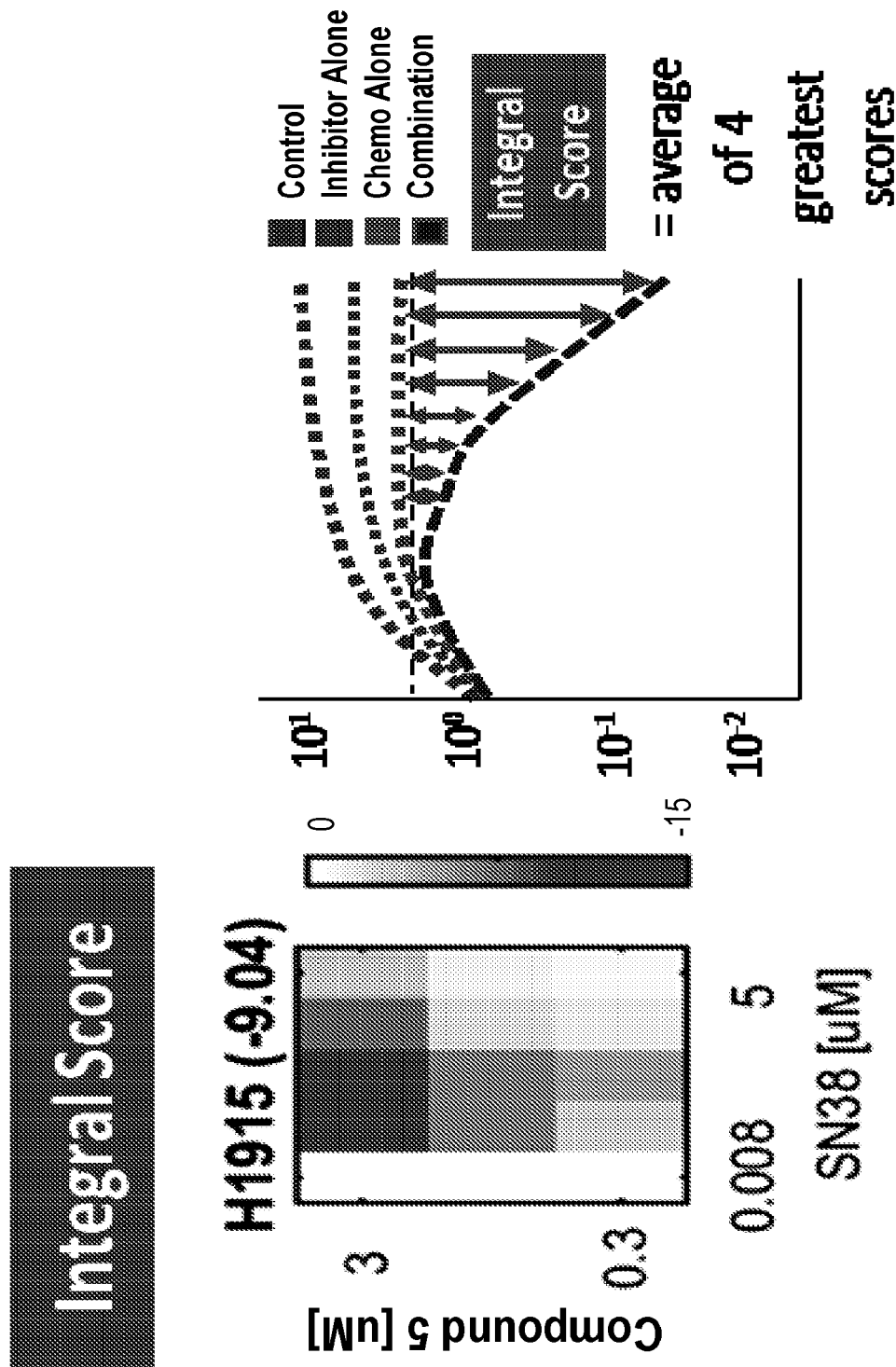
FIG. 34 A schematic illustrating how the integral score is calculated for each well in the dynamic cell viability assay.

A panel of fluorescently labeled cell lines was profiled for various proteins involved in the DNA damage pathway. Parental cancer cell lines were transduced with a NucLight Red lentivirus and selected with puromycin. Basal protein levels were measured and quantified by Western blot analysis. When quantification was performed, the PD marker signal was normalized to the beta actin signal. Protein levels were correlated with the cell line's "integral score", a measure of the in vitro cellular response to Compound 5 and chemotherapy combination treatment. The integral score can be calculated as follows:

Referring to FIGS. 33 and 34, cell lines were seeded in 96 well plates and each well was exposed to a dose matrix of Compound 5 and chemotherapy for 4 days. Dynamic cell viability was measured using an Incucyte assay. For each drug combination in the dose matrix, a dose combination-specific integral score was calculated by summing the area under normalized cell proliferation curve. A cell line specific integral score was computed by averaging the four largest scores over the dose matrix.

Figure 35:
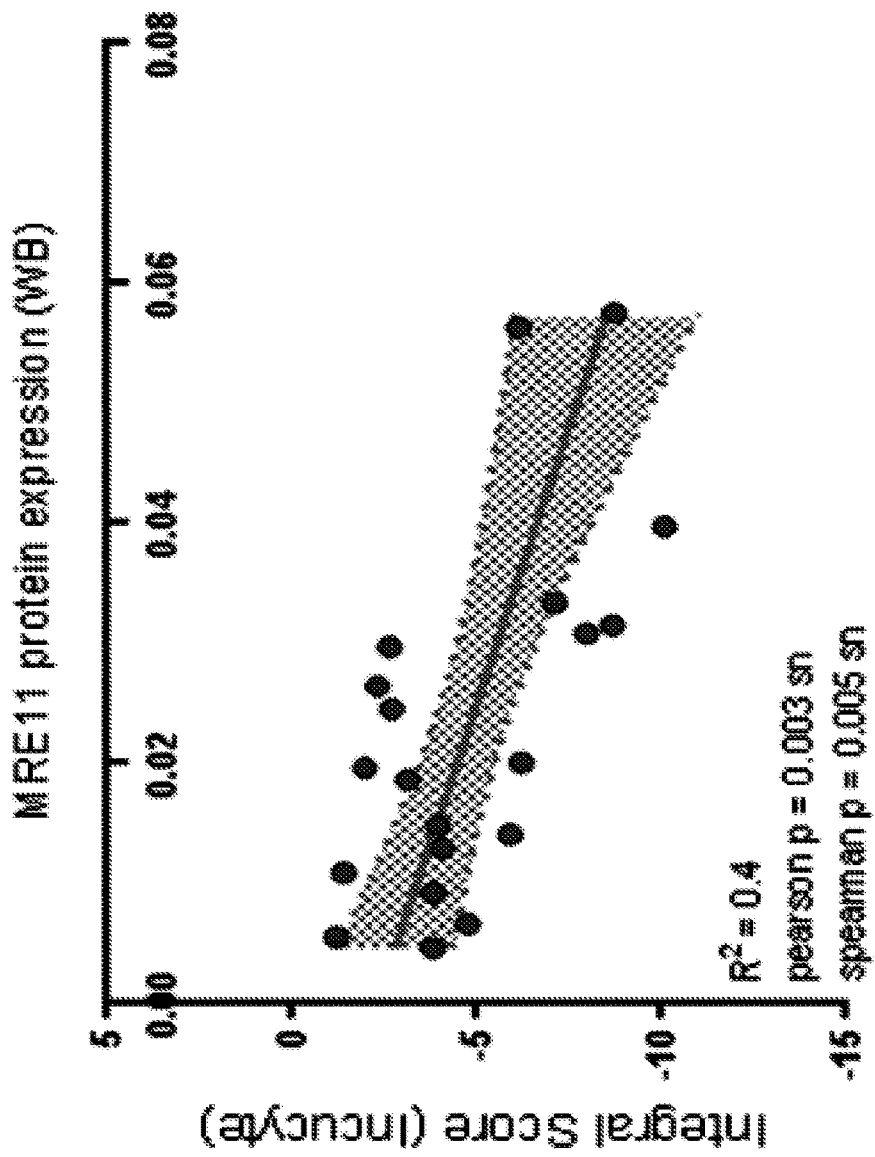
FIG. 35 Correlation of basal MRE11 protein expression (quantified by Western blot) and the integral score, a measure of dynamic cell viability, across lung cancer cell lines exposed to the ATR inhibitor Compound 5 and/or SN38.
Figure 36:
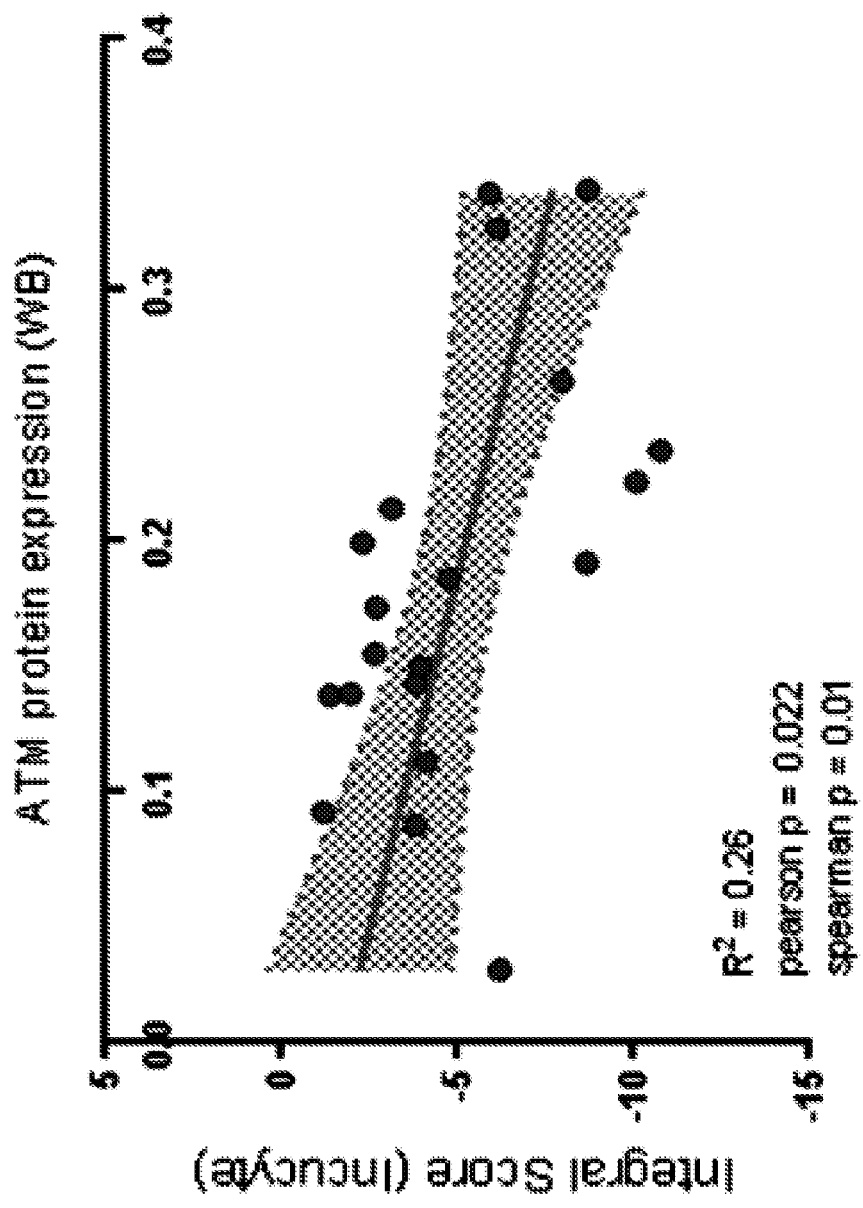
FIG. 36 Correlation of basal ATM protein expression (quantified by Western blot) and the integral score, a measure of dynamic cell viability, across lung cancer cell lines exposed to the ATR inhibitor Compound 5 and/or SN38.
Figure 37:
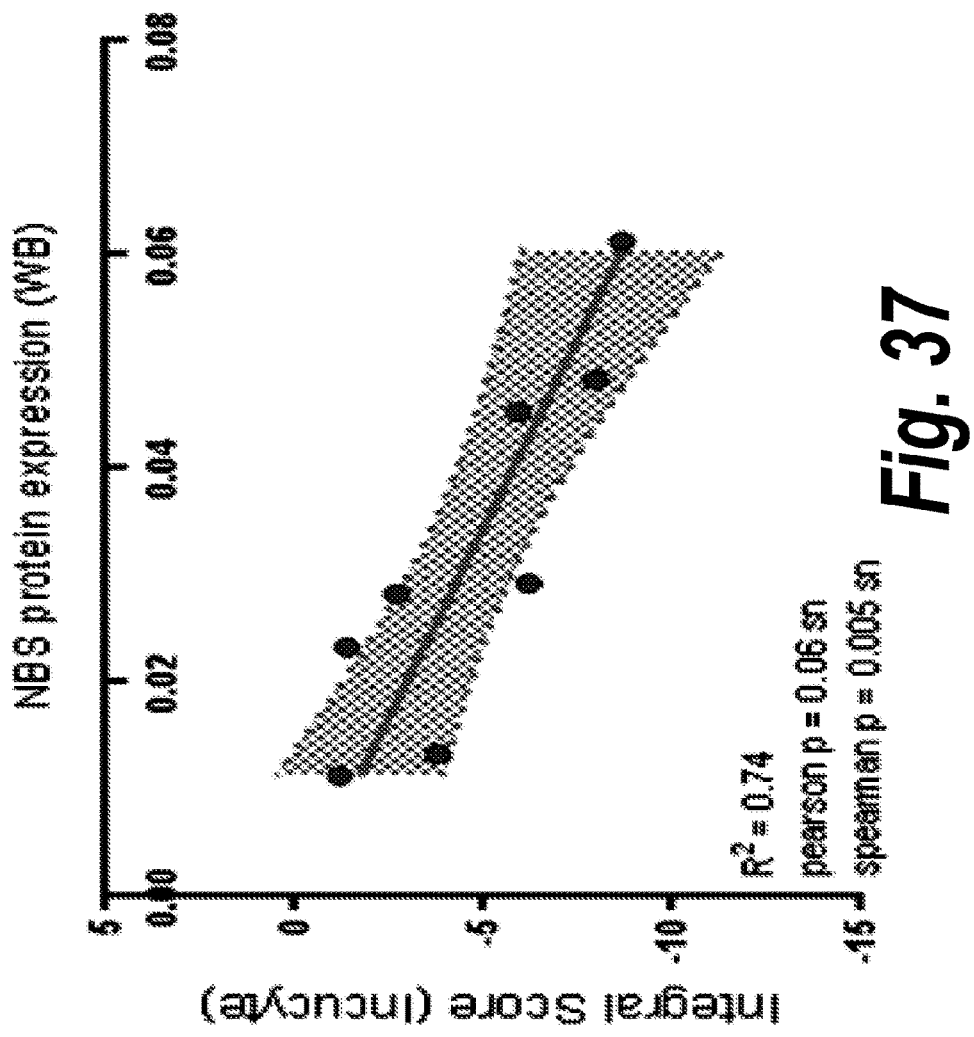
FIG. 37 Correlation of basal NBS protein expression (quantified by Western blot) and the integral score, a measure of dynamic cell viability, across lung cancer cell lines exposed to the ATR inhibitor Compound 5 and/or SN38.
Figure 38:
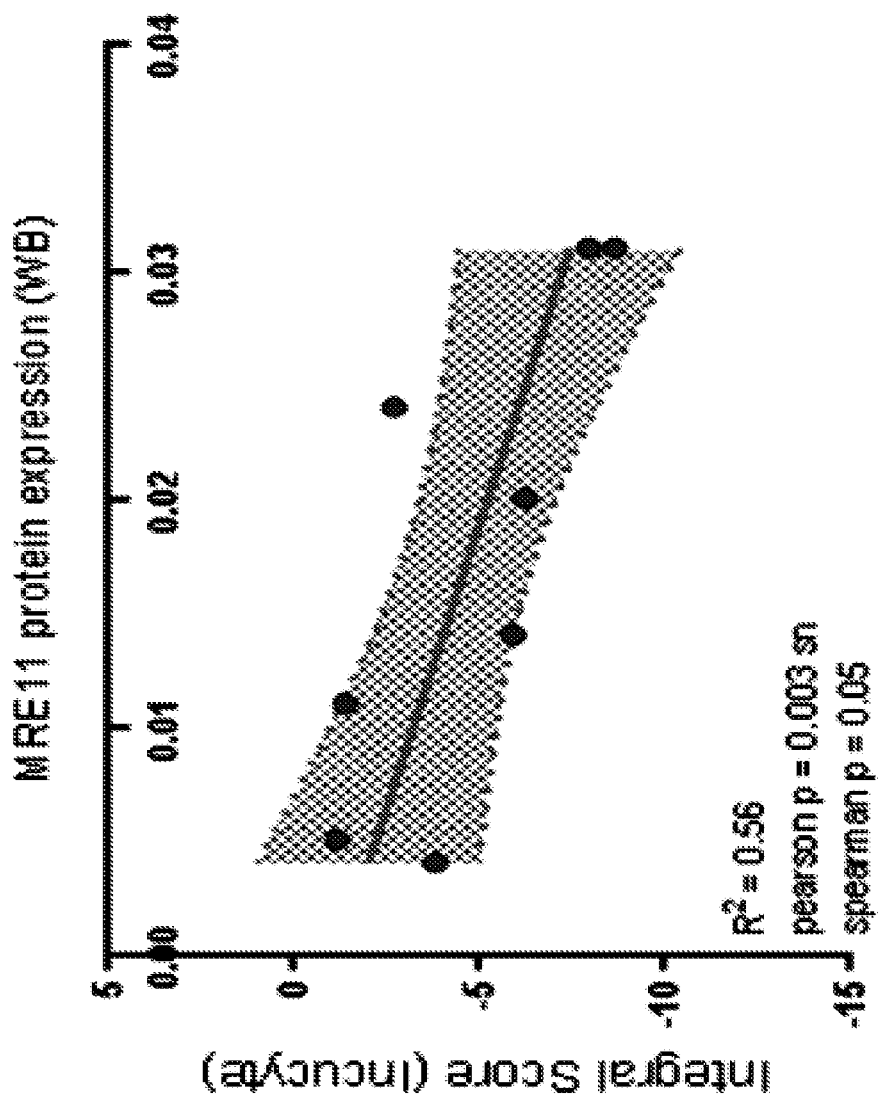
FIG. 38 Correlation of basal NBS protein expression (quantified by Western blot) and the integral score, a measure of dynamic cell viability, across p53 functionally impaired lung cancer cell lines exposed to the ATR inhibitor Compound 5 and/or SN38.
Figure 39:
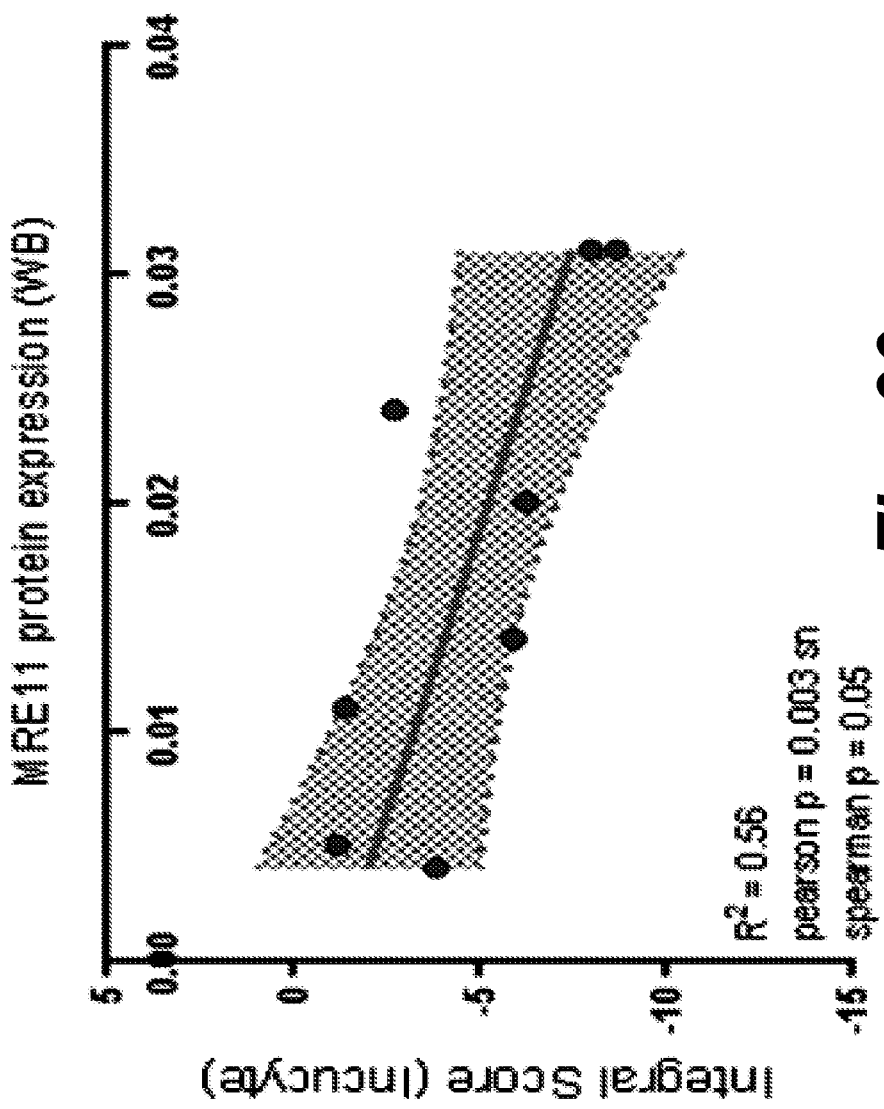
FIG. 39 Correlation of basal NBS protein expression (quantified by Western blot) and the integral score, a measure of dynamic cell viability, across p53 functionally impaired lung cancer cell lines exposed to the ATR inhibitor Compound 5 and/or SN38.
Figure 40A:
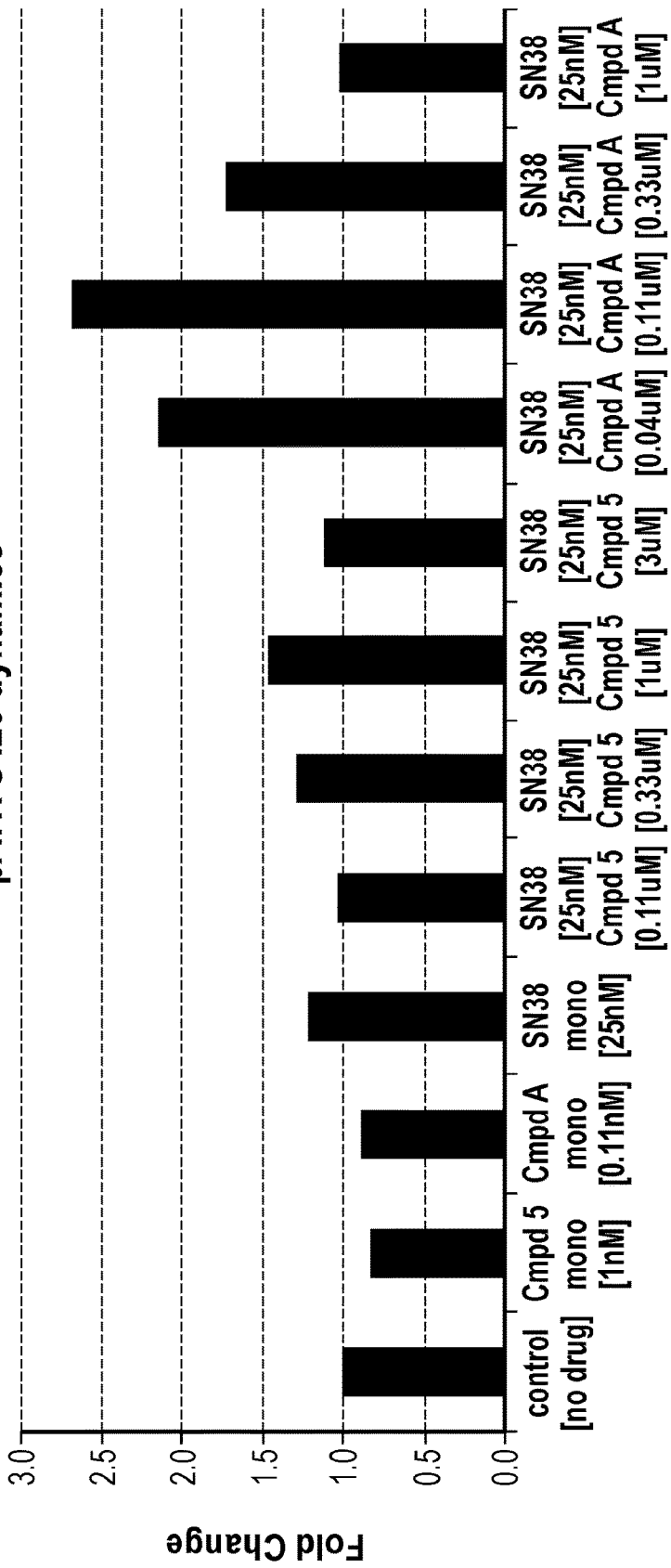
FIG. 40A-F Fold change in cancer cell line NCIH1299 pharmacodynamics markers after exposure to ATR inhibition and/or SN38.
Figure 40B:
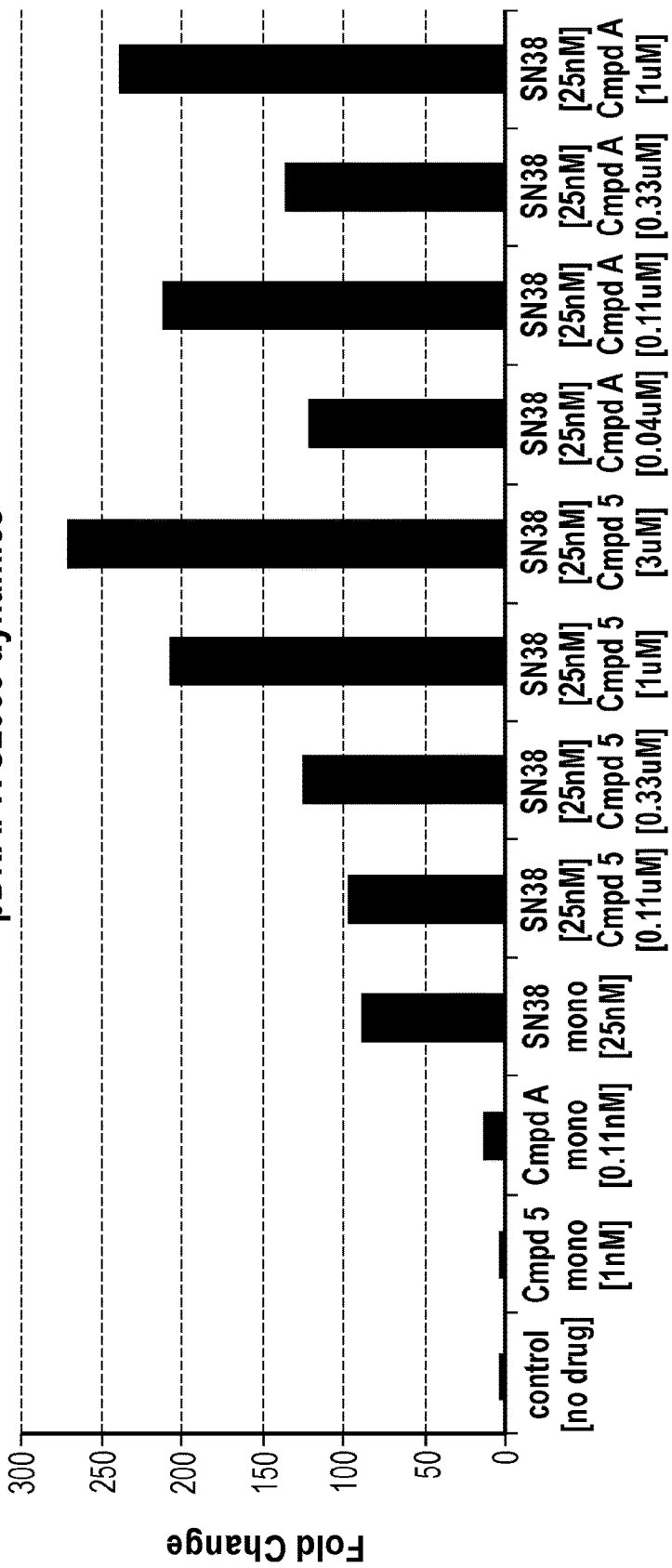
Figure 40C:
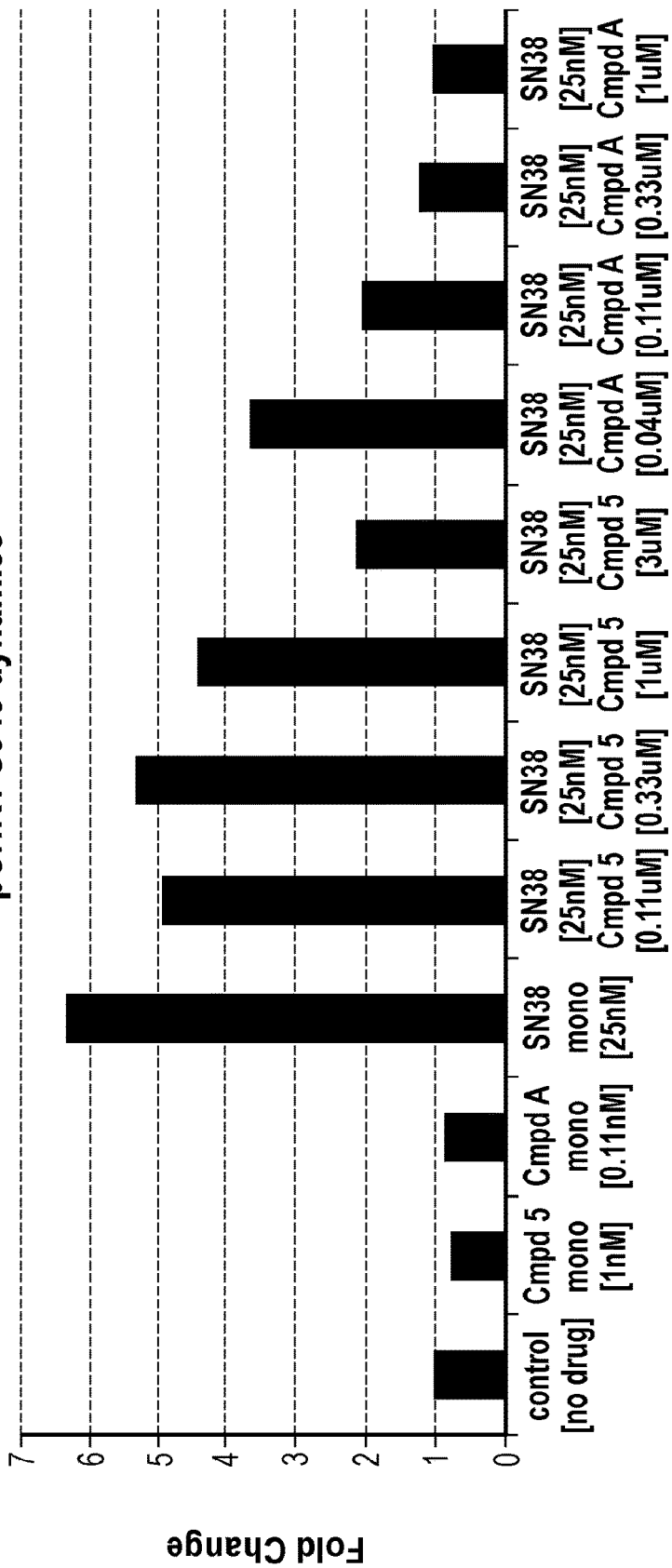
Figure 40D:
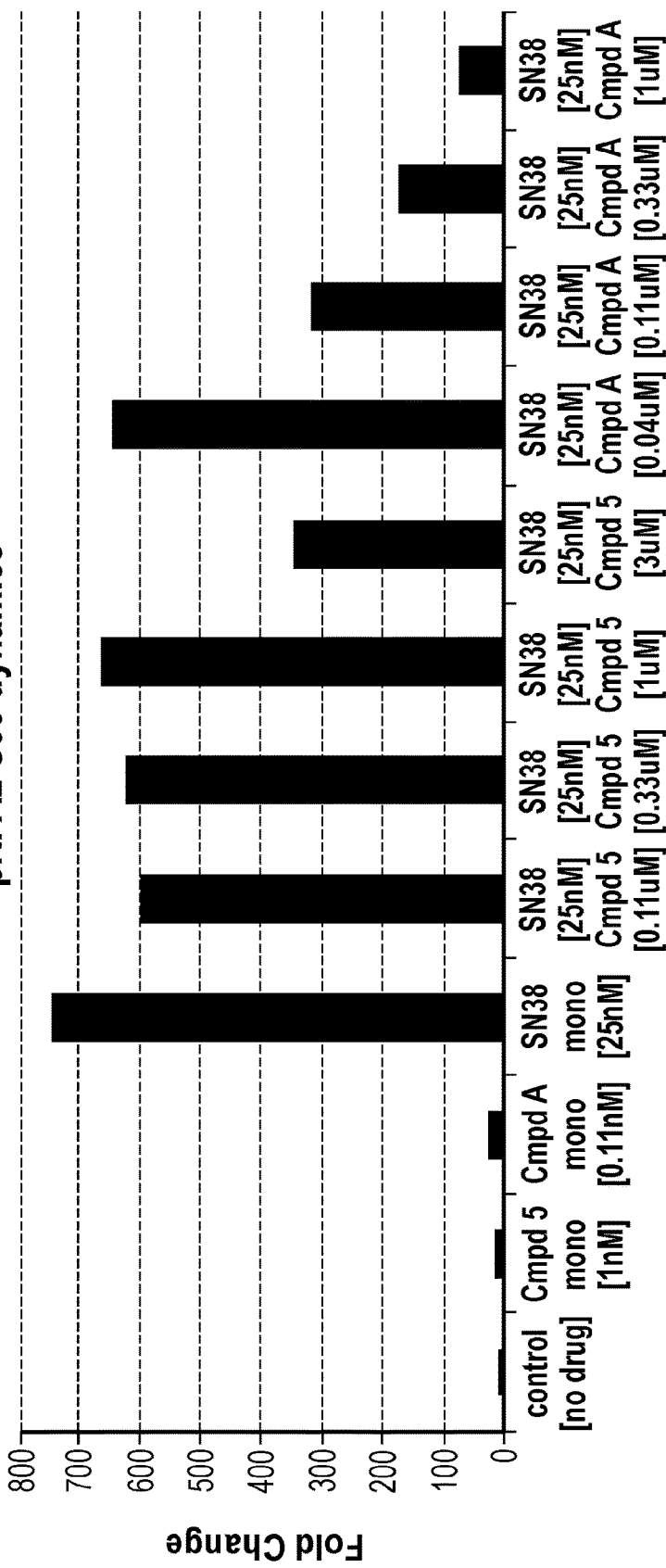
Figure 40E:
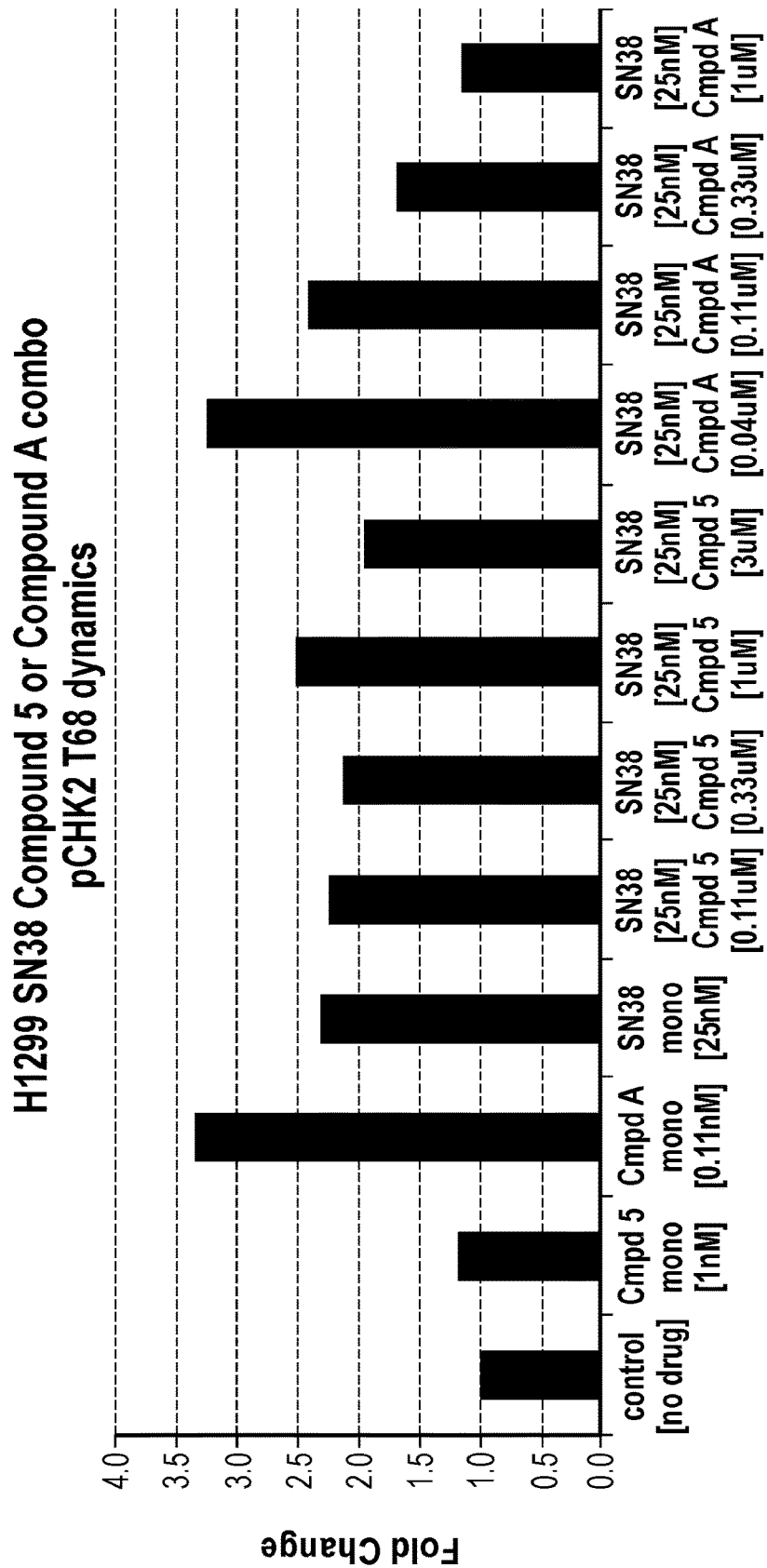
Figure 40E:
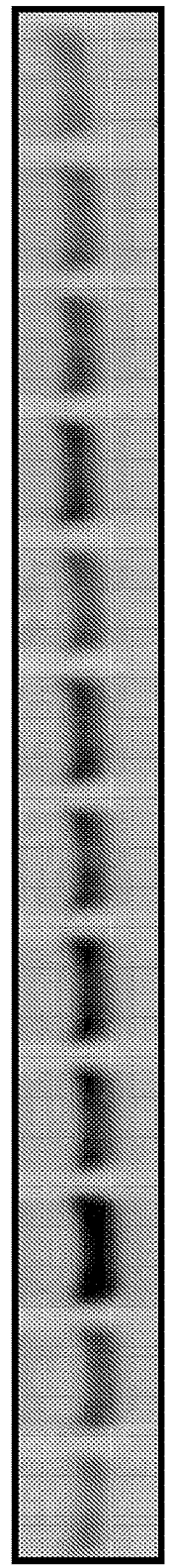
Figure 40F:
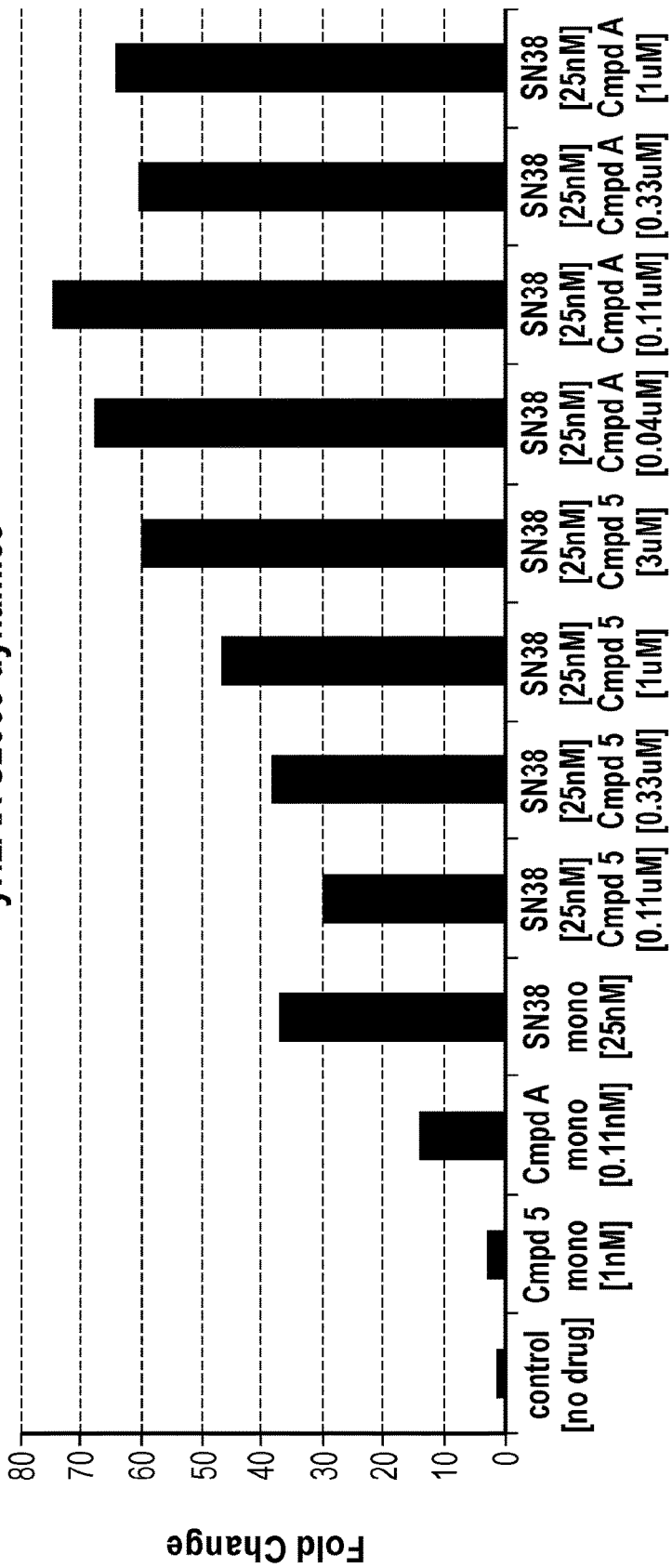
Figure 40F:
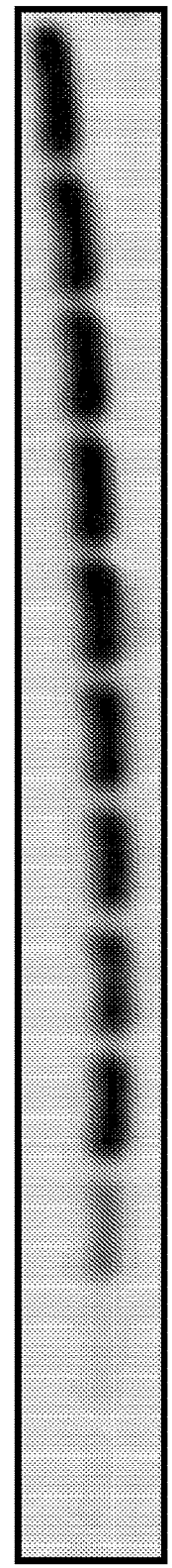
Figure 41A:
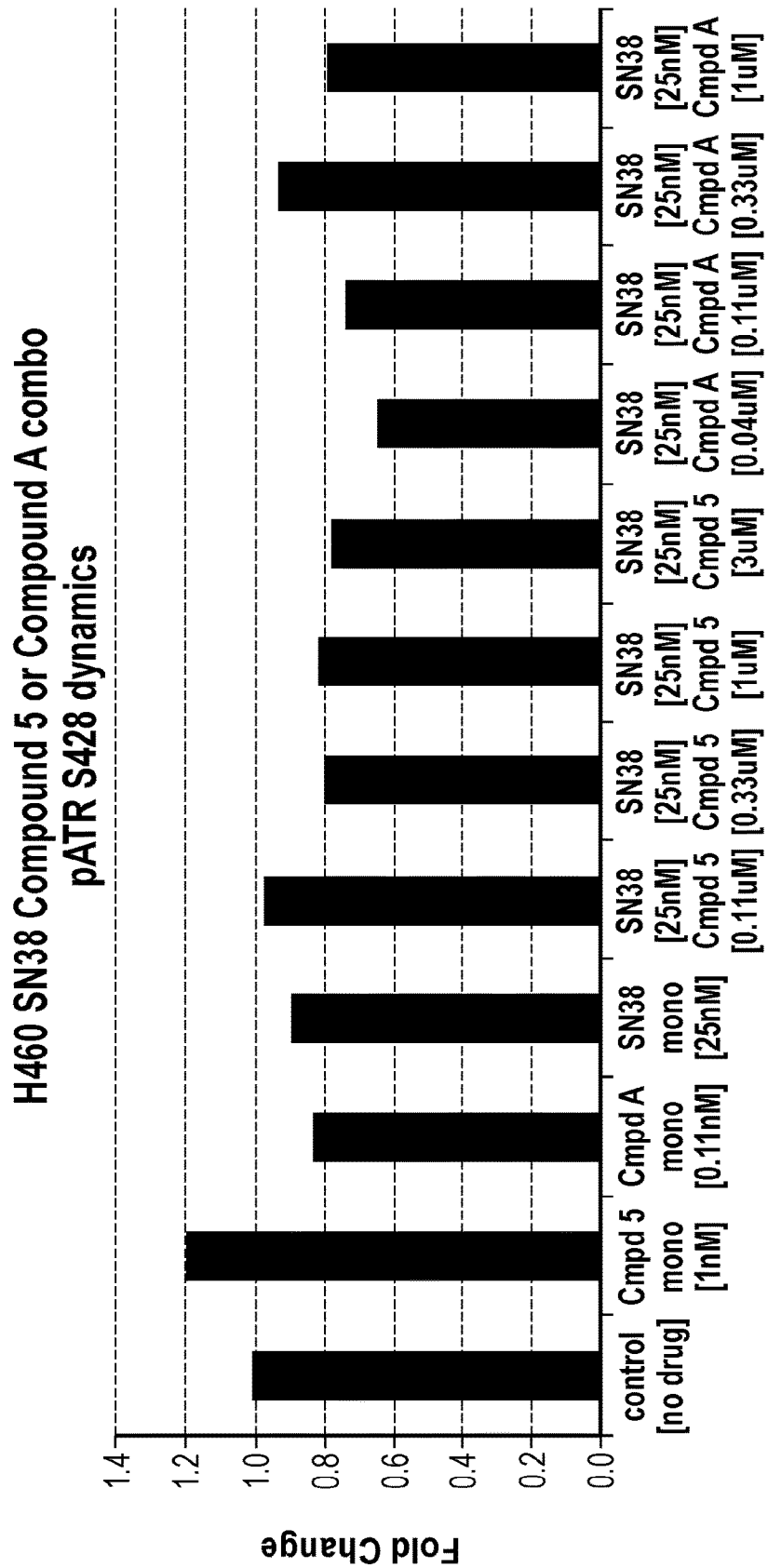
FIG. 41A-F Fold change in cancer cell line NCIH460 pharmacodynamics markers after exposure to ATR inhibition and/or SN38.
Figure 41B:
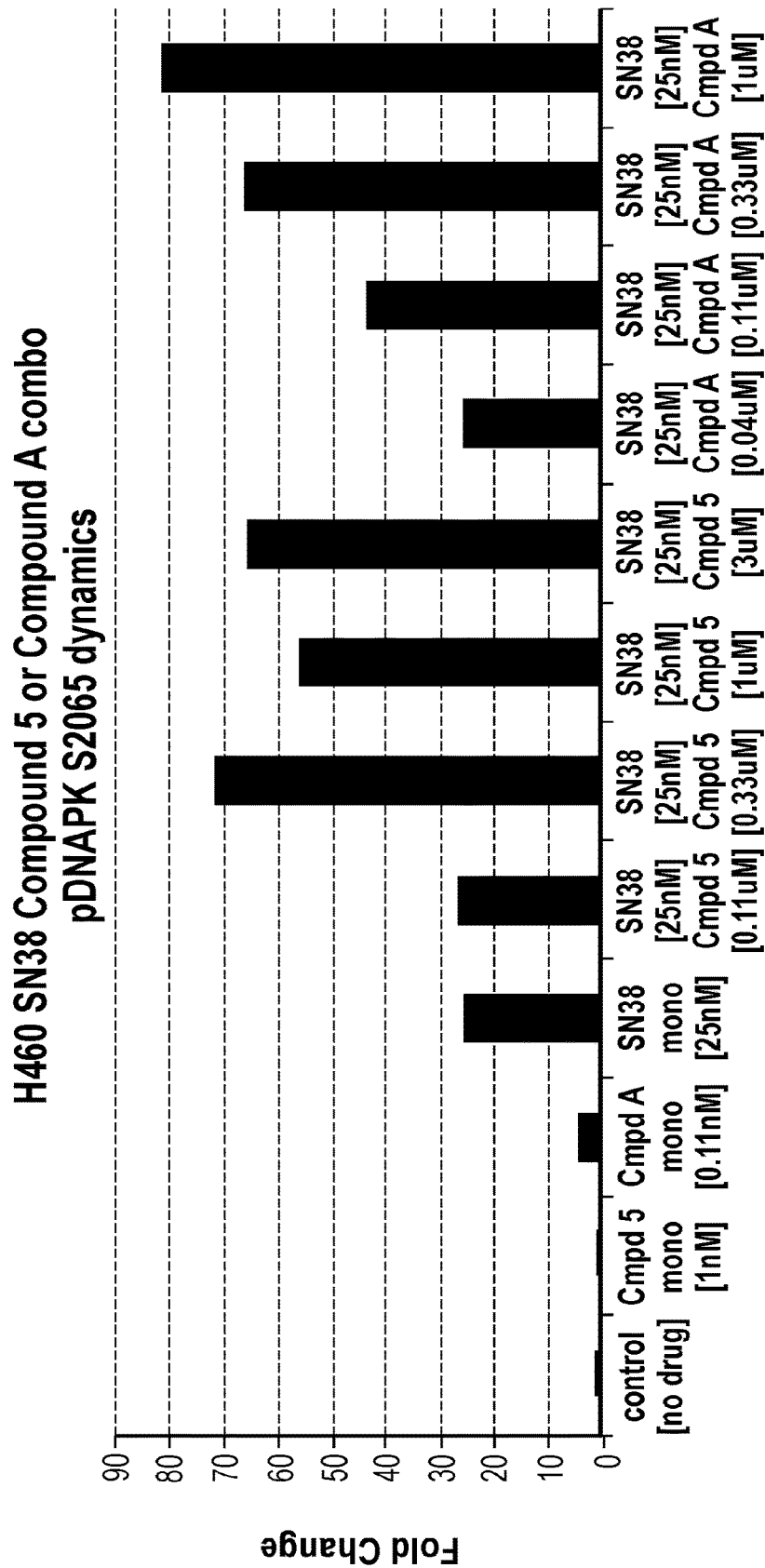
Figure 41B:
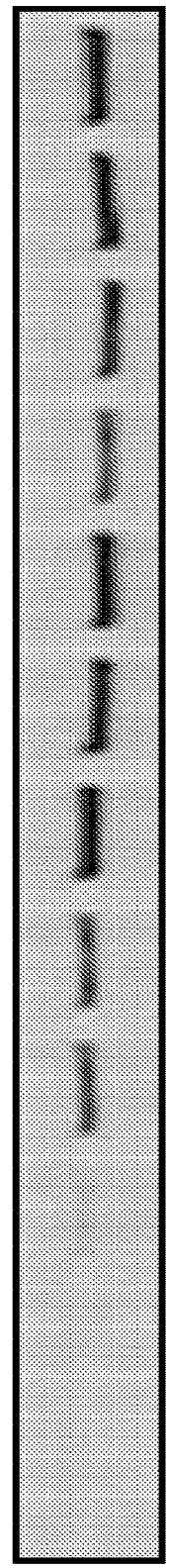
Figure 41C:
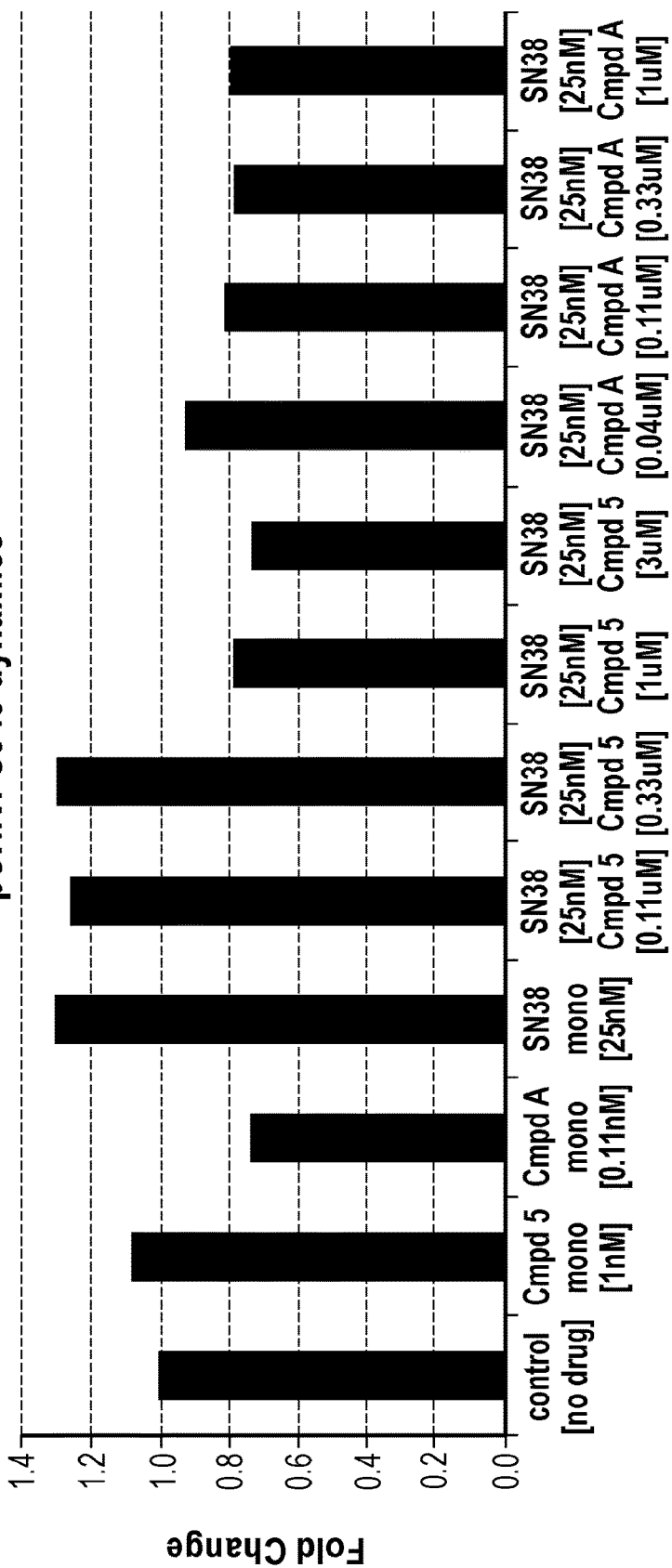
Figure 41C:
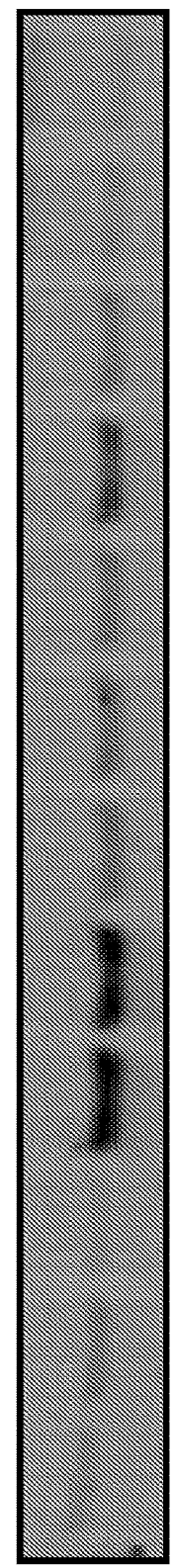
Figure 41D:
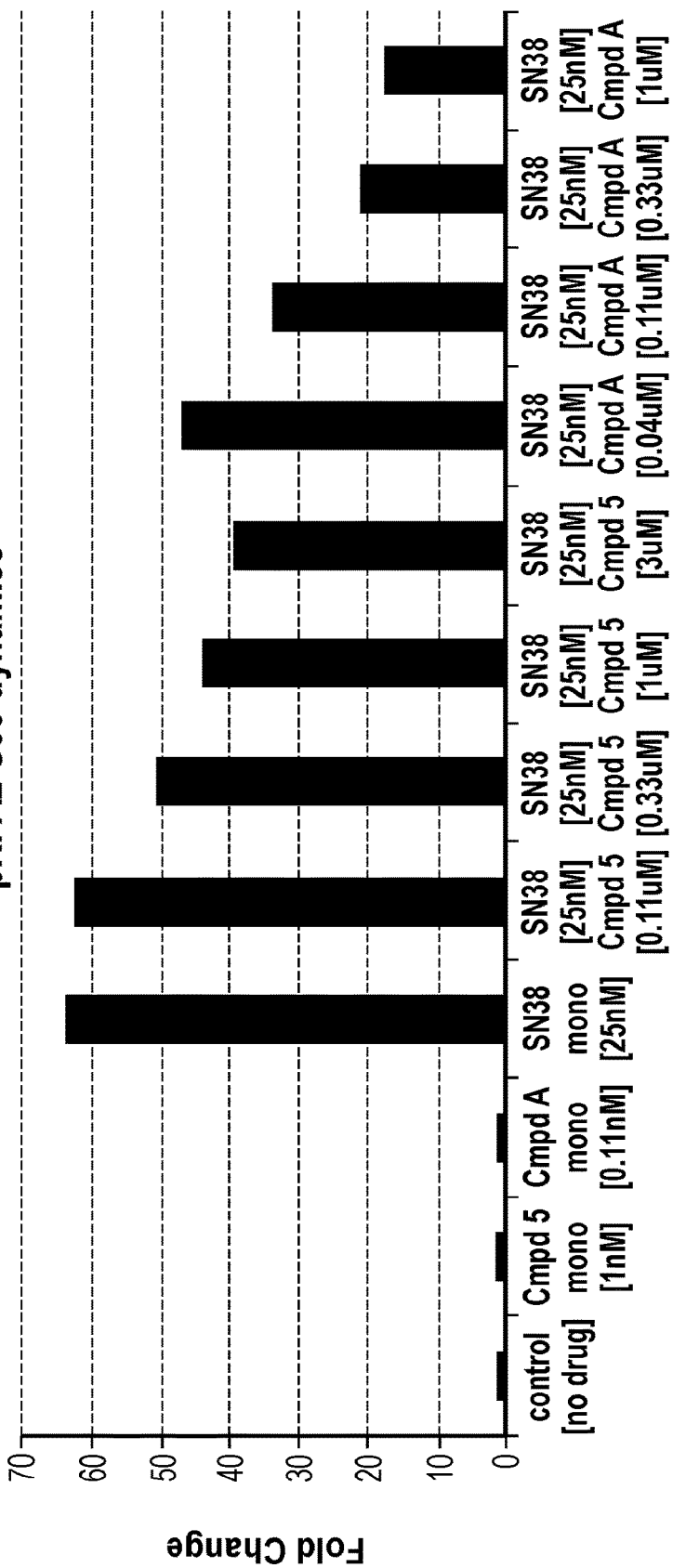
Figure 41D:
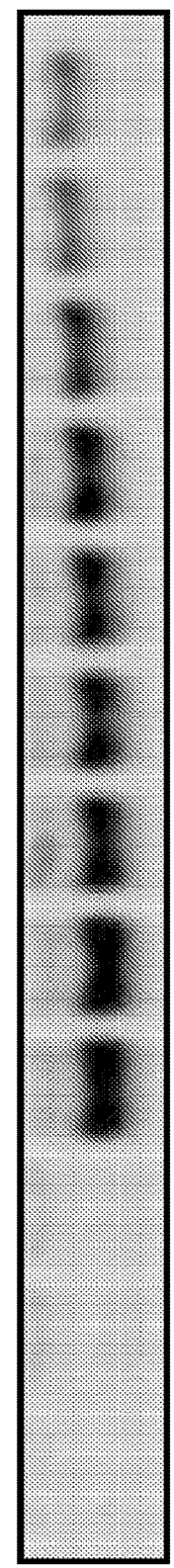
Figure 41E:
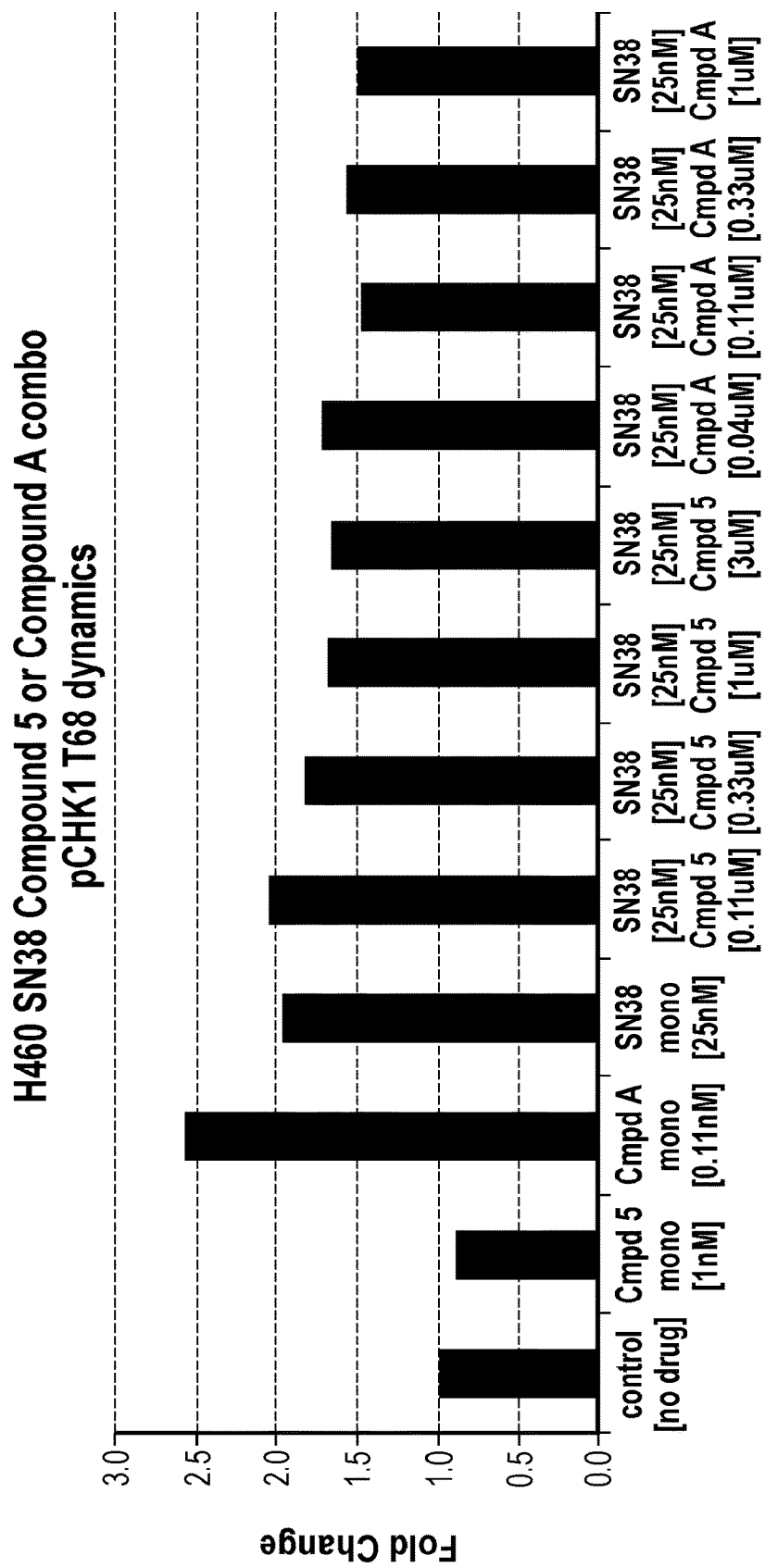
Figure 41E:
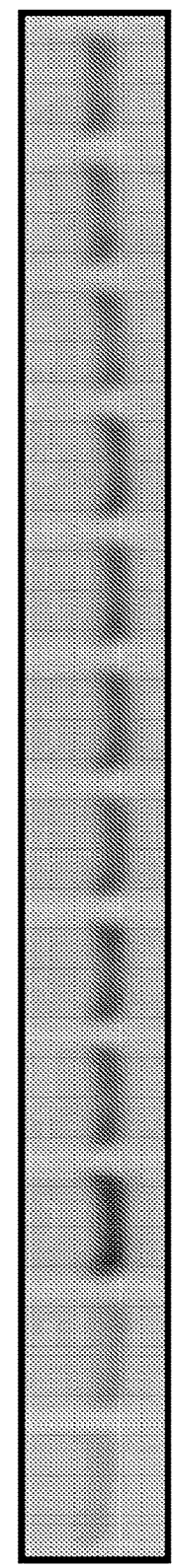
Figure 41F:
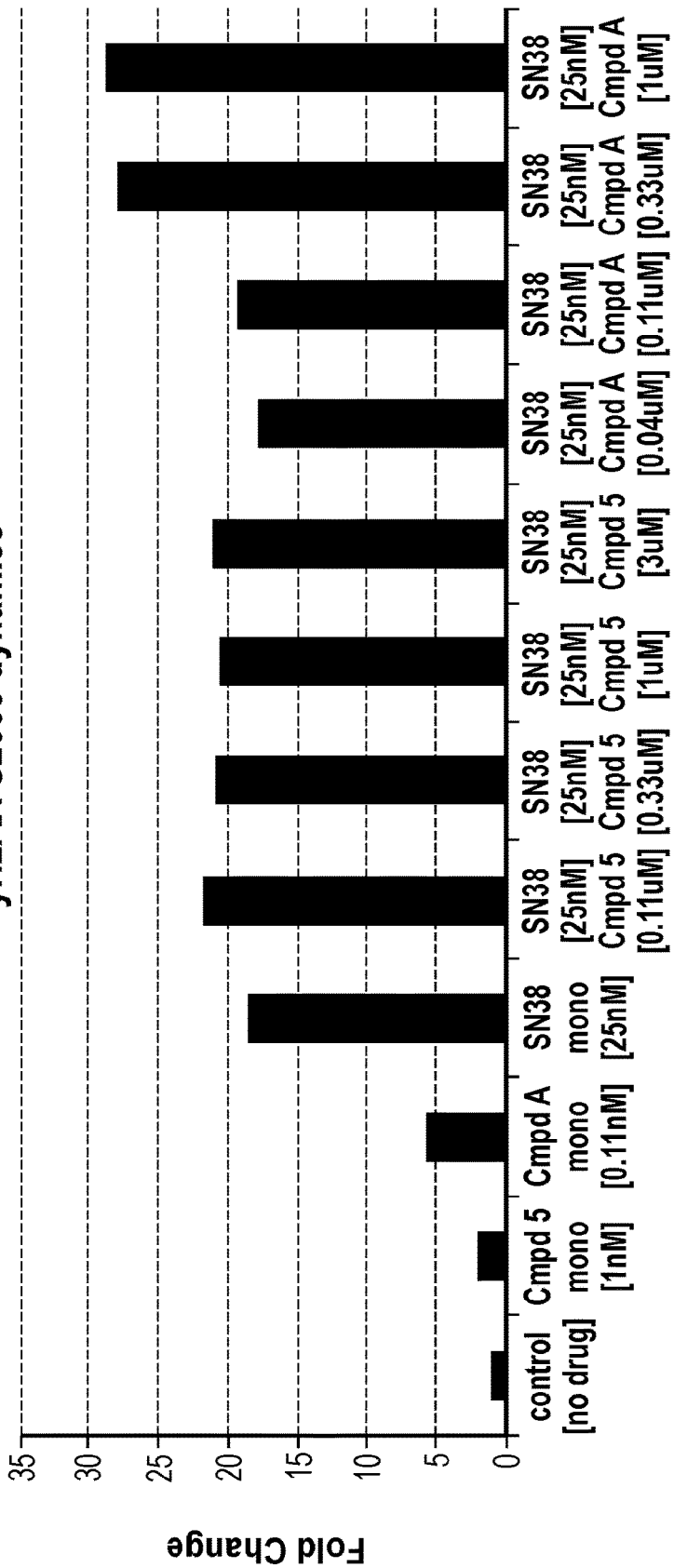
Figure 41F:
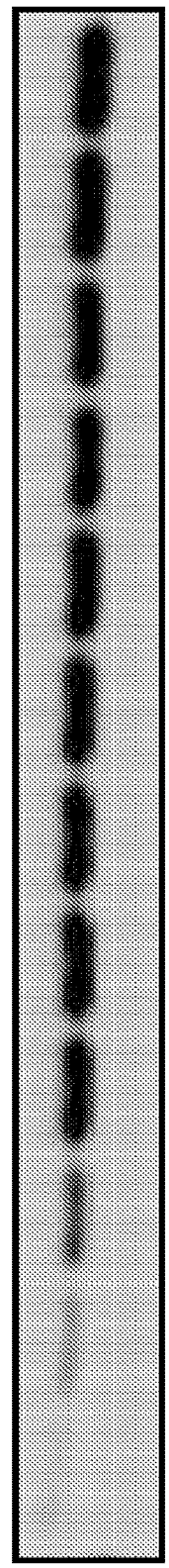
Figure 42A:
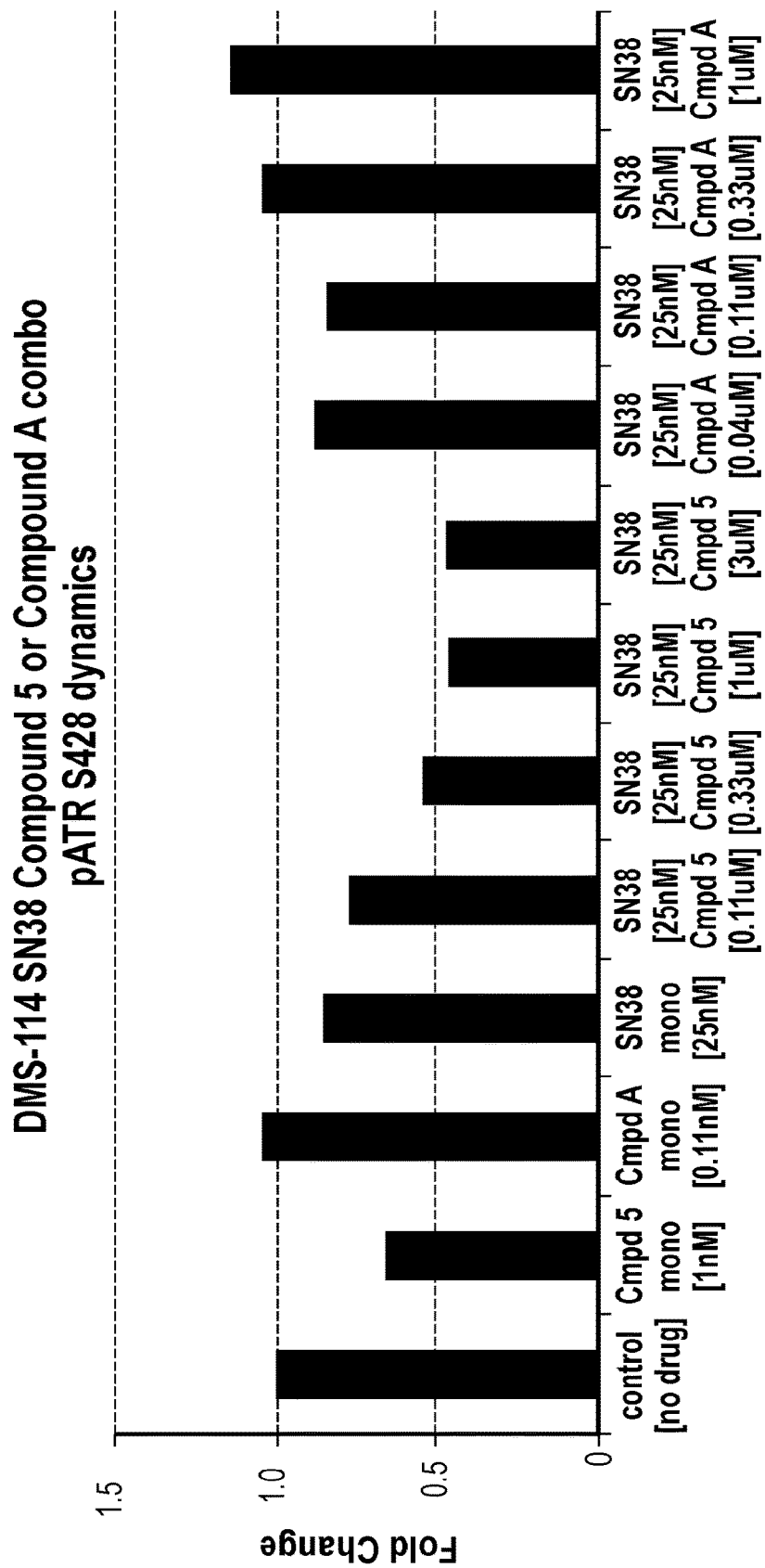
FIG. 42A-F Fold change in cancer cell line DMS 114 pharmacodynamics markers after exposure to ATR inhibition and/or SN38.
Figure 42B:
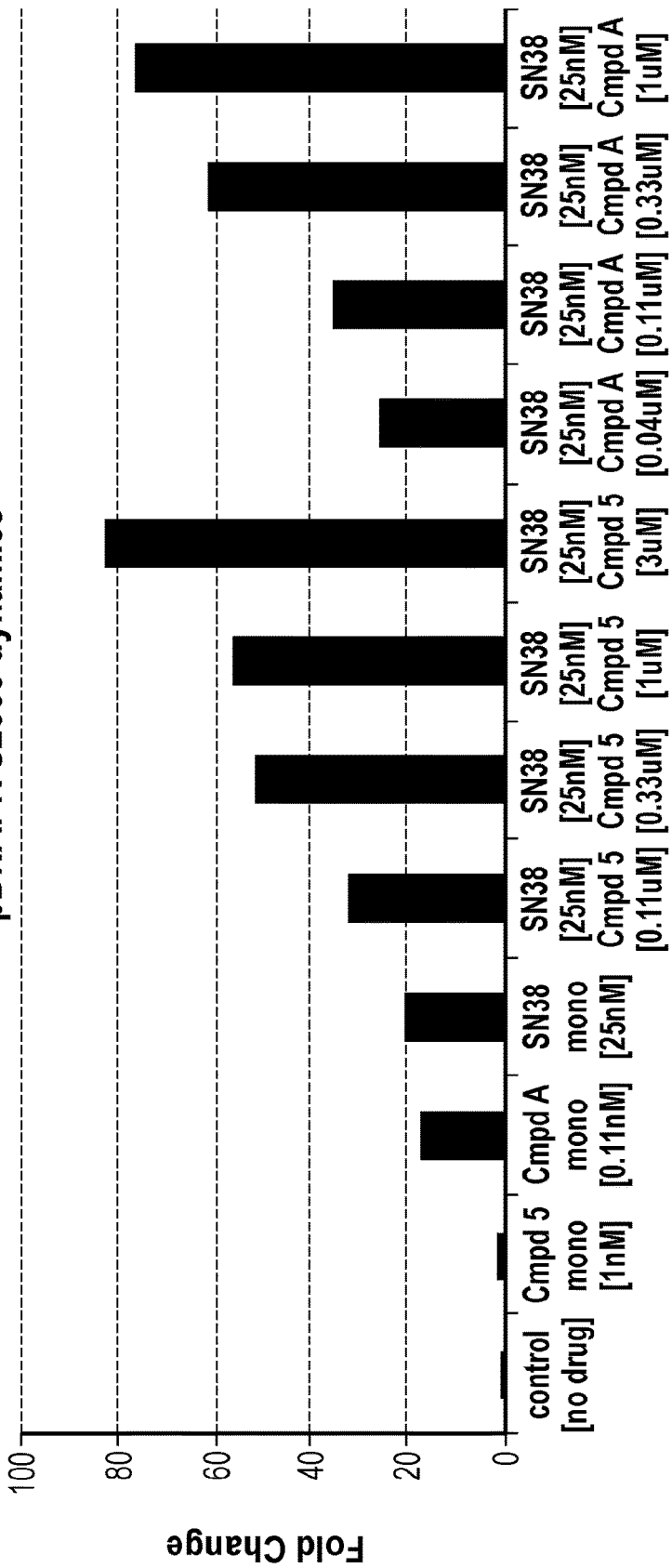
Figure 42B:
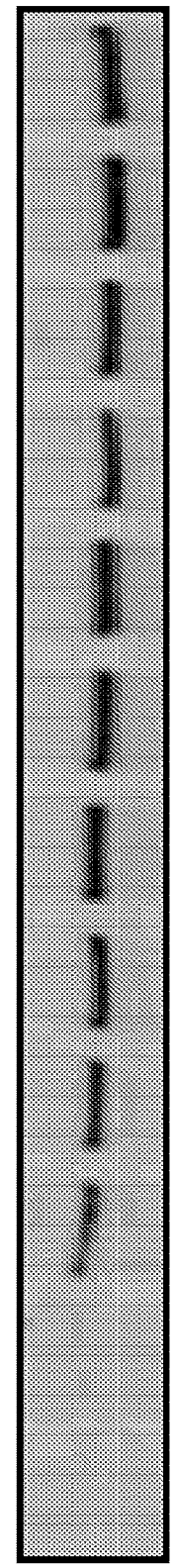
Figure 42C:
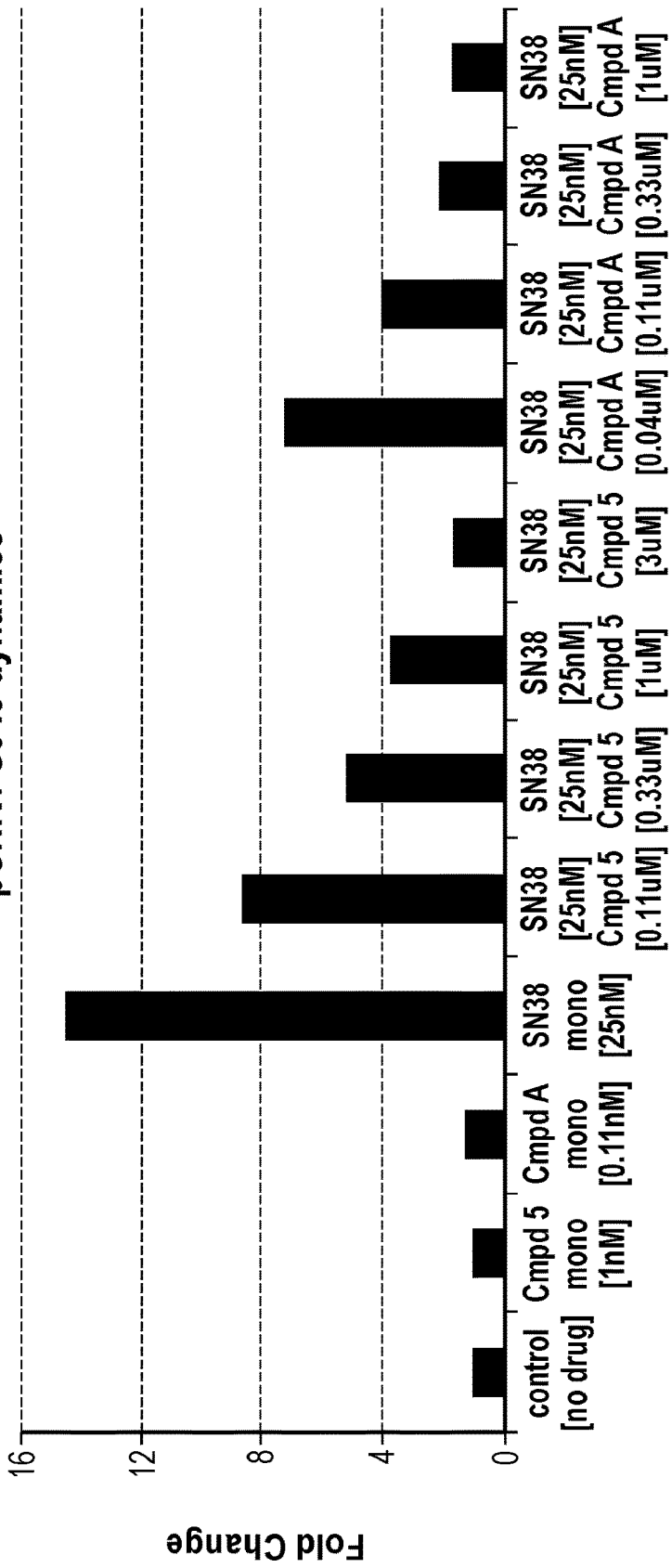
Figure 42C:
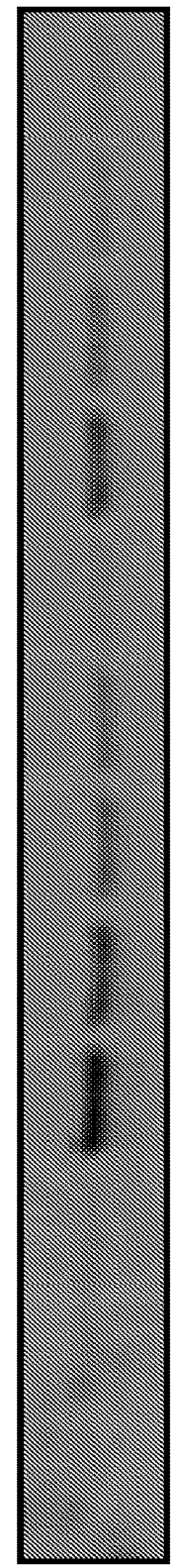
Figure 42D:
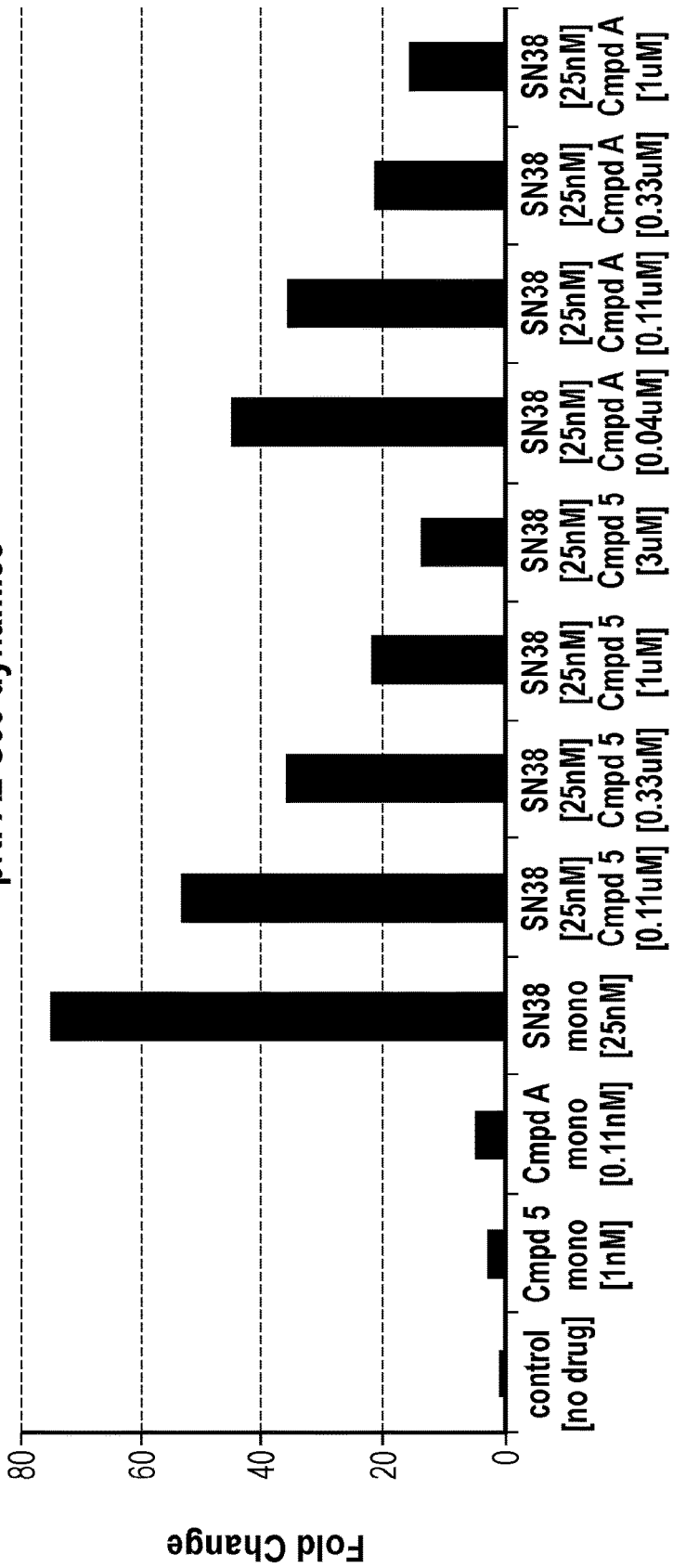
Figure 42E:
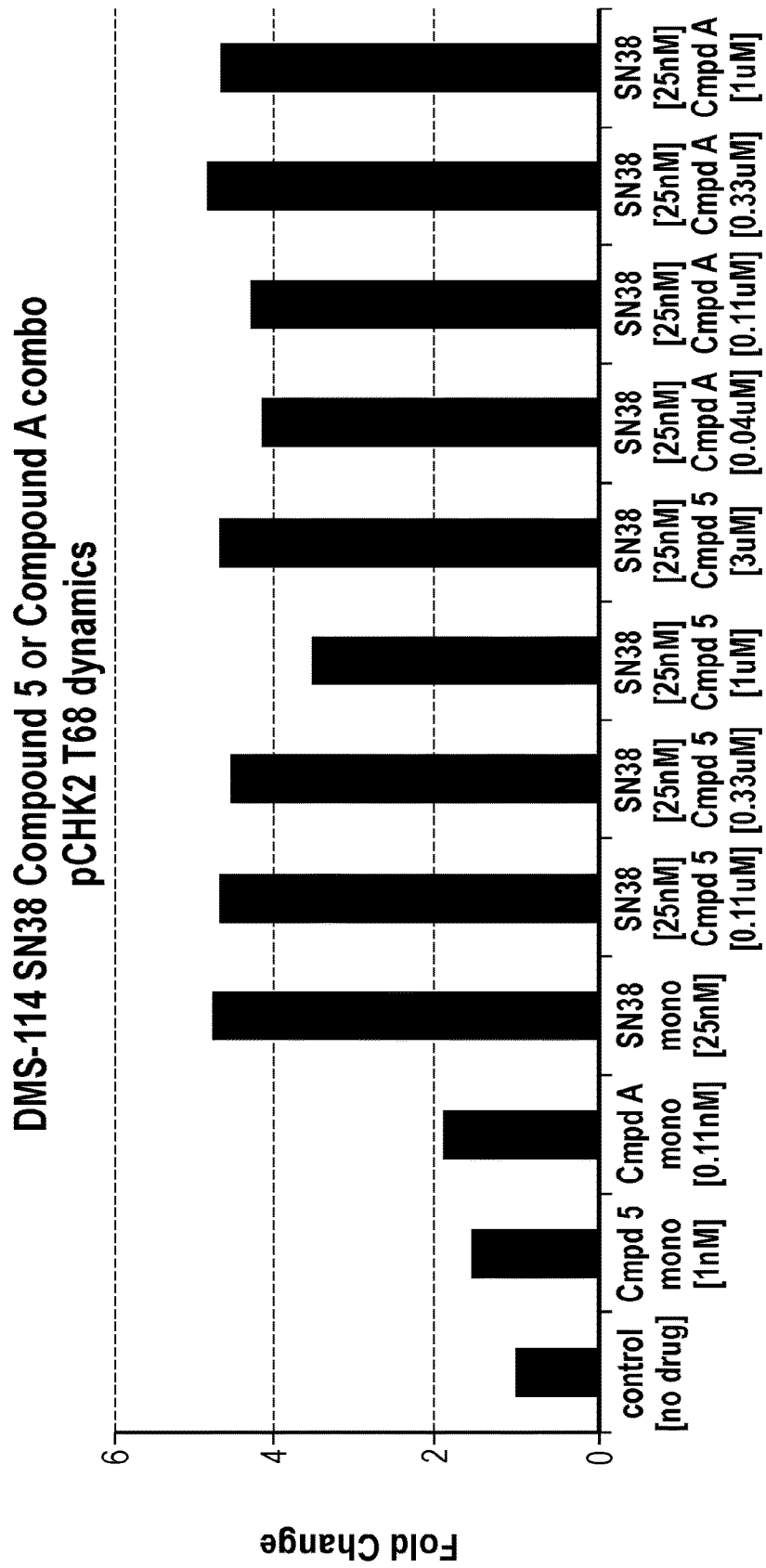
Figure 42E:
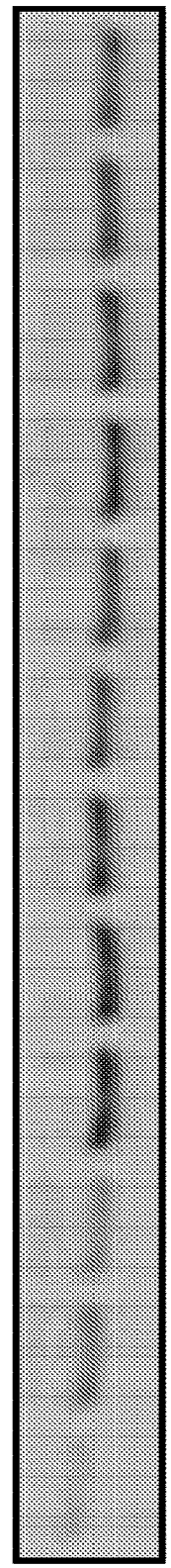
Figure 42F:
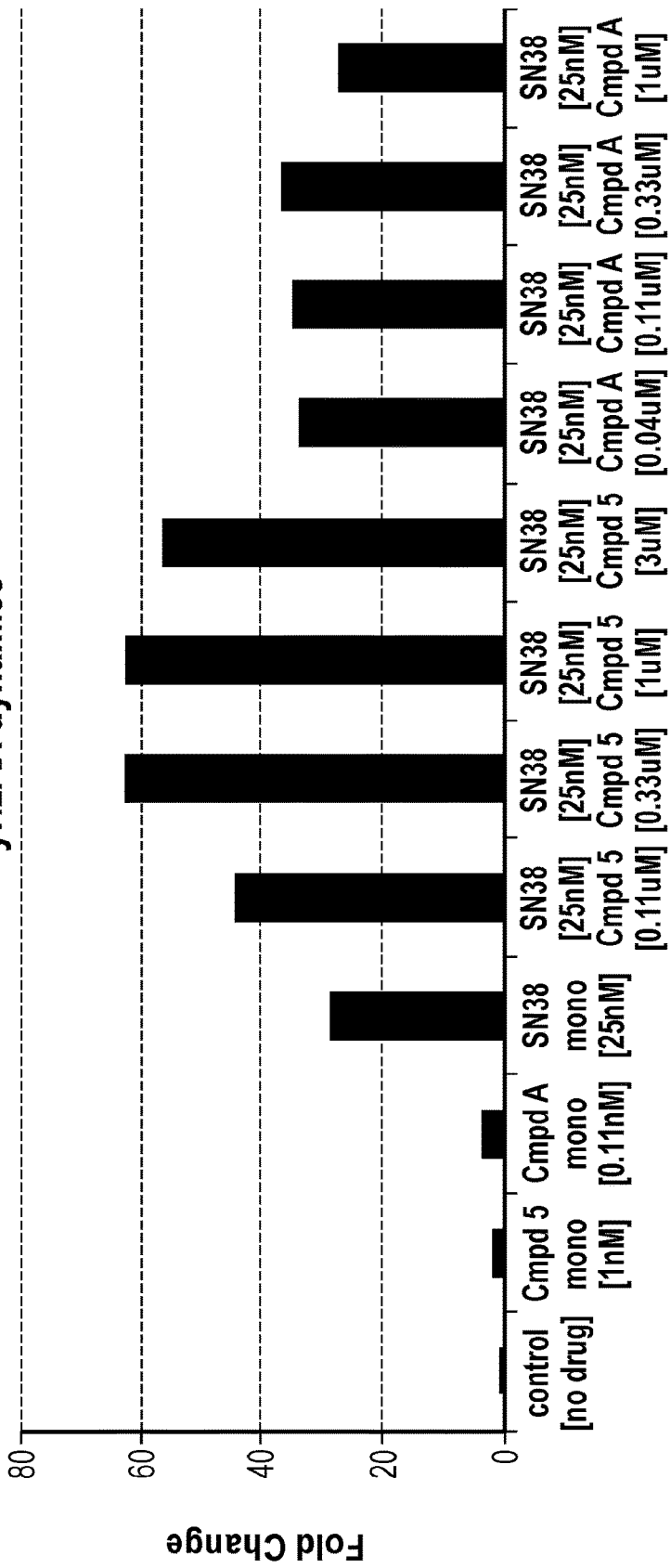
Figure 43A:
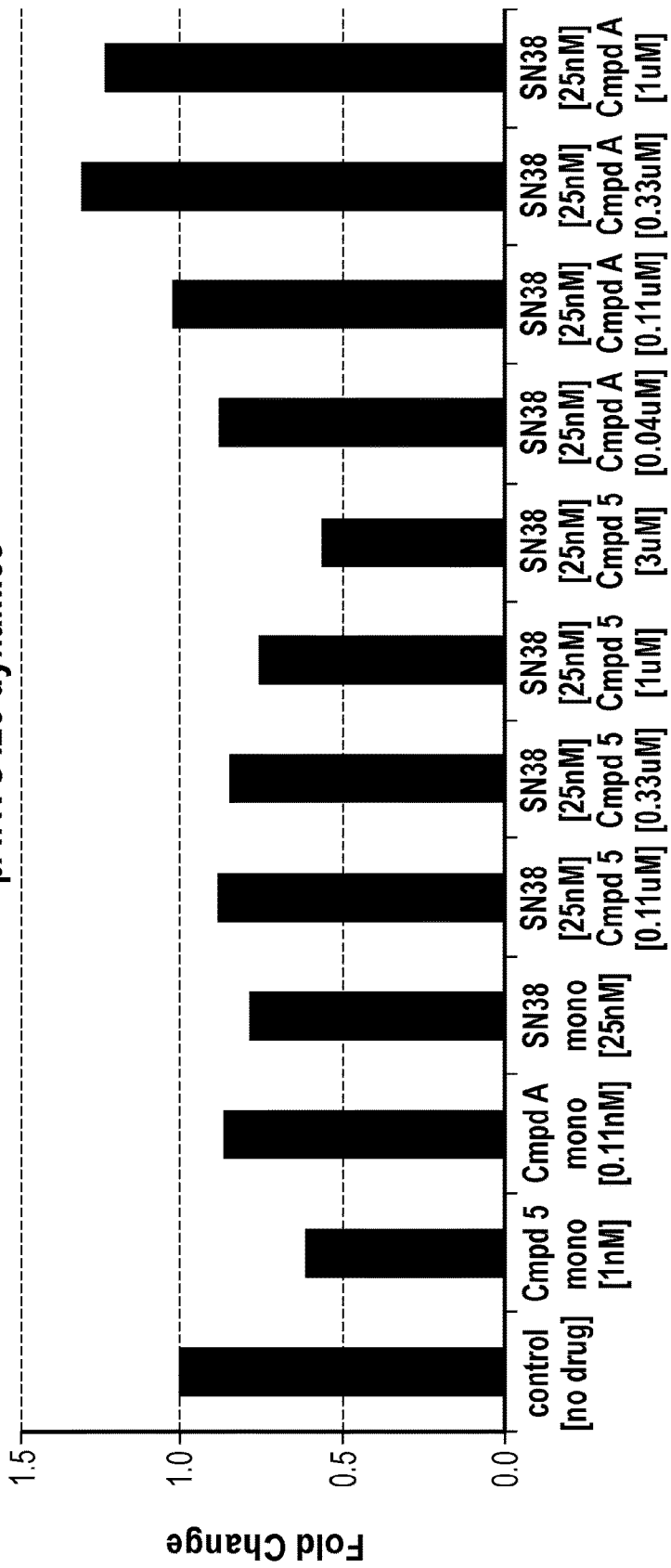
FIG. 43A-F Fold change in cancer cell line HCC70 pharmacodynamics markers after exposure to ATR inhibition and/or SN38.
Figure 43B:
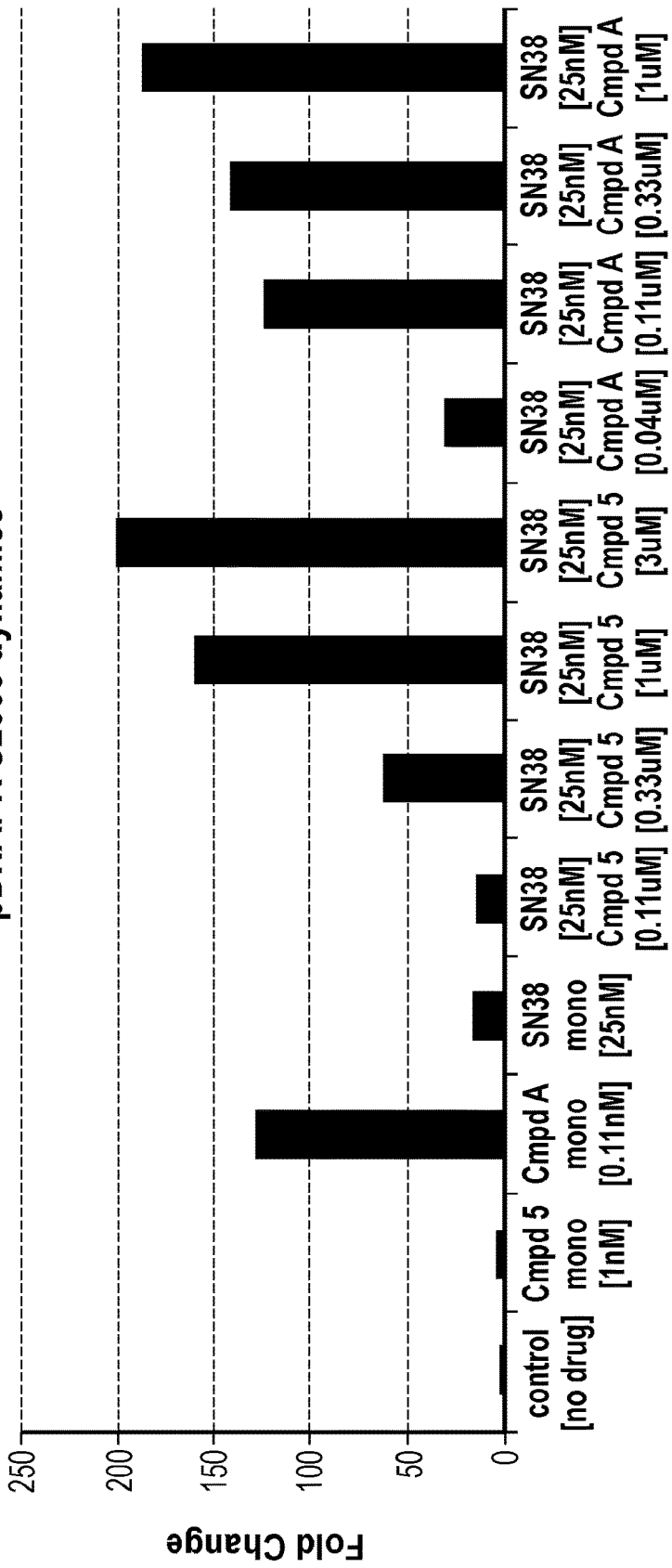
Figure 43B:
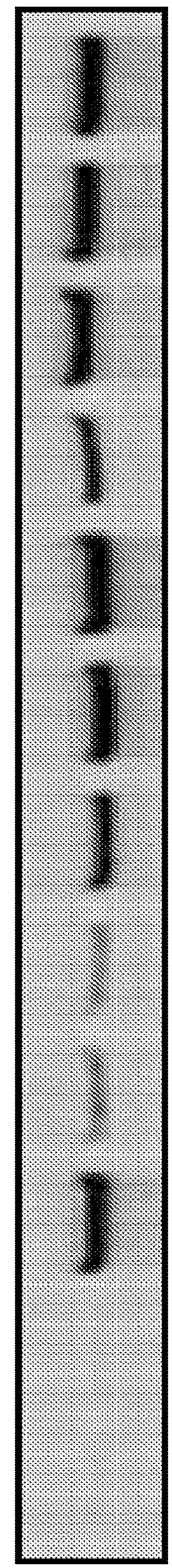
Figure 43C:
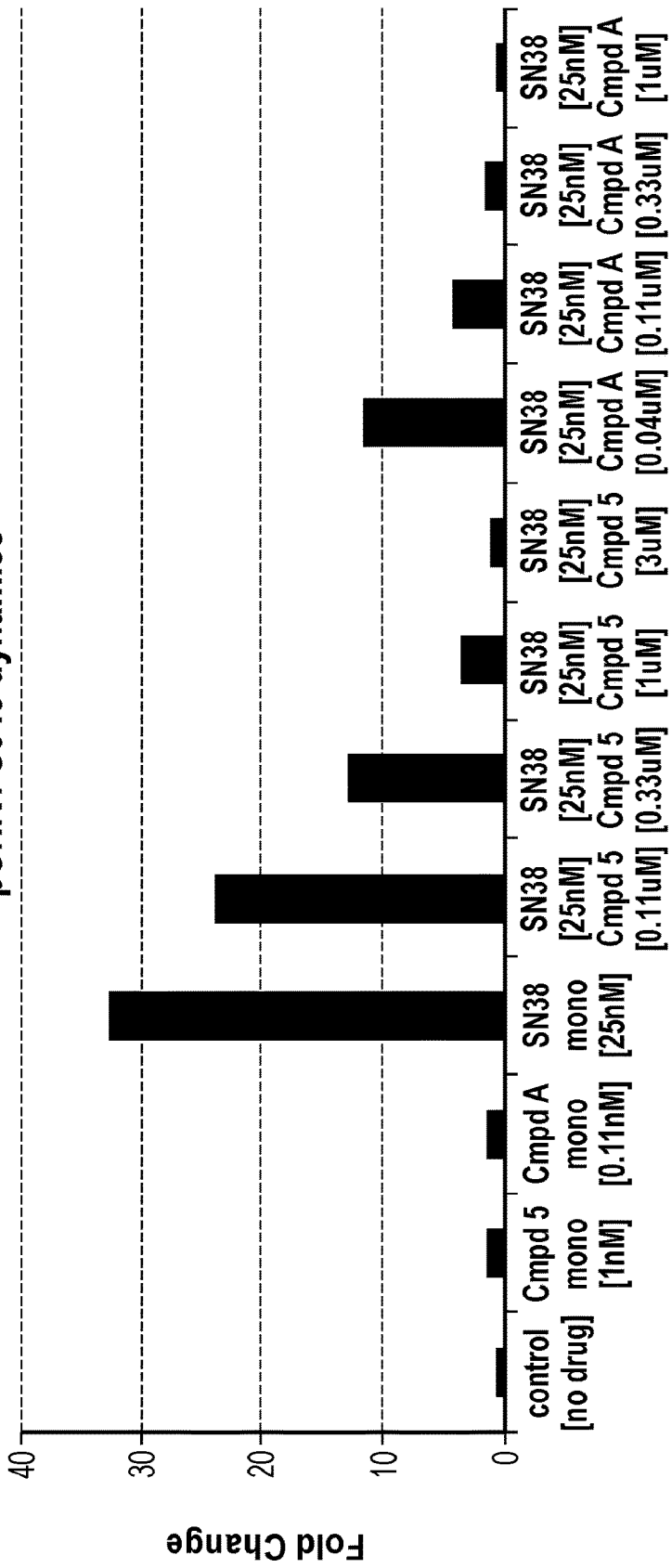
Figure 43D:
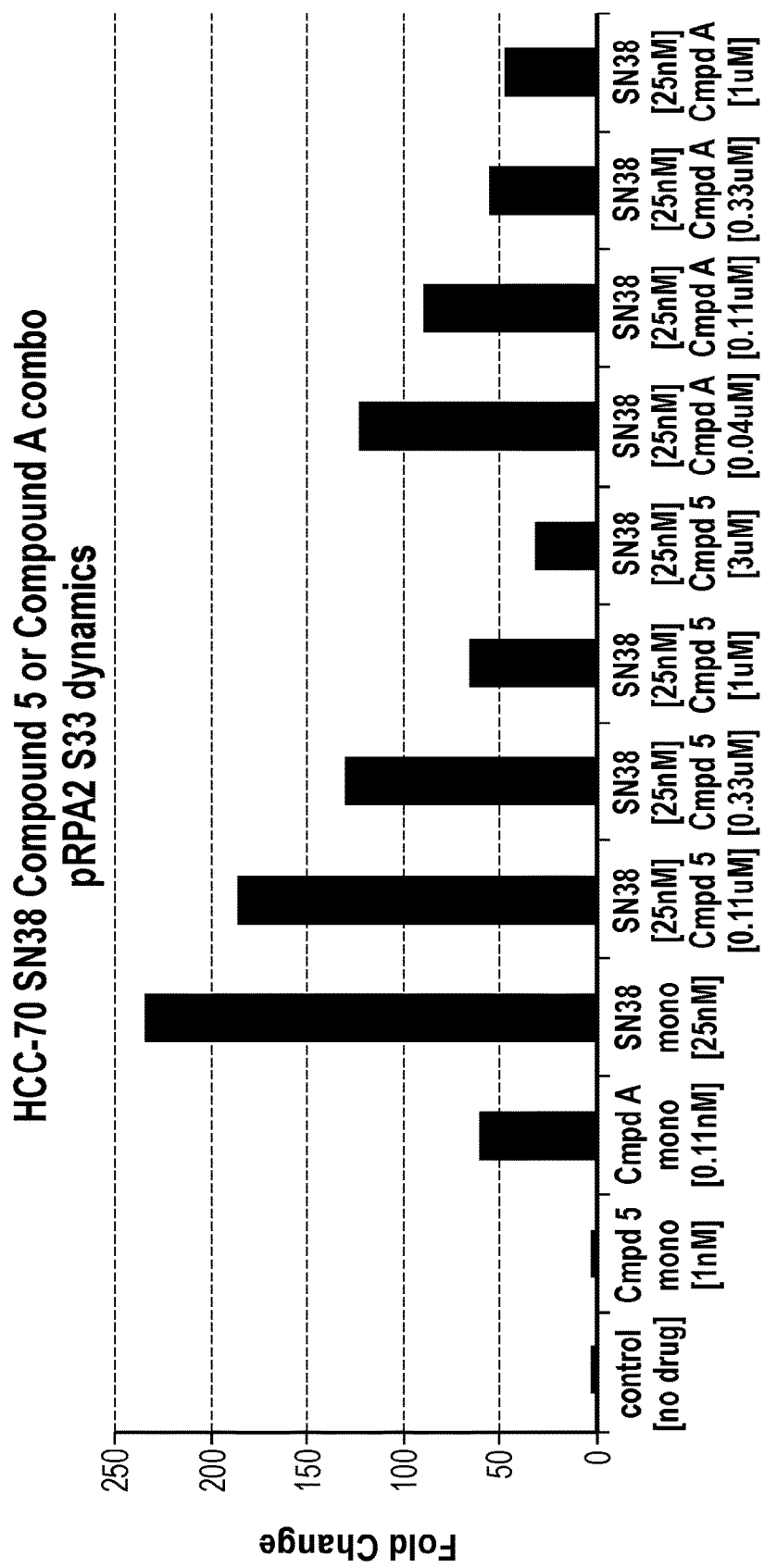
Figure 43D:
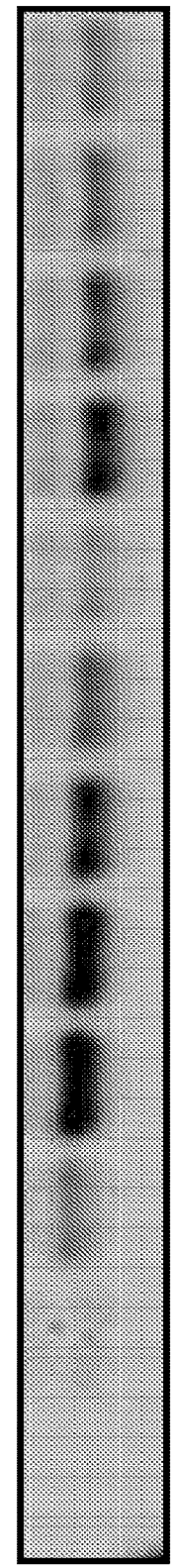
Figure 43E:
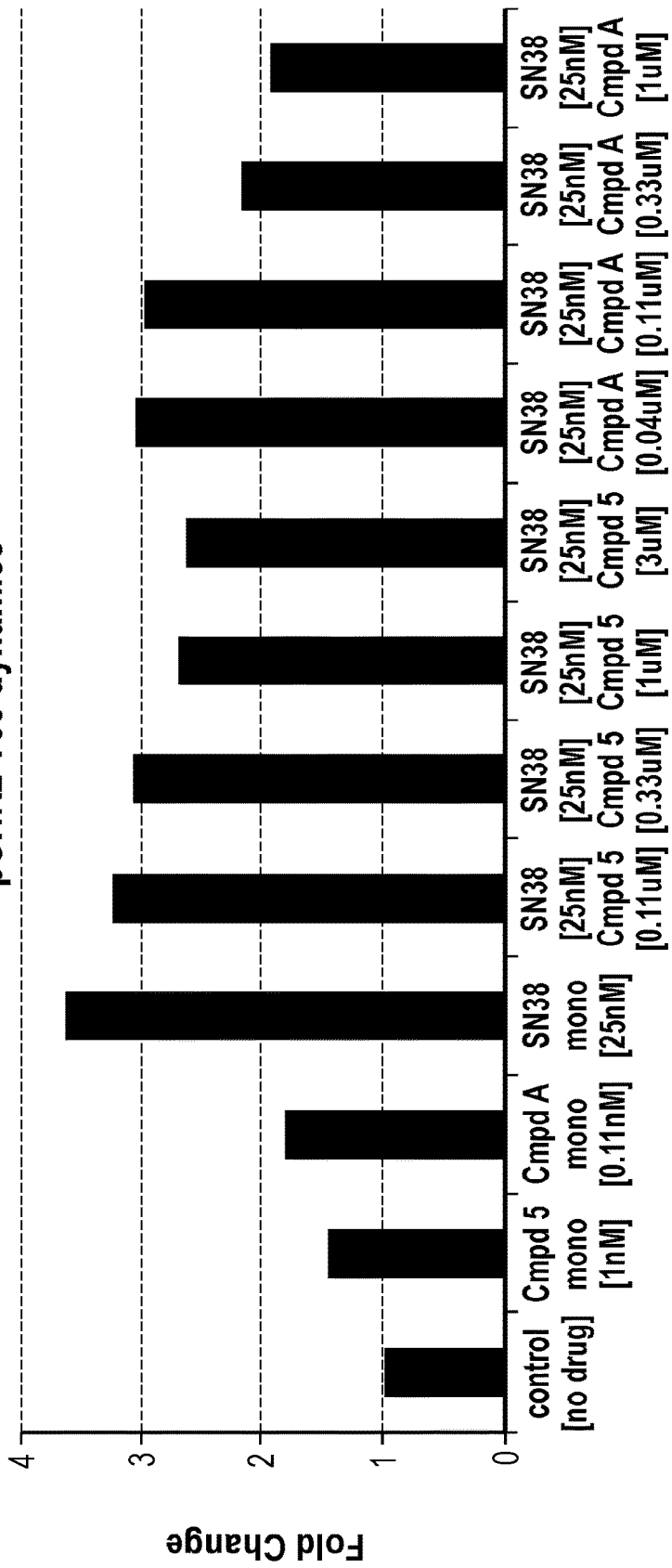
Figure 43F:
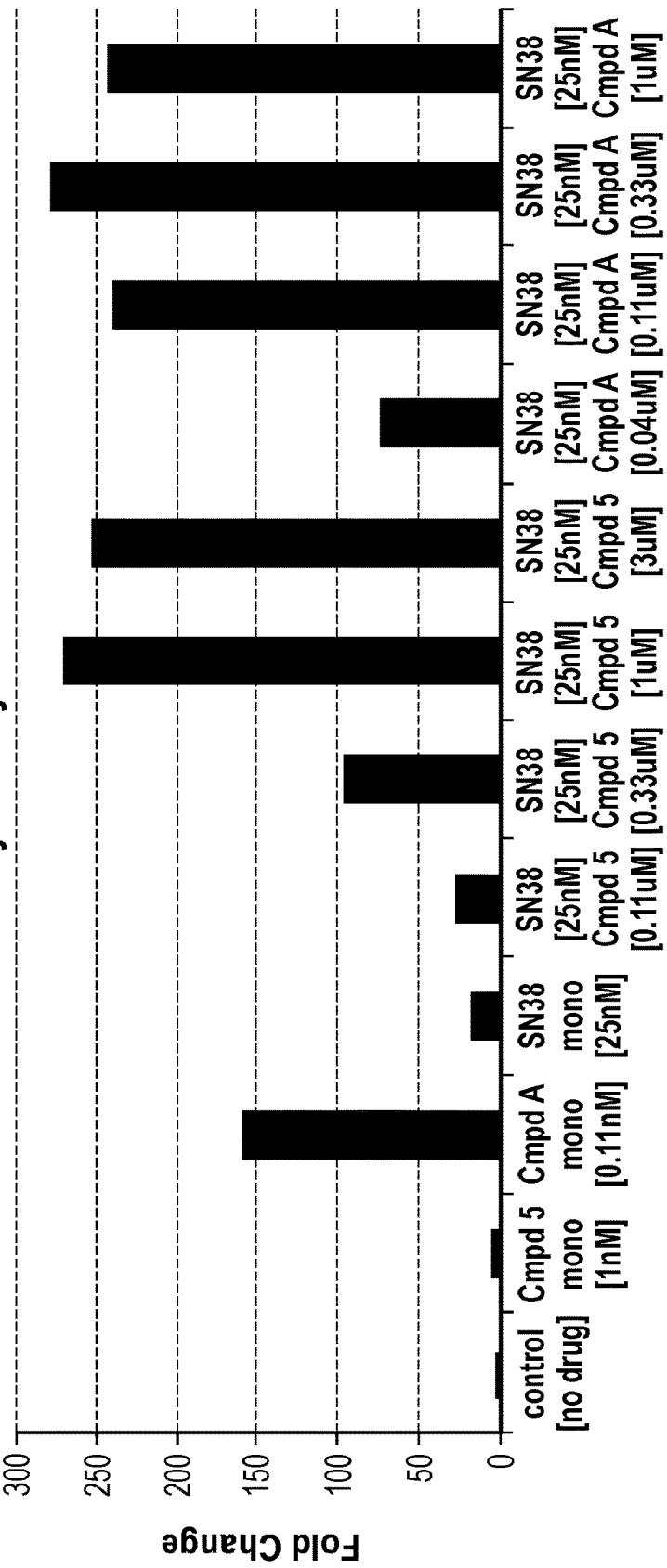
Figure 43F:
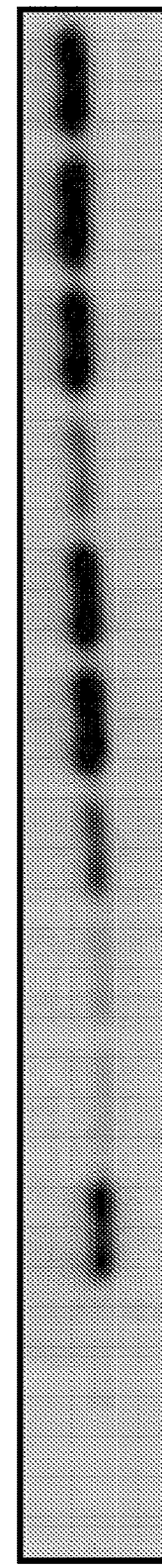
Figure 44A:
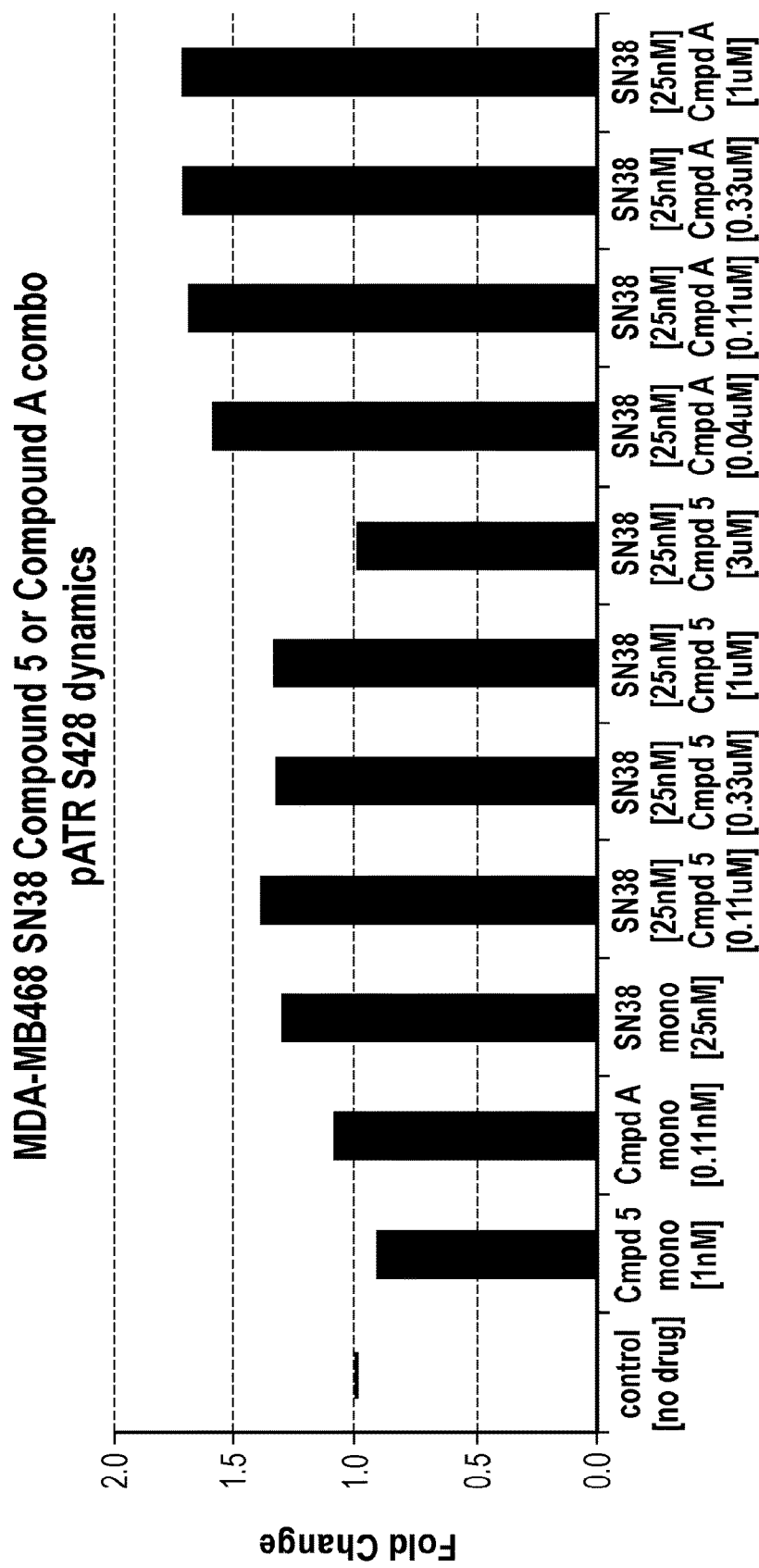
FIG. 44A-F Fold change in cancer cell line MDAMB468 pharmacodynamics markers after exposure to ATR inhibition and/or SN38.
Figure 44B:
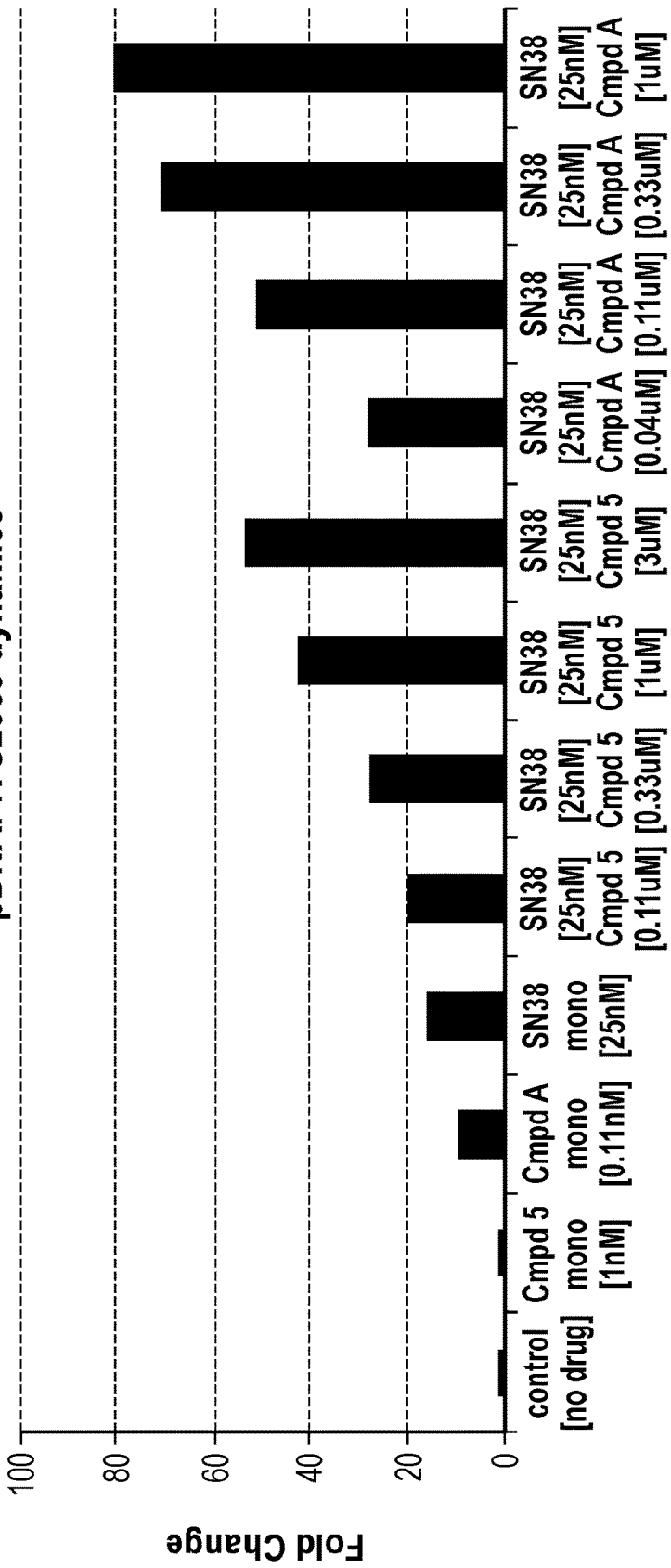
Figure 44B:
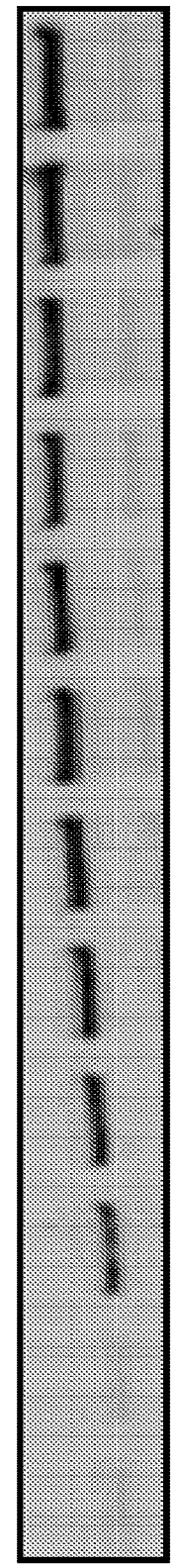
Figure 44C:
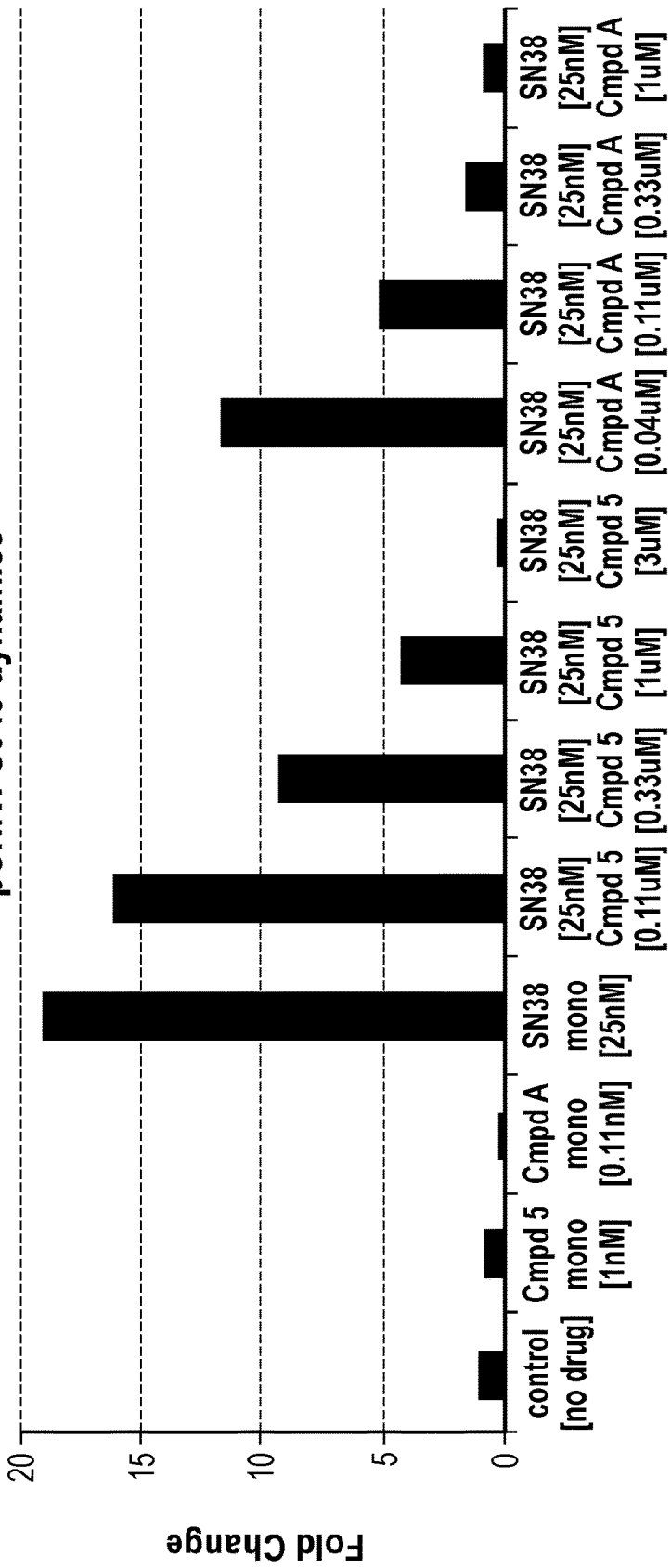
Figure 44D:
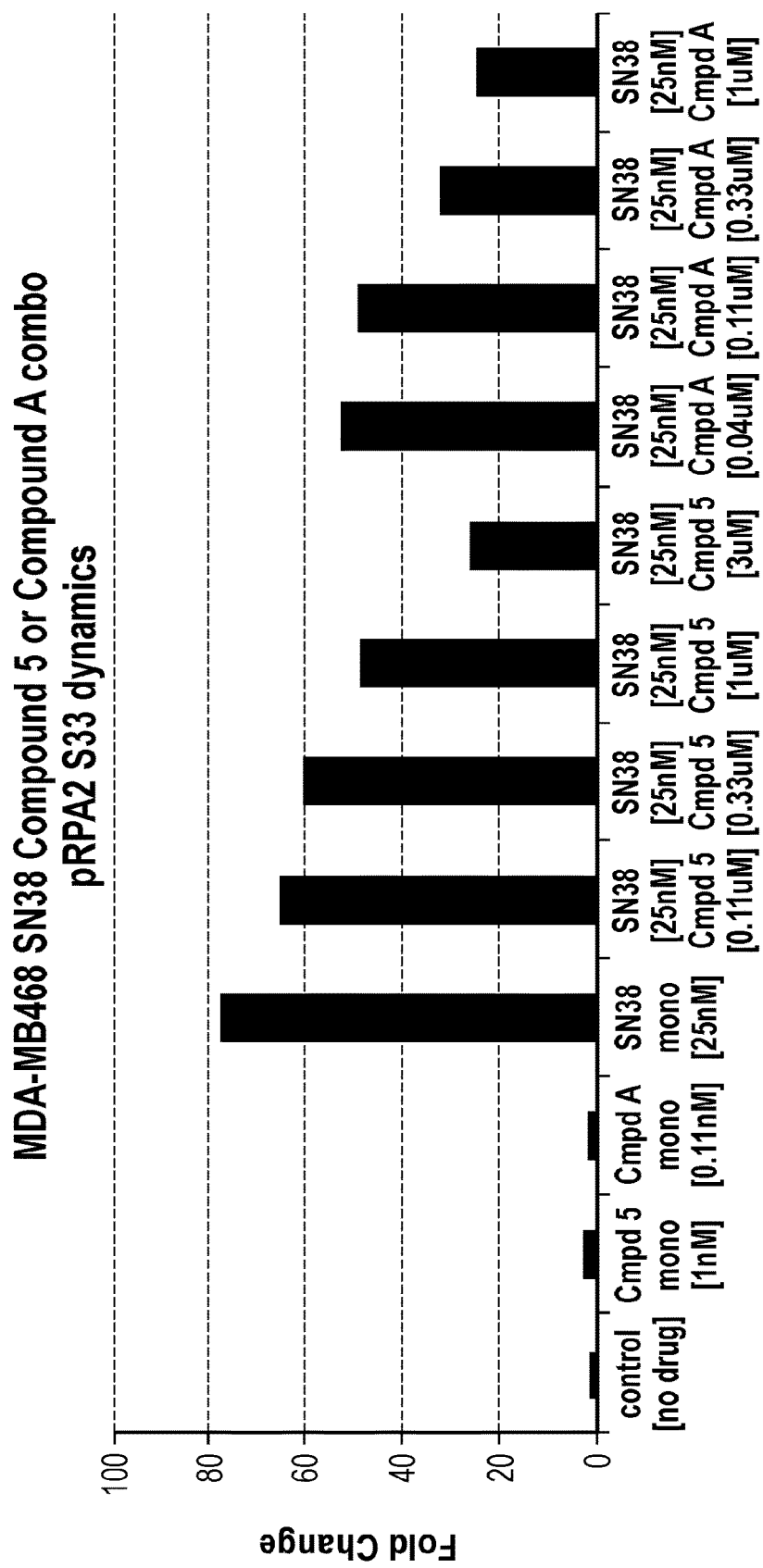
Figure 44D:
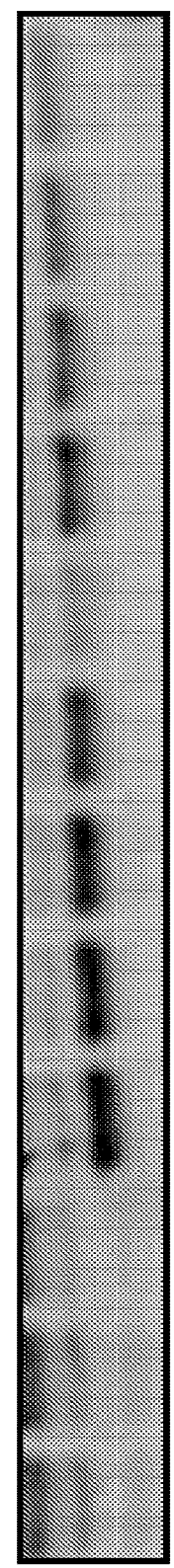
Figure 44E:
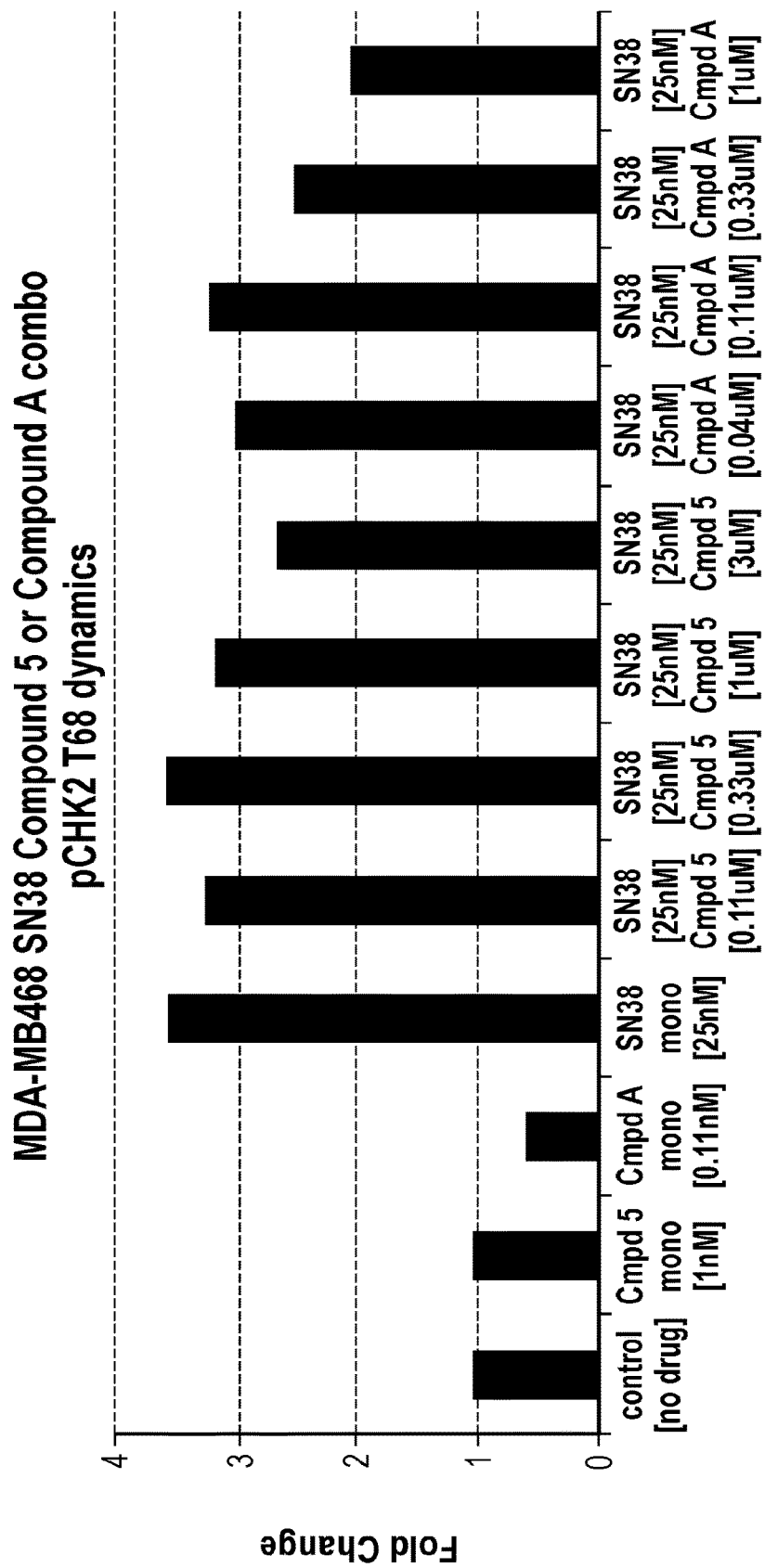
Figure 44F:
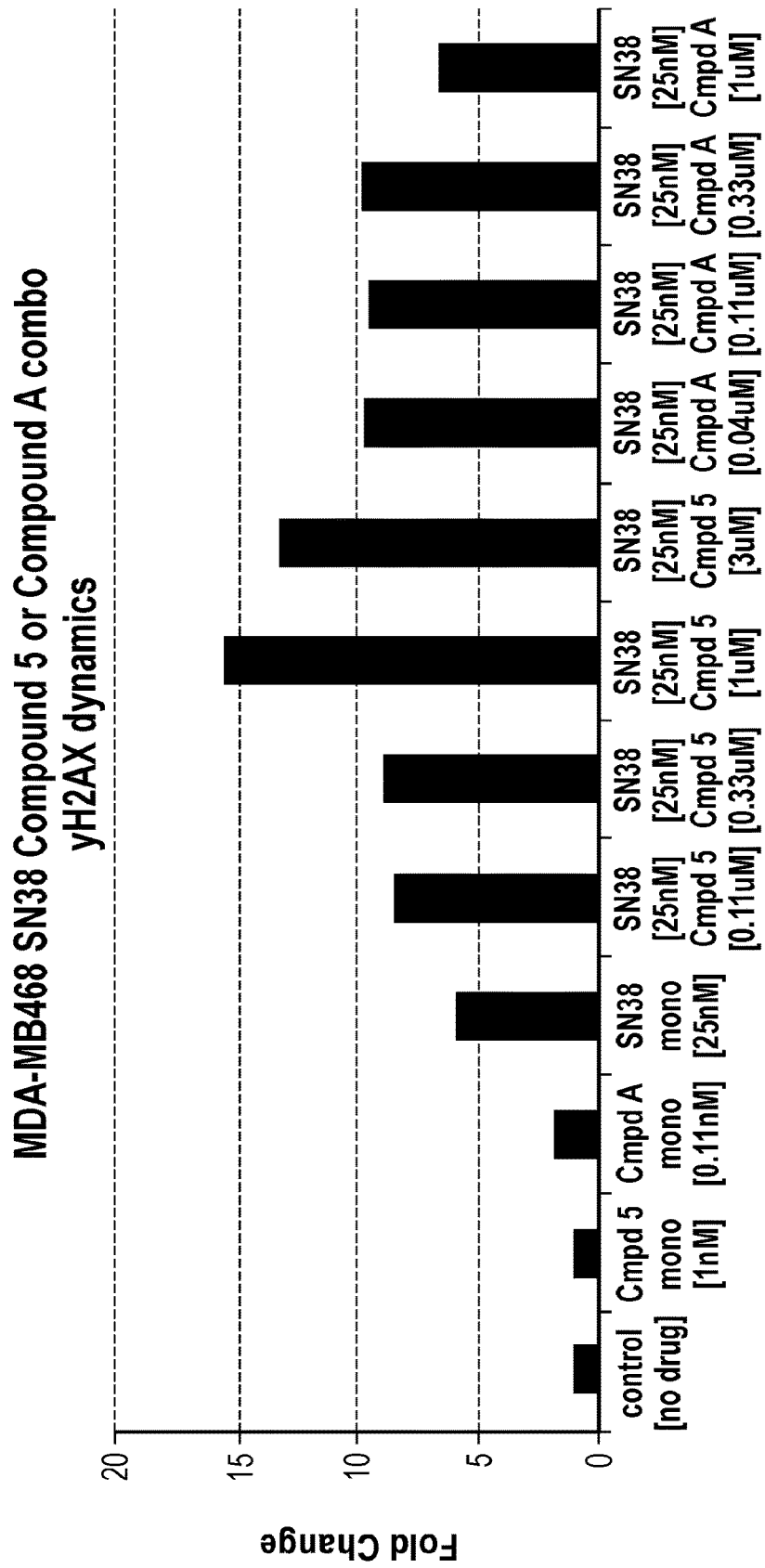
Figure 44F:
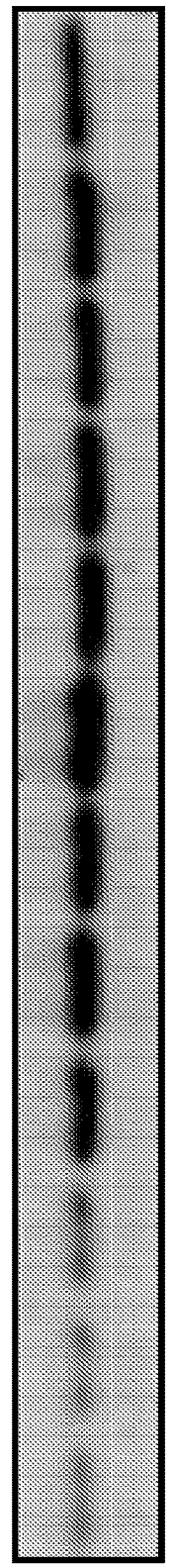
Figure 45:
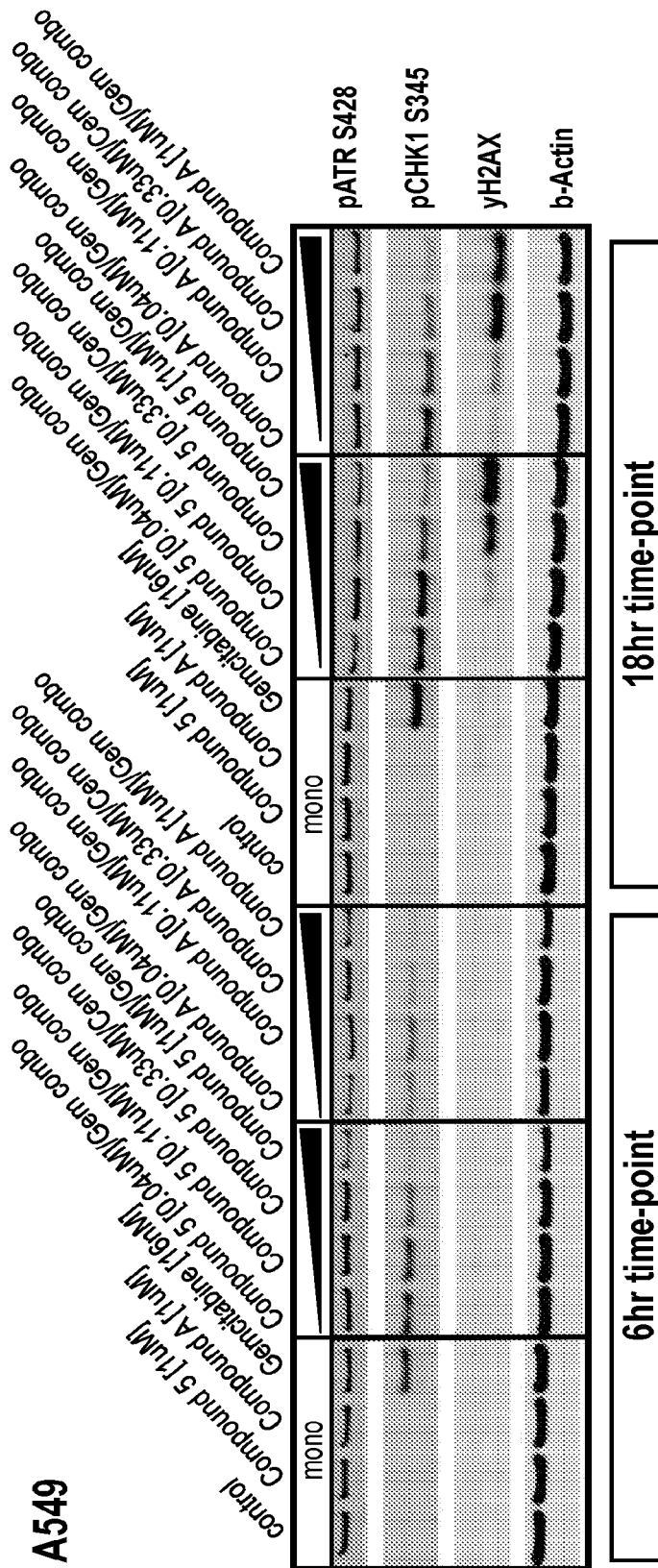
FIG. 45 Western blots of pharmacodynamics markers in cancer cell line A549 after 6 or 18 hours exposure to ATR inhibition and/or gemcitabine.
Figure 46:
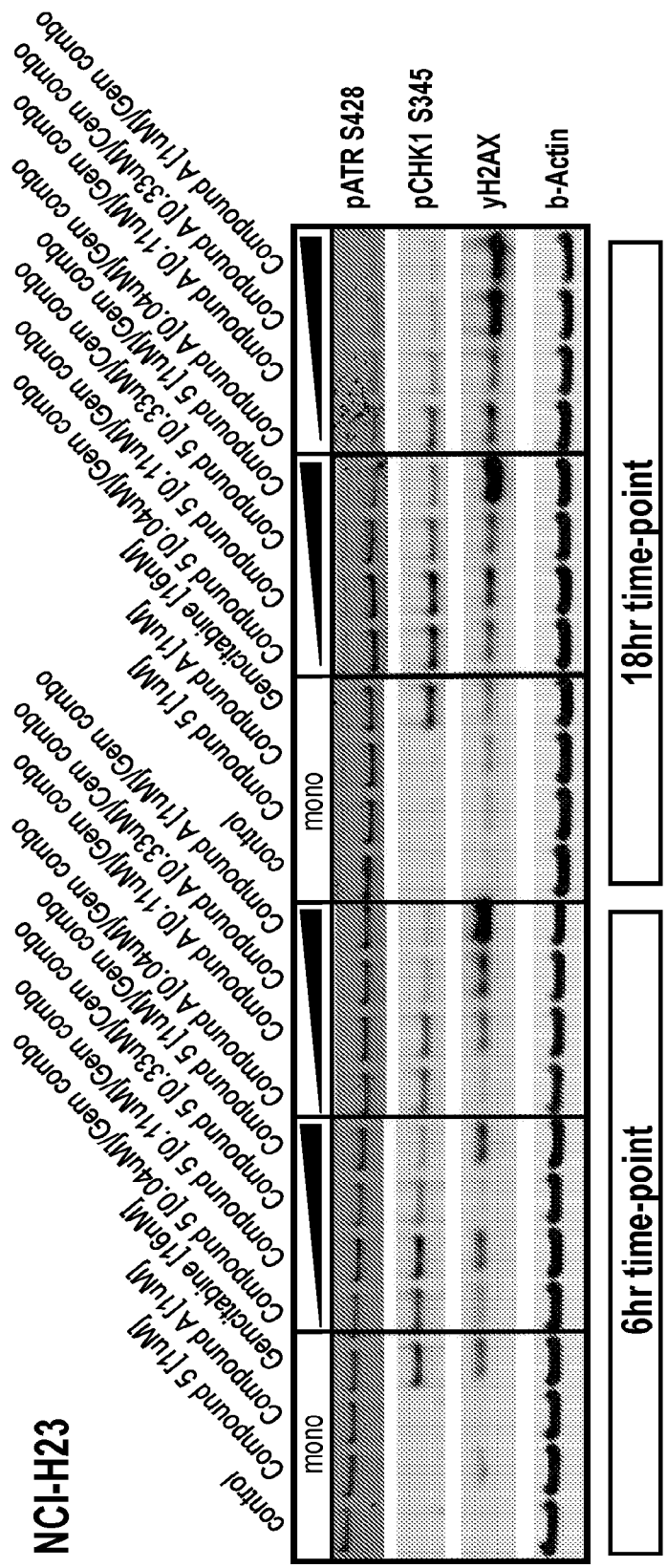
FIG. 46 Western blots of pharmacodynamics markers in cancer cell line NCIH23 after 6 or 18 hours exposure to ATR inhibition and/or gemcitabine.
Figure 47:
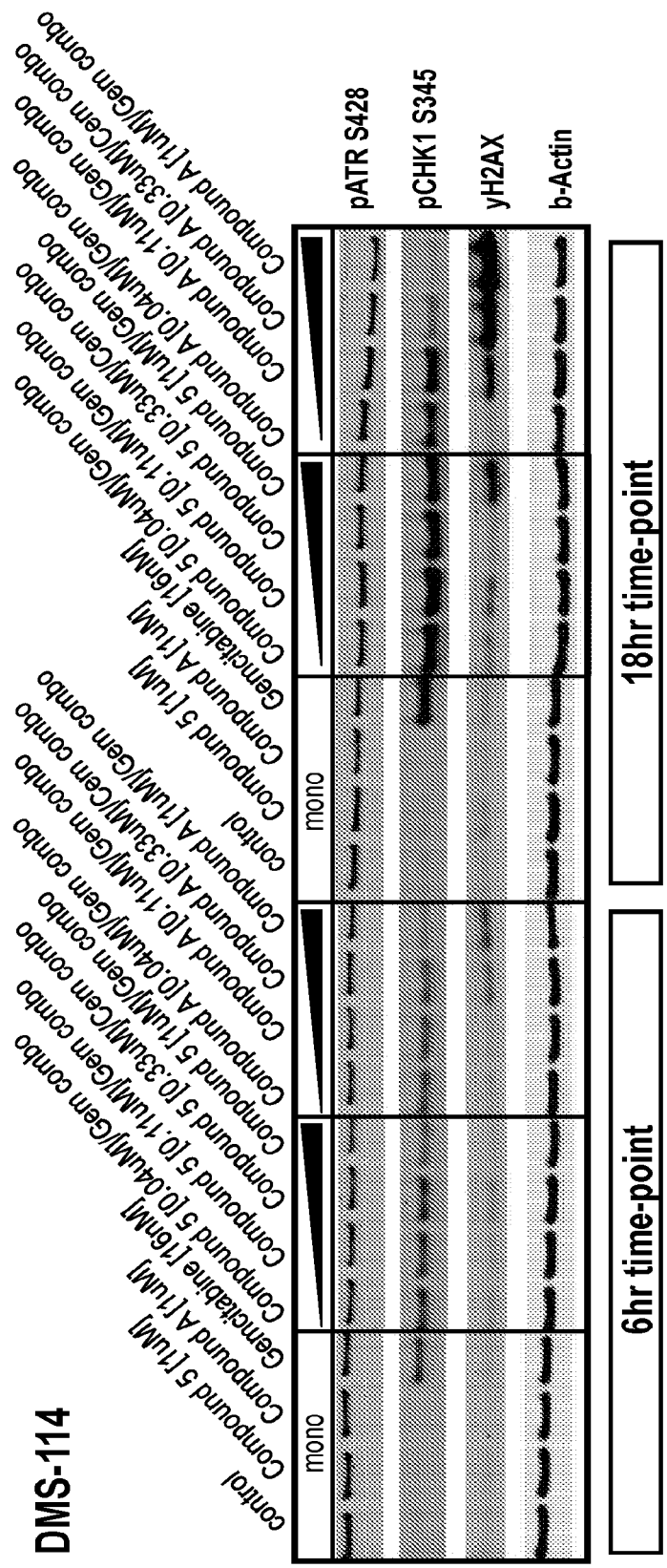
FIG. 47 Western blots of pharmacodynamics markers in cancer cell line DMS114 after 6 or 18 hours exposure to ATR inhibition and/or gemcitabine.
Figure 48:
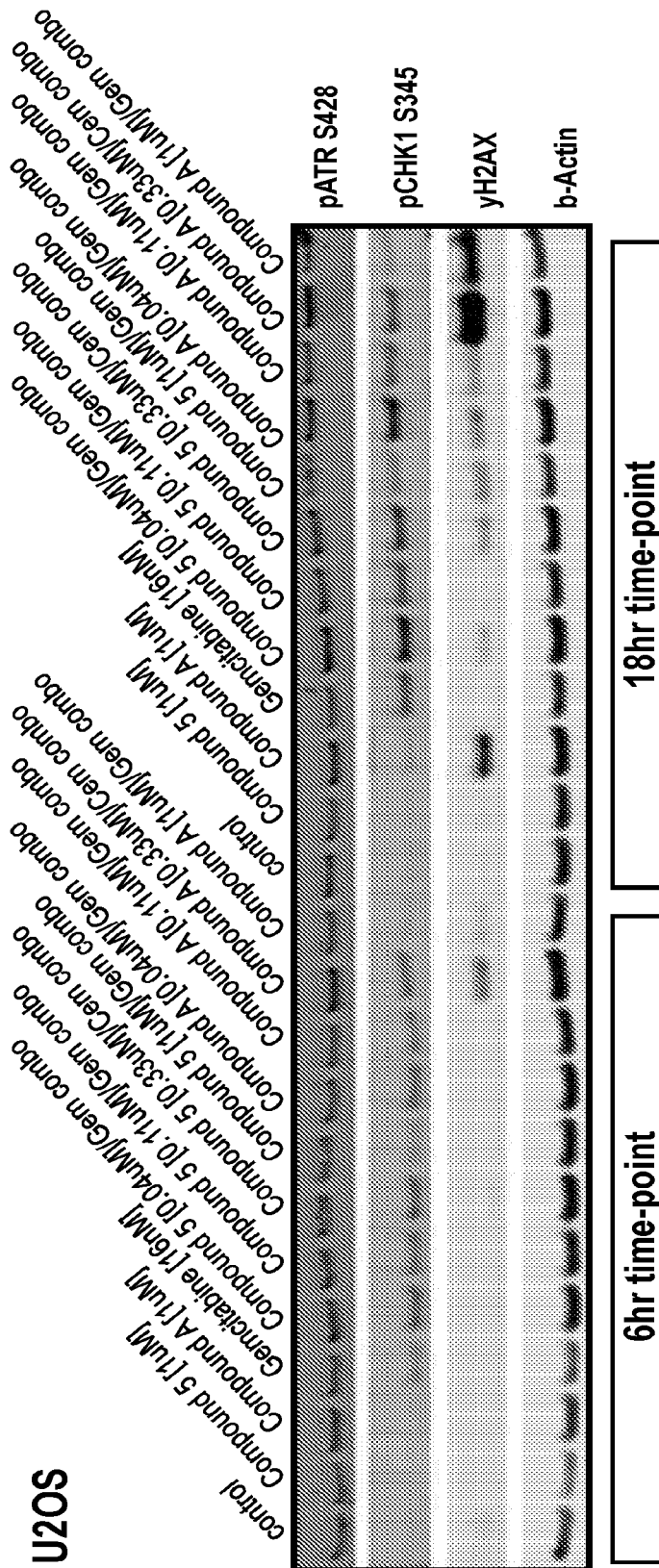
FIG. 48 Western blots of pharmacodynamics markers in cancer cell line U2OS after 6 or 18 hours exposure to ATR inhibition and/or gemcitabine.
Figure 49:
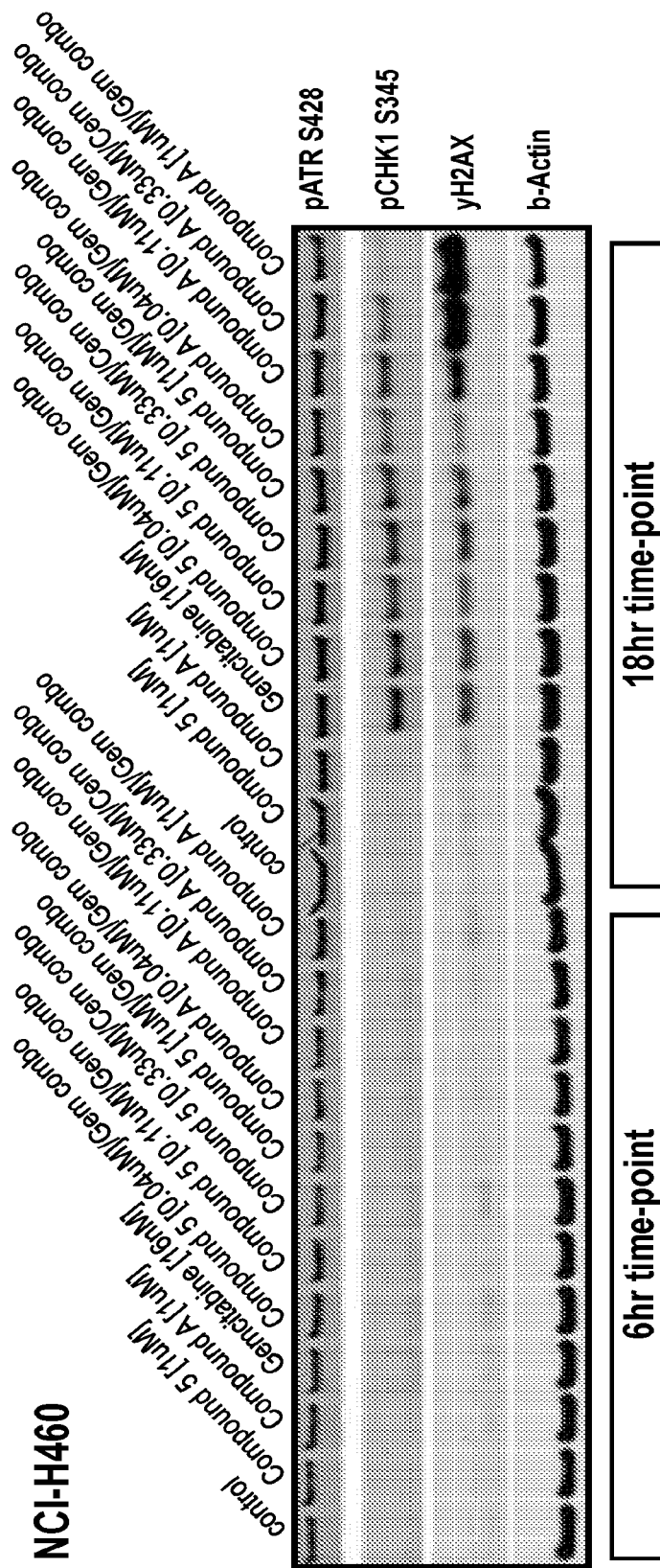
FIG. 49 Western blots of pharmacodynamics markers in cancer cell line NCIH460 after 6 or 18 hours exposure to ATR inhibition and/or gemcitabine.
Figure 50:
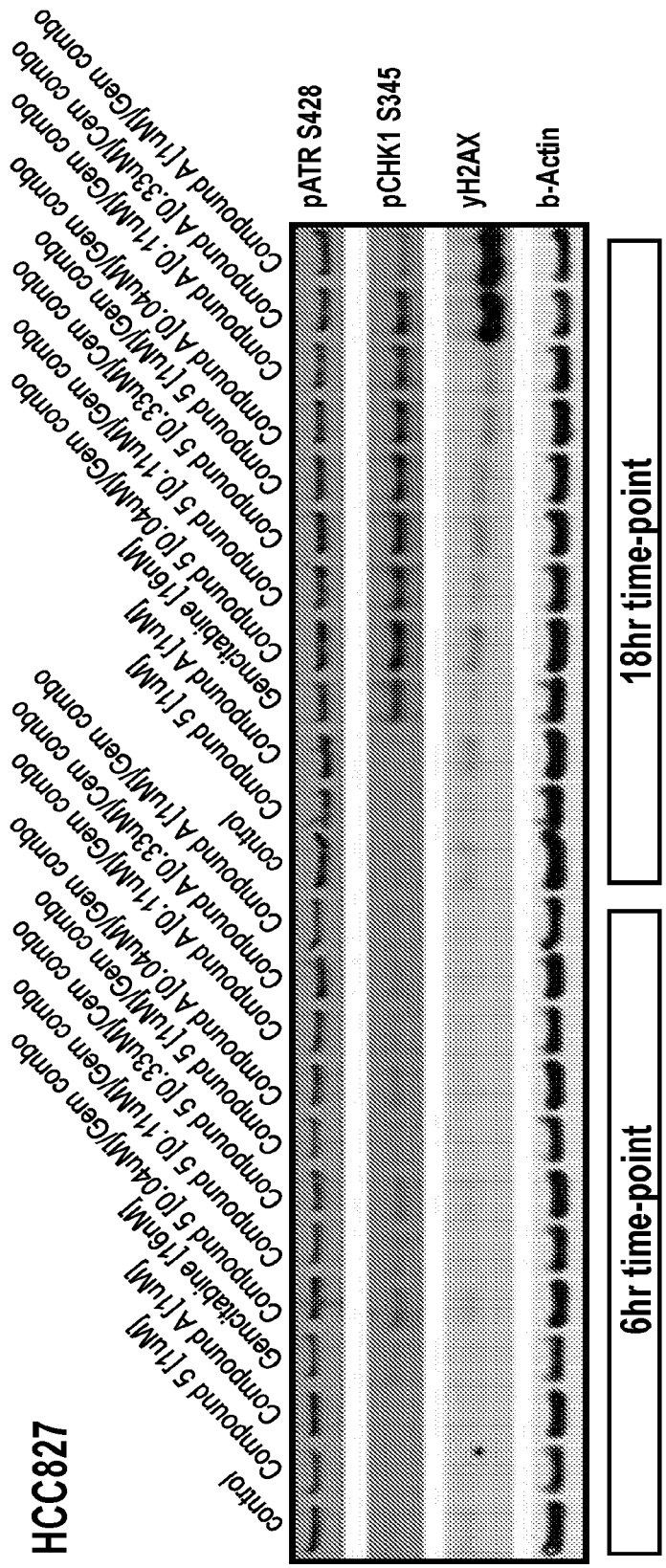
FIG. 50 Western blots of pharmacodynamics markers in cancer cell line HCC827 after 6 or 18 hours exposure to ATR inhibition and/or gemcitabine.
Figure 51:
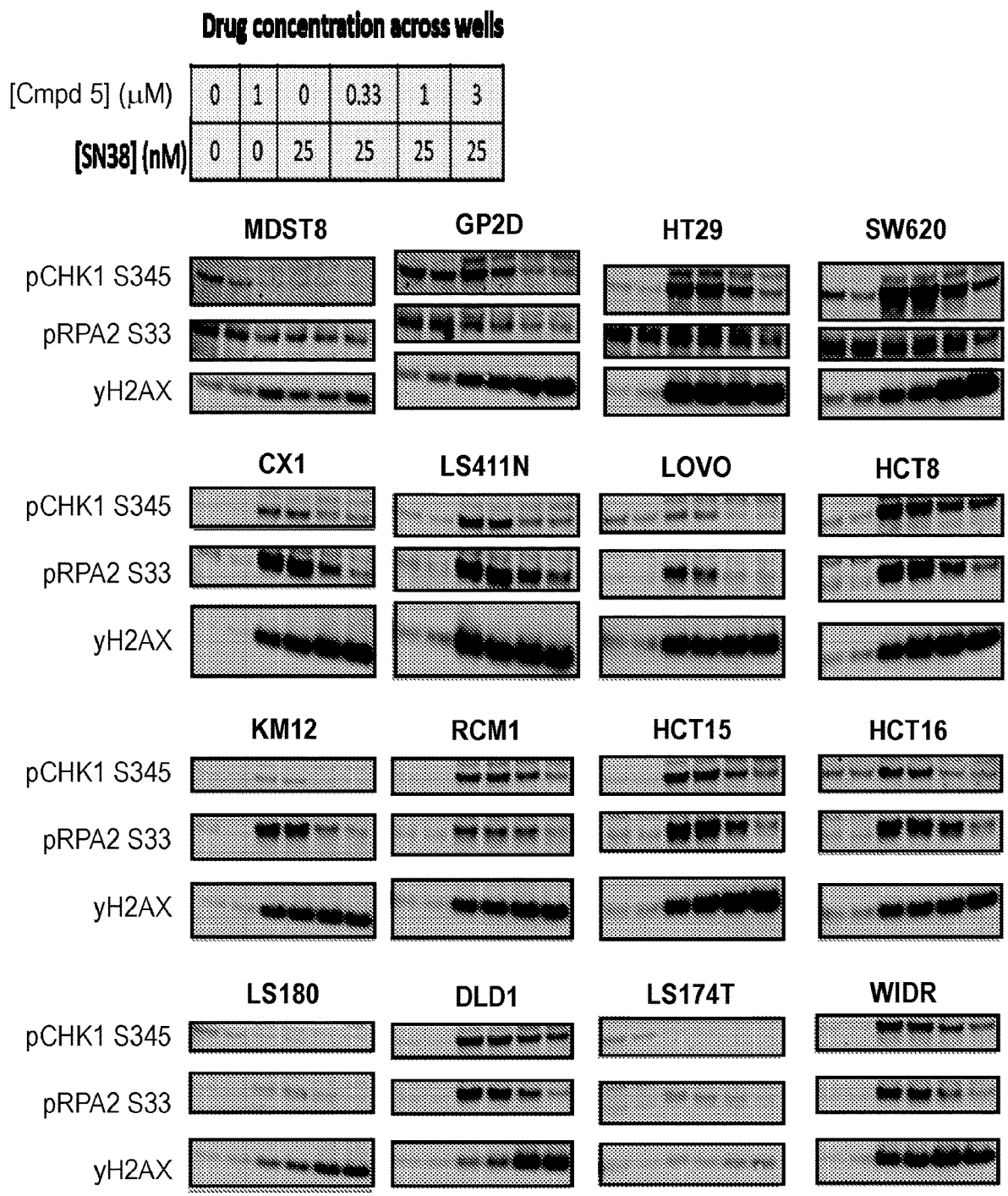
FIG. 51 Western blots of pharmacodynamics markers in a panel of colorectal cancer cell lines after 18 hours exposure to Compound 5 and/or SN38.
Figure 52:
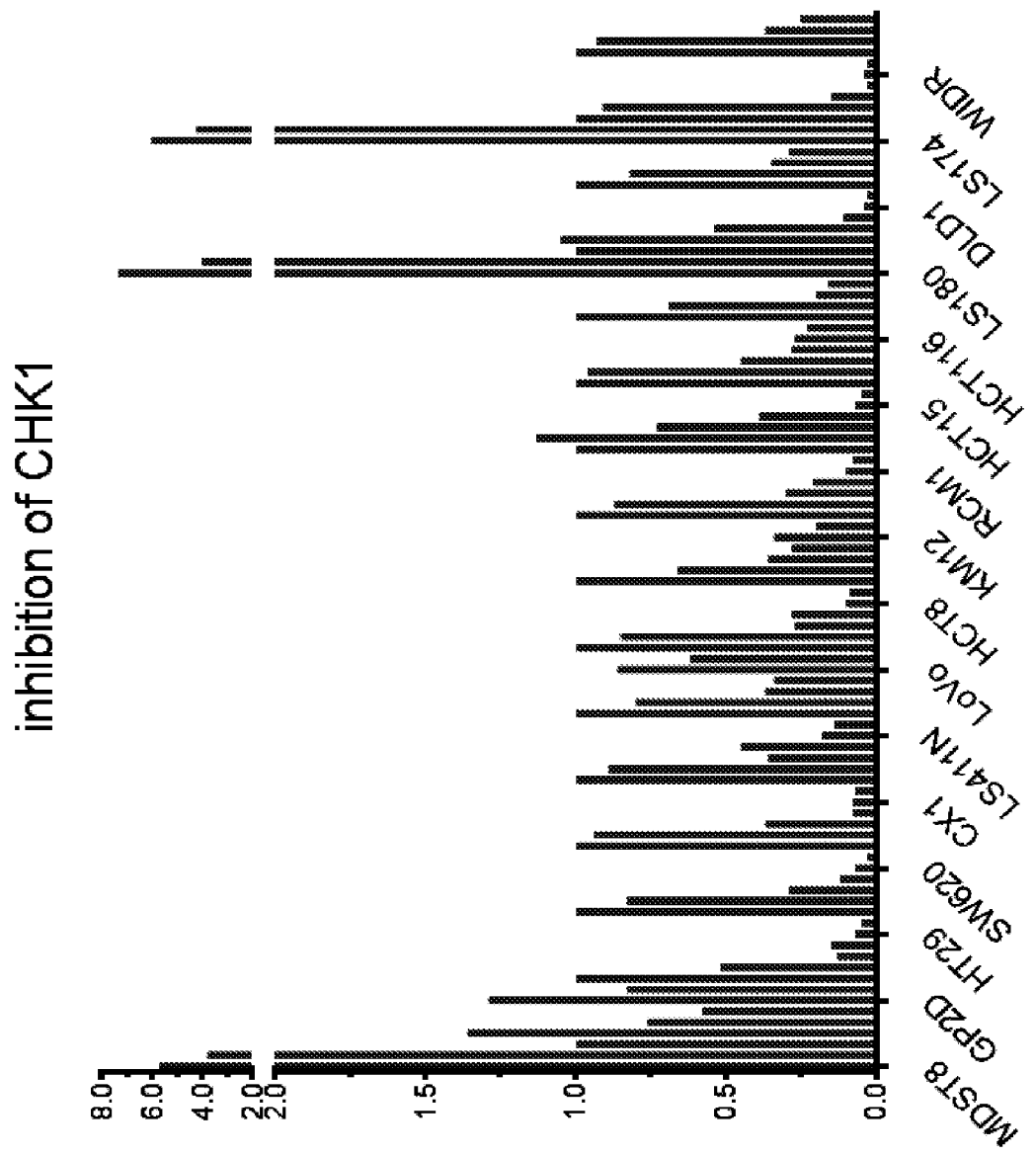
FIG. 52 Normalized quantification of phosphorylated Chk1 levels in a panel of colorectal cancer cell lines after 18 hours exposure to Compound 5 and/or SN38 (the signal for each cell line is normalized to the signal in the presence of SN38 alone).
Figure 53:
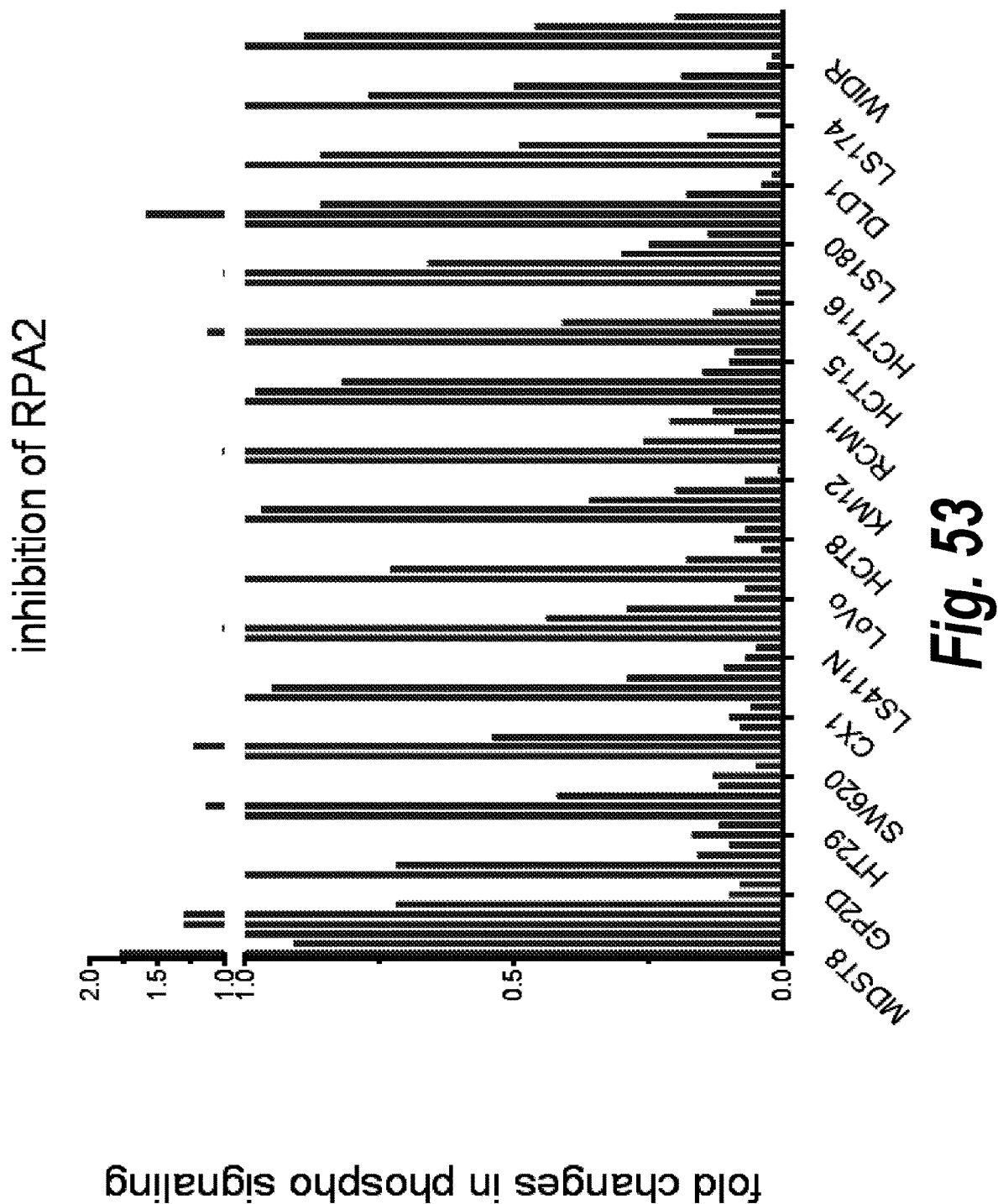
FIG. 53 Normalized quantification of phosphorylated RPA2 levels in a panel of colorectal cancer cell lines after 18 hours exposure to Compound 5 and/or SN38 (the signal for each cell line is normalized to the signal in the presence of SN38 alone).
Figure 54:
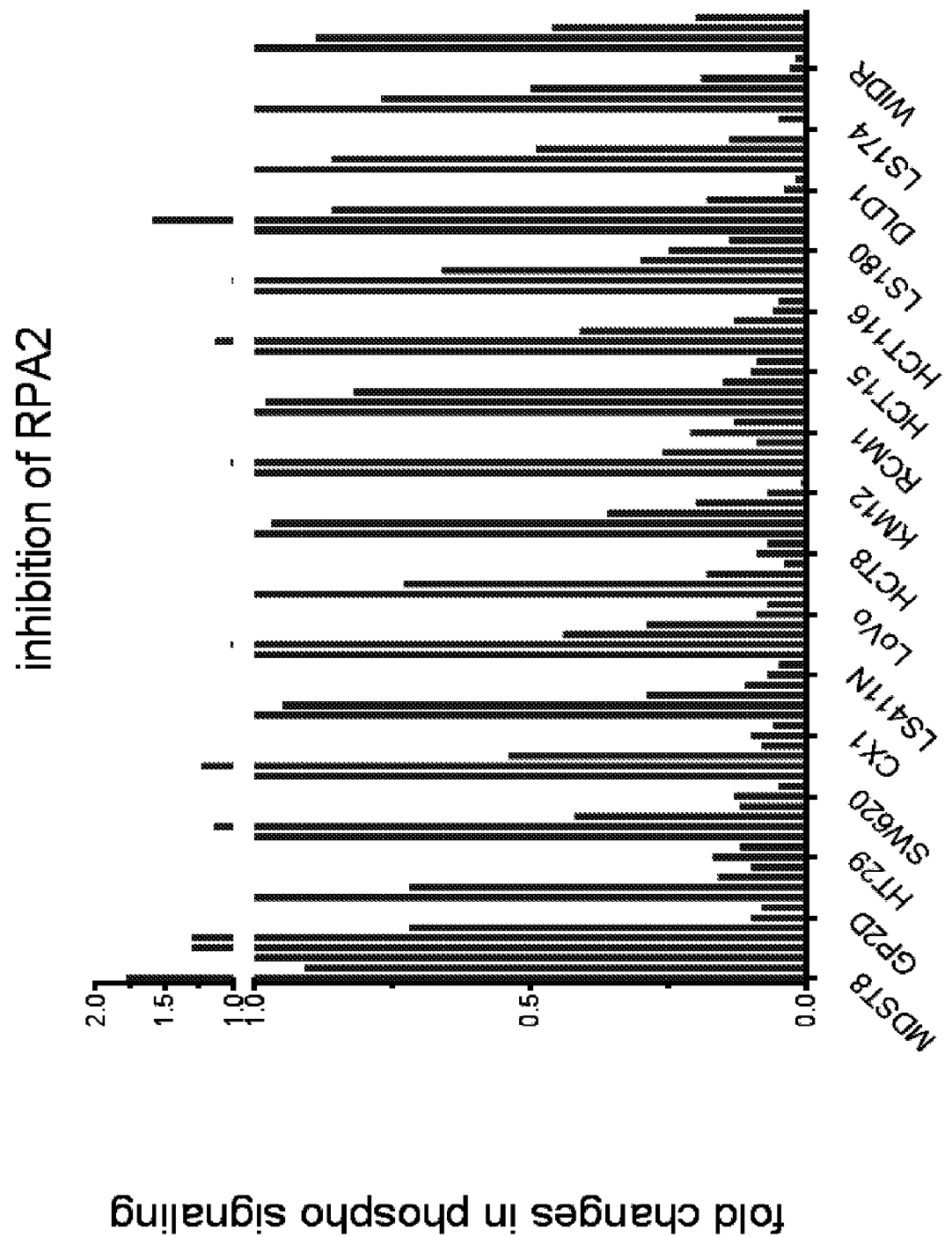
FIG. 54 Normalized quantification of γH2AX levels in a panel of colorectal cancer cell lines after 18 hours exposure to Compound 5 and/or SN38 (the signal for each cell line is normalized to the signal in the presence of SN38 alone).

Referring to FIGS. 35 and 36, it was observed that in lung cancer cell lines exposed to Compound 5 and SN38, basal MRE11 protein levels and basal ATM levels both correlated significantly with the cell line integral scores. In lung cancer cells that have a p53 compromised background and were exposed to Compound 5 and SN38, the integral score correlates with NBS, MRE11 and RAD50 protein levels. "Compromised p53" cells are those that have non-zero basal p53 protein levels (in most cells, p53 levels are only visible in Western blots after treatment). (See FIG. 37, FIG. 38 and FIG. 39).

Example 23: Signaling Experiment: Compound 5 vs. Compound a in Combination with SN38: 6 Different PD Markers Referring to FIGS. 40-44: Pharmacodynamics markers pChk1, pRPA2, pATR, pDNAPK, pChk2 and γH2AX were quantified by Western blot after cancer cell lines were exposed to various doses of Compound 5 or Compound A in combination with SN38. HCC70, DMS114, MDAMB468, NCIH1299 and NCIH460 cells were seeded in 12 well plates, allowed to incubate overnight then exposed to SN38 and/or the ATR inhibitor. After 24 hours of drug exposure, cells were lysed for Western blotting. When quantification was performed, the PD marker signal was normalized to the beta actin signal.

Example 24: Signaling Experiment: Compound 5 vs. Compound a in Combination with Gemcitabine: 3 Different PD Markers Referring to FIGS. 45-50: Six fluorescently labeled cell lines were profiled for various proteins involved in the DNA damage pathway after exposure to an ATR inhibitor and/or gemcitabine. Parental cancer cell lines were transduced with a NucLight Red lentivirus and selected with puromycin. Pharmacodynamics markers pChk1, pATR, and γH2AX were quantified by Western blot after cancer cell lines were exposed to various doses of Compound 5 or Compound A in combination with 16 nM gemcitabine. A549, NCIH23, DMS114, U2OS, HCC827 and NCIH460 cells were seeded in 12 well plates, allowed to incubate overnight then exposed to SN38 and/or the ATR inhibitor. After 6 or 18 hours of drug exposure, cells were lysed for Western blotting. When quantification was performed, the PD marker signal was normalized to the beta actin signal.

We claim:

1. A liposome composition comprising an ATR protein kinase inhibitor, or a pharmaceutically acceptable salt thereof encapsulated in a liposome, wherein the ATR protein kinase inhibitor is a compound of formula (I):

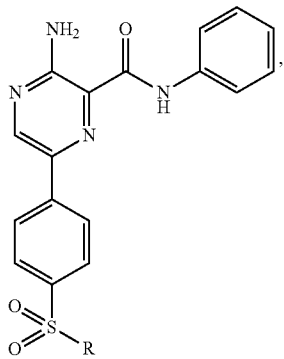

(I)

wherein R is a moiety comprising an amine with a $pK_a$ of greater than 7.0;
and the liposome comprises cholesterol.

2. The liposome composition of claim 1, wherein R is a moiety comprising an amine with a $pK_a$ of at least about 9.5.

3. The liposome composition of claim 1, wherein the ATR protein kinase inhibitor is a compound of formula (I), or a pharmaceutically acceptable salt thereof:

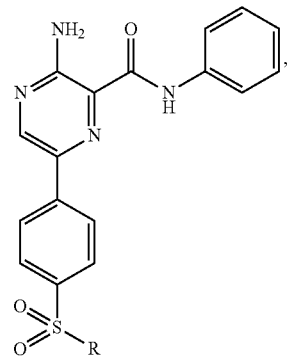

(I)

wherein R is:

i)

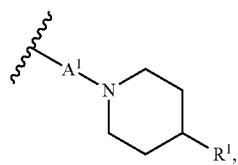

wherein $A^1$ is either absent or $C_1$-$C_4$ alkyl, and $R^1$ is $C_1$-$C_4$ alkylamino;

ii) —N(H)($C_1$-$C_4$ alkyl)-$NR^aR^b$, wherein $R^a$ and $R^b$ are each independently $C_1$-$C_4$ alkyl;

iii) -(G)-$NR^aR^b$; wherein $R^a$ and $R^b$ are each independently $C_1$-$C_4$ alkyl; and G is $C_1$-$C_4$ alkyl, wherein G can be optionally substituted with $C_1$-$C_4$ alkyl; or iv)

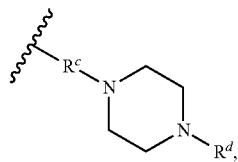

wherein $R^c$ and $R^d$ are each independently $C_1$-$C_4$ alkyl.

4. The liposome composition of claim 1, wherein the liposome further comprises PEG(2000)-distearoylglycerol (PEG-DSG).

5. The liposome composition of claim 4, wherein the liposome comprises cholesterol and PEG-DSG in a molar ratio of about 2:0.15.

6. The liposome composition of claim 1, wherein the liposome comprises one or more phospholipids.

7. The liposome composition of claim 6, wherein the phospholipid is 1,2-distearoyl-sn-glycero-3-phosphocholine (DSPC).

8. The liposome composition of claim 1, wherein the ATR protein kinase inhibitor is a compound selected from the group consisting of:
Compound 1
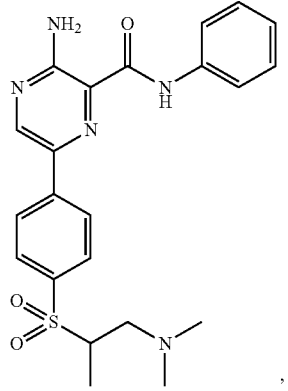
Compound 2
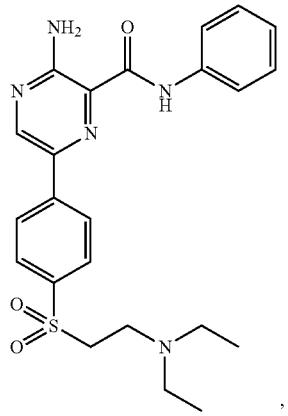
Compound 3
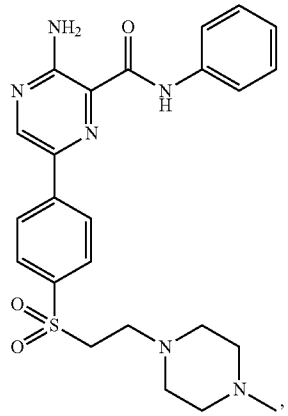
Compound 4
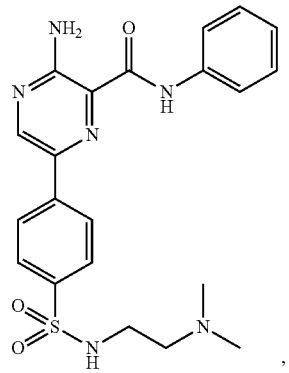
Compound 5
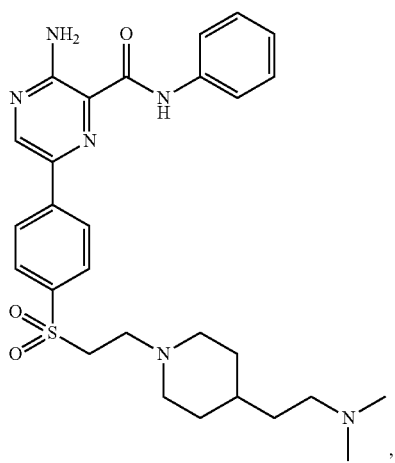
, and
Compound 6
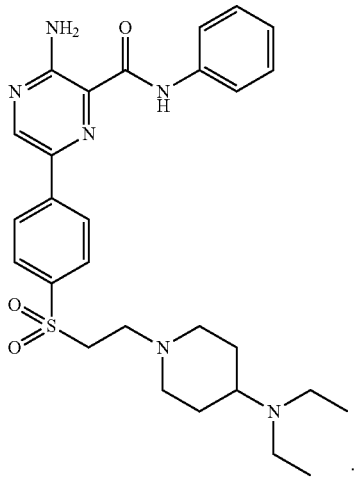
.

9. The liposome composition of claim 8, wherein the ATR protein kinase inhibitor is a compound selected from the group consisting of:

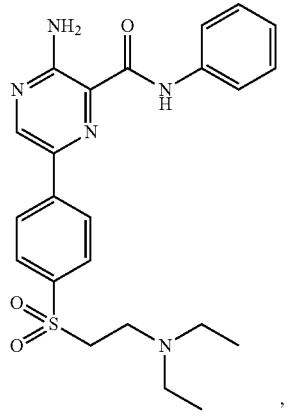

Compound 2

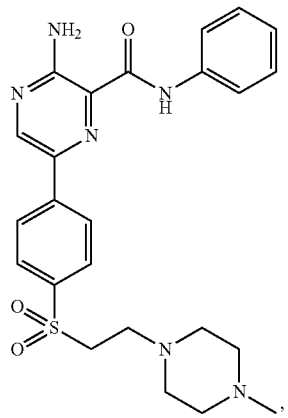

Compound 3

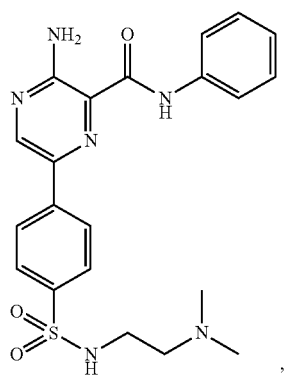

Compound 4

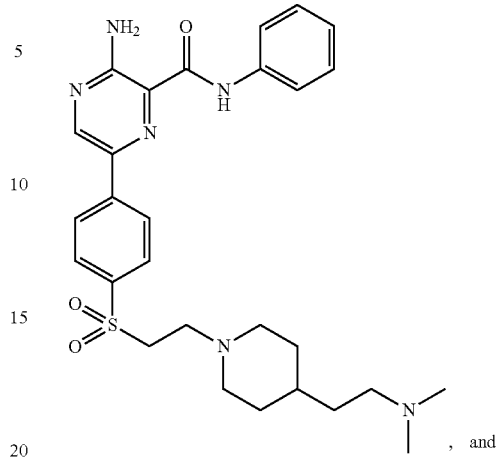

Compound 5

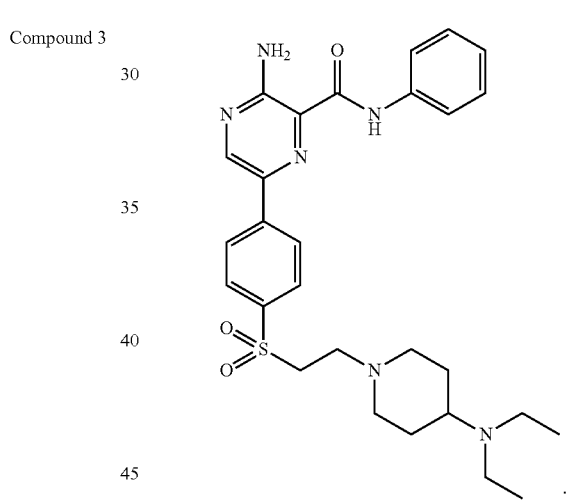

Compound 6

, and

.

10. The liposome composition of claim 8, wherein the liposome further comprises PEG(2000)-distearoylglycerol (PEG-DSG).

11. The liposome composition of claim 8, wherein the liposome comprises cholesterol and PEG-DSG in a molar ratio of about 2:0.15.

12. The liposome composition of claim 8, wherein the liposome comprises one or more phospholipids.

13. The liposome composition of claim 12, wherein the phospholipid is 1,2-distearoyl-sn-glycero-3-phosphocholine (DSPC).

14. The liposome composition of claim 1, wherein the ATR protein kinase inhibitor is:

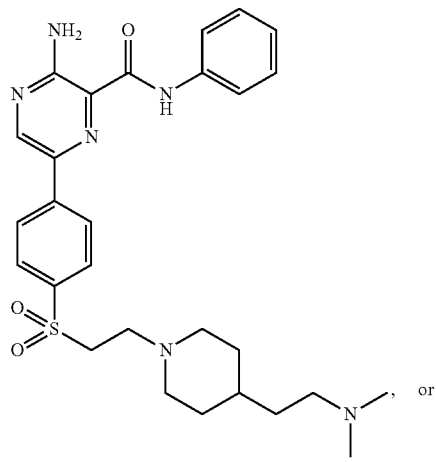

Compound 5

, or

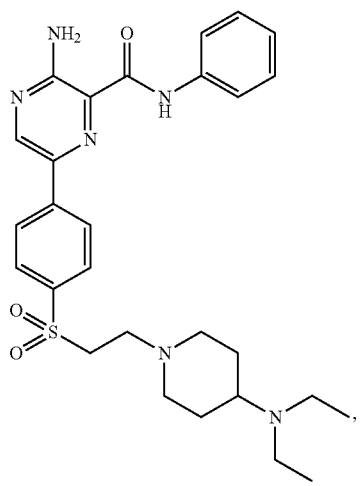

Compound 6 or a pharmaceutically acceptable salt thereof.

15. The liposome composition of claim 14, wherein the ATR protein kinase inhibitor is Compound 5:

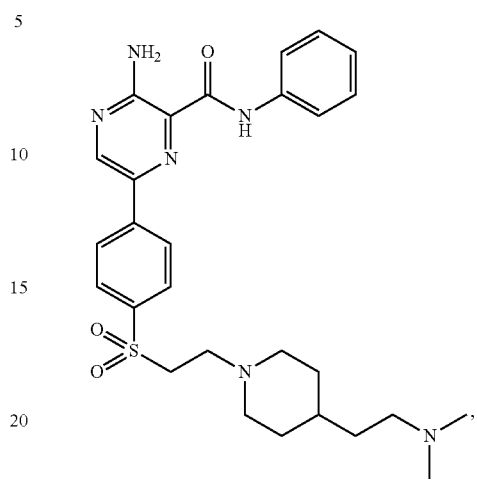

Compound 5 or a pharmaceutically acceptable salt thereof.

16. The liposome composition of claim 14, wherein the ATR protein kinase inhibitor is Compound 6, Compound 6 or a pharmaceutically acceptable salt thereof.

17. The liposome composition of claim 14, wherein the liposome further comprises PEG(2000)-distearoylglycerol (PEG-DSG).

18. The liposome composition of claim 14, wherein the liposome comprises cholesterol and PEG-DSG in a molar ratio of about 2:0.15.

19. The liposome composition of claim 14, wherein the liposome comprises one or more phospholipids.

20. The liposome composition of claim 19, wherein the phospholipid is 1,2-distearoyl-sn-glycero-3-phosphocholine (DSPC).

* * * * *